US009732390B2

(12) United States Patent
Lo et al.

(10) Patent No.: US 9,732,390 B2
(45) Date of Patent: Aug. 15, 2017

(54) NON-INVASIVE DETERMINATION OF METHYLOME OF FETUS OR TUMOR FROM PLASMA

(71) Applicant: THE CHINESE UNIVERSITY OF HONG KONG, Shatin, New Territories (CN)

(72) Inventors: Yuk-Ming Dennis Lo, Kowloon (CN); Rossa Wai Kwun Chiu, Shatin (CN); Kwan Chee Chan, Kowloon (CN); Miu Fan Lun, Kwai Chung (CN); Wai Man Chan, Shaukeiwan (CN); Peiyong Jiang, Shatin (CN)

(73) Assignee: The Chinese University of Hong Kong, Shatin (CN)

( * ) Notice: Subject to any disclaimer, the term of this patent is extended or adjusted under 35 U.S.C. 154(b) by 0 days.

(21) Appl. No.: 13/842,209

(22) Filed: Mar. 15, 2013

(65) Prior Publication Data
US 2014/0080715 A1     Mar. 20, 2014

Related U.S. Application Data

(60) Provisional application No. 61/703,512, filed on Sep. 20, 2012.

(51) Int. Cl.
*C12Q 1/68* (2006.01)
*G06F 19/22* (2011.01)

(52) U.S. Cl.
CPC ......... *C12Q 1/6886* (2013.01); *C12Q 1/6809* (2013.01); *C12Q 1/6874* (2013.01);
(Continued)

(58) Field of Classification Search
None
See application file for complete search history.

(56) References Cited

U.S. PATENT DOCUMENTS

2009/0068660 A1    3/2009  Hoon et al.
2009/0280479 A1   11/2009  Hoon et al.
(Continued)

FOREIGN PATENT DOCUMENTS

CN    101535502 A    9/2009
WO    2004046332 A2    6/2004
(Continued)

OTHER PUBLICATIONS

Google Scholar search results for "methylation-aware", obtained Jan. 25, 2016.*
(Continued)

*Primary Examiner* — Karen S Weiler
(74) *Attorney, Agent, or Firm* — Kilpatrick Townsend & Stockton LLP; David B. Raczkowski

(57) ABSTRACT

Systems, methods, and apparatuses can determine and use methylation profiles of various tissues and samples. Examples are provided. A methylation profile can be deduced for fetal/tumor tissue based on a comparison of plasma methylation (or other sample with cell-free DNA) to a methylation profile of the mother/patient. A methylation profile can be determined for fetal/tumor tissue using tissue-specific alleles to identify DNA from the fetus/tumor when the sample has a mixture of DNA. A methylation profile can be used to determine copy number variations in genome of a fetus/tumor. Methylation markers for a fetus have been identified via various techniques. The methylation profile can be determined by determining a size parameter of a size distribution of DNA fragments, where reference values for the size parameter can be used to determine methylation levels. Additionally, a methylation level can be used to determine a level of cancer.

26 Claims, 45 Drawing Sheets

(52) U.S. Cl.
CPC .......... *C12Q 1/6881* (2013.01); *G06F 19/22* (2013.01); *C12Q 2600/154* (2013.01)

(56) References Cited

U.S. PATENT DOCUMENTS

| | | |
|---|---|---|
| 2010/0240549 A1 | 9/2010 | Brown |
| 2011/0028333 A1 | 2/2011 | Christensen et al. |
| 2013/0079241 A1 | 3/2013 | Luo et al. |
| 2013/0116127 A1 | 5/2013 | Schuetz et al. |
| 2013/0143214 A1 | 6/2013 | Schutz et al. |

FOREIGN PATENT DOCUMENTS

| | | |
|---|---|---|
| WO | 2007132166 A2 | 11/2007 |
| WO | 2011038507 A1 | 4/2011 |
| WO | 2011057094 A1 | 5/2011 |
| WO | 2011091046 A1 | 7/2011 |
| WO | 2011/092592 A2 | 8/2011 |
| WO | 2012012703 A2 | 1/2012 |

OTHER PUBLICATIONS

Broquet et al. (2004) "Quantifying genotyping errors in noninvasive population genetics" Molecular Ecology 13:3601-3608.*
Li et al. (2010) "Whole genome DNA methylation analysis based on high throughput sequencing technology" Methods 52(3):203-212.*
Google Scholar search of "BS-Seq", conducted Sep. 22, 2016, 1$^{st}$ page.*
Flanagan, J.M., et al., "DNA methylome of familial breast cancer identifies distinct profiles defined by mutation status," The American Journal of Human Genetics, 2010, vol. 86, pp. 420-433.
Ogoshi, K., et al., "Genome-wide profiling of DNA methylation in human cancer cells," Genomics, 2011, vol. 98, pp. 280-287.
Yuen, R.K.C., et al., "Genome-wide mapping of imprinted differentially methylated regions by DNA methylation profiling of human placentas from triploidies," Epigenetics & Chromatin, 2011, vol. 4, Article No. 10, 16 pages.
Saied, M.H., et al., "Genome wide analysis of acute myeloid leukemia reveal leukemia specific methylome and subtype specific hypomethylation of repeats," PloS ONE, Mar. 2012, vol. 7, No. 3, 12 pages.
Kuo, H., et al., "DBCAT: database of CpG islands and analytical tools for identifying comprehensive methylation profiles in cancer cells," Journal of Computational Biology, 2011, vol. 18, No. 8, pp. 1013-1017.
Price, E.M., et al., "Different measures of "genome-wide" DNA methylation exhibit unique properties in placental and somatic tissues," Epigenetics, Jun. 2012, vol. 7, No. 6, pp. 652-663.
International Search Report and Written Opinion mailed Feb. 12, 2014 in PCT/AU2013/001088, 15 pages.
Agostini, M., et al., "Circulating cell-free DNA: A promising marker of regional lymphonode metastasis in breast cancer patients," Cancer Biomarkers, 2012, vol. 11, pp. 89-98.
Beck, Julia, et al., "Next Generation Sequencing of Serum Circulating Nucleic Acids from Patients with Invasive Ductal Breast Cancer Reveals Differences to Healthy and Nonmalignant Controls," Molecular Cancer Research, Mar. 9, 2010, 9 pages.
Jiang, Peiyong, et al., "FetalQuant: deducing fractional fetal DNA concentration from massively parallel sequencing of DNA in maternal plasma," Bioinformatics, 2012, vol. 28, No. 22, pp. 2883-2890.
Chan, K.C. Allen, et al., "Hypermethylated RASSFIA in Maternal Plasma: A Universal Fetal DNA Marker that Improves the Reliability of Noninvasive Prenatal Diagnosis," Clinical Chemistry, 2006, vol. 52, No. 12, pp. 2211-2218.
Korshunova, Yulia, et al., "Massively parallel bisulphite pyrosequencing reveals the molecular complexity of breast cancer-associated cytosine-methylation patterns obtained from tissue and serum DNA," Genome Research, 2008, 12 pages.

Hannum, Gregory, et al., "Genome-wide Methylation Profiles Reveal Quantitative Views of Human Aging Rates," Molecular Cell, 2013, vol. 49, pp. 359-367.
Heitzer, Ellen, et al., "Tumor-associated copy number changes in the circulation of patients with prostate cancer identified through whole-genome sequencing," Genome Medicine, 2013, vol. 5, No. 30, pp. 16 pages.
Li, Yingrui, et al., "The DNA Methylome of Human Peripheral Blood Mononuclear Cells," PloS Biology, Nov. 2010, vol. 8, Issue 11, 9 pages.
Lister, Ryan, et al., "Highly Integrated Single-Base Resolution Maps of the Epigenome in Arabidopsis," Cell, May 2, 2008, vol. 133, pp. 523-536.
Lister, Ryan, et al., "Human DNA methylomes at base resolution show widespread epigenomic differences," Nature, Nov. 19, 2009, vol. 462, pp. 315-322.
Mendelsohn, Andrew R. and Larrick, James W., "The DNA Methylome as a Biomarker for Epigenetic Instability and Human Aging," Rejuvenation Research, Nov. 1, 2013, vol. 16, pp. 74-77.
Müller, Hannes, M, et al., "DNA Methylatin Changes in Sera of Women in Early Pregnancy are Similar to Those in Advanced Breast Cancer Patients," Clinical Chemistry, 2004, vol. 50, 4 pages.
Flusberg, Benjamin, A., et al., "Direct detection of DNA methylation during single-molecule, real-time sequencing," Nature Methods, Jun. 2010, vol. 7, No. 6, pp. 461-467.
Papageorgiou, Elisavet, A., et al., "Sites of Differential DNA Methylation between Placenta and Peripheral Blood," The American Journal of Pathology, May 2009, vol. 174, No. 5, pp. 1609-1618.
Papageorgiou, Elisavet, A., et al., "Fetal-specific DNA methylation ratio permits noninvasive prenatal diagnosis of trisomy 21," Nature Medicine, Apr. 2011, vol. 17, No. 4, pp. 510-514.
Tang, Man-Hung Eric, et al., "Major chromosomal breakpoint intervals in breast cancer co-localize with differentially methylated regions," Dec. 2012, vol. 2, Article 197, 12 pages.
Tong, Yu Kwan, et al., "Technical concerns about immunoprecipitation of methylated fetal DNA for noninvasive trisomy 21 diagnosis," Nature Medicine, Sep. 2012, vol. 18, No. 9, pp. 1327-1328.
Tsaliki, Evdokia, et al., "MeDIP real-time qPCR of maternal peripheral bold reliably identifies trisomy 21," Prenatal Diagnosis, 2012, vol. 32, 6 pages.
Umetani, Naoyuki, et al., "Increased Integrity of Free Circulating DNA in Sera Patients with Colorectal or Periampullary Cancer: Direct Quantitative PCR for ALU Repeats," Clinical Chemistry, 2006, vol. 52, No. 6, pp. 1062-1069.
Xie, Hehuang, et al., "Genome-wide quantitative assessment of variation in DNA methylation patterns," Nucleic Acids Research, 2011, vol. 39, No. 10, pp. 4099-4108.
Frommer, Marianne, et al., "A genomic sequencing protocol that yields a positive display of 5-methylcytosine residues in individual DNA strands," Proc. Natl. Acad. Sci. USA, Mar. 1992, vol. 89, pp. 1827-1831.
Vogelstein, Bert, et al., "Digital PCR," Proc. Natl. Acad. Sci. USA, Aug. 1999, vol. 96, pp. 9236-9241.
Shim, Jiwook, et al., "Detection and Quantification of Methylation in DNA using Solid-State Nanopores," Scientific Reports, Mar. 11, 2013, 8 pages.
Lo, Y.M. Dennis, et al., "Maternal Plasma DNA Sequencing Reveals the Genome-Wide Genetic and Mutational Profile of the Fetus," www.ScienceTranslationalMedicine.org, Dec. 8, 2010, vol. 2, Issue 61, 14 pages.
Zheng, Yama W.L., et al., "Nonhematopoietically Derived DNA is Shorter than Hematopoietically Derived DNA in Plasma: A Transplantation Model," Clinical Chemistry, 2012, vol. 58, No. 3, pp. 549-558.
Booth, Michael, J., et al., "Quantitative Sequencing of 5-Methycytosine and 5-Hydroxymethylcytosine at Single-Base Resolution," Science, May 18, 2012, vol. 336, 5 pages.
Booth, Michael, J., et al., "Oxidative bisulfite sequencing of 5-methylcytosine and 5-hydroxyethylcytosine," Nature Protocols, 2013, vol. 8, No. 10, 11 pages.

(56) References Cited

OTHER PUBLICATIONS

Yu, Miao, et al., "Tet-assisted bisulfite sequencing of 5-hydroxyethylcytosine," Nature Protocols, 2012, vol. 7, No. 12, 12 pages.
Clark, Christine, et al., "A Comparison to the Whole Genome Approach of MeDIPSeq to the Targeted Approach of the Infinium HumanMethylation450 BeadChip for Methylome Profiling," PLOS One, Nov. 2012, vol. 7, Issue 11, 13 pages.
Hiura, Hitoshi, et al., "Characterization of DNA methylation errors in patients with imprinting disorders conceived by assisted reproduction technologies," Human Reproduction, 2012, vol. 27, No. 8, pp. 2541-2548.
Chu, Tianjiao, et al., "Structural and Regulatory Characterization of the Placental Epigenome at Its Maternal Interface," PLOS One, Feb. 2011, vol. 6, Issue 2, 15 pages.
Novakovic, B, et al., "The ever growing complexity of placental epigenetics—Role in adverse pregnancy outcomes and fetal programming," Placenta, 2012, vol. 33, pp. 959-970.
Chan, K.C. Allen, et al., "Cancer Genome Scanning in Plasma: Detection of Tumor-Associated Copy Number Aberrations, Single-Nucleotide Variants, and Tumoral Heterogeneity by Massively Parallel Sequencing," Clinical Chemistry, 2013, vol. 59, No. 1, pp. 211-224.
Leary, Rebecca, J., et al., "Detection of Chromosomal Alterations in the Circulation of Cancer Patients with Whole-Genome Sequencing," Sci Transl Med., Nov. 28, 2012, vol. 4, No. 162, 21 pages.
Lo, Y.M., Dennis, et al., "Presence of donor-specific DNA in plasma of kidney and liver-transplant recipients," The Lancet, May 2, 1998, vol. 351, 2 pages.
Snyder, Thomas, M., et al., "Universal noninvasive detection of solid organ transplant rejection," PNAS, Apr. 12, 2011, vol. 108, No. 15, pp. 6229-6234.
Lo, Y.M., Dennis, et al., "Quantitative Analysis of Fetal DNA in Maternal Plasma and Serum: Implications for Noninvasive Prenatal Diagnosis," Am. J. Hum. Genet., 1998, vol. 62, pp. 768-775.
Krzywinski, Martin, et al., "Circos: An information aesthetic for comparative genomics," Genome Research, 2009, vol. 19, pp. 1639-1645.
Fujita, Pauline, A., et al., "The UCSC Genome Browser Database: Update 2011," Nucleic Acids Research, 2011, vol. 39, D876-D882.
Gardiner-Garden, M., et al., "CpG Islands in Vertebrate Genomes," J. Mol. Biol., 1987, vol. 196, pp. 261-282.
Haworth, Kim E., "Combined influence of gene-specific cord blood methylation and maternal smoking habit on birth weight," Epigenomics, 2013, vol. 5, No. 1, pp. 37-49.
Chiu, Rossa, W.K., et al., "Hypermethylation of RASSF1A in Human and Rhesus Placentas," The American Journal of Pathology, Mar. 2007, vol. 170, No. 3, 10 pages.
Chim, Stephen, S.C., et al., "Systematic Search for Placental DNA-Methylation Markers on Chromosome 21: Toward a Maternal Plasma-Based Epigenetic Test for Fetal Trisomy 21," Clinical Chemistry, 2008, vol. 54, No. 3, pp. 500-511.
Chim, Stephen, S.C., et al., "Detection of the placental epigenetic signature of the maspin gene in maternal plasma," PNAS, Oct. 11, 2005, vol. 102, No. 41, pp. 14753-14758.
Tsui, Dana, W.Y., et al., "Systematic Identification of Placental Epigenetic Signatures for the Noninvasive Prenatal Detection of Edwards Symdrome," PLOS One, Nov. 2010, vol. 5, Issue 11, 12 pages.
Chiu, Rossa, W.K., et al., "Non-invasive prenatal assessment of trisomy 21 by multiplexed maternal plasma DNA sequencing: large scale validity study," BMJ, 2011, 9 pages.
Chiu, Rossa, W.K., et al.,"Noninvasive prenatal diagnosis of fetal chromosomal aneuploidy by massively parallel genomic sequencing of DNA in maternal plasma," PNAS, Dec. 23, 2008, vol. 105, No. 51, pp. 20458-20463.
Bianchi, Diana, W., et al., "Genome-Wide Fetal Aneuploidy Detection by Maternal Plasma DNA Sequencing," Obstetrics & Gynecology, May 2012, vol. 119, No. 5, 12 pages.
Sparks, Andrew, B., "Noninvasive prenatal detection and selective analysis of cell-free DNA obtained from maternal blood: evaluation for trisomy 21 and trisomy 18," AJOG, Apr. 2012, 9 pages.
Zimmermann, Bernhard, et al., "Non-invasive prenatal aneuploidy testing at chromosomes 13, 18, 21, X and Y, using targeted sequencing of polymorphic loci," Prenat. Diagn., Dec. 2012, vol. 32, No. 13, pp. 1233-1241.
Liao, Gary, J.W., "Noninvasive Prenatal Diagnosis of Fetal Trisomy 21 by Allelic Ratio Analysis Using Targeted Massively Parallel Sequencing of Maternal Plasma DNA," PLOS One, May 2012, vol. 7, Issue 5, 7 pages.
Jiang, Xinyin, et al., "Maternal choline intake alters the epigenetic state of fetal cortisol-regulating genes in humans," The FASEB Journal, 2012, 12 pages.
Srinivasan, Anupama, et al., "Noninvasive Detection of Fetal Subchromosome Abnormalities via Deep Sequencing of Maternal Plasma," The American Journal of Human Genetics, Feb. 7, 2013, vol. 92, pp. 167-176.
Yu, Stephanie C.Y., et al., "Noninvasive Prenatal Molecular Karyotyping from Maternal Plasma," PLOS One, Apr. 2013, vol. 8, Issue 4, 8 pages.
Lo, Y.M., Dennis, et al., "Digital PCR for the molecular detection of fetal chromosomal aneuploidy," PNAS, Aug. 7, 2007, vol. 104, No. 32, pp. 13116-13121.
Chan, K.C., Allen, et al., "Size Distributions of Maternal and Fetal DNA in Maternal Plasma," Clinical Chemistry, 2004, vol. 50, No. 1, pp. 88-92.
Poon, Leo, L.M., et al., "Differential DNA Methylation between Fetus and Mother as a Strategy for Detecting Fetal DNA in Maternal Plasma," Clinical Chemistry, 2002, vol. 48, No. 1, pp. 35-41.
Woodfine, Kathryn, et al., "Quantitative analysis of DNA methylation at all human imprinted regions reveals preservation of epigenetic stability in adult somatic tissue," Epigenetics & Chromatin, 2011, vol. 4, No. 1, 13 pages.
Herman, James, G., "Gene Silencing in Cancer in Association with Promoter Hypermethylation," The New England Journal of Medicine, Nov. 20, 2003, 13 pages.
Gama-Sosa, Miguel A., et al., "The 5-methylcytosin content of DNA from human tumors," Nucleic Acids Research, 1983, vol. 11, No. 19, 12 pages.
Jiang, Peiyong, et al., "Methy-Pipe: An Integrated Bioinformatics Data Analysis Pipeline for Whole Genome Methylome Analysis," 2010 IEEE International Conference on Bioinformatics and Biomedicine Workshops, pp. 585-590.
El Hajj, Nady, et al., "Metabolic Programming of MEST DNA Methylation by Intrauterine Exposure to Gestational Diabetes Mellitus," Diabetes, Apr. 2013, vol. 62, 9 pages.
Lui, Yanni, Y.N., et al., "Predominant Hematopoietic Origin of Cell-free DNA in plasma and Serum after Sex-mismatched Bone Marrow Transplantation," Clinical Chemistry, 2002, vol. 48, No. 3, pp. 421-427.
Tangkijvanich, Pisit, et al., "Serum LINE-1 hypomethylation as a potential prognostic marker for hepatocellular carcinoma," Clinica Chimica Acta, 2007, vol. 379, pp. 127-133.
Chen, Ming-Luan, et al., "Quantification of 5-Methylcytosine and 5-Hydroxymethylcytosine in Genomic DNA from Hepatocellular Carcinoma Tissues by Capillary Hydrophilic-Interaction Liquid Chromatography/Quadrupole TOF Mass Spectometry," Clinical Chemistry, 2013, vol. 59, No. 5, pp. 824-832.
Lian, Christine Guo, et al., "Loss of 5-Hydroxymethylcytosine as an Epigenetic Hallmark of Melanoma," Cell, Sep. 14, 2012, vol. 150, No. 6, pp. 1135-1146.
Hannum, Gregory, et al., "Genome-wine Methylation Profiles Reveal Quantitative Views of Human Aging Rates," Molecular Cell, Jan. 24, 2013, vol. 49, pp. 359-367.
Futscher, Bernard, W., et al., "Role of DNA methylation in the control of cell type-specific maspin expression," Nature Genetics, Jun. 2002, vol. 31, 5 pages.
Lun, Fiona, M.F., et al., "Noninvasive Prenatal Methylomic Analysis by Genomewide Bisulfite Sequencing of Maternal Plasma DNA," Clinical Chemistry, 2013, vol. 59, No. 11, pp. 1583-1594.

(56) References Cited

OTHER PUBLICATIONS

Baylin, Stephen, et al., "A decade of exploring the cancer epigenome—biological and translational implications," Nature, Oct. 2011, vol. 11, 9 pages.
Jones, Peter A., et al., "The Epigenomics of Cancer," Cell, Feb. 23, 2007, vol. 128, pp. 683-692.
Esteller, Manel, et al., "Cancer epigenomics: DNA methylomes and histone-modificaiton maps," Nature, Apr. 2007, vol. 8, 13 pages.
Ehrlich, Melanie, "DNA methylation in cancer: too much, but also too little," Oncogene, 2002, vol. 21, pp. 5400-5413.
Li, Ruiqiang, et al., "SOAP2: an improved ultrafast tool for short read alignment," Bioinformatics, 2009, vol. 25, No. 15, pp. 1966-1967.
Chen, Eric, Z, et al., "Noninvasive Prenatal Diagnosis of Fetal Trisomy 18 and Trisomy 13 by Maternal Plasma DNA Sequencing," PLOS One, Jul. 2011, vol. 6, Issue 7, 7 pages.
Gebhart, E., "Comparative genomic hybridization (CGH): ten years of substantial progress in human solid tumor molecular cytogenetics," Cytogenetic and Genome Research, 2004, vol. 104, pp. 352-358.
Laurent, Louise, et al., "Dynamic changes in the human methylome during differentiation," Genome Research, Feb. 4, 2010, vol. 20, pp. 320-331.
Kulis, Marta, et al., "Epigenomic analysis detects widespread gene-body DNA hypomethylation in chronic lymphocytic leukemia," Nature Genetics, Nov. 2012, vol. 44, No. 11, 9 pages.
Gonzalgo, Mark L. et al.; "Low Frequency of p16/CDKN2A Methylation in Sporadic Melanoma: Comparative Approaches for Methylation Analysis of Primary Tumors"; Cancer Research; 1997; 57; pp. 5336-5347.
Eads, Cindy A. et al.; "MethyLight: a high-throughput assay to measure DNA methylation"; Nucleic Acids Research; 2000; vol. 28, No. 8; 8 pages.
Eads, Cindy A. et al.; "Epigenetic Patterns in the Progression of Esophageal Adenocarcinoma"; Cancer Research; 2001; 61; pp. 3410-3418.
Extended European Search Report dated Apr. 8, 2016 in EP Patent Application No. 13838770.9. 7 pages.
Zhai, Rihong et al ; "Genome-wide DNA Methylation Profiling of Cell-Free Serum DNA in Esophageal Adenocarcinoma and Barrett Esophagus"; Neoplasia; Jan. 2012; pp. 29-33; vol. 14, No. 1; 6 pages.
Further Examination Report dated Mar. 17, 2016 in NZ Patent Application 706269. 3 pages.
Patent Examination Report No. 1 dated Sep. 16, 2016 in AU Patent Application No. 2013317708. 4 pages.
English translation of Official Notification dated Sep. 20, 2016 in EA Patent Application No. 201500327. 4 pages.
Written Opinion dated Sep. 13, 2016 in SG Patent Application No. 11201501927V. 13 pages.
Non-Final Office Action dated Nov. 4, 2016 in U.S. Appl. No. 14/495,791, filed Sep. 24, 2014. 35 pages.
Bock, Christoph et al.; "Quantitative comparison of genome-wide DNA methylation mapping technologies"; Nature Biotechnology; 2010; vol. 28, No. 10; pp. 1106-1114.
Robinson, Mark D. et al.; "Evaluation of affinity-based genome-wide DNA methylation data: Effects of CpG density, amplification bias, and copy number variation"; Genome Research; 2010; 20; pp. 1719-1729.
Fackler, Mary Jo et al.; "Quantitative Multiplex Methylation-Specific PCR Assay for the Detection of Promoter Hypermethylation in Multiple Genes in Breast Cancer"; Cancer Research; 2004; vol. 64, Issue 13; pp. 4442-4452.
Quackenbush, John; "Microarray data normalization and transformation"; Nature Genetics Supplement; 2002; vol. 32; pp. 496-501.
English translation of Office Action dated May 16, 2017 in JP Patent Application No. 2015-532250. 5 pages.
Li, Lian et al.; "DNA Methylation in Peripheral Blood: A Potential Biomarker for Cancer Molecular Epidemiology"; J Epidemiol; Epub Aug. 4, 2012; 22(5); pp. 384-394; doi:10.2188/jea. JE20120003.
English translation of Search Report dated Jun. 12, 2017 in TW Patent Application No. 102134227. 1 page.

* cited by examiner

FIG. 1A

| | Adult male blood | | Adult female blood | | Adult male plasma | | Adult female plasma | |
|---|---|---|---|---|---|---|---|---|
| | Watson | Crick | Watson | Crick | Watson | Crick | Watson | Crick |
| Raw read counts | 196544792 | 196544792 | 197367755 | 197367755 | 179888600 | 179888600 | 141199439 | 141199439 |
| Total mappability (%) | 43.52 | 42.97 | 44.94 | 44.35 | 22.47 | 22.23 | 18.98 | 18.79 |
| Total mappable reads | 85525774 | 84462486 | 88695242 | 87542953 | 40380938 | 40048964 | 26735699 | 26537762 |
| Ambiguous rate (%)[a] | 6.05 | 6.13 | 6.29 | 6.37 | 6.09 | 6.14 | 6.29 | 6.35 |
| Duplication rate (%)[b] | 1.99 | 1.73 | 1.88 | 1.53 | 7.89 | 7.64 | 11.71 | 11.47 |
| Whole genome depth after removal of ambiguous and lambda conversion rate (%)[c] | 4.13 | 4.09 | 4.28 | 4.24 | 1.83 | 1.82 | 1.16 | 1.15 |
| | 99.96 | 99.97 | 99.97 | 99.97 | 99.96 | 99.97 | 99.96 | 99.97 |
| Genomic C seq M count[d] | 127154245 | 125487793 | 124983462 | 122238508 | 55049489 | 54630306 | 37403328 | 37048480 |
| Genomic C seq U count | 2047971831 | 2026731827 | 2058153525 | 2039985644 | 936186429 | 933377753 | 596496591 | 594974253 |
| Genomic C coverage (%) | 51.56 | 51.55 | 55.17 | 55.06 | 43.76 | 43.66 | 38.33 | 38.28 |
| Genomic C seq depth | 3.72 | 3.66 | 3.74 | 3.70 | 1.70 | 1.69 | 1.09 | 1.08 |
| Genomic C methylation density (%) | 5.85 | 5.83 | 5.72 | 5.70 | 5.54 | 5.53 | 5.88 | 5.86 |
| CpG seq M count | 125161042 | 123578650 | 123020928 | 121374309 | 54155037 | 53756413 | 36738819 | 36453865 |
| CpG seq U count | 49564325 | 49936003 | 47582383 | 47812716 | 21930864 | 21830555 | 13971713 | 13867179 |
| CpG coverage (%) | 73.37 | 73.25 | 76.24 | 76.12 | 63.93 | 63.80 | 57.87 | 57.77 |
| CpG seq depth | 6.20 | 6.16 | 6.06 | 6.01 | 2.70 | 2.66 | 1.80 | 1.79 |
| CpG methylation density (%) | 71.63 | 71.22 | 72.12 | 71.74 | 71.18 | 71.12 | 72.48 | 72.44 |
| NonCpG seq M count | 1979410 | 1899750 | 1951160 | 1856542 | 894139 | 873671 | 614025 | 594289 |
| NonCpG seq U count | 1960312392 | 1950307695 | 1976031365 | 1956232257 | 915375235 | 910910430 | 563173346 | 560050464 |
| NonCpG coverage (%) | 0.10 | 0.10 | 0.11 | 0.11 | 0.08 | 0.08 | 0.07 | 0.07 |
| NonCpG seq depth | 0.69 | 0.69 | 0.70 | 0.70 | 0.32 | 0.32 | 0.21 | 0.21 |
| NonCpG methylation density (%) | 0.10 | 0.10 | 0.10 | 0.09 | 0.10 | 0.10 | 0.11 | 0.10 |
| CHG seq M count | 618974 | 596717 | 594336 | 573203 | 279945 | 272311 | 191120 | 186135 |
| CHG seq U count | 612387335 | 610126595 | 607312325 | 605093927 | 283916067 | 282626050 | 160374803 | 179612404 |
| CHG coverage (%) | 63.24 | 63.11 | 65.75 | 65.62 | 54.69 | 54.55 | 46.57 | 46.45 |
| CHG seq depth | 4.96 | 4.94 | 4.91 | 4.90 | 2.30 | 2.29 | 1.45 | 1.45 |
| CHG methylation density (%) | 0.10 | 0.10 | 0.10 | 0.09 | 0.10 | 0.10 | 0.11 | 0.10 |
| CHH seq M count | 1360436 | 1301053 | 1356824 | 1283439 | 614184 | 601360 | 422905 | 408154 |
| CHH seq U count | 1347925056 | 1340180699 | 1368718940 | 1351138330 | 631459168 | 628084440 | 402798543 | 400438060 |
| CHH coverage (%) | 46.93 | 46.83 | 50.48 | 50.38 | 39.32 | 39.22 | 34.20 | 34.11 |
| CHH seq depth | 3.12 | 3.10 | 3.17 | 3.15 | 1.46 | 1.45 | 0.93 | 0.93 |
| CHH methylation density (%) | 0.10 | 0.10 | 0.10 | 0.09 | 0.10 | 0.10 | 0.10 | 0.10 |

FIG. 1A (Cont.)

| | | | Methylation density (sequencing data) | | | Deduction | | | Methylation status in literatures | |
|---|---|---|---|---|---|---|---|---|---|---|
| No. | Gene locus | Genomic location | Maternal blood (BKG) | Placenta | Maternal plasma (MP) | Deduced values (D)[1] | Methylation predictive score (MPS)[2] | Deduced categories[3] | Placental methylation level[4] | Placental status[5] | References |
| 1 | RASSF1A | chr3:50352938-50353234 | 0.000 | 0.637 | 0.067 | 0.506 | 1.060 | High | Inter | Hypermethylated | (1) |
| 2 | CGI009 | chr21:25856489-25856756 | 0.001 | 0.432 | 0.050 | 0.374 | 0.849 | High | Inter | Hypermethylated | (2) |
| 3 | CGI028 | chr21:33221942-33222182 | 0.035 | 0.331 | 0.040 | 0.073 | 0.367 | Low | Low | Hypermethylated | (2) |
| 4 | CGI051 | chr21:36995232-36995509 | 0.043 | 0.303 | 0.046 | 0.072 | 0.365 | Low | Low | Hypermethylated | (2) |
| 5 | CGI071 | chr21:41140466-41140898 | 0.031 | 0.531 | 0.046 | 0.146 | 0.483 | Inter | Inter | Hypermethylated | (2) |
| 6 | CGI113 | chr21:44953820-44953972 | 0.013 | 0.547 | 0.051 | 0.306 | 0.739 | Inter | Inter | Hypermethylated | (2) |
| 7 | CGI137 | chr21:46249872-46250196 | 0.940 | 0.413 | 0.820 | 0.030 | 0.299 | Low | Inter | Hypomethylated | (2) |
| 8 | CGI149 | chr21:46911575-46912533 | 0.004 | 0.440 | 0.030 | 0.202 | 0.573 | Inter | Inter | Hypermethylated | (2) |
| 9 | HLCS | chr21:37274945-37275031 | 0.038 | 0.576 | 0.059 | 0.203 | 0.575 | Inter | Inter | Hypermethylated | (2) |
| 10 | PDE9A | chr21:42979270-42979525 | 0.950 | 0.303 | 0.823 | -0.018 | 0.222 | Low | Low | Hypomethylated | (2) |
| 11 | - | chr21:36589647-36589995 | 0.952 | 0.149 | 0.827 | 0.007 | 0.262 | Low | Low | Hypomethylated | Unpublished |
| 12 | SERPINB5 | chr18:59294739-59295038 | 0.936 | 0.530 | 0.856 | 0.329 | 0.777 | Inter | Inter | Hypomethylated | (3) |
| 13 | VAPA | chr18:10022563-10023186 | 0.036 | 0.752 | 0.082 | 0.382 | 0.861 | High | Inter | Hypermethylated | (4) |
| 14 | CABLES1 | chr18:19035954-19036069 | 0.335 | 0.801 | 0.491 | 1.519 | 2.680 | High | High | Hypermethylated | (4) |
| 15 | B4GALT6 | chr18:27486040-27486932 | 0.113 | 0.827 | 0.331 | 1.764 | 3.072 | High | High | Hypermethylated | (4) |

| | | | | | BS-Seq[c] | | | DMR[d] | | | | | | | |
|---|---|---|---|---|---|---|---|---|---|---|---|---|---|---|---|
| No.[a] | Gene locus | Genomic location[b] | Size[b] | Placental status[b] | Maternal blood cells | CVS | Meth diff | Chr | Start | End | Size | Maternal blood cells | CVS | p value | Meth diff | Class[b] |
| 1 | RASSF1A | chr3:50352938-50353234 | 297 | Hypermethylated | 0.00 | 63.73 | 63.73 | chr3 | 50351000 | 50354000 | 3000 | 6.26 | 66.68 | 0.00E+00 | 60.42 | TP |
| 2 | CGI009 | chr21:25856489-25856756 | 268 | Hypermethylated | 0.08 | 43.20 | 43.13 | chr21 | 25855500 | 25857500 | 2000 | 4.97 | 48.70 | 0.00E+00 | 43.73 | TP |
| 3 | CGI028 | chr21:33321942-33322182 | 241 | Hypermethylated | 3.51 | 33.10 | 29.59 | chr21 | 33316400 | 33323900 | 7500 | 4.52 | 23.85 | 0.00E+00 | 19.33 | FN |
| 4 | CGI051 | chr21:36995232-36995509 | 278 | Hypermethylated | 4.26 | 30.33 | 26.07 | chr21 | 36992800 | 37003900 | 11100 | 3.12 | 21.91 | 0.00E+00 | 18.79 | FN |
| 5 | CGI071 | chr21:41140466-41140898 | 433 | Hypermethylated | 3.09 | 53.06 | 49.97 | chr21 | 41140000 | 41141000 | 1000 | 3.40 | 52.00 | 0.00E+00 | 48.60 | TP |
| 6 | CGI113 | chr21:44953820-44953972 | 153 | Hypermethylated | 1.27 | 54.69 | 53.42 | chr21 | 44948500 | 44954700 | 6200 | 7.18 | 57.23 | 0.00E+00 | 50.05 | TP |
| 7 | CGI137 | chr21:46249872-46250196 | 325 | Hypomethylated | 94.00 | 41.34 | 52.65 | chr21 | 46227800 | 46250400 | 22600 | 89.74 | 52.67 | 0.00E+00 | 37.07 | TP |
| 8 | CGI149 | chr21:46911575-46912533 | 959 | Hypermethylated | 0.40 | 43.95 | 43.56 | chr21 | 46911200 | 46912700 | 1500 | 5.31 | 46.17 | 0.00E+00 | 40.86 | TP |
| 9 | HLCS | chr21:37274945-37275031 | 87 | Hypermethylated | 3.77 | 57.61 | 53.85 | chr21 | 37274200 | 37275200 | 1000 | 7.33 | 54.24 | 0.00E+00 | 46.91 | TP |
| 10 | PDE9A | chr21:42979270-42979525 | 256 | Hypomethylated | 95.01 | 30.33 | 64.68 | chr21 | 42978100 | 43004800 | 26700 | 89.97 | 51.44 | 0.00E+00 | 38.53 | TP |
| 11 | - | chr21:36589647-36589995 | 349 | Hypomethylated | 95.17 | 14.89 | 80.28 | chr21 | 36589200 | 36590200 | 1000 | 94.49 | 19.27 | 0.00E+00 | 75.22 | TP |
| 12 | SERPINB5 | chr18:59294739-59295038 | 300 | Hypomethylated | 93.64 | 53.00 | 40.64 | chr18 | 59294800 | 59296300 | 1500 | 88.47 | 40.76 | 3.33E-27 | 47.71 | TP |
| 13 | VAPA | chr18:10022563-10023187 | 625 | Hypermethylated | 3.63 | 75.17 | 71.54 | chr18 | 10021800 | 10023300 | 1500 | 24.08 | 80.33 | 0.00E+00 | 56.25 | TP |
| 14 | CABLES1 | chr18:19035954-19036070 | 117 | Hypermethylated | 33.47 | 80.09 | 46.62 | - | - | - | - | - | - | - | - | FN |
| 15 | B4GALT6 | chr18:27486040-27486933 | 894 | Hypermethylated | 11.34 | 82.75 | 71.41 | chr18 | 27486100 | 27487100 | 1000 | 11.34 | 82.75 | 9.6408E-86 | 71.41 | TP |
| 16 | CASP8 | chr2:201830342-201831885 | 1544 | Hypermethylated | 0.52 | 47.54 | 47.03 | chr2 | 201830200 | 201832200 | 2000 | 3.77 | 49.13 | 4.22E-42 | 45.36 | TP |
| 17 | RARB | chr3:25444840-25445090 | 251 | Hypermethylated | 2.28 | 26.93 | 24.65 | chr3 | 25443900 | 25445400 | 1500 | 3.44 | 22.97 | 9.65E-50 | 19.53 | FN |
| 18 | APC | chr5:112100999-112101943 | 945 | Hypermethylated | 0.71 | 45.78 | 45.06 | chr5 | 112100300 | 112101800 | 1500 | 3.59 | 48.09 | 0.00E+00 | 44.50 | TP |
| 19 | DAB2IP_ori | chr9:121541221-121541460 | 240 | Hypomethylated | 84.87 | 52.63 | 32.24 | chr9 | 121540400 | 121541500 | 1100 | 85.21 | 36.86 | 5.2605E-10 | 48.35 | TP |
| 20 | DAB2IP_ex | chr9:123128261-123129077 | 817 | Hypomethylated | 95.09 | 32.99 | 62.10 | chr9 | 123127700 | 123129200 | 1500 | 90.72 | 50.61 | 1.4706E-19 | 40.11 | TP |
| 21 | THY1 | chr11:118798952-118799382 | 431 | Hypermethylated | 0.88 | 39.32 | 38.44 | chr11 | 118797600 | 118799600 | 2000 | 2.25 | 27.28 | 0.00E+00 | 25.03 | TP |
| 22 | PTPN6 | chr12:6930211-6933772 | 3562 | Hypermethylated | 1.52 | 79.80 | 78.29 | chr12 | 6930000 | 6934000 | 4000 | 4.26 | 80.13 | 0.00E+00 | 75.87 | TP |
| 23 | PYCARD_ex | chr16:31121808-31122146 | 339 | Hypermethylated | 4.90 | 46.51 | 41.61 | - | - | - | - | - | - | - | - | FN |
| 24 | chr18A | chr18:55090284-55090606 | 323 | Hypermethylated | 6.14 | 31.79 | 25.65 | chr18 | 55089700 | 55094200 | 4500 | 4.78 | 22.91 | 0.00E+00 | 18.13 | FN |
| 25 | chr21A | chr21:39279723-39280004 | 282 | Hypermethylated | 12.80 | 64.02 | 51.21 | chr21 | 39279300 | 39279800 | 500 | 4.74 | 62.07 | 7.17E-62 | 57.33 | TP |
| 26 | chr21B | chr21:44161027-44161371 | 345 | Hypermethylated | 0.86 | 83.90 | 83.04 | chr21 | 44160700 | 44161700 | 1000 | 11.06 | 77.32 | 0.00E+00 | 66.26 | TP |
| 27 | chr21C | chr21:33320544-33320829 | 286 | Hypermethylated | 5.49 | 37.92 | 32.43 | chr21 | 33316400 | 33323900 | 7500 | 4.52 | 23.85 | 0.00E+00 | 19.33 | FN |
| 28 | chr21D | chr21:42188223-42189683 | 461 | Hypermethylated | 13.02 | 85.84 | 72.82 | chr21 | 42188700 | 42189700 | 1000 | 7.78 | 81.67 | 3.62E-77 | 73.89 | TP |
| 29 | chr21EI | chr21:42355712-42355908 | 197 | Hypermethylated | 0.00 | 57.85 | 57.85 | chr21 | 42355000 | 42357500 | 2500 | 5.21 | 62.23 | 0.00E+00 | 57.02 | TP |
| 30 | chr21EII | chr21:42357215-42357341 | 127 | Hypermethylated | 3.57 | 48.25 | 44.68 | chr21 | 42355000 | 42357500 | 2500 | 5.21 | 62.23 | 0.00E+00 | 57.02 | TP |
| 31 | chr21H | chr21:32268803-32268943 | 141 | Hypermethylated | 0.49 | 78.84 | 78.35 | chr21 | 32268300 | 32269300 | 1000 | 20.49 | 85.25 | 4.9563E-34 | 64.76 | TP |
| 32 | chr21I | chr21:44079235-44079535 | 301 | Hypermethylated | 1.23 | 67.44 | 66.21 | chr21 | 44079400 | 44080400 | 1000 | 15.19 | 68.06 | 4.9E-59 | 52.87 | TP |
| 33 | SERPINB5_P | chr18:59294811- | 465 | Hypomethylated | 91.96 | 39.71 | 52.25 | chr18 | 59294800 | 59296300 | 1500 | 88.47 | 40.76 | 3.3294E- | 47.71 | TP |

| | | BS-Seq | | | DMR[c] | | | | | | | |
|---|---|---|---|---|---|---|---|---|---|---|---|---|
| No.[a] | Gene locus | Maternal blood cells | Placenta | Meth diff[b] | Chr | Start | End | Size | Maternal blood cells | Placenta | p value | Meth diff | Class[d] |
| 1 | RASSF1A | 0.00 | 60.84 | 60.84 | chr3 | 50352100 | 50354100 | 2000 | 2.16 | 62.21 | 0.00E+00 | 60.05 | TP |
| 2 | CGI009 | 0.08 | 20.50 | 20.43 | chr21 | 25855600 | 25857100 | 1500 | 2.04 | 24.37 | 0.00E+00 | 22.33 | TP |
| 3 | CGI028 | 3.51 | 17.38 | 13.86 | - | - | - | - | - | - | - | - | TN |
| 4 | CGI051 | 4.26 | 13.93 | 9.67 | - | - | - | - | - | - | - | - | TN |
| 5 | CGI071 | 3.09 | 24.85 | 21.76 | chr21 | 41139900 | 41141400 | 1500 | 6.83 | 29.28 | 0.00E+00 | 22.45 | TP |
| 6 | CGI113 | 1.27 | 40.24 | 38.97 | chr21 | 44948500 | 44954700 | 6200 | 7.18 | 45.00 | 0.00E+00 | 37.82 | TP |
| 7 | CGI137 | 94.00 | 37.10 | 56.90 | chr21 | 46248400 | 46250400 | 2000 | 92.28 | 43.85 | 1.66E-76 | 48.43 | TP |
| 8 | CGI149 | 0.40 | 22.19 | 21.79 | chr21 | 46911200 | 46912700 | 1500 | 5.31 | 25.73 | 0.00E+00 | 20.42 | TP |
| 9 | HLCS | 3.77 | 58.49 | 54.72 | chr21 | 37274200 | 37275200 | 1000 | 7.33 | 56.83 | 0.00E+00 | 49.50 | TP |
| 10 | PDE9A | 95.01 | 32.41 | 62.60 | chr21 | 42978900 | 42990100 | 11200 | 90.89 | 44.38 | 0.00E+00 | 46.51 | TP |
| 11 | - | 95.17 | 19.92 | 75.24 | chr21 | 36589200 | 36590200 | 1000 | 94.49 | 22.66 | 0.00E+00 | 71.83 | TP |
| 12 | SERPINB5 | 93.64 | 28.06 | 65.57 | chr18 | 59294500 | 59295500 | 1000 | 92.11 | 36.53 | 3.85E-31 | 55.58 | TP |
| 13 | VAPA | 3.63 | 73.88 | 70.25 | chr18 | 10022100 | 10023100 | 1000 | 11.67 | 75.76 | 0.00E+00 | 64.09 | TP |
| 14 | CABLES1 | 33.47 | 81.40 | 47.93 | - | - | - | - | - | - | - | - | FN |
| 15 | B4GALT6 | 11.34 | 88.57 | 77.23 | chr18 | 27485800 | 27486800 | 1000 | 28.97 | 90.00 | 4.3779E-59 | 61.03 | TP |
| 16 | CASP8 | 0.52 | 56.27 | 55.75 | chr2 | 201830200 | 201832200 | 2000 | 3.77 | 57.60 | 1.33E-52 | 53.83 | TP |
| 17 | RARB | 2.28 | 38.18 | 35.90 | chr3 | 25444000 | 25445000 | 1000 | 2.36 | 24.42 | 8.00E-54 | 22.06 | TP |
| 18 | APC | 0.71 | 34.89 | 34.18 | chr5 | 112100700 | 112101700 | 1000 | 0.38 | 32.97 | 0.00E+00 | 32.59 | TP |
| 19 | DAB2IP_ori | 84.87 | 40.28 | 44.60 | chr9 | 121540400 | 121541400 | 1000 | 84.79 | 30.63 | 1.7338E-14 | 54.16 | TP |
| 20 | DAB2IP_ex | 95.09 | 16.14 | 78.95 | chr9 | 123128600 | 123129100 | 500 | 95.14 | 17.42 | 9.6247E-47 | 77.72 | TP |
| 21 | THY1 | 0.88 | 22.28 | 21.40 | chr11 | 118797800 | 118799300 | 1500 | 1.22 | 20.50 | 0.00E+00 | 19.28 | FN |
| 22 | PTPN6 | 1.52 | 81.33 | 79.82 | chr12 | 6930000 | 6934000 | 4000 | 4.26 | 81.58 | 0.00E+00 | 77.32 | TP |
| 23 | PYCARD_ex | 4.90 | 48.73 | 43.83 | chr16 | 31121700 | 31122200 | 500 | 4.85 | 32.87 | 1.1158E-34 | 28.02 | TP |
| 24 | chr18A | 6.14 | 16.25 | 10.10 | - | - | - | - | - | - | - | - | TN |
| 25 | chr21A | 12.80 | 74.65 | 61.85 | chr21 | 39278300 | 39280300 | 2000 | 9.96 | 75.07 | 0.00E+00 | 65.11 | TP |
| 26 | chr21B | 0.86 | 81.56 | 80.70 | chr21 | 44160700 | 44161700 | 1000 | 11.06 | 78.6 | 0.00E+00 | 67.54 | TP |
| 27 | chr21C | 5.49 | 14.91 | 9.42 | - | - | - | - | - | - | - | - | TN |
| 28 | chr21D | 13.02 | 88.71 | 75.70 | chr21 | 42188700 | 42189700 | 1000 | 7.78 | 84.42 | 3.5806E-77 | 76.64 | TP |
| 29 | chr21EI | 0.00 | 73.21 | 73.21 | chr21 | 42355300 | 42357800 | 2500 | 4.66 | 79.19 | 0.00E+00 | 74.53 | TP |
| 30 | chr21EII | 3.57 | 84.00 | 80.43 | chr21 | 42355300 | 42357800 | 2500 | 4.66 | 79.19 | 0.00E+00 | 74.53 | TP |
| 31 | chr21H | 0.49 | 77.49 | 77.00 | chr21 | 32268400 | 32268900 | 500 | 18.4 | 83.85 | 2.1972E-30 | 65.45 | TP |
| 32 | chr21I | 1.23 | 58.62 | 57.39 | chr21 | 44079300 | 44080300 | 1000 | 12.16 | 72.55 | 2.3559E-60 | 60.39 | TP |
| 33 | SERPINB5_P | 91.96 | 28.61 | 63.35 | chr18 | 59294500 | 59295500 | 1000 | 92.11 | 36.53 | 3.85E-31 | 55.58 | TP |

FIG. 15B

|  | First trimester maternal plasma | | Third trimester maternal plasma | |
| --- | --- | --- | --- | --- |
|  | Hypermethylated[a] | Hypomethylated[b] | Hypermethylated[a] | Hypomethylated[b] |
| No. predicted loci | 3081 | 44455 | 1746 | 14930 |
| No. loci with methylation densities > 40% in the placental tissue[c] data | 1,678 | N/A | 1,525 | N/A |
| No. loci with methylation densities < 60% in the placental tissue[c] data | N/A | 23468 | N/A | 13475 |
| No. of loci overlapped with DMRs mined from the placental tissue[c] and maternal blood cell data | 1457 | 21812 | 1279 | 12677 |

FIG. 16         1600

|  | HCC patient | | | |
|---|---|---|---|---|
| Chromosome | Buffy coat | Non-tumoral liver tissue | Tumor tissue | Pre-operative plasma |
| 1 | 65.4% | 65.7% | 44.1% | 60.2% |
| 2 | 68.3% | 68.2% | 42.0% | 58.6% |
| 3 | 68.2% | 68.5% | 44.6% | 60.9% |
| 4 | 68.9% | 67.7% | 37.8% | 56.9% |
| 5 | 67.4% | 66.7% | 37.8% | 56.9% |
| 6 | 67.4% | 67.7% | 43.2% | 59.9% |
| 7 | 69.1% | 68.8% | 43.0% | 60.0% |
| 8 | 69.1% | 68.0% | 40.4% | 60.0% |
| 9 | 66.4% | 66.2% | 44.9% | 60.6% |
| 10 | 68.9% | 68.2% | 40.8% | 58.5% |
| 11 | 65.5% | 65.6% | 41.6% | 58.5% |
| 12 | 67.6% | 67.4% | 45.9% | 62.0% |
| 13 | 69.8% | 68.8% | 40.6% | 60.2% |
| 14 | 66.4% | 66.2% | 41.4% | 59.2% |
| 15 | 66.1% | 66.8% | 44.6% | 61.0% |
| 16 | 68.9% | 67.6% | 45.6% | 60.7% |
| 17 | 64.0% | 64.9% | 45.8% | 60.2% |
| 18 | 69.9% | 69.1% | 42.9% | 60.0% |
| 19 | 62.3% | 62.7% | 47.5% | 61.0% |
| 20 | 66.0% | 65.3% | 39.1% | 57.8% |
| 21 | 61.8% | 61.1% | 39.9% | 57.7% |
| 22 | 67.9% | 67.6% | 49.1% | 63.8% |
| All autosomes | 67.1% | 66.9% | 42.9% | 59.7% |

FIG. 21A         2100

| Summary | Raw read count | Mapped read count | non-duplicate fragments (Autosomes only) | Proportion of reads usable % | Depth per strand | CpG coverage % | Depth on CpG sites with reads covered per strand |
|---|---|---|---|---|---|---|---|
| Control 1 | 159554637 | 56323206 | 41653660 | 26% | 1.12 | 54.86% | 3.56 |
| Control 2 | 118056735 | 49232079 | 45741385 | 39% | 1.23 | 60.26% | 3.24 |
| Control 3 | 181913746 | 75753907 | 68081010 | 37% | 1.82 | 65.74% | 4.37 |
| Control 4 | 142782870 | 50195168 | 42370350 | 30% | 1.13 | 59.15% | 3.14 |
| C06 | 262763161 | 197344994 | 88266088 | 33% | 2.11 | 64.31% | 3.65 |
| Buffy coat | 579329822 | 439663895 | 375814248 | 65% | 10.07 | 78.49% | 21.67 |
| Non-cancer liver tissue | 549773334 | 417736311 | 355154964 | 65% | 9.51 | 84.89% | 18.21 |
| Tumor tissue | 568004640 | 487494291 | 176985129 | 31% | 4.74 | 83.48% | 8.32 |
| Pre-operative plasma | 796183998 | 637735722 | 474751039 | 60% | 12.72 | 87.18% | 18.69 |
| Post-operative plasma | 921833848 | 624851729 | 550104801 | 60% | 14.73 | 89.94% | 24.81 |

| Chr | Plasma DNA methylation density | | | | | |
|---|---|---|---|---|---|---|
| | HCC Patient | | Control 1 | Control 2 | Control 3 | Control 4 |
| | Pre-operative | Post-operative | | | | |
| 1 | 60.2% | 69.6% | 70.0% | 70.3% | 70.1% | 71.3% |
| 2 | 58.6% | 71.9% | 72.2% | 72.4% | 72.3% | 73.5% |
| 3 | 60.9% | 72.3% | 72.7% | 73.1% | 72.9% | 73.9% |
| 4 | 56.9% | 71.8% | 71.9% | 72.2% | 72.2% | 73.4% |
| 5 | 56.9% | 70.9% | 71.0% | 71.3% | 71.3% | 72.6% |
| 6 | 59.9% | 71.2% | 71.6% | 71.9% | 71.7% | 72.8% |
| 7 | 60.0% | 72.2% | 72.8% | 72.8% | 72.5% | 73.9% |
| 8 | 60.0% | 72.0% | 72.6% | 72.6% | 72.4% | 73.7% |
| 9 | 60.6% | 70.4% | 71.0% | 71.1% | 71.0% | 72.2% |
| 10 | 58.5% | 71.7% | 72.0% | 72.1% | 72.0% | 73.2% |
| 11 | 58.5% | 69.6% | 70.2% | 70.4% | 70.2% | 71.6% |
| 12 | 62.0% | 71.0% | 71.6% | 71.7% | 71.5% | 72.7% |
| 13 | 60.2% | 72.8% | 73.2% | 73.4% | 73.2% | 74.3% |
| 14 | 59.2% | 70.2% | 70.7% | 70.9% | 70.8% | 72.0% |
| 15 | 61.0% | 70.5% | 70.6% | 71.0% | 70.9% | 72.0% |
| 16 | 60.7% | 71.3% | 72.4% | 71.8% | 71.6% | 73.3% |
| 17 | 60.2% | 68.6% | 69.3% | 69.4% | 69.3% | 70.8% |
| 18 | 60.0% | 72.7% | 72.9% | 73.1% | 73.0% | 74.2% |
| 19 | 61.0% | 66.9% | 68.1% | 68.1% | 67.6% | 69.3% |
| 20 | 57.8% | 69.6% | 70.3% | 70.3% | 70.3% | 71.6% |
| 21 | 57.7% | 67.0% | 64.0% | 64.5% | 65.7% | 67.4% |
| 22 | 63.8% | 71.4% | 72.5% | 72.0% | 71.9% | 73.3% |
| All autosomes | 59.7% | 70.8% | 71.2% | 71.3% | 71.2% | 72.5% |

| z-scores | Pre-operative plasma (No. of bins) | Post-operative plasma (No. of bins) |
|---|---|---|
| <-3 | 186 (80.9%) | 19 (8.3%) |
| -3 to 3 | 42 (18.3%) | 209 (90.3%) |
| >3 | 2 (0.9%) | 2 (0.9%) |
| Total | 230 (100%) | 230 (100%) |

| z-score | Pre-operative plasma (No. of bins) | Post-operative plasma (No. of bins) | C06 | Control 1 (No. of bins) | Control 2 (No. of bins) | Control 3 (No. of bins) | Control 4 (No. of bins) |
|---|---|---|---|---|---|---|---|
| <-3 | 2330 (85.2%) | 171 (6.3%) | 29 (1.1%) | 0 (0%) | 0 (0%) | 0 (0%) | 0 (0%) |
| -3 to 3 | 362 (13.3%) | 2556 (93.5%) | 2688 (98.3%) | 2734 (100%) | 2734 (100%) | 2734 (100%) | 2734 (100%) |
| >3 | 42 (1.5%) | 7 (0.2%) | 17 (0.62%) | 0 (0%) | 0 (0%) | 0 (0%) | 0 (0%) |
| Total | 2734 (100%) | 2734 (100%) | 2734 (100%) | 2734 (100%) | 2734 (100%) | 2734 (100%) | 2734 (100%) |

FIG. 26C                                                                 2640

|  | Proportion of methylated CHH | Proportion of methylated CHG | Proportion of methylated cytosines | Proportion of methylated CpG (methylation density) |
|---|---|---|---|---|
| Buffy coat of HCC patient | 0.13 | 0.14 | 5.74 | 67.08 |
| Non-tumor liver tissue | 0.16 | 0.15 | 5.45 | 66.85 |
| tumor tissue | 0.09 | 0.09 | 3.29 | 42.88 |
| Pre-op plasma | 0.09 | 0.10 | 3.99 | 59.67 |
| Post-op plasma | 1.25 | 0.96 | 6.52 | 70.75 |
| Control plasma 1 | 0.12 | 0.12 | 6.38 | 71.17 |
| Control plasma 2 | 0.10 | 0.10 | 5.62 | 71.33 |
| Control plasma 3 | 0.09 | 0.09 | 5.57 | 71.20 |
| Control plasma 4 | 0.10 | 0.10 | 5.93 | 72.48 |

| | raw read count | Mapped read count | Nonduplicate fragments | Proportion of reads usable % | Depth per strand | CpG coverage % | Depth on CpG sites with reads covered oer strand |
|---|---|---|---|---|---|---|---|
| CL1 | 120807588 | 91750018 | 76890830 | 64% | 0.69 | 33.32% | 2.87 |
| CL2 | 101344850 | 76473792 | 66246435 | 65% | 0.59 | 30.26% | 2.79 |
| NPC1 | 101883643 | 75281330 | 57236188 | 56% | 0.51 | 27.87% | 2.72 |
| NPC2 | 102745073 | 74211781 | 56841611 | 55% | 0.51 | 28.74% | 2.70 |
| CRC1 | 87732645 | 66456695 | 56112543 | 64% | 0.50 | 27.38% | 2.63 |
| CRC2 | 109955730 | 82594007 | 67253101 | 61% | 0.60 | 29.91% | 2.90 |
| NE1 | 105514000 | 79923333 | 64534726 | 61% | 0.58 | 27.86% | 2.58 |
| SMS1 | 94727279 | 71698718 | 64426529 | 68% | 0.58 | 29.23% | 2.79 |

2790

| z-score | CL1 | CL2 | NPC1 | NPC2 | CRC1 | CRC2 | NE1 | SMS1 |
|---|---|---|---|---|---|---|---|---|
| <-3 | 34.9% | 33.9% | 17.6% | 54.3% | 13.5% | 9.8% | 98.1% | 11.2% |
| -3 to 3 | 65.0% | 65.9% | 82.4% | 45.6% | 86.5% | 90.2% | 1.7% | 70.8% |
| >3 | 0.07% | 0.15% | 0.04% | 0% | 0.07% | 0% | 0.15% | 18.0% |

FIG. 27J

| depth diluting factor at 5% | Sequencing depth (times haploid genome) | No. of hypomethylated bins (z-scores <-3) in Pre-operative plasma | % of hypomethylated bins (z-scores <-3) in Pre-operative plasma |
|---|---|---|---|
| 0.8 | 1.76 | 1314 | 48.06 |
| 0.6 | 1.32 | 1323 | 48.39 |
| 0.4 | 0.88 | 1220 | 44.62 |
| 0.2 | 0.44 | 1094 | 40.01 |
| 0.1 | 0.22 | 900 | 32.92 |
| 0.05 | 0.11 | 645 | 23.59 |
| 0.01 | 0.022 | 207 | 7.57 |

| depth diluting factor at 2% | Sequencing depth (times haploid genome) | No. of hypomethylated bins (z-scores <-3) in Pre-operative plasma | % of hypomethylated bins (z-scores <-3) in Pre-operative plasma |
|---|---|---|---|
| 0.8 | 1.76 | 491 | 17.96 |
| 0.6 | 1.32 | 493 | 18.03 |
| 0.4 | 0.88 | 460 | 16.83 |
| 0.2 | 0.44 | 439 | 16.06 |
| 0.1 | 0.22 | 356 | 13.02 |
| 0.05 | 0.11 | 297 | 10.86 |
| 0.01 | 0.022 | 231 | 8.45 |

FIG. 32A          3200

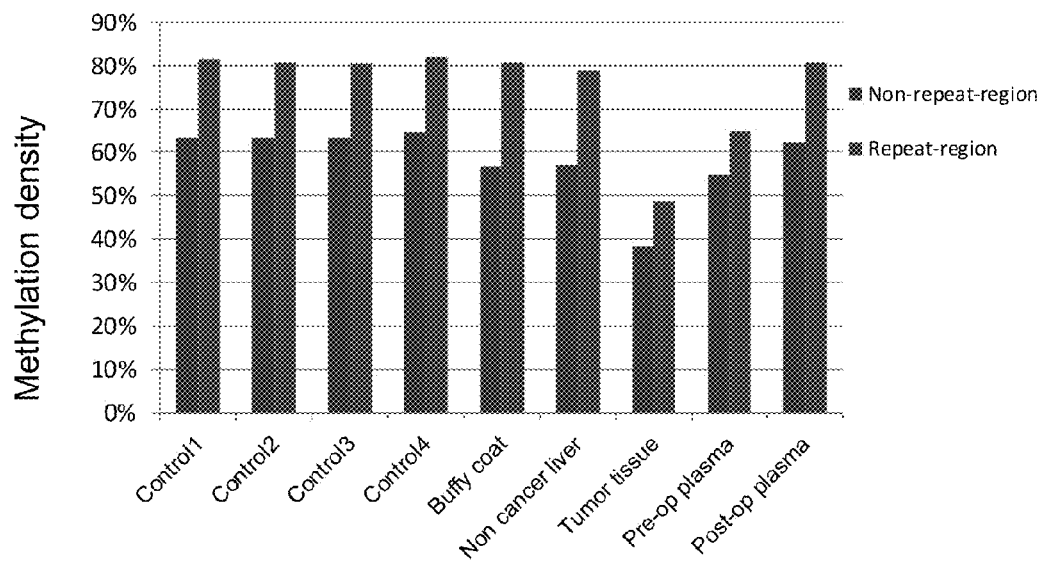

FIG. 32B          3250

NON-INVASIVE DETERMINATION OF METHYLOME OF FETUS OR TUMOR FROM PLASMA

CROSS-REFERENCES TO RELATED APPLICATION

This application is a non-provisional of and claims the benefit of U.S. Provisional Patent Application No. 61/703,512, entitled "Method Of Determining The Whole Genome DNA Methylation Status Of The Placenta By Massively Parallel Sequencing Of Maternal Plasma," filed on Sep. 20, 2012, which is herein incorporated by reference in its entirety for all purposes.

FIELD

The present disclosure relates generally a determination of a methylation pattern (methylome) of DNA, and more particularly to analyzing a biological sample (e.g., plasma) that includes a mixture of DNA from different genomes (e.g., from fetus and mother, or from tumor and normal cells) to determine the methylation pattern (methylome) of the minority genome. Uses of the determined methylome are also described.

BACKGROUND

Embryonic and fetal development is a complex process and involves a series of highly orchestrated genetic and epigenetic events. Cancer development is also a complex process involving typically multiple genetic and epigenetic steps. Abnormalities in the epigenetic control of developmental processes are implicated in infertility, spontaneous abortion, intrauterine growth abnormalities and postnatal consequences. DNA methylation is one of the most frequently studied epigenetic mechanisms. Methylation of DNA mostly occurs in the context of the addition of a methyl group to the 5' carbon of cytosine residues among CpG dinucleotides. Cytosine methylation adds a layer of control to gene transcription and DNA function. For example, hypermethylation of gene promoters enriched with CpG dinucleotides, termed CpG islands, is typically associated with repression of gene function.

Despite the important role of epigenetic mechanisms in mediating developmental processes, human embryonic and fetal tissues are not readily accessible for analysis (tumors may similarly not be accessible). Studies of the dynamic changes of such epigenetic processes in health and disease during the prenatal period in humans are virtually impossible. Extraembryonic tissues, particularly the placenta, which can be obtained as part of prenatal diagnostic procedures or after birth, have provided one of the main avenues for such investigations. However, such tissues require invasive procedures.

The DNA methylation profile of the human placenta has intrigued researchers for decades. The human placenta exhibits a plethora of peculiar physiological features involving DNA methylation. On a global level, placental tissues are hypomethylated when compared with most somatic tissues. At the gene level, the methylation status of selected genomic loci is a specific signature of placental tissues. Both the global and locus-specific methylation profiles show gestational-age dependent changes. Imprinted genes, namely genes for which expression is dependent on the parental origin of alleles serve key functions in the placenta. The placenta has been described as pseudomalignant and hypermethylation of several tumor suppressor genes have been observed.

Studies of the DNA methylation profile of placental tissues have provided insights into the pathophysiology of pregnancy-associated or developmentally-related diseases, such as preeclampsia and intrauterine growth restriction. Disorders in genomic imprinting are associated with developmental disorders, such as Prader-Willi syndrome and Angelman syndrome. Altered profiles of genomic imprinting and global DNA methylation in placental and fetal tissues have been observed in pregnancies resulting from assisted reproductive techniques (H. Hiura et al. 2012 Hum Reprod; 27: 2541-2548). A number of environmental factors such as maternal smoking (K. E. Haworth et al. 2013 Epigenomics; 5: 37-49), maternal dietary factors (X. Jiang et al. 2012 FASEB J; 26: 3563-3574) and maternal metabolic status such as diabetes (N. Hajj et al., Diabetes. doi: 10.2337/db12-0289) have been associated with epigenetic aberrations of the offsprings.

Despite decades of efforts, there had not been any practical means available to study the fetal or tumor methylome and to monitor the dynamic changes throughout pregnancy or during disease processes, such as malignancies. Therefore, it is desirable to provide methods for analyzing all or portions of a fetal methylome and a tumor methylome noninvasively.

SUMMARY

Embodiments provide systems, methods, and apparatuses for determining and using methylation profiles of various tissues and samples. Examples are provided. A methylation profile can be deduced for fetal/tumor tissue based on a comparison of plasma methylation (or other sample with cell-free DNA) to a methylation profile of the mother/patient. A methylation profile can be determined for fetal/tumor tissue using tissue-specific alleles to identify DNA from the fetus/tumor when the sample has a mixture of DNA. A methylation profile can be used to determine copy number variations in genome of a fetus/tumor. Methylation markers for a fetus have been identified via various techniques. The methylation profile can be determined by determining a size parameter of a size distribution of DNA fragments, where reference values for the size parameter can be used to determine methylation levels.

Additionally, a methylation level can be used to determine a level of cancer. In the context of cancer, the measurement of the methylomic changes in plasma can allow one to detect the cancer (e.g. for screening purposes), for monitoring (e.g. to detect response following anti-cancer treatment; and to detect cancer relapse) and for prognostication (e.g. for measuring the load of cancer cells in the body or for staging purposes or for assessing the chance of death from disease or disease progression).

A better understanding of the nature and advantages of embodiments of the present invention may be gained with reference to the following detailed description and the accompanying drawings.

BRIEF DESCRIPTION OF THE DRAWINGS

Figure 1A:
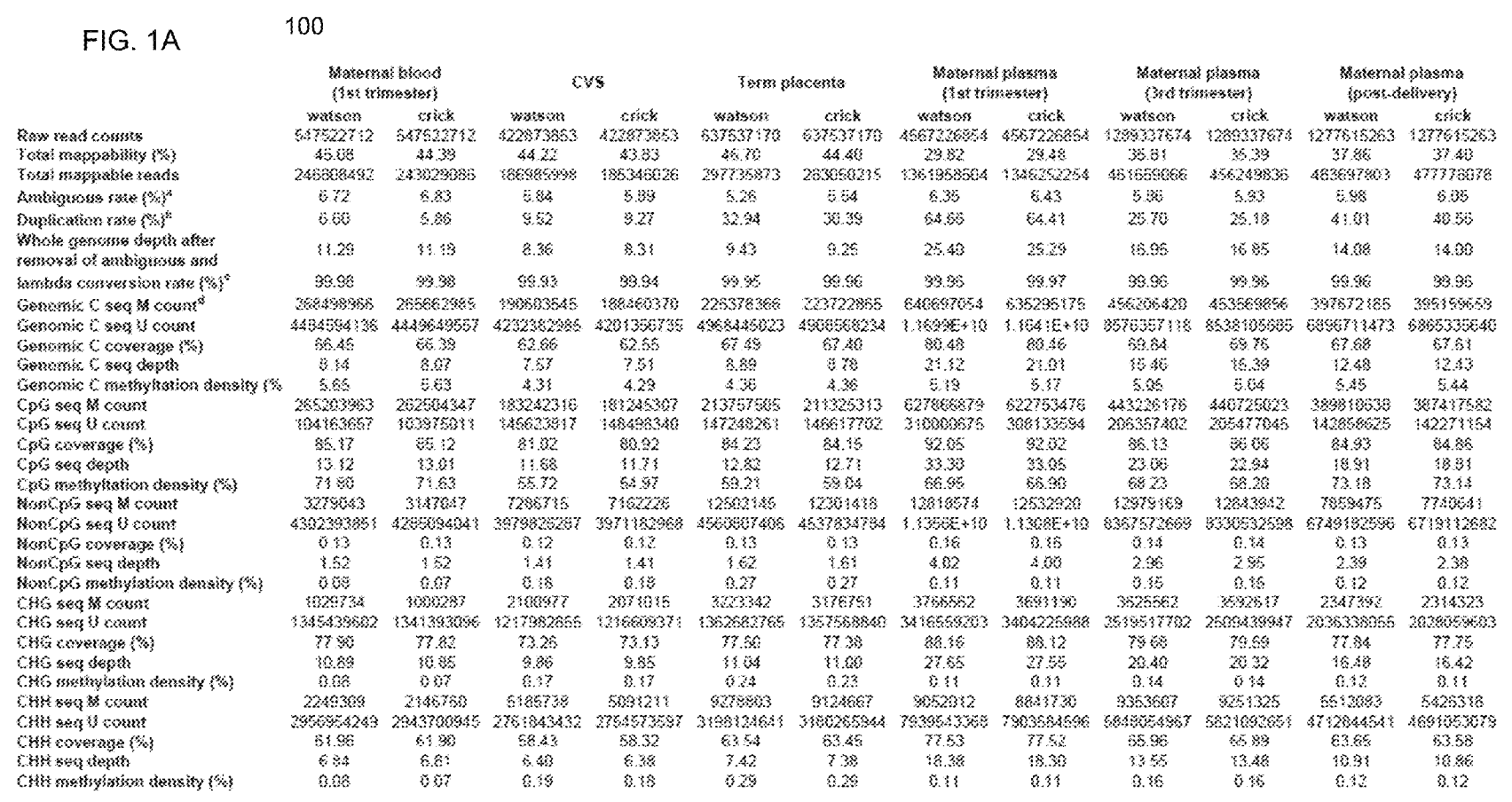

FIG. 1A shows a table 100 of sequencing results for maternal blood, placenta, and maternal plasma according to embodiments of the present invention.

FIG. 12A is a table 1200 showing details of 15 selected genomic loci for methylation prediction according to embodiments of the present invention.

FIG. 15A is a table 1500 showing a performance of first trimester differentially methylated region (DMR) identification algorithm using placental methylome with reference to 33 previously reported first trimester markers. FIG. 15B is a table 1550 showing a performance of third trimester DMR identification algorithm using the placental methylome measured using the placenta sample obtained at delivery.

FIG. 16 is a table 1600 showing the numbers of loci predicted to be hypermethylated or hypomethylated based on direct analysis of the maternal plasma bisulfite-sequencing data.

FIG. 21A is a table 2100 showing the methylation densities of the pre-operative plasma and the tissue samples of an HCC patient. FIG. 21B is a table 2150 showing the number of sequence reads and the sequencing depth achieved per sample.

FIG. 22 is a table 220 showing the methylation densities in the autosomes ranged from 71.2% to 72.5% in the plasma samples of the healthy controls.

FIG. 26C is a table 2640 showing a distribution of the z-scores of the 1 Mb bins for the whole genome in both the pre-operative and post-operative plasma samples of the HCC patient. FIG. 26D is a table 2660 showing the methylation levels of the tumor tissue and pre-operative plasma sample overlapped with some of the control plasma samples when using the CHH and CHG contexts.

FIG. 27I is table 2780 showing the number of sequence reads and the sequencing depth achieved per sample. FIG. 27J is a table 2790 showing a distribution of the z-scores of the 1 Mb bins for the whole genome in plasma of patients with different malignancies. CL=adenocarcinoma of lung; NPC=nasopharyngeal carcinoma; CRC=colorectal carcinoma; NE=neuroendocrine carcinoma; SMS=smooth muscle sarcoma.

FIG. 32A is a table 3200 showing the effect of reducing the sequencing depth when the plasma sample contained 5% or 2% tumor DNA.

FIG. 32B is a graph 3250 showing the methylation densities of the repeat elements and non-repeat regions in the plasma of the four healthy control subjects, the buffy coat, the normal liver tissue, the tumor tissue, the pre-operative plasma and the post-operative plasma samples of the HCC patient.

DEFINITIONS

Figure 1B:
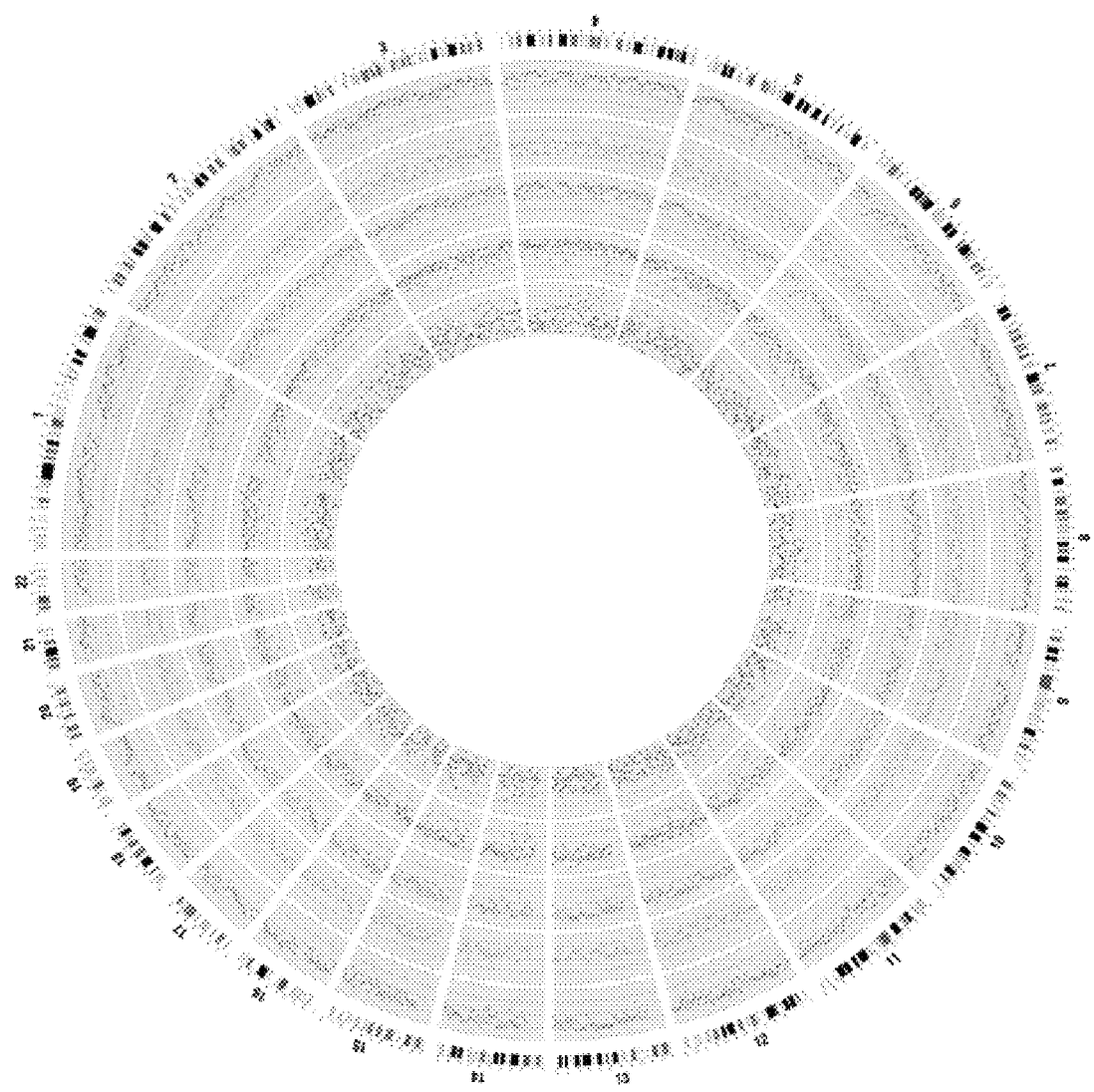
FIG. 1B shows methylation density in 1-Mb windows of sequenced samples according to embodiments of the present invention.

A "methylome" provides a measure of an amount of DNA methylation at a plurality of sites or loci in a genome. The methylome may correspond to all of the genome, a substantial part of the genome, or relatively small portion(s) of the genome. A "fetal methylome" corresponds to the methylome of a fetus of a pregnant female. The fetal methylome can be determined using a variety of fetal tissues or sources of fetal DNA, including placental tissues and cell-free fetal DNA in maternal plasma. A "tumor methylome" corresponds to the methylome of a tumor of an organism (e.g., a human). The tumor methylome can be determined using tumor tissue or cell-free tumor DNA in maternal plasma. The fetal methylome and the tumor methylome are examples of a methylome of interest. Other examples of methylomes of interest are the methylomes of organs that can contribute DNA into a bodily fluid (e.g. methylomes of brain cells, bones, the lungs, the heart, the muscles and the kidneys, etc.). The organs may be transplanted organs.

A "plasma methylome" is the methylome determined from the plasma or serum of an animal (e.g., a human). The plasma methylome is an example of a cell-free methylome since plasma and serum include cell-free DNA. The plasma methylome is also an example of a mixed methylome since it is a mixture of fetal/maternal methylome or tumor/patient methylome. The "placental methylome" can be determined from a chorionic villus sample (CVS) or a placental tissue sample (e.g. obtained following delivery). The "cellular methylome" corresponds to the methylome determined from cells (e.g., blood cells) of the patient. The methylome of the blood cells is called the blood cell methylome (or blood methylome).

A "site" corresponds to a single site, which may be a single base position or a group of correlated base positions, e.g., a CpG site. A "locus" may correspond to a region that includes multiple sites. A locus can include just one site, which would make the locus equivalent to a site in that context.

The "methylation index" for each genomic site (e.g., a CpG site) refers to the proportion of sequence reads showing methylation at the site over the total number of reads covering that site. The "methylation density" of a region is the number of reads at sites within the region showing methylation divided by the total number of reads covering the sites in the region. The sites may have specific characteristics, e.g., be CpG sites. Thus, the "CpG methylation density" of a region is the number of reads showing CpG methylation divided by the total number of reads covering CpG sites in the region (e.g., a particular CpG site, CpG sites within a CpG island, or a larger region). For example, the methylation density for each 100-kb bin in the human genome can be determined from the total number of unconverted cytosines (which corresponds to methylated cytosine) at CpG sites as a proportion of all CpG sites covered by sequence reads mapped to the 100-kb region. This analysis can also be performed for other bin sizes, e.g. 50-kb or 1-Mb, etc. A region could be the entire genome or a chromosome or part of a chromosome (e.g. a chromosomal arm). The methylation index of a CpG site is the same as the methylation density for a region when the region only includes that CpG site. The "proportion of methylated cytosines" refers the number of cytosine sites, "C's", that are shown to be methylated (for example unconverted after bisulfite conversion) over the total number of analyzed cytosine residues, i.e. including cytosines outside of the CpG context, in the region. The methylation index, methylation density and proportion of methylated cytosines are examples of "methylation levels."

A "methylation profile" (also called methylation status) includes information related to DNA methylation for a region. Information related to DNA methylation can include, but not limited to, a methylation index of a CpG site, a methylation density of CpG sites in a region, a distribution of CpG sites over a contiguous region, a pattern or level of methylation for each individual CpG site within a region that contains more than one CpG site, and non-CpG methylation. A methylation profile of a substantial part of the genome can be considered equivalent to the methylome. "DNA methylation" in mammalian genomes typically refers to the addition of a methyl group to the 5' carbon of cytosine residues (i.e. 5-methylcytosines) among CpG dinucleotides. DNA methylation may occur in cytosines in other contexts, for example CHG and CHH, where H is adenine, cytosine or thymine. Cytosine methylation may also be in the form of 5-hydroxymethylcytosine. Non-cytosine methylation, such as N6-methyladenine, has also been reported.

A "tissue" corresponds to any cells. Different types of tissue may correspond to different types of cells (e.g., liver, lung, or blood), but also may correspond to tissue from different organisms (mother vs. fetus) or to healthy cells vs. tumor cells. A "biological sample" refers to any sample that is taken from a subject (e.g., a human, such as a pregnant woman, a person with cancer, or a person suspected of having cancer, an organ transplant recipient or a subject suspected of having a disease process involving an organ (e.g. the heart in myocardial infarction, or the brain in stroke) and contains one or more nucleic acid molecule(s) of interest. The biological sample can be a bodily fluid, such as blood, plasma, serum, urine, vaginal fluid, uterine or vaginal flushing fluids, plural fluid, ascitic fluid, cerebrospinal fluid, saliva, sweat, tears, sputum, bronchioalveolar lavage fluid, etc. Stool samples can also be used.

The term "level of cancer" can refer to whether cancer exists, a stage of a cancer, a size of tumor, whether there is metastasis, the total tumor burden of the body, and/or other measure of a severity of a cancer. The level of cancer could be a number or other characters. The level could be zero. The level of cancer also includes premalignant or precancerous conditions (states) associated with mutations or a number of mutations. The level of cancer can be used in various ways.

For example, screening can check if cancer is present in someone who is not known previously to have cancer. Assessment can investigate someone who has been diagnosed with cancer to monitor the progress of cancer, study the effectiveness of therapies or to determine the prognosis. Detection can mean 'screening' or can mean checking if someone, with suggestive features of cancer (e.g. symptoms or other positive tests), has cancer.

DETAILED DESCRIPTION

Epigenetic mechanisms play an important role in embryonic and fetal development. However, human embryonic and fetal tissues (including placental tissues) are not readily accessible (U.S. Pat. No. 6,927,028). Certain embodiments have addressed this problem by analyzing a sample that has cell-free fetal DNA molecules present in maternal circulation. The fetal methylome can be deduced in a variety of ways. For example, the maternal plasma methylome can be compared to a cellular methylome (from blood cells of the mother) and the difference is shown to be correlated to the fetal methylome. As another example, fetal-specific alleles can be used to determine the methylation of the fetal methylome at specific loci. Additionally, the size of a fragment can be used as an indicator of a methylation percentage, as a correlation between size and methylation percentage is shown.

In one embodiment, genome-wide bisulfite sequencing is used to analyze the methylation profile (part or all of a methylome) of maternal plasma DNA at single nucleotide resolution. By exploiting the polymorphic differences between the mother and the fetus, the fetal methylome could be assembled from maternal blood samples. In another implementation, polymorphic differences were not used, but a differential between the plasma methylome and the blood cell methylome can be used.

In another embodiment, by exploiting single nucleotide variations and/or copy number aberrations between a tumor genome and a nontumor genome, and sequencing data from plasma (or other sample), methylation profiling of a tumor can be performed in the sample of a patient suspected or known to have cancer. A difference in a methylation level in a plasma sample of a test individual when compared with the plasma methylation level of a healthy control or a group of healthy controls can allow the identification of the test individual as harboring cancer. Additionally, the methylation profile can act as a signature that reveals the type of cancer, for example, from which organ, that the person has developed and whether metastasis has occurred.

Due to the noninvasive nature of this approach, we were able to serially assess the fetal and maternal plasma methylomes from maternal blood samples collected in the first trimester, third trimester and after delivery. Gestation-related changes were observed. The approach can also be applied to samples obtained during the second trimester. The fetal methylome deduced from maternal plasma during pregnancy resembled the placental methylome. Imprinted genes and differentially methylated regions were identified from the maternal plasma data.

We have therefore developed an approach to study the fetal methylome noninvasively, serially and comprehensively, thus offering the possibility for identifying biomarkers or direct testing of pregnancy-related pathologies. Embodiments can also be used to study the tumor methylome noninvasively, serially and comprehensively, for screening or detecting if a subject is suffering from cancer, for monitoring malignant diseases in a cancer patient and for prognostication. Embodiments can be applied to any cancer type, including, but not limited to, lung cancer, breast cancer, colorectal cancer, prostate cancer, nasopharyngeal cancer, gastric cancer, testicular cancer, skin cancer, cancer affecting the nervous system, bone cancer, ovarian cancer, liver cancer, hematologic malignancies, pancreatic cancer, endometriocarcinoma, kidney cancer etc.

A description of how to determine a methylome or methylation profile is first discussed, and then different methylomes are described (such as fetal methylomes, a tumor methylome, methylomes of the mother or a patient, and a mixed methylome, e.g., from plasma). The determination of a fetal methylation profile is then described using fetal-specific markers or by comparing a mixed methylation profile to a cellular methylation profile. Fetal methylation markers are determined by comparing methylation profiles. A relationship between size and methylation is discussed. Uses of methylation profiles to detect cancer are also provided.

I. Determination of a Methylome

A myriad of approaches have been used to investigate the placental methylome, but each approach has its limitations. For example, sodium bisulfite, a chemical that modifies unmethylated cytosine residues to uracil and leaves methylated cytosine unchanged, converts the differences in cytosine methylation into a genetic sequence difference for further interrogation. The gold standard method of studying cytosine methylation is based on treating tissue DNA with sodium bisulfite followed by direct sequencing of individual clones of bisulfite-converted DNA molecules. After the analysis of multiple clones of DNA molecules, the cytosine methylation pattern and quantitative profile per CpG site can be obtained. However, cloned bisulfite sequencing is a low throughput and labor-intensive procedure that cannot be readily applied on a genome-wide scale.

Methylation-sensitive restriction enzymes that typically digest unmethylated DNA provide a low cost approach to study DNA methylation. However, data generated from such studies are limited to loci with the enzyme recognition motifs and the results are not quantitative. Immunoprecipitation of DNA bound by anti-methylated cytosine antibodies can be used to survey large segments of the genome but tends to bias towards loci with dense methylation due to higher strength of antibody binding to such regions. Microarray-based approaches are dependent on the a priori design of the interrogation probes and hybridization efficiencies between the probes and the target DNA.

To interrogate a methylome comprehensively, some embodiments use massively parallel sequencing (MPS) to provide genome-wide information and quantitative assessment of the level of methylation on a per nucleotide and per allele basis. Recently, bisulfite conversion followed by genome-wide MPS has become feasible (R. Lister et al 2008 Cell; 133: 523-536).

Among the small number of published studies (R. Lister et al. 2009 Nature; 462: 315-322); L. Laurent et al. 2010 Genome Res; 20: 320-331; Y. Li et al. 2010 PLoS Biol; 8: e1000533; and M. Kulis et al. 2012 Nat Genet; 44: 1236-1242) that applied genome-wide bisulfite sequencing for the investigation of human methylomes, two studies focused on embryonic stem cells and fetal fibroblasts (R. Lister et al. 2009 and L. Laurent et al 2010). Both studies analyzed cell-line derived DNA.

A. Genome-Wide Bisulfite Sequencing

Certain embodiments can overcome the aforesaid challenges and enable interrogation of a fetal methylome comprehensively, noninvasively and serially. In one embodiment, genome-wide bisulfite sequencing was used to analyze cell-free fetal DNA molecules that are found in the circulation of pregnant women. Despite the low abundance and fragmented nature of plasma DNA molecules, we were able to assemble a high resolution fetal methylome from maternal plasma and serially observe the changes with pregnancy progression. Given the intense interest in noninvasive prenatal testing (NIPT), embodiments can provide a powerful new tool for fetal biomarker discovery or serve as a direct platform for achieving NIPT of fetal or pregnancy-associated diseases. Data from the genome-wide bisulfite sequencing of various samples, from which the fetal methylome can be derived, is now provided. In one embodiment, this technology can be applied for methylation profiling in pregnancies complicated with preeclampsia, or intrauterine growth retardation, or preterm labor. For such complicated pregnancies, this technology can be used serially because of its noninvasive nature, to allow for the monitoring and/or prognostication and/or response to treatment.

FIG. 1A shows a table 100 of sequencing results for maternal blood, placenta, and maternal plasma according to embodiments of the present invention. In one embodiment, whole genome sequencing was performed on bisulfite-converted DNA libraries, prepared using methylated DNA library adaptors (Illumina) (R. Lister et al. 2008), of blood cells of the blood sample collected in the first trimester, the CVS, the placental tissue collected at term, the maternal plasma samples collected during the first and third trimesters and the postpartum period. Blood cell and plasma DNA samples obtained from one adult male and one adult non-pregnant female were also analyzed. A total of 9.5 billion pairs of raw sequence reads were generated in this study. The sequencing coverage of each sample is shown in table 100.

The sequence reads that were uniquely mappable to the human reference genome reached average haploid genomic coverages of 50 folds, 34 folds and 28 folds, respectively, for the first trimester, third trimester and post-delivery maternal plasma samples. The coverage of the CpG sites in the genome ranged from 81% to 92% for the samples obtained from the pregnancy. The sequence reads that spanned CpG sites amounted to average haploid coverages of 33 folds per strand, 23 folds per strand and 19 folds per strand, respectively, for the first trimester, third trimester and post-delivery maternal plasma samples. The bisulfite conversion efficiencies for all samples were >99.9% (table 100).

In table 100, ambiguous rate (marked "a") refers to the proportion of reads mapped onto both the Watson and Crick strands of the reference human genome. Lambda conversion rate refers to the proportion of unmethylated cytosines in the internal lambda DNA control being converted to the "thymine" residues by bisulfite modification. H generically equates to A, C, or T. "a" refers to reads that could be mapped to a specific genomic locus but cannot be assigned to the Watson or Crick strand. "b" refers to paired reads with identical start and end coordinates. For "c", lambda DNA was spiked into each sample before bisulfite conversion. The lambda conversion rate refers to the proportion of cytosine nucleotides that remain as cytosine after bisulfite conversion and is used as an indication of the rate of successful bisulfite conversion. "d" refers to the number of cytosine nucleotides present in the reference human genome and remaining as a cytosine sequence after bisulfite conversion.

During bisulfite modification, unmethylated cytosines are converted to uracils and subsequently thymines after PCR amplifications while the methylated cytosines would remain intact (Frommer M, et al. 1992 Proc Natl Acad Sci USA; 89:1827-31). After sequencing and alignment, the methylation status of an individual CpG site could thus be inferred from the count of methylated sequence reads "M" (methylated) and the count of unmethylated sequence reads "U" (unmethylated) at the cytosine residue in CpG context. Using the bisulfite sequencing data, the entire methylomes of maternal blood, placenta and maternal plasma were constructed. The mean methylated CpG density (also called methylation density m) of specific loci in the maternal plasma can be calculated using the equation:

$$m = \frac{M}{M+U}$$

where M is the count of methylated reads and U is the count of unmethylated reads at the CpG sites within the genetic locus. If there is more than one CpG site within a locus, then M and U correspond to the counts across the sites.

B. Various Techniques

As described above, methylation profiling can be performed using massively parallel sequencing (MPS) of bisulfite converted plasma DNA. The MPS of the bisulfite converted plasma DNA can be performed in a random or shotgun fashion. The depth of the sequencing can be varied according to the size of the region of interest.

In another embodiment, the region(s) of interest in the bisulfite converted plasma DNA can be first captured using a solution-phase or solid-phase hybridization-based process, followed by the MPS. The massively parallel sequencing can be performed using a sequencing-by-synthesis platform such as the Illumina, a sequencing-by-ligation platform such as the SOLiD platform from Life Technologies, a semiconductor-based sequencing system such as the Ion Torrent or Ion Proton platforms from Life Technologies, or single molecule sequencing system such as the Helicos system or the Pacific Biosciences system or a nanopore-based sequencing system. Nanopore-based sequencing including nanopores that are constructed using lipid bilayers and protein nanopore, and solid-state nanopores (such as those that are graphene based). As selected single molecule sequencing platforms would allow the methylation status of DNA molecules (including N6-methyladenine, 5-methylcytosine and 5-hydroxymethylcytosine) to be elucidated directly without bisulfite conversion (B. A. Flusberg et al. 2010 Nat Methods; 7: 461-465; J. Shim et al. 2013 Sci Rep; 3:1389. doi: 10.1038/srep01389), the use of such platforms would allow the methylation status of non-bisulfite converted sample DNA (e.g. plasma DNA) to be analyzed.

Besides sequencing, other techniques can be used. In one embodiment, methylation profiling can be done by methylation-specific PCR or methylation-sensitive restriction enzyme digestion followed by PCR or ligase chain reaction followed by PCR. In yet other embodiments, the PCR is a form of single molecule or digital PCR (B. Vogelstein et al. 1999 Proc Natl Acad Sci USA; 96: 9236-9241). In yet further embodiments, the PCR can be a real-time PCR. In other embodiments, the PCR can be multiplex PCR.

II. Analysis of Methylomes

Some embodiments can determine the methylation profile of plasma DNA using whole genome bisulfite sequencing. The methylation profile of a fetus can be determined by sequencing maternal plasma DNA samples, as is described below. Thus, the fetal DNA molecules (and fetal methylome) were accessed noninvasively during the pregnancy, and changes were monitored serially as the pregnancy progressed. Due to the comprehensiveness of the sequencing data, we were able to study the maternal plasma methylomes on a genome-wide scale at single nucleotide resolution.

Since the genomic coordinates of the sequenced reads were known, these data enabled one to study the overall methylation levels of the methylome or any region of interest in the genome and to make comparison between different genetic elements. In addition, multiple sequence reads covered each CpG site or locus. A description of some of the metrics used to measure the methylome are now provided.

A. Methylation of Plasma DNA Molecules

DNA molecules are present in human plasma at low concentrations and in a fragmented form, typically in lengths resembling mononucleosomal units (Y. M. D. Lo et al. 2010 Sci Transl Med; 2: 61ra91; and Zheng at al. 2012 Clin Chem; 58: 549-558). Despite these limitations, a genome-wide bisulfite-sequencing pipeline was able to analyze the methylation of the plasma DNA molecules. In other embodiments, as selected single molecule sequencing platforms would allow the methylation status of DNA molecules to be elucidated directly without bisulfite conversion (Flusberg B A et al. 2010 Nat Methods; 7: 461-465; Shim J et al. 2013 Sci Rep; 3:1389. doi: 10.1038/srep01389), the use of such platforms would allow the non-bisulfite converted plasma DNA to be used to determine the methylation levels of plasma DNA or to determine the plasma methylome. Such platforms can detect N6-methyladenine, 5-methylcytosine and 5-hydroxymethylcytosine.

FIG. 1B shows methylation density in 1-Mb windows of sequenced samples according to embodiments of the present invention. Plot 150 is a Circos plot depicting the methylation density in the maternal plasma and genomic DNA in 1-Mb windows across the genome. From outside to inside: chromosome ideograms can be oriented pter-qter in a clockwise direction (centromeres are shown in red), maternal blood (red), placenta (yellow), maternal plasma (green), shared reads in maternal plasma (blue), and fetal-specific reads in maternal plasma (purple). The overall CpG methylation levels (i.e., density levels) of maternal blood cells, placenta and maternal plasma can be found in table 100. The methylation level of maternal blood cells is in general higher than that of the placenta across the whole genome.

B. Comparison of Bisulfite Sequencing to Other Techniques

We studied the placental methylome using massively parallel bisulfite sequencing. In addition, we studied the placental methylome using an oligonucleotide array platform that covered about 480,000 CpG sites in the human genome (Illumina) (M. Kulis et al. 2012 Nat Genet; 44: 1236-1242; and C. Clark et al. 2012 PLoS One; 7: e50233). In one embodiment using beadchip-based genotyping and methylation analysis, genotyping was performed using the Illumina HumanOmni2.5-8 genotyping array according to the manufacturer's protocol. Genotypes were called using the GenCall algorithm of the Genome Studio Software (Illumina). The call rates were over 99%. For the microarray based methylation analysis, genomic DNA (500-800 ng) was treated with sodium bisulfite using the Zymo EZ DNA Methylation Kit (Zymo Research, Orange, Calif., USA) according to the manufacturer's recommendations for the Illumina Infinium Methylation Assay.

The methylation assay was performed on 4 µl bisulfite-converted genomic DNA at 50 ng/µl according to the Infinium HD Methylation Assay protocol. The hybridized beadchip was scanned on an Illumina iScan instrument. DNA methylation data were analyzed by the GenomeStudio (v2011.1) Methylation Module (v1.9.0) software, with normalization to internal controls and background subtraction. The methylation index for individual CpG site was represented by a beta value (β), which was calculated using the ratio of fluorescent intensities between methylated and unmethylated alleles:

$$\beta = \frac{\text{Intensity of methylated allele}}{\text{Intensity of unmethylated allele} + \text{Intensity of methylated allele} + 100}$$

For CpG sites that were represented on the array and sequenced to coverage of at least 10 folds, we compared the beta-value obtained by the array to the methylation index as determined by sequencing of the same site. Beta-values represented the intensity of methylated probes as a proportion of the combined intensity of the methylated and unmethylated probes covering the same CpG site. The methylation index for each CpG site refers to the proportion of methylated reads over the total number of reads covering that CpG.

Figure 2A:
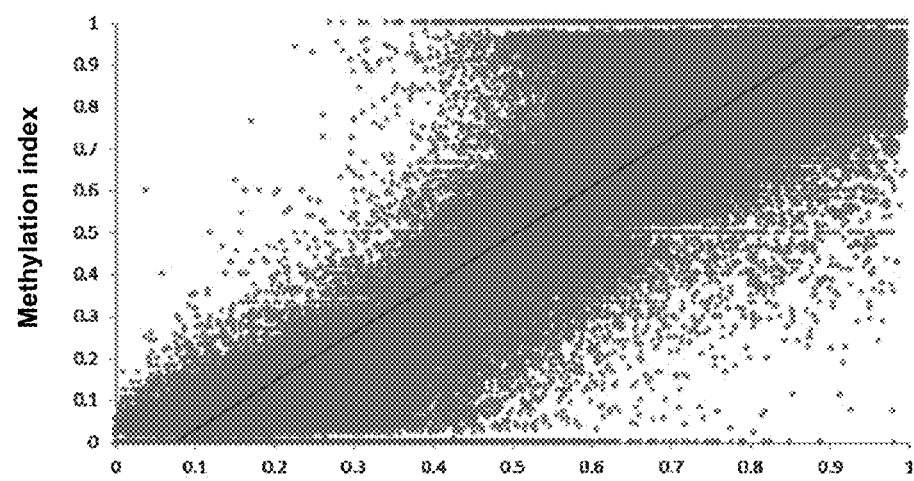
FIGS. 2A-2C show plots of the beta-values against the methylation indices: (A) Maternal blood cells, (B) Chorionic villus sample, (C) Term placental tissue.
Figure 2B:
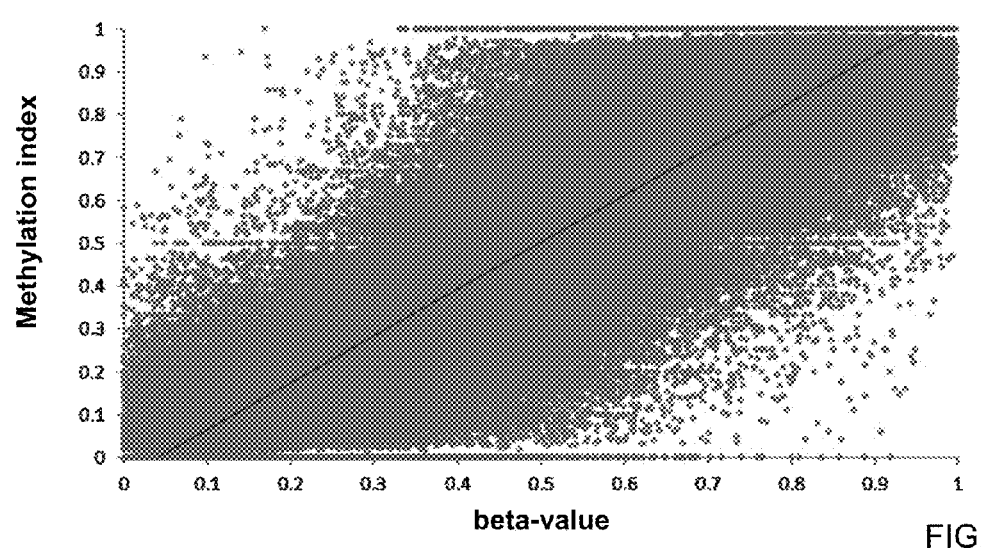
Figure 2C:
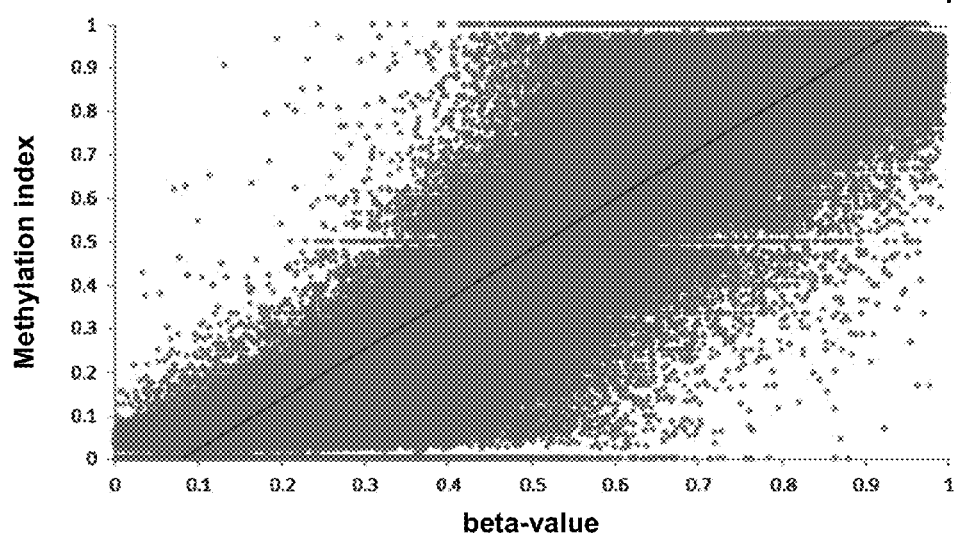

FIGS. 2A-2C show plots of the beta-values determined by the Illumina Infinium HumanMethylation 450K beadchip array against the methylation indices determined by genome-wide bisulfite sequencing of corresponding CpG sites that were interrogated by both platforms: (A) Maternal blood cells, (B) Chorionic villus sample, (C) Term placental tissue. The data from both platforms were highly concordant and the Pearson correlation coefficients were 0.972, 0.939 and 0.954, and $R^2$ values were 0.945, 0.882 and 0.910 for the maternal blood cells, CVS and term placental tissue, respectively.

We further compared our sequencing data with those reported by Chu et al, who investigated the methylation profiles of 12 pairs of CVS and maternal blood cell DNA samples using an oligonucleotide array that covered about 27,000 CpG sites (T. Chu et al. 2011 PLoS One; 6: e14723). The correlation data between the sequencing results of the CVS and maternal blood cell DNA and each of the 12 pairs of samples in the previous study are an average Pearson coefficient (0.967) and $R^2$ (0.935) for maternal blood and an average Pearson coefficient (0.943) and $R^2$ (0.888) for the CVS. Among the CpG sites represented on both arrays, our data correlated highly with the published data. The rates of non-CpG methylation were <1% for the maternal blood cells, CVS and placental tissues (table 100). These results were consistent with current belief that substantial amounts of non-CpG methylation were mainly restricted to pluripotent cells (R. Lister et al. 2009 and L. Laurent et al 2010).

C. Comparison of Plasma and Blood Methylomes for Non Pregnant Subjects

Figure 3A:
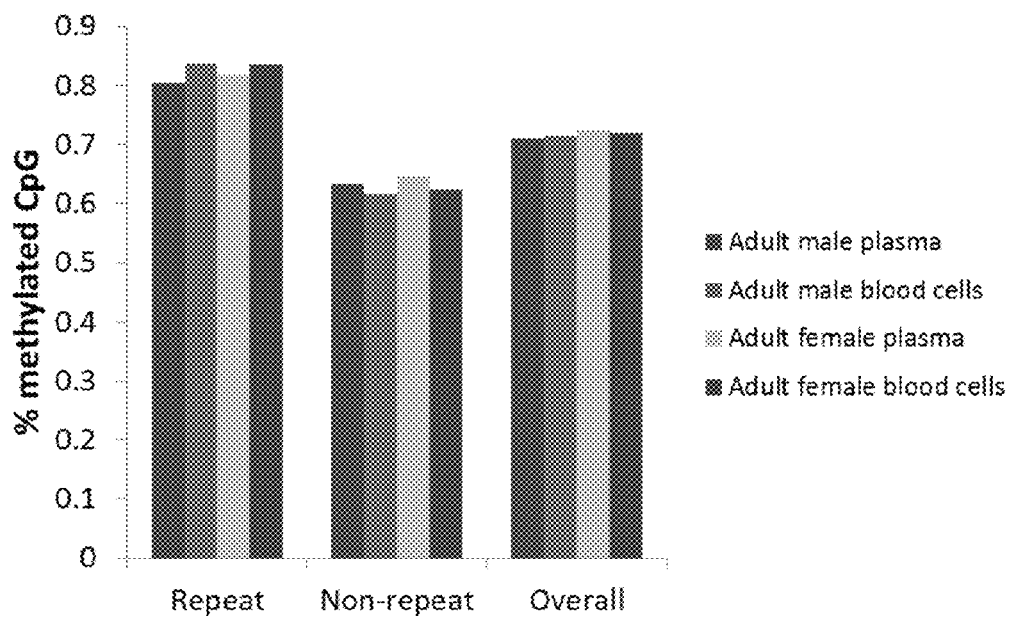
FIGS. 3A and 3B show bar charts of percentage of methylated CpG sites in plasma and blood cells collected from an adult male and a non-pregnant adult female: (A) Autosomes, (B) Chromosome X.
Figure 3B:
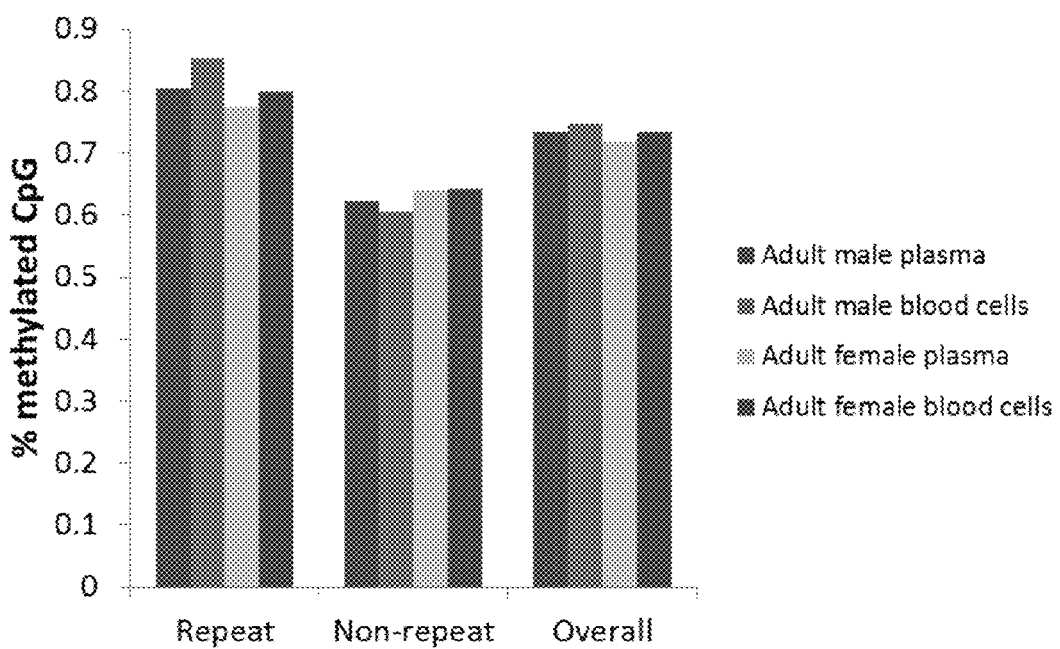

FIGS. 3A and 3B show bar charts of percentage of methylated CpG sites in plasma and blood cells collected from an adult male and a non-pregnant adult female: (A) Autosomes, (B) Chromosome X. The charts show a similarity between plasma and blood methylomes of a male and a non-pregnant female. The overall proportions of CpG sites that were methylated in the male and non-pregnant female plasma samples were almost the same as the corresponding blood cell DNA (table 100 and FIGS. 2A and 2B).

We next studied the correlation of the methylation profiles of the plasma and blood cell samples in a locus-specific manner. We determined the methylation density of each 100-kb bin in the human genome by determining the total number of unconverted cytosines at CpG sites as a proportion of all CpG sites covered by sequence reads mapped to the 100-kb region. The methylation densities were highly concordant between the plasma sample and corresponding blood cell DNA of the male as well as the female samples.

Figure 4A:
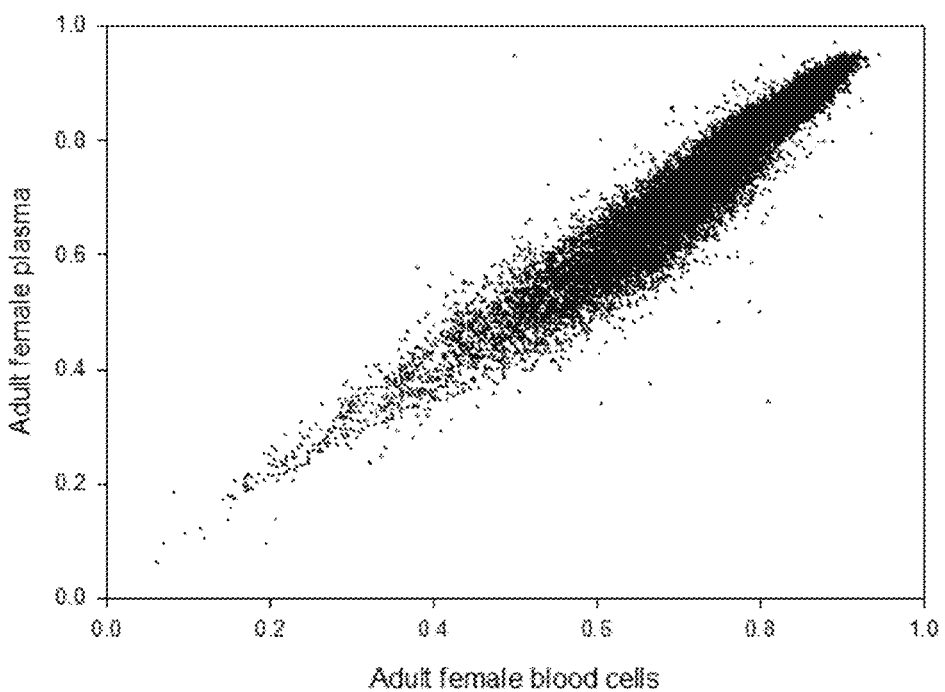
FIGS. 4A and 4B show plots of methylation densities of corresponding loci in blood cell DNA and plasma DNA: (A) Non-pregnant adult female, (B) Adult male.
Figure 4B:
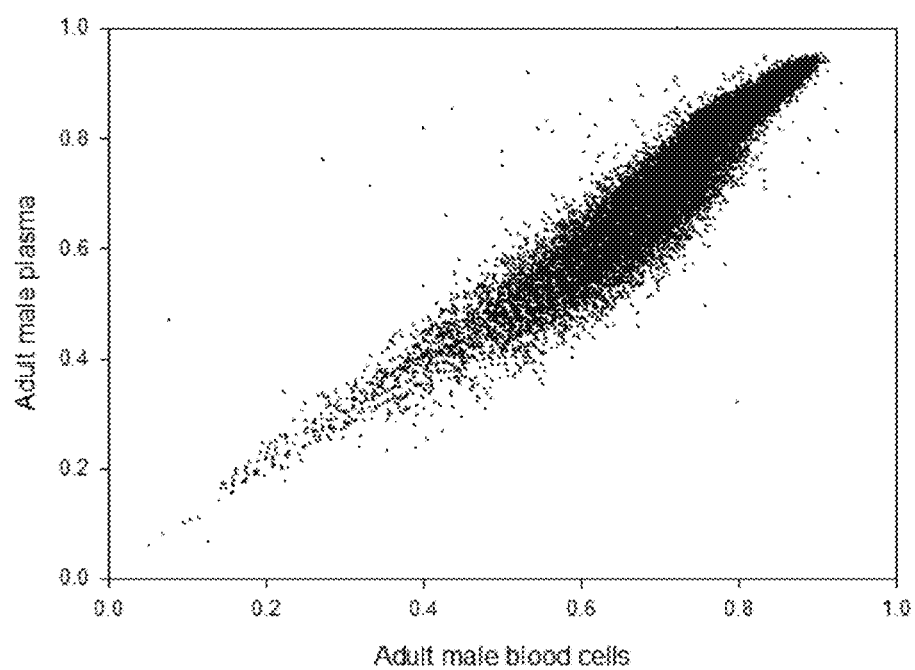

FIGS. 4A and 4B show plots of methylation densities of corresponding loci in blood cell DNA and plasma DNA: (A) Non-pregnant adult female, (B) Adult male. The Pearson correlation coefficient and $R^2$ value for the non-pregnant female samples were respectively 0.963 and 0.927, and that for the male samples were respectively 0.953 and 0.908. These data are consistent with previous findings based on the assessment of genotypes of plasma DNA molecules of recipients of allogenic hematopoietic stem cell transplantation which showed that hematopoietic cells are the predominant source of DNA in human plasma (Zheng at al., 2012).

D. Methylation Levels Across Methylomes

We next studied the DNA methylation levels of maternal plasma DNA, maternal blood cells, and placental tissue to determine methylation levels. The levels were determined for repeat regions, non-repeat regions, and overall.

Figure 5A:
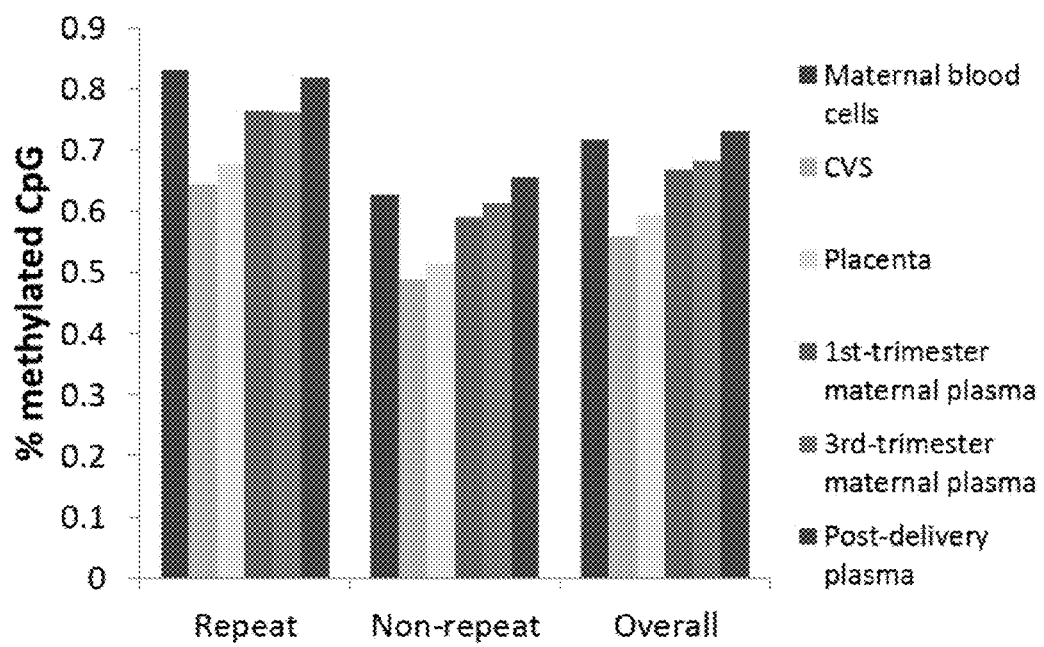
FIGS. 5A and 5B show bar charts of percentage of methylated CpG sites among samples collected from the pregnancy: (A). Autosomes, (B) Chromosome X.
Figure 5B:
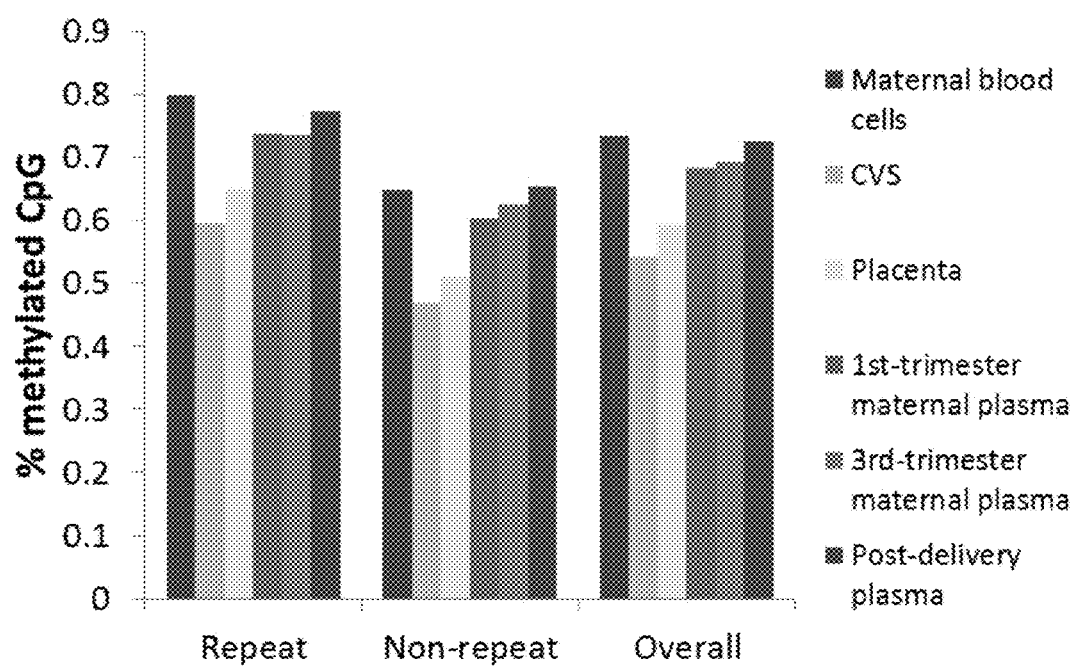

FIGS. 5A and 5B show bar charts of percentage of methylated CpG sites among samples collected from the pregnancy: (A). Autosomes, (B) Chromosome X. The overall proportions of methylated CpGs were 67.0% and 68.2% for the first and third trimester maternal plasma samples, respectively. Unlike the results obtained from the non-pregnant individuals, these proportions were lower than that of the first trimester maternal blood cell sample but higher than that of the CVS and term placental tissue samples (table 100). Of note, the percentage of methylated CpGs for the post-delivery maternal plasma sample was 73.1% which was similar to the blood cell data (table 100). These trends were observed in CpGs distributed over all autosomes as well as chromosome X and spanned across both the non-repeat regions and multiple classes of repeat elements of the human genome.

Both the repeat and non-repeat elements in the placenta were found to be hypomethylated relative to maternal blood cells. The results were concordant to the findings in literatures that the placenta is hypomethylated to other tissues, including peripheral blood cells.

Between 71% to 72% of the sequenced CpG sites were methylated in the blood cell DNA from the pregnant woman, non-pregnant woman and adult male (table 100 of FIG. 1). These data are comparable with the report of 68.4% of CpG sites of blood mononuclear cells reported by Li et al 2010. Consistent with the previous reports on the hypomethylated nature of placental tissues, 55% and 59% of the CpG sites were methylated in the CVS and term placental tissue, respectively (table 100).

Figure 6:
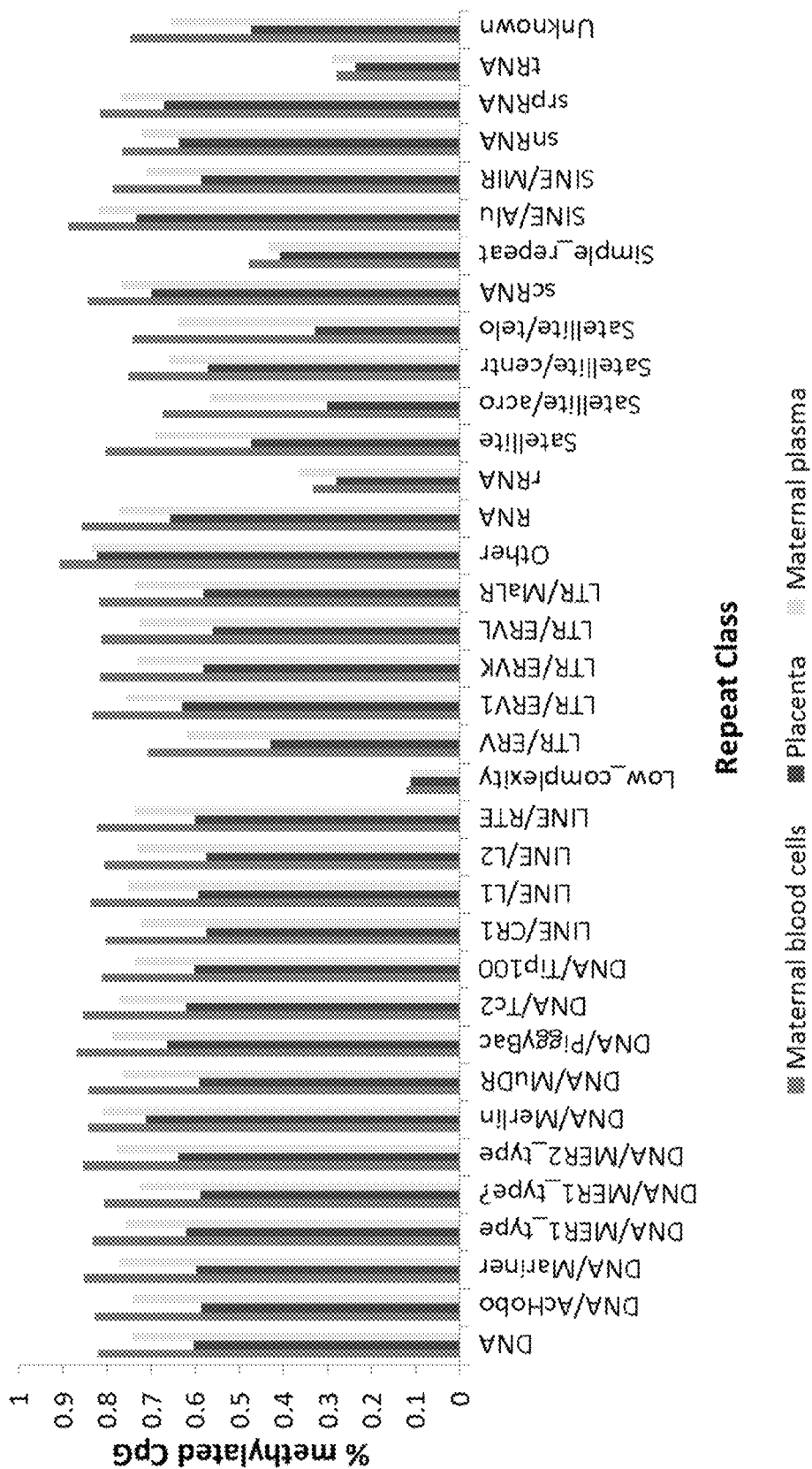
FIG. 6 shows a bar chart of methylation level of different repeat classes of the human genome for maternal blood, placenta and maternal plasma.

FIG. 6 shows a bar chart of methylation level of different repeat classes of the human genome for maternal blood, placenta and maternal plasma. The repeat classes are as defined by the UCSC genome browser. Data shown are from the first trimester samples. Unlike earlier data suggesting that the hypomethylated nature of placental tissues was mainly observed in certain repeat classes in the genome (B. Novakovic et al. 2012 Placenta; 33: 959-970), here we show that the placenta was in fact hypomethylated in most classes of genomic elements with reference to blood cells.

E. Similarity of Methylomes

Embodiments can determine the methylomes of placental tissues, blood cells and plasma using the same platform. Hence, direct comparisons of the methylomes of those biological sample types were possible. The high level of resemblance between methylomes of the blood cells and plasma for the male and non-pregnant female as well as between the maternal blood cells and the post-delivery maternal plasma sample further affirmed that hematopoietic cells were the main sources of DNA in human plasma (Zheng at al., 2012).

The resemblances are evident both in terms of the overall proportion of methylated CpGs in the genome as well as from the high correlation of methylation densities between corresponding loci in the blood cell DNA and plasma DNA. Yet, the overall proportions of methylated CpGs in the first trimester and third trimester maternal plasma samples were reduced when compared with the maternal blood cell data or the post-delivery maternal plasma sample. The reduced methylation levels during pregnancy were due to the hypomethylated nature of the fetal DNA molecules present in maternal plasma.

The reversal of the methylation profile in the post-delivery maternal plasma sample to become more similar to that of the maternal blood cells suggests that the fetal DNA molecules had been removed from the maternal circulation. Calculation of the fetal DNA concentrations based on SNP markers of the fetus indeed showed that the concentration changed from 33.9% before delivery to just 4.5% in the post-delivery sample.

F. Other Applications

Embodiments have successfully assembled DNA methylomes through the MPS analysis of plasma DNA. The ability to determine the placental or fetal methylome from maternal plasma provides a noninvasive method to determine, detect and monitor the aberrant methylation profiles associated with pregnancy-associated conditions such as preeclampsia, intrauterine growth restriction, preterm labor and others. For example, the detection of a disease-specific aberrant methylation signature allows the screening, diagnosis and monitoring of such pregnancy-associated conditions. The measuring of the maternal plasma methylation level allows the screening, diagnosis and monitoring of such pregnancy-associated conditions. Besides the direct applications on the investigation of pregnancy-associated conditions, the approach could be applied to other areas of medicine where plasma DNA analysis is of interest. For example, the methylomes of cancers could be determined from plasma DNA of cancer patients. Cancer methylomic analysis from plasma, as described herein, is potentially a synergistic technology to cancer genomic analysis from plasma (K. C. A. Chan at al. 2013 Clin Chem; 59:211-224 and Leary R J et al. 2012 Sci Transl Med; 4:162ra154).

For example, the determination of a methylation level of a plasma sample could be used to screen for cancer. When the methylation level of the plasma sample shows aberrant levels compared with healthy controls, cancer may be suspected. Then further confirmation and assessment of the type of cancer or tissue origin of the cancer may be performed by determining the plasma profile of methylation at different genomic loci or by plasma genomic analysis to detect tumor-associated copy number aberrations, chromosomal translocations and single nucleotide variants. Alternatively, radiological and imaging investigations (e.g. computed tomography, magnetic resonance imaging, positron emission tomography) or endoscopy (e.g. upper gastrointestinal endoscopy or colonoscopy) could be used to further investigate individuals who were suspected of having cancer based on the plasma methylation level analysis.

For cancer screening or detection, the determination of a methylation level of a plasma (or other biologic) sample can be used in conjunction with other modalities for cancer screening or detection such as prostate specific antigen measurement (e.g. for prostate cancer), carcinoembryonic antigen (e.g. for colorectal carcinoma, gastric carcinoma, pancreatic carcinoma, lung carcinoma, breast carcinoma, medullary thyroid carcinoma), alpha fetoprotein (e.g. for liver cancer or germ cell tumors) and CA19-9 (e.g. for pancreatic carcinoma).

Additionally, other tissues may be sequenced to obtain a cellular methylome. For example, liver tissue can be analyzed to determine a methylation pattern specific to the liver, which may be used to identify liver pathologies. Other tissues which can also be analyzed include brain cells, bones, the lungs, the heart, the muscles and the kidneys, etc. The methylation profiles of various tissues may change from time to time, e.g. as a result of development, aging, disease processes (e.g. inflammation or cirrhosis) or treatment (e.g. treatment with demethylating agents such as 5-azacytidine and 5-azadeoxycytidine). The dynamic nature of DNA methylation makes such analysis potentially very valuable for monitoring of physiological and pathological processes. For example, if one detects a change in the plasma methylome of an individual compared to a baseline value obtained when they were healthy, one could then detect disease processes in organs that contribute plasma DNA.

Also, the methylomes of transplanted organs could be determined from plasma DNA of organ transplantation recipients. Transplant methylomic analysis from plasma, as described in this invention, is potentially a synergistic technology to transplant genomic analysis from plasma (Y. W. Zheng at al, 2012; Y. M. D. Lo at al. 1998 Lancet; 351: 1329-1330; and T. M. Snyder et al. 2011 Proc Natl Acad Sci USA; 108: 6229-6234).

III. Determining Fetal Methylome Using SNPs

As described above, the plasma methylome corresponds to the blood methylome for a non-pregnant normal person. However, for a pregnant female, the methylomes differ. Fetal DNA molecules circulate in maternal plasma among a majority background of maternal DNA (Y. M. D. Lo et al. 1998 Am J Hum Genet; 62: 768-775). Thus, for a pregnant female, the plasma methylome is largely a composite of the placental methylome and the blood methylome. Accordingly, one can extract the placental methylome from plasma.

In one embodiment, single nucleotide polymorphism (SNP) differences between the mother and the fetus are used to identify the fetal DNA molecules in maternal plasma. An aim was to identify SNP loci where the mother was homozygous, but the fetus is heterozygous; the fetal-specific allele can be used to determine which DNA fragments are from the fetus. Genomic DNA from the maternal blood cells was analyzed using a SNP genotyping array, the Illumina HumanOmni2.5-8.

A. Correlation of Methylation of Fetal-Specific Reads and Placental Methylome

Loci having two different alleles, where the amount of one allele (B) was significantly less than the other allele (A), were identified from sequencing results of a biological sample. Reads covering the B alleles were regarded as fetal-specific (fetal-specific reads). The mother is determined to be homozygous for A and the fetus heterozygous for A/B, and thus reads covering the A allele were shared by the mother and fetus (shared reads).

The mother was found to be homozygous at 1,945,516 loci on the autosomes. The maternal plasma DNA sequencing reads that covered these SNPs were inspected. Reads carrying a non-maternal allele was detected at 107,750 loci and these were considered the informative loci. At each informative SNP, the allele that was not from the mother was termed a fetal-specific allele while the other one was termed a shared allele.

A fractional fetal/tumor DNA concentration (also called fetal DNA percentage) in the maternal plasma can be determined. In one embodiment, the fractional fetal DNA concentration in the maternal plasma, f, is determined by the equation:

$$f = \frac{2p}{p+q}$$

where p is the number of sequenced reads with the fetal-specific allele and q is the number of sequenced reads with the shared allele between the mother and the fetus (Y. M. D. Lo et al. 2010 Sci Transl Med; 2:61ra91). The fetal DNA proportions in the first trimester, third trimester and post-delivery maternal plasma samples were found to be 14.4%, 33.9% and 4.5%, respectively. The fetal DNA proportions were also calculated using the numbers of reads that aligned to chromosome Y. Based on the chromosome Y data, the results were 14.2%, 34.9% and 3.7%, respectively, in the first trimester, third trimester and post-delivery maternal plasma samples.

By separately analyzing the fetal-specific or shared sequence reads, embodiments demonstrate that the circulating fetal DNA molecules were much more hypomethylated than the background DNA molecules. Comparisons of the methylation densities of corresponding loci in the fetal-specific maternal plasma reads and the placental tissue data for both the first and third trimesters revealed high levels of correlation. These data provided genome level evidence that the placenta is the predominant source of fetal-derived DNA molecules in maternal plasma and represented a major step forward compared with previous evidence based on information derived from selected loci.

We determined the methylation density of each 1-Mb region in the genome using either the fetal-specific or shared reads that covered CpG sites adjacent to the informative SNPs. The fetal and non-fetal-specific methylomes assembled from the maternal plasma sequence reads can be displayed, for example, in Circos plots (M. Krzywinski et al. 2009 Genome Res; 19: 1639-1645). The methylation densities per 1-Mb bin were also determined for the maternal blood cells and placental tissue samples.

Figure 7A:
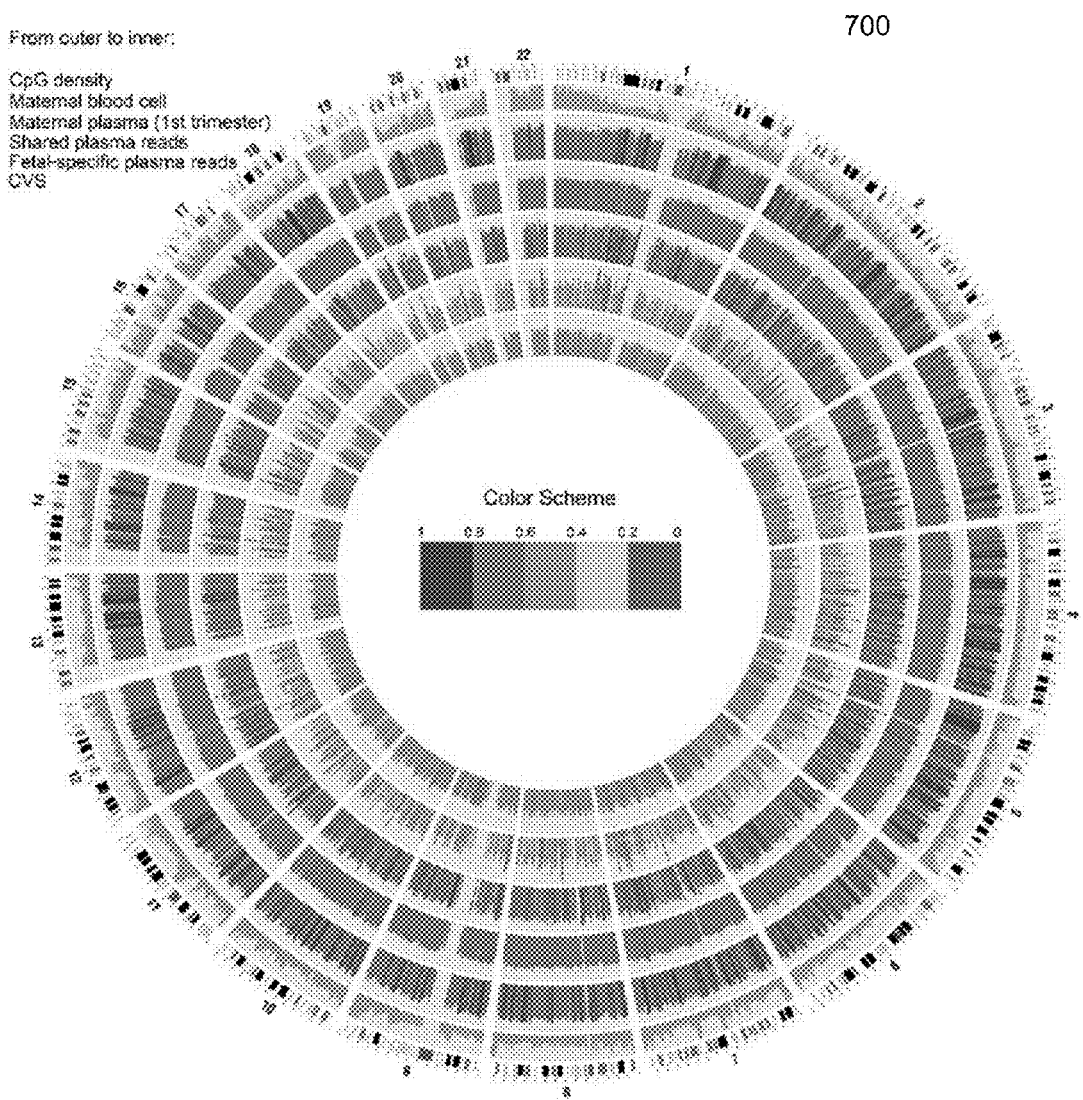
FIG. 7A shows a Circos plot 700 for first trimester samples.
Figure 7B:
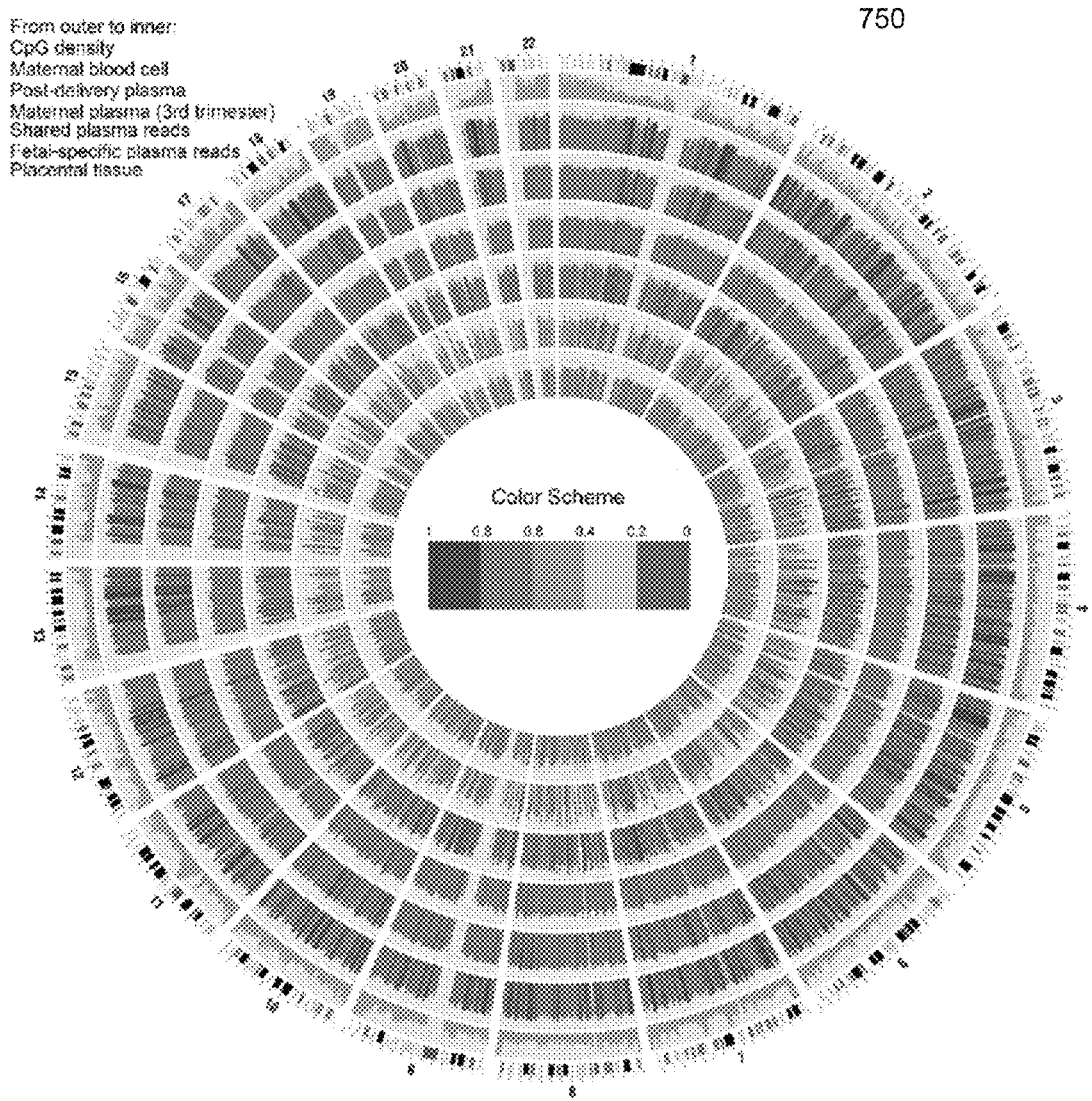
FIG. 7B shows a Circos plot 750 for third trimester samples.

FIG. 7A shows a Circos plot 700 for first trimester samples. FIG. 7B shows a Circos plot 750 for third trimester samples. The plots 700 and 750 show methylation density per 1-Mb bin. Chromosome ideograms (outermost ring) are oriented pter-qter in a clockwise direction (centromeres are shown in red). The second outermost track shows the number of CpG sites in the corresponding 1-Mb regions up to 20,000 sites. The methylation densities of the corresponding 1-Mb regions are shown in the other tracks based on the color scheme shown in the center.

For the first trimester samples (FIG. 7A), from inside to outside, the tracks are: chorionic villus sample, fetal-specific reads in maternal plasma, maternal-specific reads in maternal plasma, combined fetal and non-fetal reads in maternal plasma, and maternal blood cells. For the third trimester samples (FIG. 7B), the tracks are: term placental tissue, fetal-specific reads in maternal plasma, maternal-specific reads in maternal plasma, combined fetal and non-fetal reads in maternal plasma, post-delivery maternal plasma and maternal blood cells (from the first trimester blood sample). It can be appreciated that for both the first and third trimester plasma samples, the fetal methylomes were more hypomethylated than those of the non-fetal-specific methylomes.

The overall methylation profile of the fetal methylomes more closely resembled that of the CVS or placental tissue samples. On the contrary, the DNA methylation profile of the shared reads in plasma, which were predominantly maternal DNA, more closely resembled that of the maternal blood cells. We then performed a systematic locus-by-locus comparison of the methylation densities of the maternal plasma DNA reads and the maternal or fetal tissues. We determined the methylation densities of CpG sites that were present on the same sequence read as the informative SNPs and were covered by at least 5 maternal plasma DNA sequence reads.

Figure 8A:
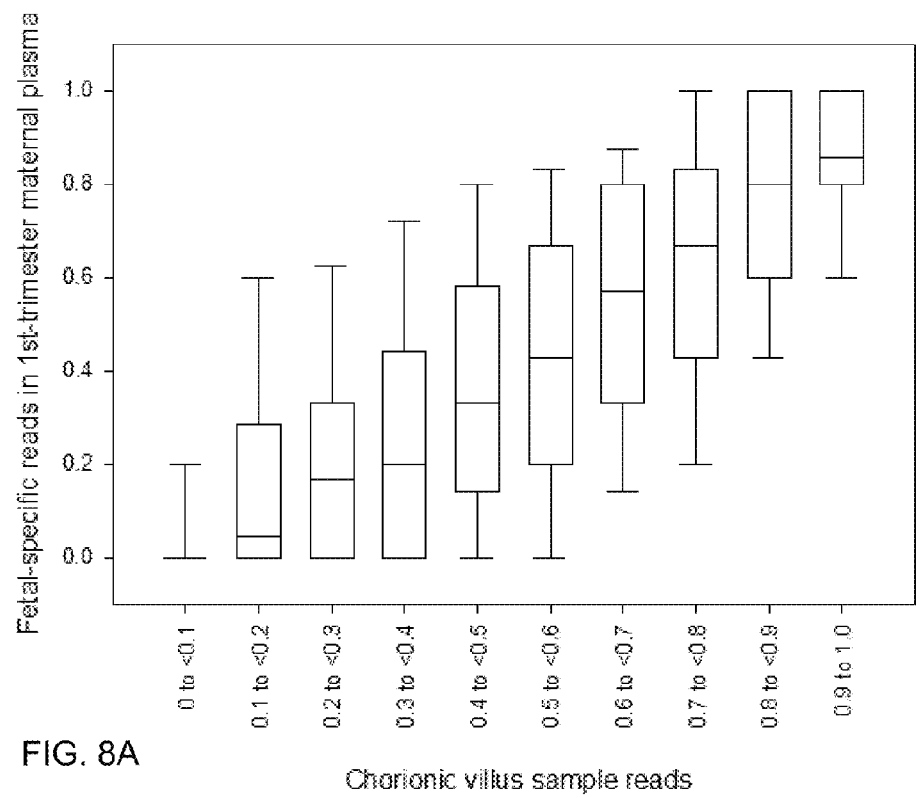
FIGS. 8A-8D shows plots of comparisons of the methylation densities of genomic tissue DNA against maternal plasma DNA for CpG sites surrounding the informative single nucleotide polymorphisms.

FIGS. 8A-8D shows plots of comparisons of the methylation densities of genomic tissue DNA against maternal plasma DNA for CpG sites surrounding the informative single nucleotide polymorphisms. FIG. 8A shows methylation densities for fetal-specific reads in the first trimester maternal plasma sample relative to methylation densities for reads in a CVS sample. As can be seen, the fetal-specific values correspond well to the CVS values.

Figure 8B:
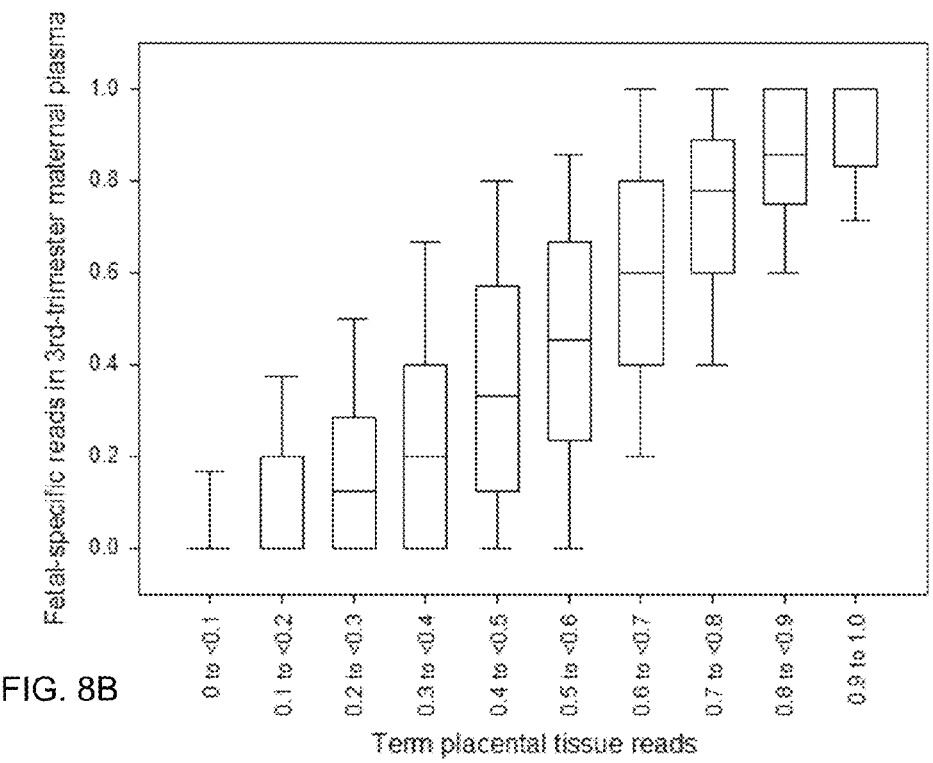

FIG. 8B shows methylation densities for fetal-specific reads in the third trimester maternal plasma sample relative to methylation densities for reads in a term placental tissue. Again, the sets of densities correspond well, indicating the a fetal methylation profile can be obtained by analyzing reads with fetal-specific alleles.

Figure 8C:
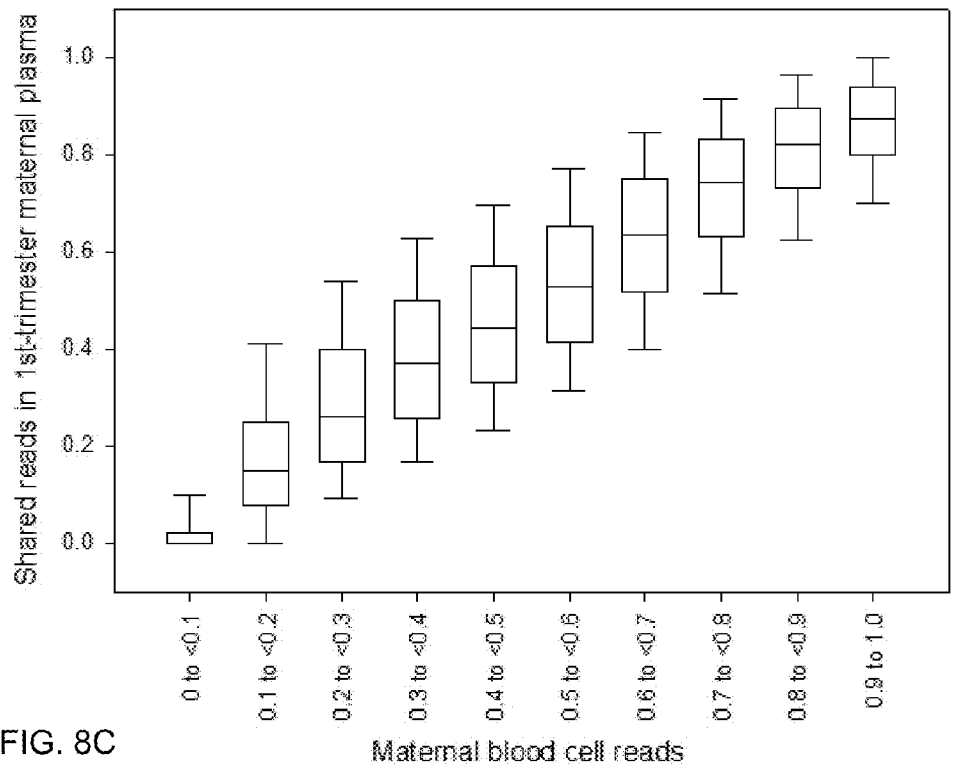
Figure 8D:
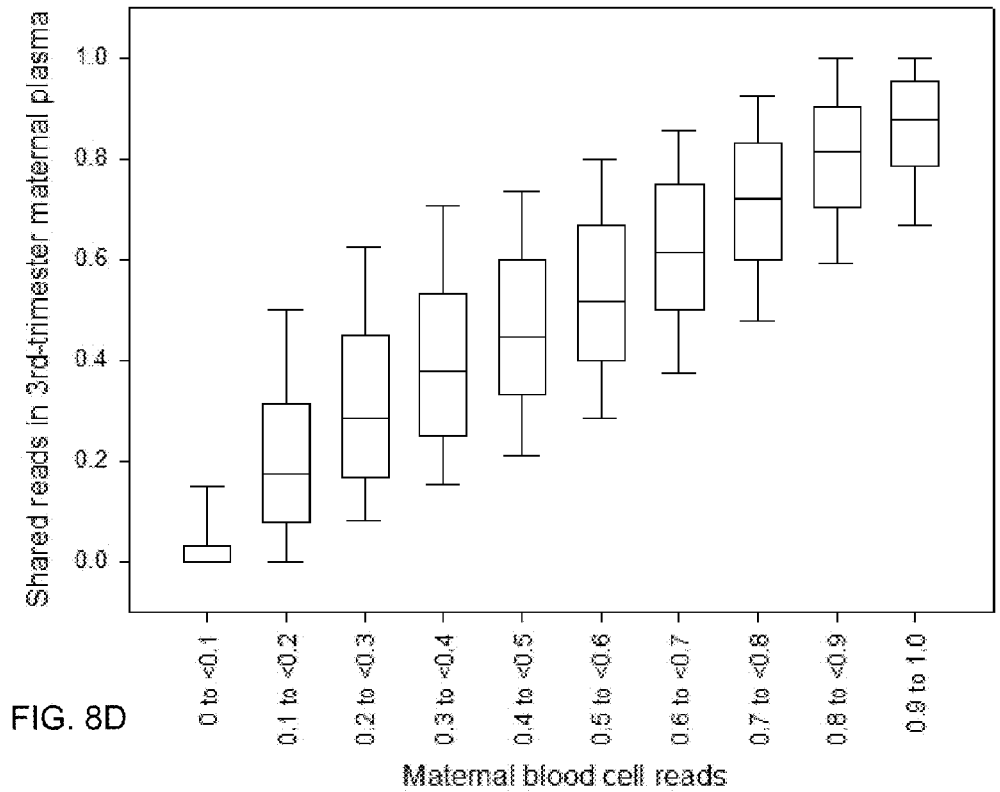

FIG. 8C shows methylation densities for shared reads in the first trimester maternal plasma sample relative to methylation densities for reads in maternal blood cells. Given that most of the shared reads are from the mother, the two sets of values correspond well. FIG. 8D shows methylation densities for shared reads in the third trimester maternal plasma sample relative to methylation densities for reads in maternal blood cells.

For the fetal-specific reads in maternal plasma, the Spearman correlation coefficient between the first trimester maternal plasma and the CVS was 0.705 ($P<2.2*e-16$); and that between the third trimester maternal plasma and term placental tissue was 0.796 ($P<2.2*e-16$) (FIGS. 8A and 8B). A similar comparison was performed for the shared reads in maternal plasma with the maternal blood cell data. The Pearson correlation coefficient was 0.653 ($P<2.2*e-16$) for the first trimester plasma sample and was 0.638 ($P<2.2*e-16$) for the third trimester plasma sample (FIGS. 8C and 8D).

B. Fetal Methylome

In one embodiment, to assemble the fetal methylome from maternal plasma, we sorted for sequence reads that spanned at least one informative fetal SNP site and contained at least one CpG site within the same read. Reads that showed the fetal-specific alleles were included in the assembly of the fetal methylome. Reads that showed the shared allele, i.e. non-fetal-specific allele, were included in the assembly of the non-fetal-specific methylome which was predominantly comprised of maternal-derived DNA molecules.

The fetal-specific reads covered 218,010 CpG sites on the autosomes for the first trimester, maternal plasma samples. The corresponding figures for the third trimester and post-delivery maternal plasma samples were 263,611 and 74,020, respectively. On average, the shared reads covered those CpG sites an average of 33.3, 21.7 and 26.3 times, respectively. The fetal-specific reads covered those CpG sites 3.0, 4.4 and 1.8 times, respectively, for the first trimester, third trimester and post-delivery maternal plasma samples.

Fetal DNA represents a minor population in maternal plasma and therefore the coverage of those CpG sites by fetal-specific reads was proportional to the fetal DNA percentage of the sample. For the first trimester maternal plasma sample, the overall percentage of methylated CpG among the fetal reads was 47.0%, while that for the shared reads was 68.1%. For the third trimester maternal plasma sample, the percentage of methylated CpG of the fetal reads was 53.3%, while that for the shared reads was 68.8%. These data showed that the fetal-specific reads in maternal plasma were more hypomethylated than the shared reads in maternal plasma C. Method The techniques described above can also be used to determine a tumor methylation profile. Methods for determining fetal and tumor methylation profiles are now described.

Figure 9:
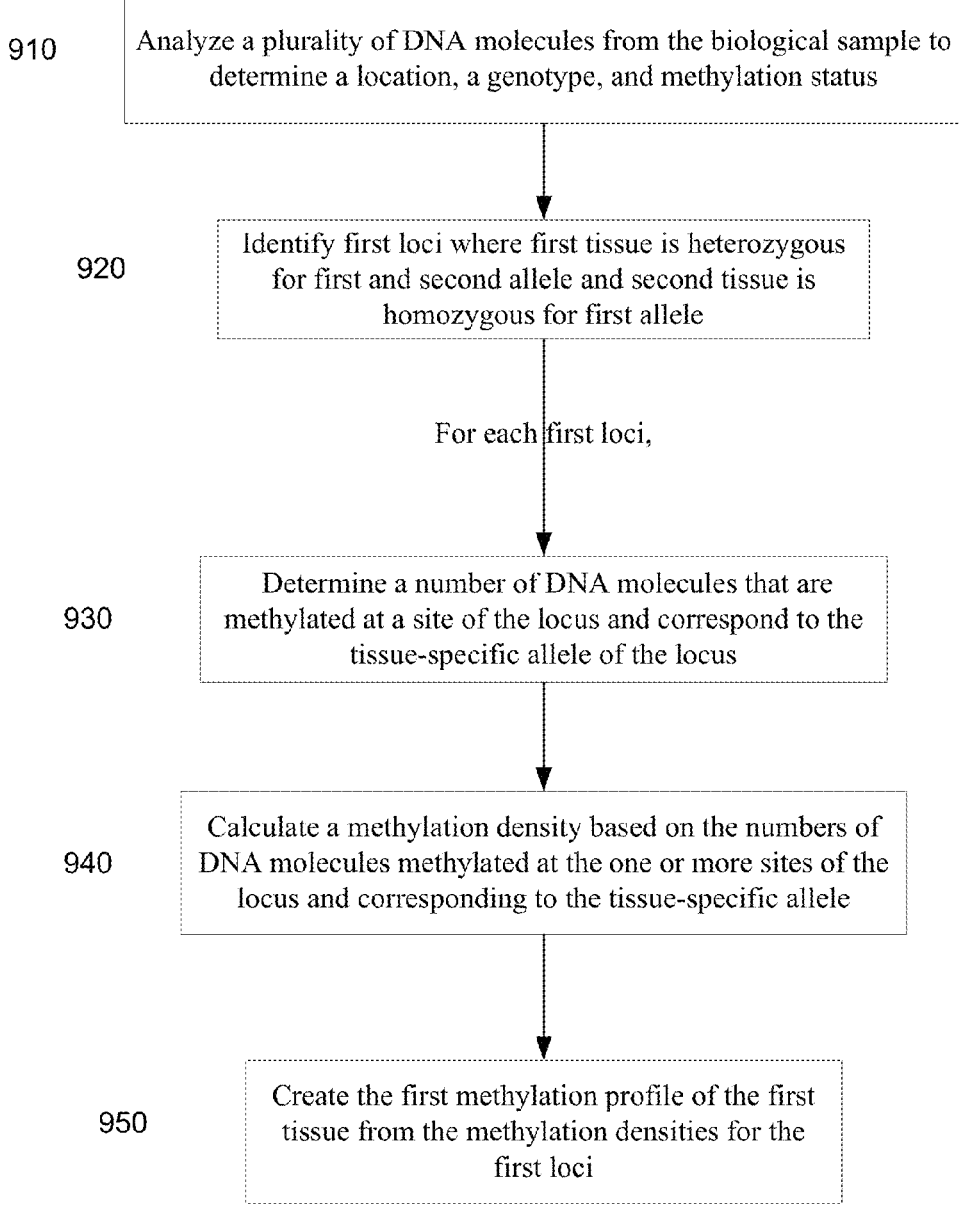
FIG. 9 is a flowchart illustrating a method 900 for determining a first methylation profile from a biological sample of an organism according to embodiments of the present invention.

FIG. 9 is a flowchart illustrating a method 900 for determining a first methylation profile from a biological sample of an organism according to embodiments of the present invention. Method 900 can construct an epigenetic map of the fetus from the methylation profile of maternal plasma. The biological sample includes cell-free DNA comprising a mixture of cell-free DNA originating from a first tissue and from a second tissue. As examples, the first tissue can be from a fetus, a tumor, or a transplanted organ.

At block 910, a plurality of DNA molecules are analyzed from the biological sample. The analysis of a DNA molecule can include determining a location of the DNA molecule in a genome of the organism, determining a genotype of the DNA molecule, and determining whether the DNA molecule is methylated at one or more sites.

In one embodiment, the DNA molecules are analyzed using sequence reads of the DNA molecules, where the sequencing is methylation aware. Thus, the sequence reads include methylation status of DNA molecules from the biological sample. The sequence reads can be obtained from various sequencing techniques, PCR-techniques, arrays, and other suitable techniques for identifying sequences of fragments. The methylation status of sites of the sequence read can be obtained as described herein.

At block 920, a plurality of first loci are identified at which a first genome of the first tissue is heterozygous for a respective first allele and a respective second allele and a second genome of the second tissue is homozygous for the respective first allele. For example, fetal-specific reads may be identified at the plurality of first loci. Or, tumor-specific reads may be identified at the plurality of first loci. The tissue-specific reads can be identified from sequencing reads where the percentage of sequence reads of the second allele fall within a particular range, e.g., about 3%-25%, thereby indicating a minority population of DNA fragment from a heterozygous genome at the locus and a majority population from a homozygous genome at the locus.

At block 930, DNA molecules located at one or more sites of each of the first locus are analyzed. A number of DNA molecules that are methylated at a site and correspond to the respective second allele of the locus are determined. There may be more than one site per locus. For example, a SNP might indicate that a fragment is fetal-specific, and that fragment may have multiple sites whose methylation status is determined. The number of reads at each site that are methylated can be determined, and the total number of methylated reads for the locus can be determined.

The locus may be defined by a specific number of sites, a specific set of sites, or a particular size for a region around a variation that comprises the tissue-specific allele. A locus can have just one site. The sites can have specific properties, e.g., be CpG sites. The determination of a number of reads that are unmethylated is equivalent, and is encompassed within the determination of the methylation status.

At block 940, for each of the first loci, a methylation density is calculated based on the numbers of DNA molecules methylated at the one or more sites of the locus and corresponding to the respective second allele of the locus. For example, a methylation density can be determined for CpG sites corresponding to a locus.

At block 950, the first methylation profile of the first tissue is created from the methylation densities for the first loci. The first methylation profile can correspond to particular sites, e.g., CpG sites. The methylation profile can be for all loci having a fetal-specific allele, or just some of those loci.

IV. Using Difference of Plasma and Blood Methylomes

Above, it was shown that the fetal-specific reads from plasma correlate to the placental methylome. As the maternal component of the maternal plasma methylome is primarily contributed by the blood cells, the difference between the plasma methylome and blood methylome can be used to determine the placental methylome for all loci, and not just locations of fetal-specific alleles.

A. Method

Figure 10:
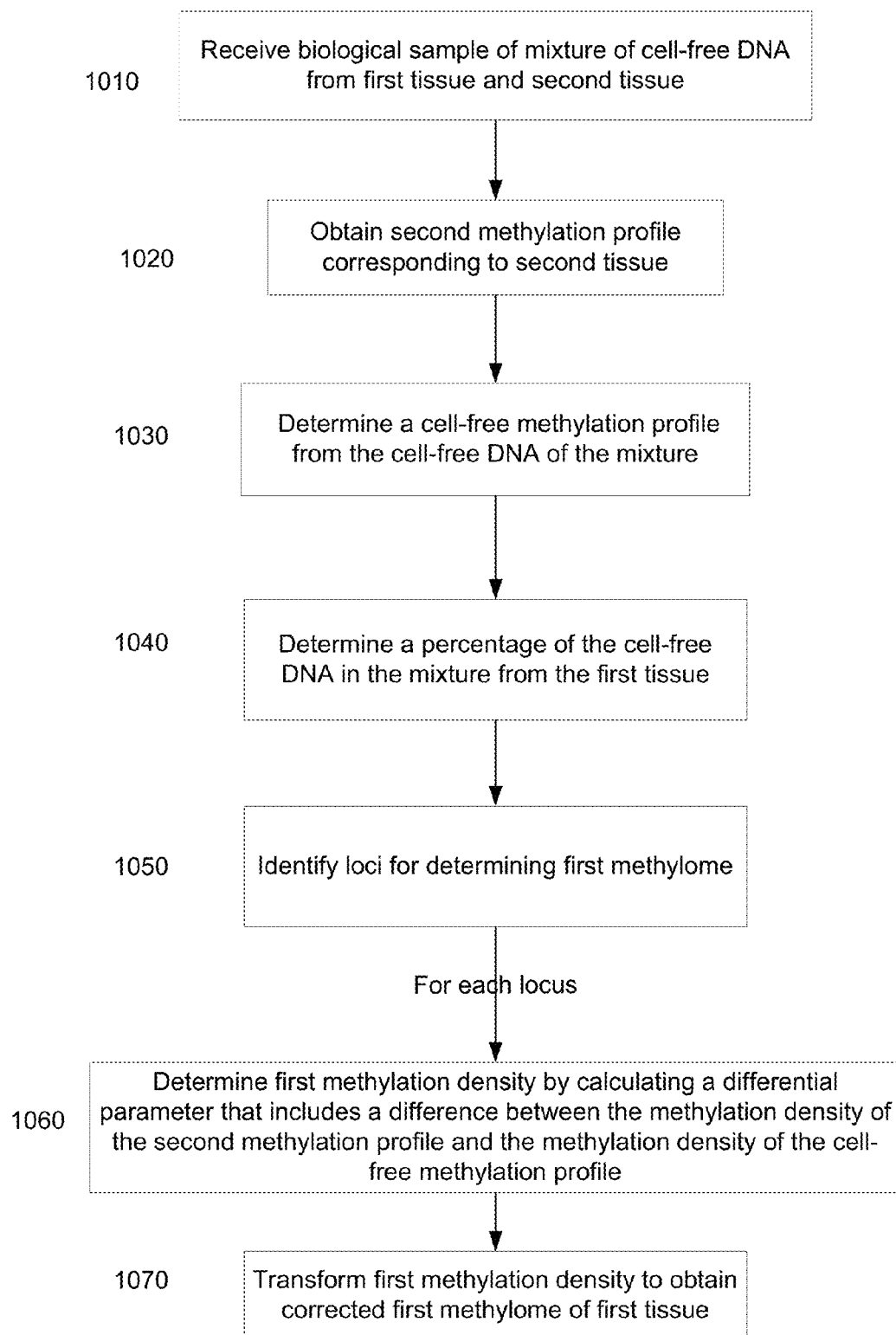
FIG. 10 is a flowchart illustrating a method 1000 of determining a first methylation profile from a biological sample of an organism according to embodiments of the present invention.

FIG. 10 is a flowchart illustrating a method 1000 of determining a first methylation profile from a biological sample of an organism according to embodiments of the present invention. The biological sample (e.g., plasma) includes cell-free DNA comprising a mixture of cell-free DNA originating from a first tissue and from a second tissue. The first methylation profile corresponds to a methylation profile of the first tissue (e.g., fetal tissue or tumor tissue). Method 1200 can provide a deduction of differentially methylated regions from maternal plasma.

At block 1010, a biological sample is received. The biological sample could simply be received at a machine (e.g., a sequencing machine). The biological sample may be in the form taken from the organism or may be in a processes form, e.g., the sample may be plasma that is extracted from a blood sample.

At block 1020, a second methylation profile corresponding to DNA of the second tissue is obtained. The second methylation profile could be read from memory, as it may have been determined previously. The second methylation profile can be determined from the second tissue, e.g., a different sample that contains only or predominantly cells of the second tissue. The second methylation profile can correspond to a cellular methylation profile and be obtained from cellular DNA. As another example, the second profile can be determined from a plasma collected before pregnancy, or before development of cancer because the plasma methylome of a non-pregnant person without cancer is very similar to the methylome of blood cells.

The second methylation profile can provide a methylation density at each of a plurality of loci in a genome of the organism. The methylation density at a particular locus corresponds to a proportion of DNA of the second tissue that is methylated. In one embodiment, the methylation density is a CpG methylation density, where CpG sites associated with the locus are used to determine the methylation density. If there is one site for a locus, then the methylation density can equal the methylation index. The methylation density also corresponds to an unmethylation density as the two values are complementary.

In one embodiment, the second methylation profile is obtained by performing methylation-aware sequencing of cellular DNA from a sample of the organism. One example of methylation-aware sequencing includes treating DNA with sodium bisulfite and then performing DNA sequencing. In another example, the methylation-aware sequencing can be performed without using sodium bisulfite, using a single molecule sequencing platform that would allow the methylation status of DNA molecules (including N6-methyladenine, 5-methylcytosine and 5-hydroxymethylcytosine) to be elucidated directly without bisulfite conversion (A. B. Flusberg et al. 2010 Nat Methods; 7: 461-465; Shim J et al. 2013 Sci Rep; 3:1389. doi: 10.1038/srep01389); or through the immunoprecipitation of methylated cytosine followed by sequencing; or through the use of methylation-sensitive restriction enzymes followed by sequencing. In another embodiment, non-sequencing techniques are used, such as arrays and digital PCR.

In another embodiment, the second methylation density of the second tissue could be obtained previously from control samples of the subject or from other subjects. The methylation density from another subject can act as a reference methylation profile having reference methylation densities. The reference methylation densities can be determined from multiple samples, where a mean level (or other statistical value) of the different methylation densities at a locus can be used as the reference methylation density at the locus.

At block 1030, a cell-free methylation profile is determined from the cell-free DNA of the mixture. The cell-free methylation profile provides a methylation density at each of the plurality of loci. The cell-free methylation profile can be determined by receiving sequence reads from a sequencing of the cell-free DNA, where the methylation information is obtained with the sequence reads. The cell-free methylation profile can be determined in a same manner as the cellular methylome.

At block 1040, a percentage of the cell-free DNA from the first tissue in the biological sample is determined. In one embodiment, the first tissue is fetal tissue, and the corresponding DNA is fetal DNA. In another embodiment, the first tissue is tumor tissue, and the corresponding DNA is tumor DNA. The percentage can be determined in a variety of ways, e.g., using a fetal-specific allele or a tumor-specific allele. Copy number can also be used to determine the percentage, e.g., as described in U.S. patent application Ser. No. 13/801,748 entitled "Mutational Analysis Of Plasma DNA For Cancer Detection" filed on Mar. 13, 3013, which is incorporated by reference.

At block 1050, a plurality of loci for determining the first methylome are identified. These loci may correspond to each of the loci used to determine the cell-free methylation profile and the second methylation profile. Thus, the plurality of loci may correspond. It is possible that more loci may be used to determine the cell-free methylation profile and the second methylation profile.

In some embodiments, loci that were hypermethylated or hypomethylated in the second methylation profile can be identified, e.g., using maternal blood cells. To identify the loci that were hypermethylated in the maternal blood cells, one can scan from one end of a chromosome for a CpG site with a methylation index ≥80%. One can then search for the next CpG site within the downstream 200-bp region. If the immediately downstream CpG site also had a methylation index ≥80%, the first and the second CpG sites can be grouped. The grouping can continue until either there were no other CpG site within the next downstream region of 200 bp; or the immediately downstream CpG site had a methylation index <80%. The region of the grouped CpG sites can be reported as hypermethylated in maternal blood cells if the region contained at least five immediately adjacent hypermethylated CpG sites. A similar analysis can be performed to search for loci that were hypomethylated in maternal blood cells for CpG sites with methylation indices ≤20%. The methylation densities for the second methylation profile can calculated for the short-listed loci and used to deduce the first methylation profile (e.g., placental tissue methylation density) of the corresponding loci, e.g., from maternal plasma bisulfite-sequencing data.

At block 1060, the first methylation profile of the first tissue is determined by calculating a differential parameter that includes a difference between the methylation density of the second methylation profile and the methylation density of the cell-free methylation profile for each of the plurality of loci. The difference is scaled by the percentage.

In one embodiment, the first methylation density of a locus in the first (e.g., placental) tissue (D) was deduced using the equation:

$$D = mbc - \frac{(mbc - mp)}{f * CN} \quad (1)$$

where mbc denotes the methylation density of the second methylation profile at a locus (e.g., a short-listed locus as determined in the maternal blood cell bisulfite-sequencing data); mp denotes the methylation density of the corresponding locus in the maternal plasma bisulfite-sequencing data; f represented the percentage of cell-free DNA from the first tissue (e.g., fractional fetal DNA concentration), and CN represents copy number at the locus (e.g., a higher value for amplifications or a lower number for deletions relative to normal). If there is no amplification or deletion in the first tissue then CN can be one. For trisomy (or a duplication of the region in a tumor or a fetus), CN would be 1.5 (as the increase is from 2 copies to 3 copies) and monosomy would have 0.5. Higher amplification can increase by increments of 0.5. In this example, D can correspond to the differential parameter.

At block 1070, the first methylation density is transformed to obtain a corrected first methylation density of the first tissue. The transformation can account for fixed differences between the differential parameters and the actual methylation profile of the first tissue. For example, the values may differ by a fixed constant or by a slope. The transformation can be linear or non-linear.

In one embodiment, the distribution of the deduced values, D, was found to be lower than the actual methylation level of the placental tissue. For example, the deduced values can be linearly transformed using data from CpG islands, which were genomic segments that had an overrepresentation of CpG sites. The genomic positions of CpG islands used in this study were obtained from the UCSC Genome Brower database (NCBI build 36/hg18) (P. A. Fujita et al. 2011 Nucleic Acids Res; 39: D876-882). For example, a CpG island can be defined as a genomic segment with GC content ≥50%, genomic length >200 bp and the ratio of observed/expected CpG number >0.6 (M. Gardiner-Garden et al 1987 J Mol Biol; 196: 261-282).

In one implementation, to derive the linear transformation equation, CpG islands with at least 4 CpG sites and an average read depth ≥5 per CpG site in the sequenced samples can be included. After determining the linear relationships between the methylation densities of CpG islands in the CVS or term placenta and the deduced values, D, the following equations were used to determine the predicted values:

First trimester predicted values=$D \times 1.6 + 0.2$

Third trimester predicted values=$D \times 1.2 + 0.05$

B. Fetal Example

As mentioned above, method 1000 can be used to deduce a methylation landscape of the placenta from maternal plasma. Circulating DNA in plasma is predominately originated from hematopoietic cells. Still there is an unknown proportion of cell-free DNA contributed from other internal organs. Moreover, placenta-derived cell-free DNA accounts for approximately 5-40% of the total DNA in maternal plasma, with a mean of approximately 15%. Thus, one can make an assumption that the methylation level in maternal plasma is equivalent to an existing background methylation plus a placental contribution during pregnancy, as described above.

The maternal plasma methylation level, MP, can be determined using the following equation:

$$MP = BKG \times (1-f) + PLN \times f$$

where BKG is the background DNA methylation level in plasma derived from blood cells and internal organs, PLN is the methylation level of placenta and f is the fractional fetal DNA concentration in maternal plasma.

The methylation level of placenta can theoretically be deduced by:

$$PLN = \frac{MP - BKG \times (1 - f)}{f} \quad (2)$$

Equations (1) and (2) are equivalent when CN equals one, D equals PLN, and BKG equals mbc.

The methylation level of maternal blood was taken to represent the background methylation of maternal plasma. Besides the loci that were hypermethylated or hypomethylated in maternal blood cells, we further explored the deduction approach by focusing on defined regions with clinical relevance, for instance, CpG islands in the human genome.

The mean methylation density of a total of 27,458 CpG islands (NCBI Build36/hg18) on the autosomes and chrX was derived from the sequencing data of maternal plasma and placenta. Only those with ≥10 CpG sites covered and an averaged read depth ≥5 per covered CpG sites in all analyzed samples, including the placenta, maternal blood and maternal plasma, were selected. As a result, 26,698 CpG islands (97.2%) remained as valid and their methylation level was deduced using the plasma methylation data and the fractional fetal DNA concentration according to the above equation.

It was noticed that the distribution of deduced PLN values was lower than the actual methylation level of CpG islands in the placental tissue. Thus, in one embodiment, the deduced PLN values, or simply deduced values (D), were used as an arbitrary unit for estimating the methylation level of CpG islands in the placenta. After a transformation, the deduced values linearly and their distribution became more alike to the actual dataset. The transformed deduced values were named methylation predictive values (MPV) and subsequently used for predicting the methylation level of genetic loci in the placenta.

Figure 12B:
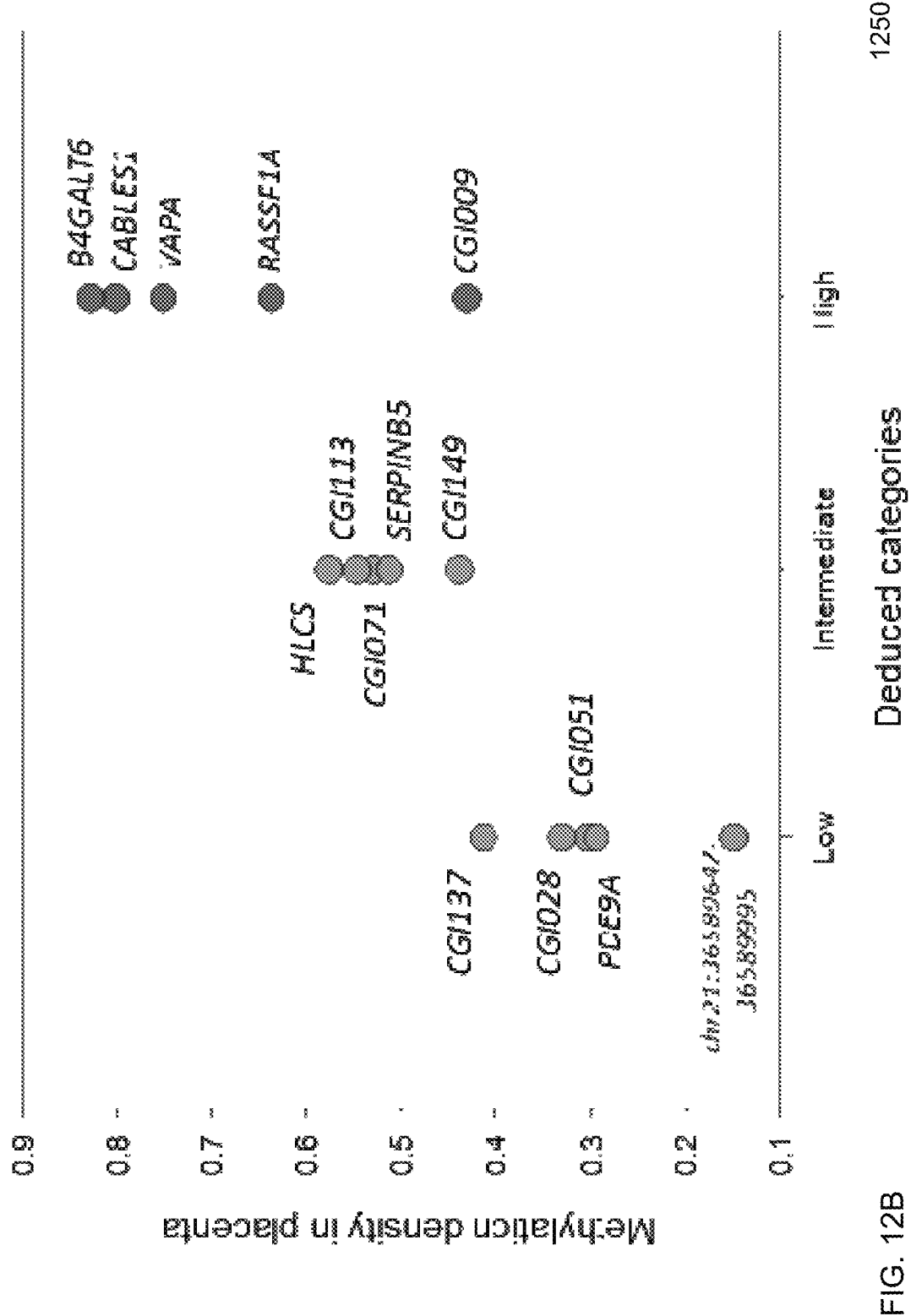
FIG. 12B is a graph 1250 showing the deduced categories of the 15 selected genomic loci are provided with their corresponding methylation levels in the placenta.

In this example, the CpG islands were classified into 3 categories based on their methylation densities in the placenta: Low (≤0.4), Intermediate (>0.4-<0.8) and High (≥0.8). Using the deduction equation, we calculated the MPV of the same set of CpG islands and then used the values to classify them into 3 categories with the same cutoffs. By comparing the actual and the deduced datasets, we found that 75.1% of the short-listed CpG islands could be matched correctly to the same categories in the tissue data according to their MPS. About 22% of the CpG islands were assigned to groups with 1-level difference (high versus intermediate, or intermediate versus low) and less than 3% would be completely misclassified (high versus low) (FIG. 12A). The overall classification performance was also determined: 86.1%, 31.4% and 68.8% of CpG islands with methylation densities ≤0.4, >0.4-<0.8 and ≥0.8 in the placenta were deduced to be "Low", "Intermediate" and "High" correctly (FIG. 12B).

Figure 11A:
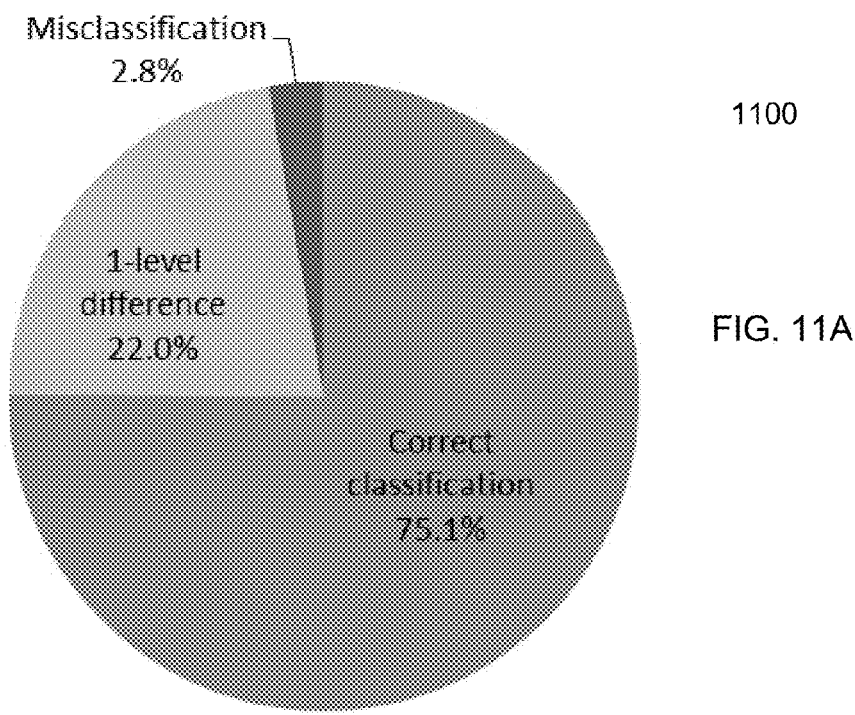
FIGS. 11A and 11B shows graphs of the performance of the predicting algorithm using maternal plasma data and fractional fetal DNA concentration according to embodiments of the present invention.
Figure 11B:
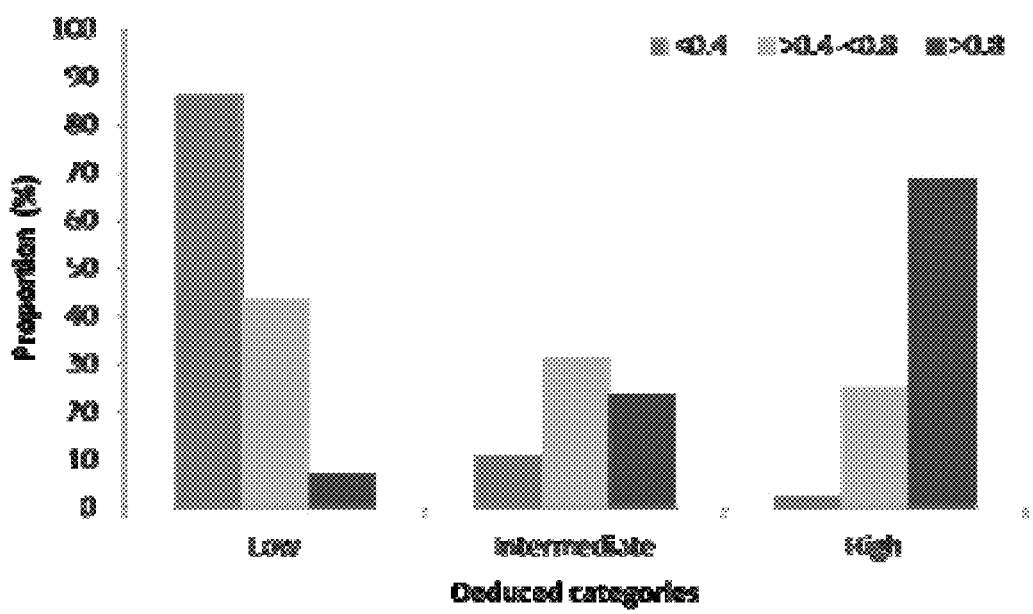

FIGS. 11A and 11B shows graphs of the performance of the predicting algorithm using maternal plasma data and fractional fetal DNA concentration according to embodiments of the present invention. FIG. 11A is a graph 1100 showing the accuracy of CpG island classification using the MPV correction classification (the deduced category matches exactly the actual dataset); 1-level difference (the deduced category is 1-level different from the actual dataset); and misclassification (the deduced category is opposite to the actual dataset). FIG. 11B is a graph 1150 showing the proportion of CpG islands classified in each deduced category.

Provided that the maternal background methylation is low in the respective genomic regions, the presence of hypermethylated placental-derived DNA in the circulation would increase the overall plasma methylation level to a degree depending on the fractional fetal DNA concentration. A marked change could be observed when the fetal DNA released is fully methylated. On the contrary, when the maternal background methylation is high, the degree of change in the plasma methylation level would become more significant if hypomethylated fetal DNA is released. Therefore, the deduction scheme may be more practical when the methylation level was deduced for genetic loci which are known to be distinct between the maternal background and the placenta, especially for those hypermethylated and hypomethylated markers in the placenta.

FIG. 12A is a table 1200 showing details of 15 selected genomic loci for methylation prediction according to embodiments of the present invention. To confirm techniques, we selected 15 differentially methylated genomic loci which were studied previously. The methylation levels of selected regions were deduced and compared to previously studied 15 differentially methylated genetic loci (R. W. K. Chiu et al. 2007 Am J Pathol; 170: 941-950; S. S. C. Chim et al. 2008 Clin Chem; 54: 500-511; S. S. C. Chim et al. 2005 Proc Natl Acad Sci USA; 102: 14753-14758; D. W. Y. Tsui et al. 2010 PLoS One; 5: e15069).

FIG. 12B is a graph 1250 showing the deduced categories of the 15 selected genomic loci are provided with their corresponding methylation levels in the placenta. Deduced methylation categories are: Low, ≤0.4; Intermediate, >0.4-<0.8; High, ≥0.8. Table 1200 and graph 1300 shows that their methylation levels in placenta could be deduced correctly with some exceptions: RASSF1A, CGI009, CGI137 and VAPA. Out of these 4 markers, only CGI009 showed a marked discrepancy with the actual dataset. The others were just marginally misclassified.

In table 1200, "1" refers to the deduced values (D) being calculated by the equation:

$$D = \frac{MP - BKG \times (1-f)}{f}$$

where f is the fraction fetal DNA concentration. The label "2" refers to the methylation predictive values (MPV) referring to the linearly transformed deduced values using the equation: MPV=D×1.6+0.25. Label "3" refers to the classification cutoff for the deduced values: Low, ≤0.4; Inter(mediate), >0.4-<0.8; High, ≥0.8. Label "4" refers to the classification cutoff for the actual placental dataset: Low, ≤0.4; Inter(mediate), >0.4-<0.8; High, ≥0.8. Label "5" denotes that placental status refers to the methylation status of placenta relative to that of maternal blood cells.

C. Calculation of Fractional Concentrations of Fetal DNA

In one embodiment, the percentage of fetal DNA from the first tissue can use a Y chromosome for a male fetus. The proportion of chromosome Y (% chrY) sequences in a maternal plasma sample was a composite of the chromosome Y reads derived from the male fetus and the number of maternal (female) reads that were misaligned to chromosome Y (R. W. K. Chiu et al. 2011 BMJ; 342: c7401). Thus, the relationship between % chrY and the fractional fetal DNA concentration (f) in the sample can be given by:

$$\% \ chrY = \% \ chrY_{male} \times f + \% \ chrY_{female} \times (1-f)$$

where % $chrY_{male}$ refers to a proportion of reads aligned to chromosome Y in a plasma sample containing 100% male DNA; and % $chrY_{female}$ refers to the proportion of reads aligned to chromosome Y in a plasma sample containing 100% female DNA.

% chrY can be determined from reads that were aligned to chromosome Y with no mismatches for a sample from a female pregnant with a male fetus, e.g., where the reads are from bisulfite-converted samples. The % $chrY_{male}$ value can be obtained from the bisulfite-sequencing of two adult male plasma samples. The % $chrY_{female}$ value can be obtained from the bisulfite-sequencing of two non-pregnant adult female plasma samples.

In other embodiments, the fetal DNA percentage can be determined from fetal-specific alleles on an autosome. As another example, epigenetic markers may be used to determine the fetal DNA percentage. Other ways of determining the fetal DNA percentage may also be used.

D. Method of Using Methylation to Determine Copy Number

The placental genome is more hypomethylated than the maternal genome. As discussed above the methylation of the plasma of a pregnant woman is dependent on the fractional concentration of placentally-derived fetal DNA in the maternal plasma. Therefore, through the analysis of the methylation density of a chromosomal region, it is possible to detect the difference in the contribution of fetal tissues to the maternal plasma. For example, in a pregnant woman carrying a trisomic fetus (e.g. suffering from trisomy 21 or trisomy 18 or trisomy 13), the fetus would contribute an additional amount of the DNA from the trisomic chromosome to the maternal plasma when compared with the disomic chromosomes. In this situation, the plasma methylation density for the trisomic chromosome (or any chromosomal region that has an amplification) would be lower than those for the disomic chromosomes. The degree of difference can be predicted by mathematical calculation by taking into account the fractional fetal DNA concentration in the plasma sample. The higher the fractional fetal DNA concentration in the plasma sample the larger the difference in methylation density between the trisomic and disomic chromosomes would be. For regions having a deletion, the methylation density would be higher.

From the previous discussion, the plasma methylation density for a disomic chromosome ($MP_{Non-aneu}$) can be calculated as: $MP_{Non-aneu}=BKG \times (1-f)+PLN \times f$, where BKG is the background DNA methylation level in plasma derived from blood cells and internal organs, PLN is the methylation level of placenta and f is the fractional fetal DNA concentration in maternal plasma.

The plasma methylation density for a trisomic chromosome ($MP_{Aneu}$) can be calculated as: $MP_{Aneu}=BKG \times (1-f)+PLN \times f \times 1.5$, where the 1.5 corresponds to the copy number CN and the addition of one more chromosome is a 50% increase. The difference between a trisomic and disomic chromosomes ($MP_{Diff}$) would be $$MP_{Diff}=PLN \times f \times 0.5.$$

In one embodiment, a comparison of the methylation density of the potentially aneuploid chromosome (or chromosomal region) to one or more other presumed non-aneuploid chromosome(s) or the overall methylation density of the genome can be used to effectively normalize the fetal DNA concentration in the plasma sample. The comparison be via a calculation of a parameter (e.g., involving a ratio or a difference) between the methylation densities of the two regions to obtain a normalized methylation density. The comparison can remove a dependence of the resulting methylation level (e.g., determined as a parameter from the two methylation densities).

If the methylation density of the potentially aneuploid chromosome is not normalized to the methylation density of one or more other chromosome(s), or other parameters that reflect the fractional concentration of fetal DNA, the fractional concentration would be a major factor affecting the methylation density in the plasma. For example, the plasma methylation density of chromosome 21 of a pregnant woman carrying a trisomy 21 fetus with a fractional fetal DNA concentration of 10% would be the same as that of a pregnant woman carrying a euploid fetus and the fractional fetal DNA concentration is 15%, whereas a normalized methylation density would show a difference.

In another embodiment, the methylation density of the potentially aneuploid chromosome can be normalized to the fractional fetal DNA concentration. For example, the following equation can be applied to normalize the methylation density: $MP_{Normalized}=MP_{non-normalized}+(BKG-PLN) \times f$, where $MP_{Normalized}$ is the methylation density normalized with the fractional fetal DNA concentration in the plasma, $MP_{non-normalized}$ is the measured methylation density, BKG is the background methylation density from maternal blood cells or tissues, PLN is the methylation density in the placental tissues, and f is the fractional fetal DNA concentration. The methylation densities of BKG and PLN could be based on reference values previously established from maternal blood cells and placental tissues obtained from healthy pregnancies. Different genetic and epigenetic methods can be used for the determination of the fractional fetal DNA concentration in the plasma sample, for example by the measurement of the percentage of sequence reads from the chromosome Y using massively parallel sequencing or PCR on non-bisulfite-converted DNA.

In one implementation, the normalized methylation density for a potentially aneuploid chromosome can be compared to a reference group which consists of pregnant woman carrying euploid fetuses. The mean and SD of the normalized methylation density of the reference group can be determined. Then the normalized methylation density of the tested case can be expressed as a z-score which indicates the number of SDs from the mean of the reference group by:

$$z-\text{score} = \frac{MP_{Normalized} - \text{Mean}}{SD},$$

where $MP_{Normalized}$ is the normalized methylation density for the tested case, Mean is the mean of the normalized methylation density of the reference cases and SD is the standard deviation of the normalized methylation density of the reference cases. A cutoff, for example z-score <−3, can be used to classify if a chromosome is significantly hypomethylated and, hence, to determine if the aneuploidy status of the sample.

In another embodiment, the $MP_{Diff}$ can be used as the normalized methylation density. In such an embodiment, PLN can be deduced, e.g., using method 1000. In some implementations, a reference methylation density (which can be normalized using f) can be determined from a methylation level of a non-aneuploid region. For example, the Mean could be determined from one or more chromosomal regions of the same sample. The cutoff could be scaled by f, or just set to a level sufficient as long as a minimum concentration exists.

Accordingly, a comparison of a methylation level for a region to a cutoff can be accomplished in various ways. The comparison can involve a normalization (e.g., as described above), which may be performed equivalently on the methylation level or the cutoff value, depending on how the values are defined. Thus, whether the determined methylation level of a region is statistically different than a reference level (determined from same sample or other samples) can be determined in a variety of ways.

The above analysis can be applied to the analysis of chromosomal regions, which can include a whole chromosome or parts of the chromosome, including contiguous or disjoint subregions of a chromosome. In one embodiment, the potentially aneuploid chromosome can be divided into a number of bins. The bins can be of the same or different sizes. The methylation density of each bin can be normalized to the fractional concentration of the sample or to the methylation density of one or more presumed non-aneuploid chromosome(s) or the overall methylation density of the genome. The normalized methylation density of each bin can then be compared with a reference group to determine if it is significantly hypomethylated. Then the percentage of bins being significantly hypomethylated can be determined. A cutoff, for examples more than 5%, 10%, 15%, 20% or 30% of the bins being significantly hypomethylated can be used to classify the aneuploidy status of the case.

When one is testing for an amplification or a deletion, one can compare the methylation density to a reference methylation density, which may be specific for a particular region being tested. Each region may have a different reference methylation density as methylation can vary from region to region, particularly depending on the size of the regions (e.g., smaller regions will show more variation).

As mentioned above, one or more pregnant women each carrying a euploid fetus can be used to define the normal range of the methylation density for a region of interest or a difference in methylation density between two chromosomal regions. A normal range can also be determined for the PLN (e.g., by direct measurement or as deduced by method 1000). In other embodiments, a ratio between two methylation densities can be used, e.g., of a potentially aneuploid chromosome and a non-aneuploid chromosome can be used for the analysis instead of their difference. This methylation analysis approach can be combined with sequence read counting approach (R W K Chiu et al. 2008 Proc Natl Acad Sci USA; 105:20458-20463) and approaches involving size analysis of plasma DNA (US patent 2011/0276277) to determine or confirm an aneuploidy.

The use of BKG can account for variations in the background between samples. For example, one female might have different BKG methylation levels than another female, but a difference between the BKG and PLN can be used across samples in such situations. The cutoff for different chromosomal regions can be different, e.g., when a methylation density of one region of the genome differs relative to another region of the genome.

This approach can be generalized to detect any chromosomal aberrations, including deletion and amplification, in the fetal genome. In addition, the resolution of this analysis can be adjusted to the desired level, for example, the genome can be divided into 10 Mb, 5 Mb, 2 Mb, 1 Mb, 500 kb, 100 kb bins. Hence, this technology can also be used for detecting subchromosomal duplication or subchromosomal deletion. This technology would thus allow a prenatal fetal molecular karyotype to be obtained noninvasively. When used in this manner, this technology can be used in combination with the noninvasive prenatal testing methods that are based on the counting of molecules (A. Srinivasan et al. 2013 Am J Hum Genet; 92:167-176). In other embodiments, the size of the bins need not be identical. For example, the size of the bins may be adjusted so that each bin contains an identical number of CpG dinucleotides. In this case, the physical size of the bins would be different.

The equation can be rewritten to apply to different types of chromosome aberrations as $MP_{Diff}=(BKG-PLN) \times f \times 0.5 \times CN$. Here CN represents the number of copy number change at the affected region. CN equals to 1 for the gain of 1 copy of a chromosome, 2 for the gain of 2 copies of a chromosome and −1 for the loss of one of the two homologous chromosomes (e.g. for detecting fetal Turner syndrome in which a female fetus has lost one of the X chromosomes, leading to a XO karyotype). This equation need not be changed when the size of the bins are changed. However, the sensitivity and specificity may reduce when smaller bin size is used because a smaller number of CpG dinucleotides (or other nucleotide combinations showing differential methylation between fetal DNA and maternal DNA) would be present in smaller bins, leading to increased stochastic variation in the measurement of methylation densities. In one embodiment, the number of reads required can be determined by analyzing the coefficient of variation of the methylation density and the desired level of sensitivity.

To demonstrate the feasibility of this approach, we have analyzed the plasma samples from 9 pregnant women. In five pregnant women, each was carrying a euploid fetus and the other four were each carrying a trisomy 21 (T21) fetus. Three of the five euploid pregnancies were randomly selected to form a reference group. The remaining two euploid pregnancy cases (Eu1 and Eu2) and the four T21 cases (T21-1, T21-2, T21-3 and T21-4) were analyzed using this approach to test for a potential T21 status. The plasma DNA was bisulfite-converted and sequenced using the Illumina HiSeq2000 platform. In one embodiment, the methylation density of individual chromosomes were calculated. The difference in methylation density between chromosome 21 and the mean of the other 21 autosomes was then determined to obtain a normalized methylation density. The mean and SD of the reference group was used for the calculated of the z-score of the five test cases.

TABLE 1

Using a cutoff of <-3 for z-score to classify a sample to be T21, the classification of all the euploid and T21 cases were correct.

| | Eu1 | Eu2 | T21-1 | T21-2 | T21-3 | T21-4 |
|---|---|---|---|---|---|---|
| z-score for $MP_{Diff}$ between chr 21 and other autosomes | −1.48 | 1.09 | −4.46 | −5.30 | −8.06 | −5.69 |

In another embodiment, the genome was divided into 1 Mb bins and the methylation density for each 1 Mb bin can be determined. The methylation density of all the bins on the potentially aneuploid chromosome can be normalized with the median methylation density of all the bins located on the presumed non-aneuploid chromosomes. In one implementation, for each bin, the difference in methylation density from the median of the non-aneuploid bins can be calculated. Then z-score can be calculated for these values using the mean and SD values of the reference group.

TABLE 2

Using 5% as a cutoff for the bins with significantly more hypomethylated on chromosome 21, all the cases were classified correctly for T21 status.

| | Eu1 | Eu2 | T21-1 | T21-2 | T21-3 | T21-4 |
|---|---|---|---|---|---|---|
| Percentage of bins on chr 21 have a z-score of $MP_{Diff}$ <-3 | 0% | 0% | 33.3% | 58.3% | 19.4% | 52.8% |

This DNA methylation-based approach for detecting fetal chromosomal or subchromosomal aberrations can be used in conjunction with those based on the counting of molecules such as by sequencing (R. W. Chiu et al. 2008 Proc Natl Acad Sci USA; 105: 20458-20463) or digital PCR (Y. M. Lo et al. 2007 Proc Natl Acad Sci USA; 104: 13116-13121), or the sizing of DNA molecules (US Patent Publication 2011/0276277). Such combination (e.g. DNA methylation plus molecular counting, or DNA methylation plus sizing, or DNA methylation plus molecular counting plus sizing) would have a synergistic effect which would be advantageous in a clinical setting, e.g. improving the sensitivity and specificity. For example, the number of DNA molecules that would need to be analyzed, e.g. by sequencing, can be reduced without adversely impacting the diagnostic accuracy. This feature would allow such tests to be done more economically. As another example, for a given number of DNA molecules analyzed, a combined approach would allow fetal chromosomal or subchromosomal aberrations to be detected at a lower fractional concentration of fetal DNA.

Figure 13:
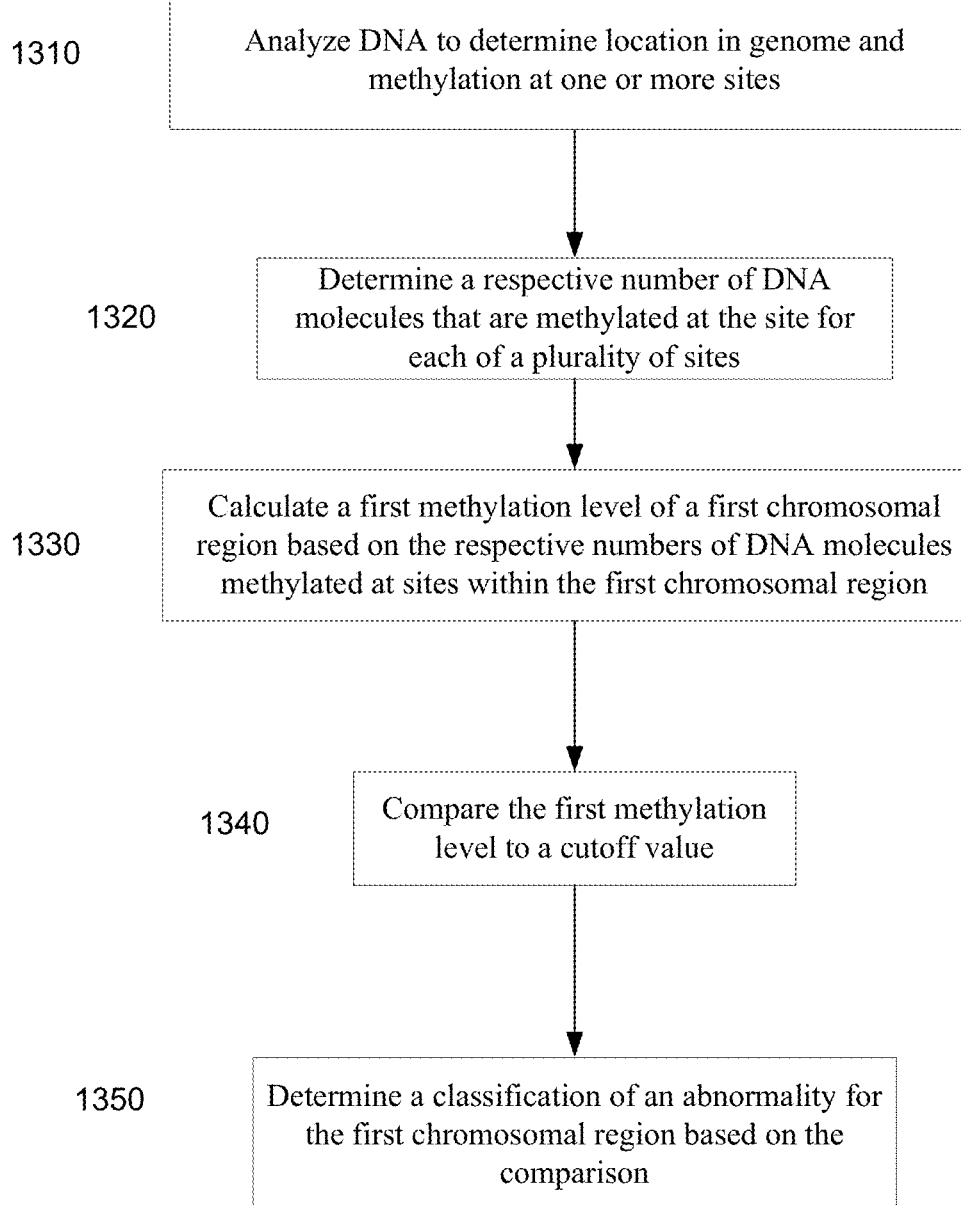
FIG. 13 is a flowchart of a method 1300 for detecting a fetal chromosomal abnormality from a biological sample of a female subject pregnant with at least one fetus.

FIG. 13 is a flowchart of a method 1300 for detecting a chromosomal abnormality from a biological sample of an organism. The biological sample includes cell-free DNA comprising a mixture of cell-free DNA originating from a first tissue and from a second tissue. The first tissue may be from a fetus or tumor and the second tissue may be from a pregnant female or a patient.

At block 1310, a plurality of DNA molecules from the biological sample are analyzed. The analysis of a DNA molecule can include determining a location of the DNA molecule in a genome of the organism and determining whether the DNA molecule is methylated at one or more sites. The analysis can be performed by receiving sequence reads from a methylation-aware sequencing, and thus the analysis can be performed just on data previously obtained from the DNA. In other embodiments, the analysis can include the actual sequencing or other active steps of obtaining the data.

The determining of a location can include mapping the DNA molecules (e.g., via sequence reads) to respective parts of the human genome, e.g., to specific regions. In one implementation, if a read does not map to a region of interest, then the read can be ignored.

At block 1320, a respective number of DNA molecules that are methylated at the site is determined for each of a plurality of sites. In one embodiment, the sites are CpG sites, and may be only certain CpG sites, as selected using one or more criteria mentioned herein. The number of DNA that are methylated is equivalent to determining the number that are unmethylated once normalization is performed using a total number of DNA molecules analyzed at a particular site, e.g., a total number of sequence reads.

At block 1330, a first methylation level of a first chromosomal region is calculated based on the respective numbers of DNA molecules methylated at sites within the first chromosomal region. The first chromosomal region can be of any size, e.g., sizes mentioned above. The methylation level can account for a total number of DNA molecules aligned to the first chromosomal region, e.g., as part of a normalization procedure.

The first chromosomal region may be of any size (e.g., a whole chromosome) and may be composed of disjoint subregions, i.e., subregions are separated from each other. Methylation levels of each subregion can be determined and the combined, e.g., as an average or median, to determine a methylation level for the first chromosomal region.

At block 1340, the first methylation level is compared to a cutoff value. The cutoff value may be a reference methylation level or be related to a reference methylation level (e.g., a specified distance from a normal level). The cutoff value may be determined from other female pregnant subjects carrying fetuses without a chromosomal abnormality for the first chromosomal region, from samples of individuals without cancer, or from loci of the organism that are known to not be associated with an aneuploidy (i.e., regions that are disomic).

In one embodiment, the cutoff value can be defined as having a difference from a reference methylation level of (BKG−PLN)×f×0.5×CN, where BKG is the background of the female (or an average or median from other subjects), f is the concentration of cell-free DNA originating from the first tissue, and CN is a copy number being tested. CN is an example of a scale factor corresponding to a type of abnormality (deletion or duplication). A cutoff for a CN of 1 can be used to test all amplifications initially, and then further cutoffs can be used to determine the degree of amplification. The cutoff value can be based on a concentration of cell-free DNA originating from the first tissue using other formula.

At block 1350, a classification of an abnormality for the first chromosomal region is determined based on the comparison. A statistically significant difference in levels can indicate increased risk of the fetus having a chromosomal abnormality. In various embodiments, the chromosomal abnormality can be trisomy 21, trisomy 18, trisomy 13, Turner syndrome, or Klinefelter syndrome. Other examples are a subchromosomal deletion, subchromosomal duplication, or DiGeorge syndrome.

V. Determination of Markers

As noted above, certain parts of the fetal genome are methylated differently than the maternal genome. These differences can be common across pregnancies. The regions of different methylation can be used to identify DNA fragments that are from the fetus.

A. Method to Determine DMRs from Placental Tissue and Maternal Tissue

The placenta has tissue-specific methylation signatures. Fetal-specific DNA methylation markers have been developed for maternal plasma detection and for noninvasive prenatal diagnostic applications based on loci that are differentially methylated between placental tissues and maternal blood cells (S. S. C. Chim et al. 2008 Clin Chem; 54: 500-511; E. A. Papageorgiou et al 2009 Am J Pathol; 174: 1609-1618; and T. Chu et al. 2011 PLoS One; 6: e14723). Embodiments for mining for such differentially methylated regions (DMRs) on a genome-wide basis are provided.

Figure 14:
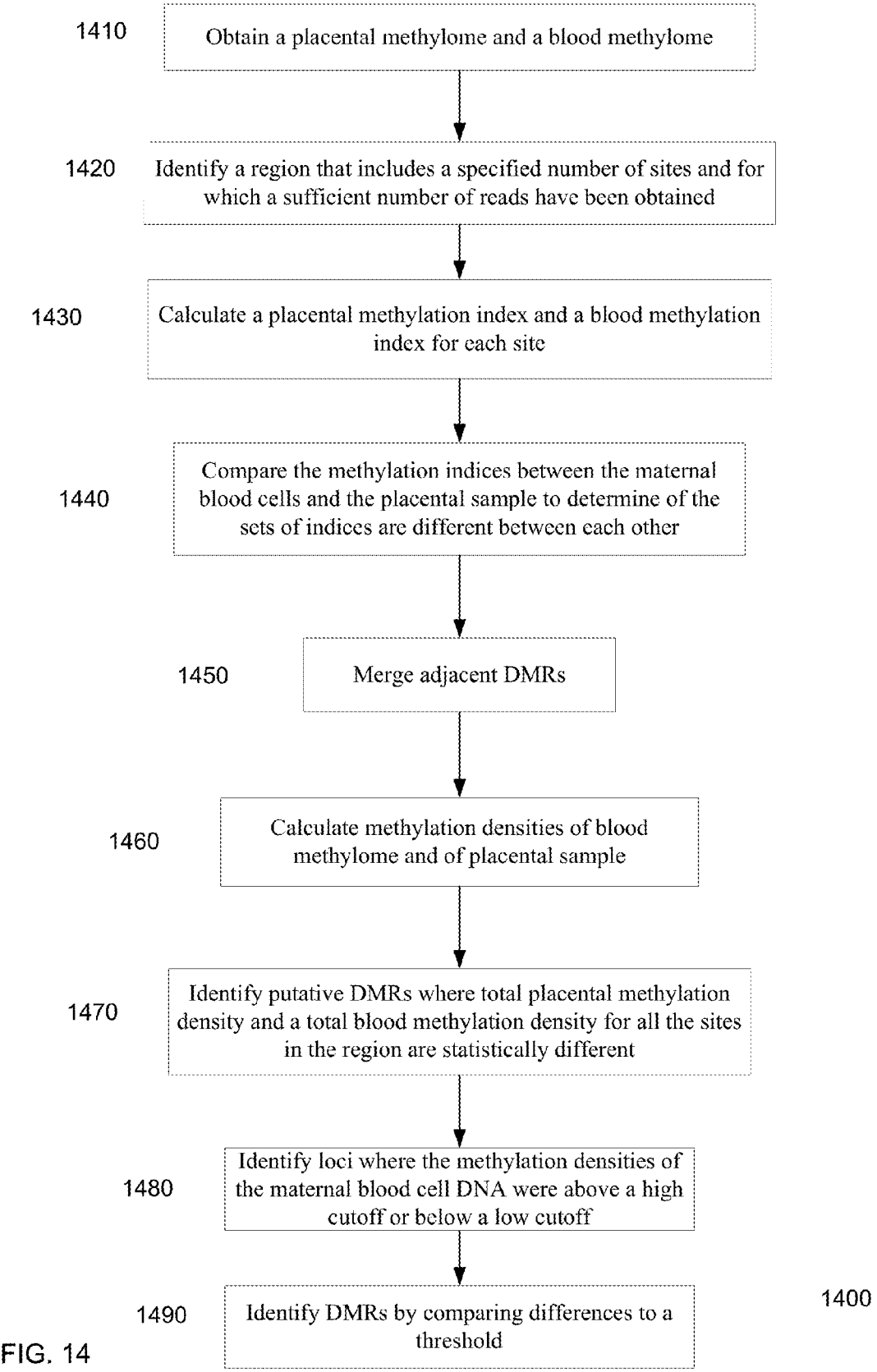
FIG. 14 is a flowchart of a method 1400 for identifying methylation markers by comparing a placental methylation profile to a maternal methylation profile according to embodiments of the present invention.

FIG. 14 is a flowchart of a method 1400 for identifying methylation markers by comparing a placental methylation profile to a maternal methylation profile (e.g., determined from blood cells) according to embodiments of the present invention. Method 1400 may also be used to determine markers for a tumor by comparing a tumor methylation profile to a methylation profile corresponding to healthy tissue.

At block 1410, a placental methylome and a blood methylome is obtained. The placental methylome can be determined from a placental sample, e.g., CVS or a term placenta. Methylome should be understood to possible include methylation densities of only part of a genome.

At block 1420, a region is identified that includes a specified number of sites (e.g., 5 CpG sites) and for which a sufficient number of reads have been obtained. In one embodiment, the identification began from one end of each chromosome to locate the first 500-bp region that contained at least five qualified CpG sites. A CpG site may be deemed qualified if the site was covered by at least five sequence reads.

At block 1430, a placental methylation index and a blood methylation index is calculated for each site. For example, the methylation index was calculated individually for all qualified CpG sites within each 500-bp region.

At block 1440, the methylation indices were compared between the maternal blood cells and the placental sample to determine if the sets of indices were different between each other. For example, the methylation indices were compared between the maternal blood cells and the CVS or the term placenta using, for example, the Mann-Whitney test. A P-value of, for example, ≤0.01 was considered as statistically significantly different, although other values may be used, where a lower number would reduce false positive regions.

In one embodiment, if the number of qualified CpG sites was less than five or the Mann-Whitney test was non-significant, the 500-bp region shifted downstream for 100 bp. The region continued to be shifted downstream until the Mann-Whitney test became significant for a 500-bp region. The next 500-bp region would then be considered. If the next region was found to exhibit statistical significance by the Mann-Whitney test, it would be added to the current region as long as the combined contiguous region is no larger than 1,000 bp.

At block 1450, adjacent regions that were statistically significantly different (e.g., by the Mann-Whitney test) can be merged. Note the difference is between the methylation indices for the two samples. In one embodiment, if the adjacent regions are within a specified distance (e.g., 1,000 bp) of each other and if they showed a similar methylation profile then they would be merged. In one implementation, the similarity of the methylation profile between adjacent regions can be defined using any of the following: (1) showing the same trend in the placental tissue with reference to the maternal blood cells, e.g. both regions were more methylated in the placental tissues than the blood cells; (2) with differences in methylation densities of less than 10% for the adjacent regions in the placental tissue; and (3) with differences in methylation densities of less than 10% for the adjacent regions in the maternal blood cells.

At block 1460, methylation densities of the blood methylome from maternal blood cell DNA and placental sample (e.g., CVS or term placental tissue) at the regions were calculated. The methylation densities can be determined as described herein.

At block 1470, putative DMRs where total placental methylation density and a total blood methylation density for all the sites in the region are statistically significantly different is determined. In one embodiment, all qualified CpG sites within a merged region are subjected to a $\chi^2$ test. The $\chi^2$ test assessed if the number of methylated cytosines as a proportion of the methylated and unmethylated cytosines among all the qualified CpG sites within the merged region was statistically significantly different between the maternal blood cells and placental tissue. In one implementation, for the $\chi^2$ test, a P-value of $\leq 0.01$ may be considered as statistically significantly different. The merged segments that showed significance by the $\chi^2$ test were considered as putative DMRs.

At block 1480, loci where the methylation densities of the maternal blood cell DNA were above a high cutoff or below a low cutoff were identified. In one embodiment, loci were identified where the methylation densities of the maternal blood cell DNA were either $\leq 20\%$ or $\geq 80\%$. In other embodiments, bodily fluids other than maternal blood can be used, including, but not limited to saliva, uterine or cervical lavage fluid from the female genital tract, tears, sweat, saliva, and urine.

A key to the successful development of DNA methylation markers that are fetal-specific in maternal plasma can be that the methylation status of the maternal blood cells are either as highly methylated or as unmethylated as possible. This can reduce (e.g., minimize) the chance of having maternal DNA molecules interfering with the analysis of the placenta-derived fetal DNA molecules which show an opposite methylation profile. Thus, in one embodiment, candidate DMRs were selected by further filtering. The candidate hypomethylated loci were those that showed methylation densities $\leq 20\%$ in the maternal blood cells and with at least 20% higher methylation densities in the placental tissues. The candidate hypermethylated loci were those that showed methylation densities $\geq 80\%$ in the maternal blood cells and with at least 20% lower methylation densities in the placental tissues. Other percentages may be used.

At block 1490, DMRs were then identified among the subset of loci where the placental methylation densities are significantly different from the blood methylation densities by comparing the difference to a threshold. In one embodiment, the threshold is 20%, so the methylation densities differed by at least 20% from the methylation densities of the maternal blood cells. Accordingly, a difference between placental methylation densities and blood methylation densities at each identified loci can be calculated. The difference can be a simple subtraction. In other embodiments, scaling factors and other functions can be used to determine the difference (e.g., the difference can be the result of a function applied to the simple subtraction).

In one implementation, using this method, 11,729 hypermethylated and 239,747 hypomethylated loci were identified from the first trimester placental sample. The top 100 hypermethylated loci are listed in table S2A of the appendix. The top 100 hypomethylated loci are listed in table S2B of the appendix. The tables list the chromosome, the start and end location, the size of the region, the methylation density in maternal blood, the methylation density in the placenta sample, the P-values (which are all very small), and the methylation difference. The locations correspond to reference genome hg18, which can be found at hgdownload.soe.ucsc.edu/goldenPath/hg18/chromosomes.

11,920 hypermethylated and 204,768 hypomethylated loci were identified from the third trimester placental sample. The top 100 hypermethylated loci for the $3^{rd}$ trimester are listed in table S2C, and the top 100 hypomethylated loci are listed in table S2D. Thirty-three loci that were previously reported to be differentially methylated between maternal blood cells and first trimester placental tissues were used to validate our list of first trimester candidates. 79% of the 33 loci had been identified as DMRs using our algorithm.

FIG. 15A is a table 1500 showing a performance of first trimester DMR identification algorithm using placental methylome with reference to 33 previously reported first trimester markers. In the table, "a" indicates that loci 1 to 15 were previously described in (R. W. K. Chiu et al. 2007 Am J Pathol; 170:941-950 and S. S. C. Chim et al. 2008 Clin Chem; 54:500-511); loci 16 to 23 were previously described in (K. C. Yuen, thesis 2007, The Chinese University of Hong Kong, Hong Kong); and loci 24 to 33 were previously described in (E. A. Papageorgiou et al. 2009 Am J Pathol; 174:1609-1618). "b" indicates that these data were derived from the above publications. "c" indicates that methylation densities of maternal blood cells and chorionic villus sample and their differences were observed from the sequencing data generated in the present study but based on the genomic coordinates provided by the original studies. "d" indicates that data on the loci identified using embodiments of method 1400 on the bisulfite sequencing data without taking reference from the publications cited above by Chiu et al (2007), Chim et al (2008), Yuen (2007) and Papageorgiou et al (2009). The span of the loci included the previously reported genomic regions but in general spanned larger regions. "e" indicates that a candidate DMR was classified as true-positive (TP) or false-negative (FN) based on the requirement of observing >0.20 difference between the methylation densities of the corresponding genome coordinates of the DMRs in maternal blood cells and chorionic villus sample.

FIG. 15B is a table 1550 showing a performance of third trimester DMR identification algorithm using the placental methylome measured using the placenta sample obtained at delivery. "a" indicates that the same list of 33 loci as described in FIG. 17A were used. "b" indicates that as the 33 loci were previously identified from early pregnancy samples, they might not be applicable to the third trimester data. Hence, the bisulfite sequencing data generated in the present study on the term placental tissue based on the genomic coordinates provided by the original studies were reviewed. A difference of >0.20 in the methylation densities between the maternal blood cell and term placental tissue was used to determine if the loci were indeed true DMRs in the third trimester. "c" indicates that the data on the loci was identified using method 1400 on the bisulfite sequencing data without taking reference from previously cited publications by Chiu et al (2007), Chim et al (2008), Yuen (2007) and Papageorgiou et al (2009). The span of the loci included the previously reported genomic regions but in general spanned larger regions. "d" indicates that candidate DMRs that contained loci which qualified as differentially methylated in the third trimester were classified as true-positive (TP) or false-negative (FN) based on the requirement of observing >0.20 difference between the methylation densities of the corresponding genome coordinates of the DMRs in maternal blood cells and term placental tissue. For loci that did not qualify as differentially methylated in the third trimester, their absence in the DMR list or the presence of a DMR containing the loci but showing methylation difference of <0.20 was considered as true negative (TN) DMRs.

B. DMRs from the Maternal Plasma Sequencing Data

One should be able to identify placental tissue DMRs directly from the maternal plasma DNA bisulfite-sequencing data provided that the fractional fetal DNA concentration of the sample was also known. It is possible because the placenta is the predominant source of fetal DNA in maternal plasma (S. S. Chim et al. 2005 Proc Natl Acad Sci USA 102, 14753-14758) and we showed in this study that the methylation status of fetal-specific DNA in maternal plasma correlated with the placental methylome.

Therefore, aspects of method 1400 may be implemented using a plasma methylome to determine a deduced placental methylome instead of using a placental sample. Thus, method 1000 and method 1400 can be combined to determine DMRs. Method 1000 can be used to determine the predicted values for the placental methylation profile and use them in method 1400. For this analysis, the example also focuses on loci that were either ≤20% or ≥80% methylated in the maternal blood cells.

In one implementation, to deduce loci that were hypermethylated in the placental tissues with respect to maternal blood cells, we sorted for loci that showed ≤20% methylation in maternal blood cells, and ≥60% methylation according to the predicted value with a difference of at least 50% between the blood cell methylation density and the predicted value. To deduce loci that were hypomethylated in the placental tissues with respect to maternal blood cells, we sorted for loci that showed ≥80% methylation in maternal blood cells, and ≤40% methylation according to the predicted value with a difference of at least 50% between the blood cell methylation density and the predicted value.

FIG. 16 is a table 1600 showing the numbers of loci predicted to be hypermethylated or hypomethylated based on direct analysis of the maternal plasma bisulfite-sequencing data. "N/A" means not applicable. "a" indicates that the search for hypermethylated loci started from the list of loci showing methylation densities <20% in the maternal blood cells. "b" indicates that the search for hypomethylated loci started from the list of loci showing methylation densities >80% in the maternal blood cells. "c" indicates that bisulfite-sequencing data from the chorionic villus sample was used for verifying the first trimester maternal plasma data, and the term placental tissue was used for verifying the third trimester maternal plasma data.

As shown in table 1600, a majority of the noninvasively deduced loci showed the expected methylation pattern in the tissues and overlapped with the DMRs mined from the tissue data and presented in the earlier section. The appendix lists DMRs identified from the plasma. Table S3A lists the top 100 loci deduced to be hypermethylated from the first trimester maternal plasma bisulfite-sequencing data. Table S3B lists the top 100 loci deduced to be hypomethylated from the first trimester maternal plasma bisulfite-sequencing data. Table S3C lists the top 100 loci deduced to be hypermethylated from the third trimester maternal plasma bisulfite-sequencing data. Table S3D lists the top 100 loci deduced to be hypomethylated from the third trimester maternal plasma bisulfite-sequencing data.

C. Gestational Variation in Placental and Fetal Methylomes

The overall proportion of methylated CpGs in the CVS was 55% while it was 59% for the term placenta (table 100 of FIG. 1). More hypomethylated DMRs could be identified from CVS than the term placenta while the number of hypermethylated DMRs was similar for the two tissues. Thus, it was evident that the CVS was more hypomethylated than the term placenta. This gestational trend was also apparent in the maternal plasma data. The proportion of methylated CpGs among the fetal-specific reads was 47.0% in the first trimester maternal plasma but was 53.3% in the third trimester maternal plasma. The numbers of validated hypermethylated loci were similar in the first (1,457 loci) and third trimester (1,279 loci) maternal plasma samples but there were substantially more hypomethylated loci in the first (21,812 loci) than the third trimester (12,677 loci) samples (table 1600 of FIG. 16).

D. Use of Markers

The differentially methylated markers, or DMRs, are useful in several aspects. The presence of such markers in maternal plasma indicates and confirms the presence or fetal or placental DNA. This confirmation can be used as a quality control for noninvasive prenatal testing. DMRs can serve as generic fetal DNA markers in maternal plasma and have advantages over markers that rely on genotyping differences between the mother and fetus, such as polymorphism based markers or those based on chromosome Y. DMRs are generic fetal markers that are useful for all pregnancies. The polymorphism based markers are only applicable to the subset of pregnancies where the fetus has inherited the marker from its father and where the mother does not possess this marker in her genome. In addition, one could measure the fetal DNA concentration in a maternal plasma sample by quantifying the DNA molecules originating from those DMRs. By knowing the profile of DMRs expected for normal pregnancies, pregnancy-associated complications, particularly those involving placental tissue changes, could be detected by observing a deviation in the maternal plasma DMR profile or methylation profile from that expected for normal pregnancies. Pregnancy-associated complications that involve placental tissue changes include but not limited to fetal chromosomal aneuploidies, such as trisomy 21, preeclampsia, intrauterine growth retardation and preterm labor.

E. Kits Using Markers

Embodiments can provide compositions and kits for practicing the methods described herein and other applicable methods. Kits can be used for carrying out assays for analyzing fetal DNA, e.g., cell-free fetal DNA in maternal plasma. In one embodiment, a kit can include at least one oligonucleotide useful for specific hybridization with one or more loci identified herein. A kit can also include at least one oligonucleotide useful for specific hybridization with one or more reference loci. In one embodiment, placental hypermethylated markers are measured. The test locus may be the methylated DNA in maternal plasma and the reference locus may be the methylated DNA in maternal plasma. A similar kit could be composed for analyzing tumor DNA in plasma.

In some cases, the kits may include at least two oligonucleotide primers that can be used in the amplification of at least a section of a target locus (e.g., a locus in the appendix) and a reference locus. Instead of or in addition to primers, a kit can include labeled probes for detecting a DNA fragment corresponding to a target locus and a reference locus. In various embodiments, one or more oligonucleotides of the kit correspond to a locus in the tables of the appendix.

Typically, the kits also provide instruction manuals to guide users in analyzing test samples and assessing the state of physiology or pathology in a test subject.

In various embodiments, a kit for analyzing fetal DNA in a biological sample containing a mixture of fetal DNA and DNA from a female subject pregnant with a fetus is provided. The kit may comprise one or more oligonucleotides for specifically hybridizing to at least a section of a genomic region listed in tables S2A, S2B, S2C, S2D, S3A, S3B, S3C, and S3D. Thus, any number of oligonucleotides from across the tables are just from one table may be used. The oligonucleotides may act as primers, and may be organized as pairs of primers, where a pair corresponds to a particular region from the tables.

VI. Relationship of Size and Methylation Density

Plasma DNA molecules are known to exist in circulation in the form of short molecules, with the majority of molecules about 160 bp in length (Y. M. D. Lo et al. 2010 Sci Transl Med; 2: 61ra91, Y. W. Zheng at al. 2012 Clin Chem; 58: 549-558). Interestingly, our data revealed a relationship between the methylation status and the size of plasma DNA molecules. Thus, plasma DNA fragment length is linked to DNA methylation level. The characteristic size profiles of plasma DNA molecules suggest that the majority are associated with mononucleosomes, possibly derived from enzymatic degradation during apoptosis.

Circulating DNA is fragmented in nature. In particular, circulating fetal DNA is shorter than maternally-derived DNA in maternal plasma samples (K C A Chan et al. 2004 Clin Chem; 50: 88-92). As paired-end alignment enables the size analysis of bisulfite-treated DNA, one could assess directly if any correlation exists between the size of plasma DNA molecules and their respective methylation levels. We explored this in the maternal plasma as well as a non-pregnant adult female control plasma sample.

Paired-end sequencing for both ends of each DNA molecule was used to analyze each sample in this study. By aligning the pair of end sequences of each DNA molecule to the reference human genome and noting the genome coordinates of the extreme ends of the sequenced reads, one can determine the lengths of the sequenced DNA molecules. Plasma DNA molecules are naturally fragmented into small molecules and the sequencing libraries for plasma DNA are typically prepared without any fragmentation steps. Hence, the lengths deduced by the sequencing represented the sizes of the original plasma DNA molecules.

In a previous study, we determined the size profiles of the fetal and maternal DNA molecules in maternal plasma (Y. M. D. Lo et al. 2010 Sci Transl Med; 2: 61ra91). We showed that the plasma DNA molecules had sizes that resembled mononucleosomes and fetal DNA molecules were shorter than the maternal ones. In this study, we have determined the relationship of the methylation status of plasma DNA molecules had to their sizes.

A. Results

Figure 17A:
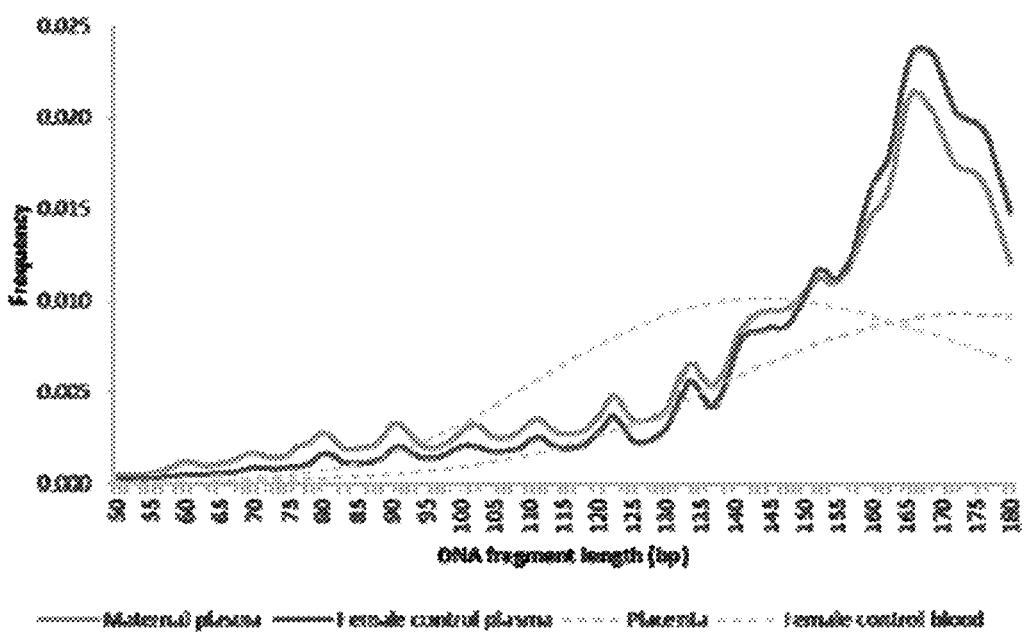
FIG. 17A is a plot 1700 showing size distribution of maternal plasma, non-pregnant female control plasma, placental and peripheral blood DNA.
Figure 17B:
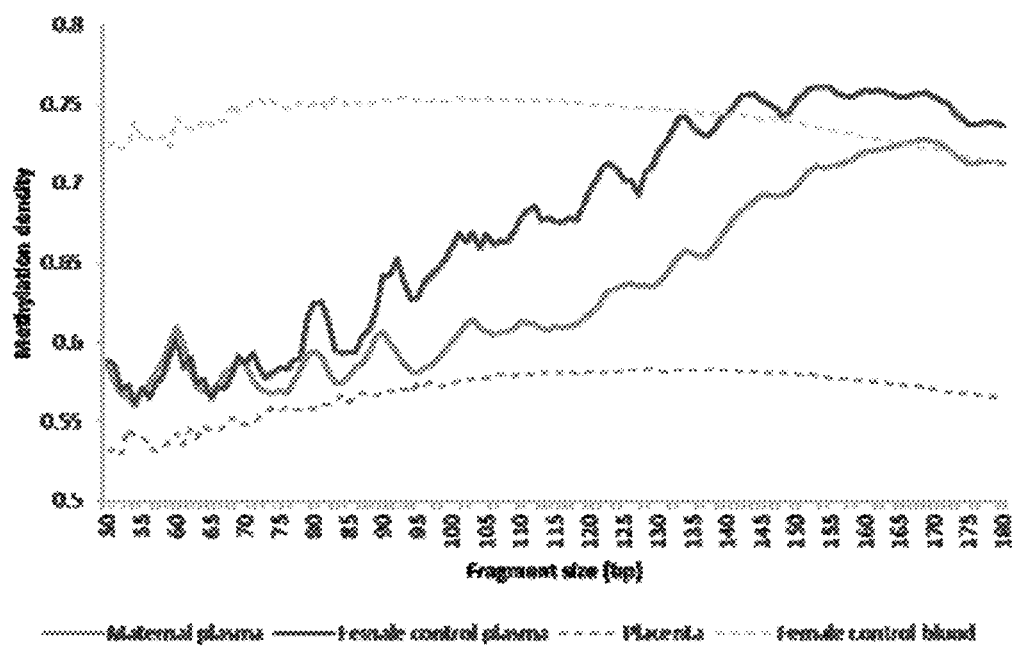
FIG. 17B is a plot 1750 of size distribution and methylation profile of maternal plasma, adult female control plasma, placental tissue and adult female control blood.

FIG. 17A is a plot 1700 showing size distribution of maternal plasma, non-pregnant female control plasma, placental and peripheral blood DNA. For the maternal sample and the non-pregnant female control plasma, the two bisulfite-treated plasma samples displayed the same characteristic size distribution as previously reported (Y. M. D. Lo et al. 2010 Sci Transl Med; 2: 61ra91) with the most abundant total sequences of 166-167 bp in length and a 10-bp periodicity of DNA molecules shorter than 143 bp FIG. 17B is a plot 1750 of size distribution and methylation profile of maternal plasma, adult female control plasma, placental tissue and adult female control blood. For DNA molecules of the same size and containing at least one CpG site, their mean methylation density was calculated. We then plotted the relationship between the sizes of the DNA molecules and their methylation densities. Specifically, the mean methylation density was determined for each fragment length ranging from 50 bp up to 180 bp for sequenced reads covering at least 1 CpG site. Interestingly, the methylation density increased with the plasma DNA size and peaked at around 166-167 bp. This pattern, however, was not observed in the placenta and control blood DNA samples which were fragmented using an ultrasonicator system.

Figure 18A:
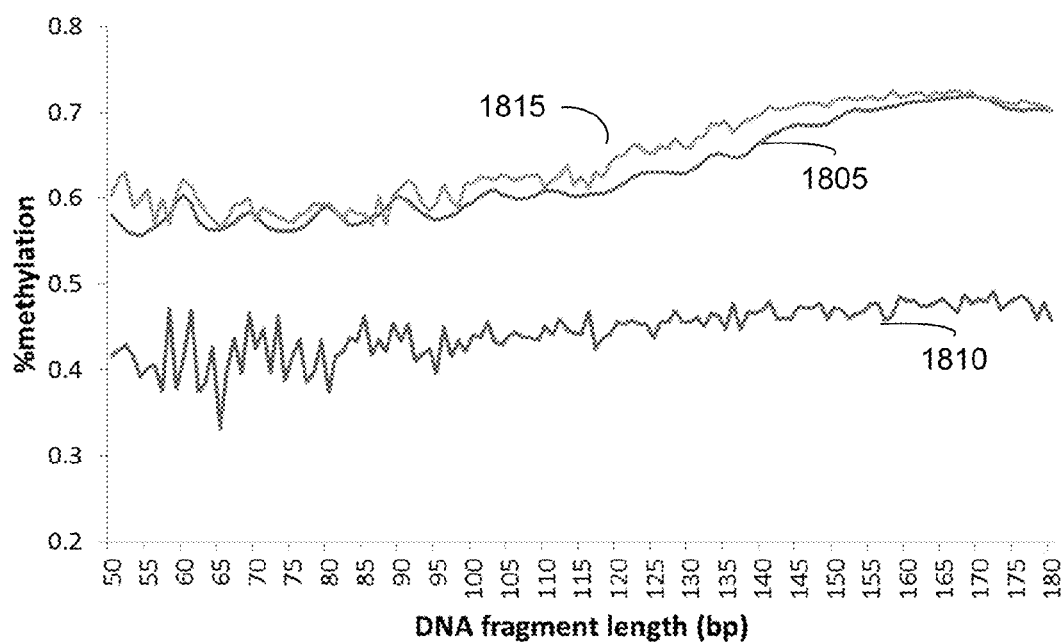
FIGS. 18A and 18B are plots of methylation densities and size of plasma DNA molecules according to embodiments of the present invention.
Figure 18B:
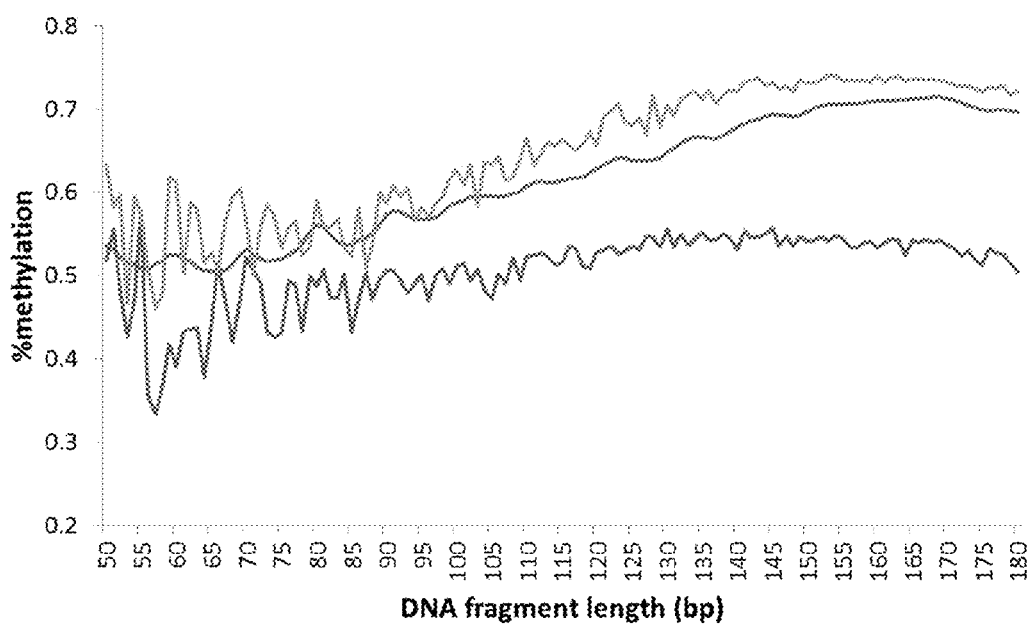

FIG. 18 shows plots of methylation densities and size of plasma DNA molecules. FIG. 18A is a plot 1800 for the first trimester maternal plasma. FIG. 18B is a plot 1850 for the third trimester maternal plasma. Data for all the sequenced reads that covered at least one CpG site are represented by the blue curve 1805. Data for reads that also contained a fetal-specific SNP allele are represented by the red curve 1810. Data for reads that also contained a maternal-specific SNP allele are represented by the green curve 1815.

Reads that contained a fetal-specific SNP allele was considered a fetal DNA molecule. Reads that contained a maternal-specific SNP allele was considered a maternal DNA molecule. In general, DNA molecules with high methylation densities were longer in size. This trend was present in both the fetal and maternal DNA molecules in both the first and third trimesters. The overall sizes of the fetal DNA molecules were shorter than the maternal ones as previously reported.

Figure 19A:
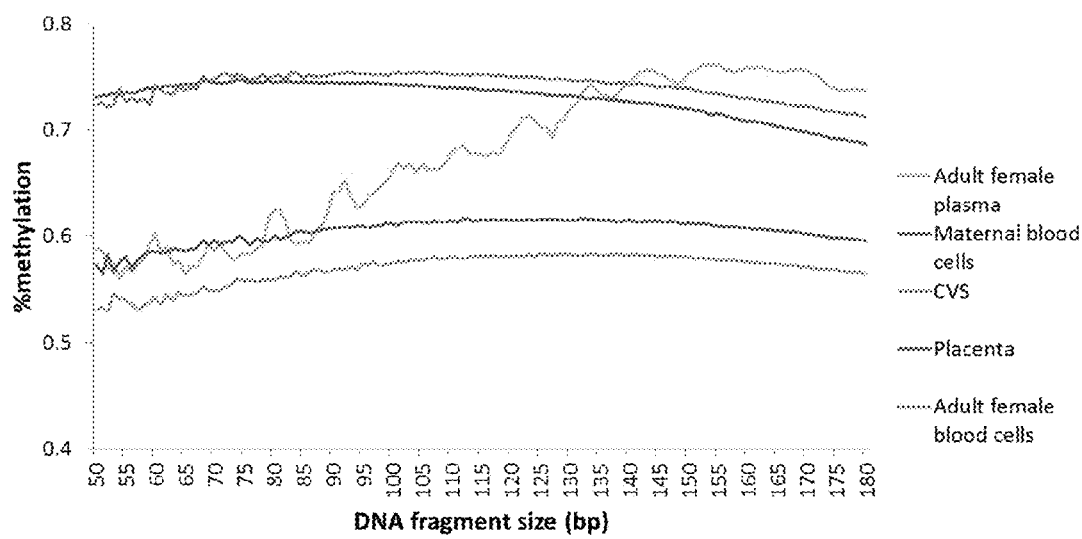
FIG. 19A shows a plot 1900 of methylation densities and the sizes of sequenced reads for an adult non-pregnant female.

FIG. 19A shows a plot 1900 of methylation densities and the sizes of sequenced reads for an adult non-pregnant female. The plasma DNA sample from the adult non-pregnant female also showed the same relationship between the sizes and methylation state of the DNA molecules. On the other hand, the genomic DNA samples were fragmented by an ultrasonication step before MPS analysis. As shown in plot 1900, the data from the blood cell and placental tissue samples did not reveal the same trend. Since the fragmentation of the cells is artificial, one would expect to have no relationship of size and density. Since the naturally fragmented DNA molecules in plasma do show a dependence on size, it can be presumed that the lower methylation densities make it more likely for molecules to break into smaller fragments.

Figure 19B:
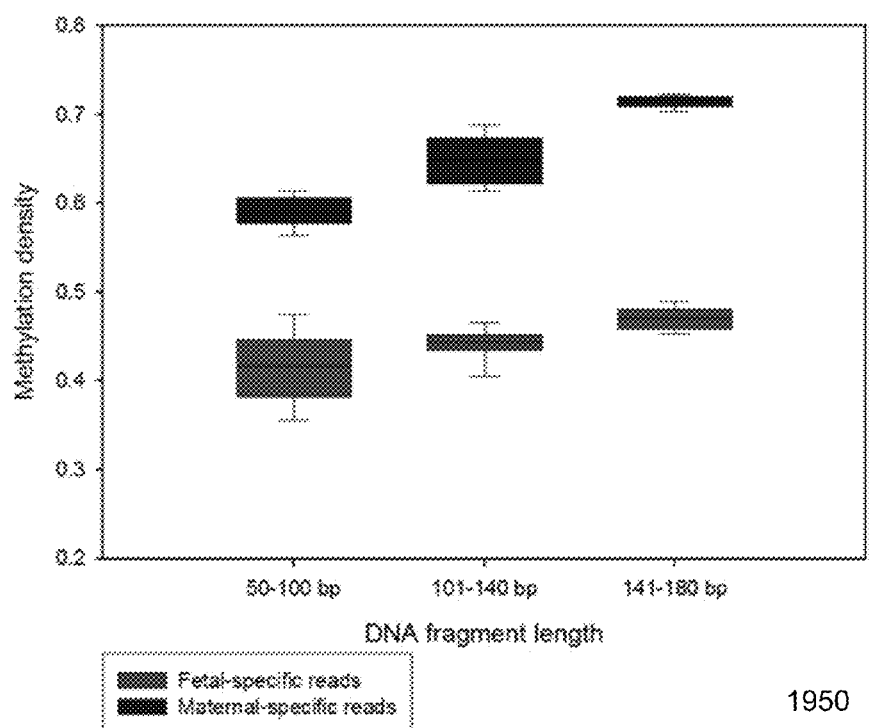
FIG. 19B is a plot 1950 showing size distribution and methylation profile of fetal-specific and maternal-specific DNA molecules in maternal plasma.

FIG. 19B is a plot 1950 showing size distribution and methylation profile of fetal-specific and maternal-specific DNA molecules in maternal plasma. Fetal-specific and maternal-specific plasma DNA molecules also exhibited the same correlation between fragment size and methylation level. Both the fragment length of placenta-derived and maternal circulating cell-free DNA increased with the methylation level. Moreover, the distribution of their methylation status did not overlap with each other, suggesting that the phenomenon exists irrespective of the original fragment length of the sources of circulating DNA molecules.

B. Method

Accordingly, a size distribution can be used to estimate a total methylation percentage of a plasma sample. This methylation measurement can then be tracked during pregnancy or during cancer treatment by serial measure of the size distributions of the plasma DNA according to the relationship shown in FIGS. 18A and 18B. The methylation measurement can also be used to look for increased or decreased release of DNA from an organ or a tissue of interest. For example, one can specifically look for DNA methylation signatures specific to a specific organ (e.g. the liver) and to measure the concentrations of these signatures in plasma. As DNA is released into plasma when cells die, an increase in levels could mean an increase in cell death or damage in that particular organ or tissue. A decrease in level from a particular organ can mean that treatment to counter damage or pathological processes in that organ is under control.

Figure 20:
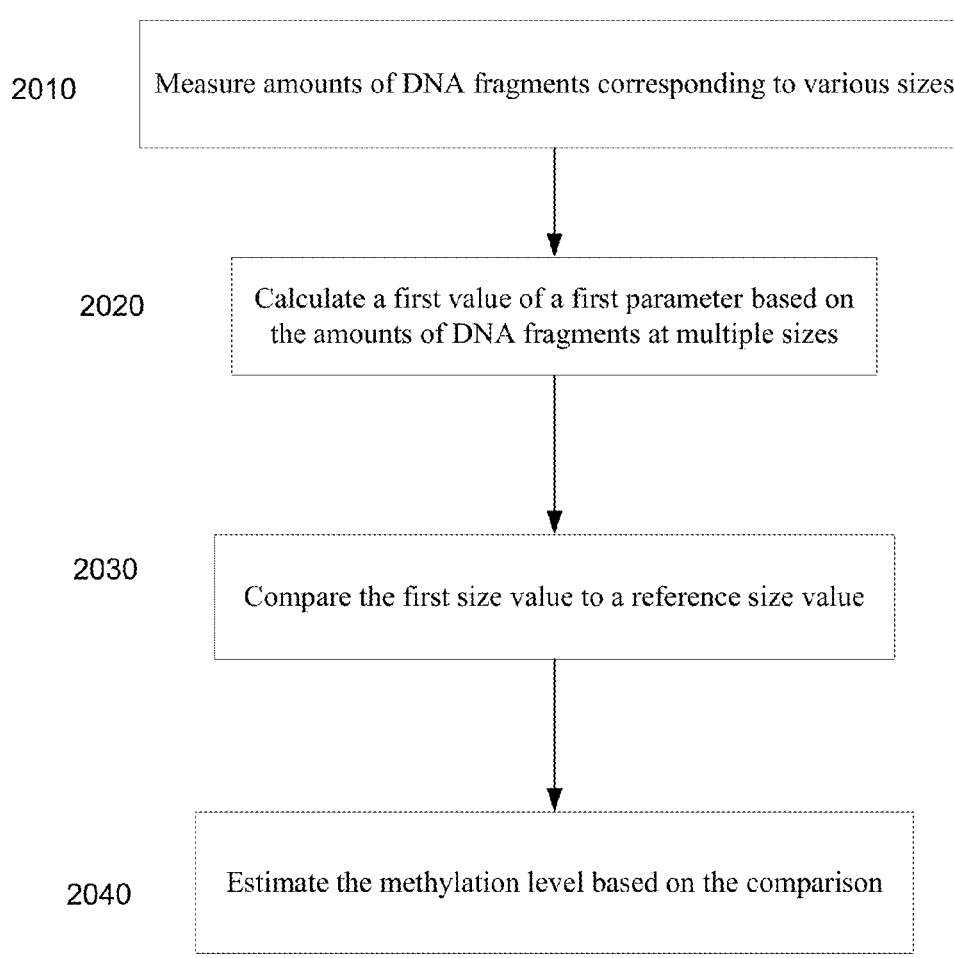
FIG. 20 is a flowchart of a method 2000 for estimating a methylation level of DNA in a biological sample of an organism according to embodiments of the present invention.

FIG. 20 is a flowchart of a method 2000 for estimating a methylation level of DNA in a biological sample of an organism according to embodiments of the present invention. The methylation level can be estimated for a particular region of a genome or the entire genome. If a specific region is desired, then DNA fragments only from that specific region may be used.

At block 2010, amounts of DNA fragments corresponding to various sizes are measured. For each size of a plurality of sizes, an amount of a plurality of DNA fragments from the biological sample corresponding to the size can be measured. For instance, the number of DNA fragments having a length of 140 bases may be measured. The amounts may be saved as a histogram. In one embodiment, a size of each of the plurality of nucleic acids from the biological sample is measured, which may be done on an individual basis (e.g., by single molecule sequencing of a whole molecule or just ends of the molecule) or on a group basis (e.g., via electrophoresis). The sizes may correspond to a range. Thus, an amount can be for DNA fragments that have a size within a particular range. When paired-end sequencing is performed, the DNA fragments (as determined by the paired sequence reads) mapping (aligning) to a particular region may be used to determine the methylation level of the region.

At block 2020, a first value of a first parameter is calculated based on the amounts of DNA fragments at multiple sizes. In one aspect, the first parameter provides a statistical measure of a size profile (e.g., a histogram) of DNA fragments in the biological sample. The parameter may be referred to as a size parameter since it is determined from the sizes of the plurality of DNA fragments.

The first parameter can be of various forms. One parameter is the percentage of DNA fragment of a particular size or range of sizes relative to all DNA fragments or relative to DNA fragments of another size or range. Such a parameter is a number of DNA fragments at a particular size divided by the total number of fragments, which may be obtained from a histogram (any data structure providing absolute or relative counts of fragments at particular sizes). As another example, a parameter could be a number of fragments at a particular size or within a particular range divided by a number of fragments of another size or range. The division can act as a normalization to account for a different number of DNA fragments being analyzed for different samples. A normalization can be accomplished by analyzing a same number of DNA fragments for each sample, which effectively provides a same result as dividing by a total number fragments analyzed. Additional examples of parameters and about size analysis can be found in U.S. patent application Ser. No. 13/789,553, which is incorporated by reference for all purposes.

At block 2030, the first size value is compared to a reference size value. The reference size value can be calculated from DNA fragments of a reference sample. To determine the reference size values, the methylation profile can be calculated and quantified for a reference sample, as well as a value of the first size parameter. Thus, when the first size value is compared to the reference size value, a methylation level can be determined.

At block 2040, the methylation level is estimated based on the comparison. In one embodiment, one can determine if the first value of the first parameter is above or below the reference size value, and thereby determine if the methylation level of the instant sample is above or below the methylation level to the reference size value. In another embodiment, the comparison is accomplished by inputting the first value into a calibration function. The calibration function can effectively compare the first value to calibration values (a set of reference size values) by identifying the point on a curve corresponding to the first value. The estimated methylation level is then provided as the output value of the calibration function.

Accordingly, one can calibrate a size parameter to a methylation level. For example, a methylation level can be measured and associated with a particular size parameter for that sample. Then data points from various samples can be fit a calibration function. In one implementation, different calibration functions can be used for different subsets of DNA. Thus, there may be some form of calibration based on prior knowledge about the relationship between methylation and size for a particular subset of DNA. For example, the calibration for fetal and maternal DNA could be different.

As shown above, the placenta is more hypomethylated when compared with maternal blood, and thus the fetal DNA is smaller due to the lower methylation. Accordingly, an average size of the fragments of a sample (or other statistical value) can be used to estimate the methylation density. As the fragment sizes can be measured using paired-end sequencing, rather than the potentially technically more complex methylation-aware sequencing, this approach would potentially be cost-effective if used clinically. This approach can be used for monitoring the methylation changes associated with the progress of pregnancy, or with pregnancy-associated disorders such as preeclampsia, preterm labor and fetal disorders (such as those caused by chromosomal or genetic abnormalities or intrauterine growth retardation).

In another embodiment, this approach can be used for detecting and monitoring cancer. For example, with the successful treatment of cancer, the methylation profile in plasma or another bodily fluid as measured using this size-based approach would change towards that of healthy individuals without cancer. Conversely, in the event that the cancer is progressing, then the methylation profile in plasma or another bodily fluid would diverge from that of healthy individuals without cancer.

In summary, the hypomethylated molecules were shorter than the hypermethylated ones in plasma. The same trend was observed in both the fetal and maternal DNA molecules. Since DNA methylation is known to influence nucleosome packing, our data suggest that perhaps the hypomethylated DNA molecules were less densely packed with histones and were therefore more susceptible to enzymatic degradation. On the other hand, the data presented in FIGS. 18A and 18B also showed that despite the fetal DNA being much more hypomethylated than the maternal reads, the size distribution of the fetal and maternal DNA does not separate from one another completely. In FIG. 19B, one can see that even for the same size category, the methylation level of fetal- and maternal-specific reads differ from one another This observation suggests that the hypomethylated state of fetal DNA is not the only factor that accounted for its relative shortness with reference to the maternal DNA.

VII. Imprinting Status of Gene Loci

Fetal-derived DNA molecules can be detected which share the same genotype but with different epigenetic signatures as the mother in maternal plasma (L. L. Poon et al. 2002 Clin Chem; 48: 35-41). To demonstrate that the sequencing approach is sensitive in picking up fetal-derived DNA molecules in maternal plasma, we applied the same strategy to detect the imprinted fetal alleles in maternal plasma sample. Two genomic imprinted regions were identified: H19 (chr11:1,977,419-1,977,821, NCBI Build36/hg18) and MEST (chr7:129,917,976-129,920,347, NCBI Build36/hg18). Both of them contain informative SNPs for differentiation between the maternal and fetal sequences. For H19, a maternally expressed gene, the mother was homozygous (A/A) and the fetus was heterozygous (A/C) for the SNP rs2071094 (chr11:1,977,740) in the region. One of the maternal A alleles is fully methylated and the other is unmethylated. In the placenta, however, the A allele is unmethylated while the paternal-inherited C allele is fully methylated. We detected two methylated reads with the C genotype, corresponding to the imprinted paternal alleles derived from the placenta, in maternal plasma.

MEST, also known as PEG1, is a paternally expressed gene. Both the mother and the fetus were heterozygous (A/G) for the SNP rs2301335 (chr7:129,920,062) within the imprinted locus. The G allele is methylated while the A allele is unmethylated in maternal blood. The methylation pattern is reversed in the placenta with the maternal A allele being methylated and the paternal G allele unmethylated. Three unmethylated G alleles, which were paternally derived, were detectable in maternal plasma. In contrast, VAV1, a non-imprinted gene locus on chromosome 19 (chr19:6,723,621-6,724,121), did not display any allelic methylation pattern in the tissue as well as in the plasma DNA samples.

Thus, methylation status can be used to determine which DNA fragments are from the fetus. For example, just detecting the A allele in maternal plasma cannot be used as a fetal marker when the mother is GA heterozygous. But if one distinguishes the methylation status of the A molecules in plasma, the methylated A molecules are fetal-specific while the unmethylated A-molecules are maternal-specific, or vice versa.

We next focused on loci that have been reported to demonstrate genomic imprinting in placental tissues. Based on the list of loci reported by Woodfine et al. (2011 Epigenetics Chromatin; 4: 1), we further sorted for those that contained SNPs within the imprinting control region. Four loci fulfilled the criteria and they were H19, KCNQ10T1, MEST and NESP.

Regarding the reads of the maternal blood cell sample for H19 and KCNQ10T1, the maternal reads were homozygous for the SNP and there were approximately equal proportions of methylated and unmethylated reads. The CVS and term placental tissue sample revealed that the fetus was heterozygous for both loci and each allele was either exclusively methylated or unmethylated, i.e. showing monoallelic methylation. In the maternal plasma samples, the paternally inherited fetal DNA molecules were detected for both loci. For H19, the paternally inherited molecules were represented by the sequenced reads that contained the fetal-specific allele and were methylated. For KCNQ10T1, the paternally inherited molecules were represented by the sequenced reads that contained the fetal-specific allele and were unmethylated.

On the other hand, the mother was heterozygous for both MEST and NESP. For MEST, both the mother and fetus were GA heterozygotes for the SNP. However, as evident from the data for the Watson strand for the maternal blood cells and placental tissue, the methylation status for the CpGs adjacent to the SNP was opposite in the mother and fetus. The A-allele was unmethylated in the mother's DNA but methylated in the fetus's DNA. For MEST, the maternal allele was methylated. Hence, one could pinpoint that the fetus had inherited the A-allele from its mother (methylated in the CVS) and the mother had inherited the A-allele from her father (unmethylated in the maternal blood cells). Interestingly, in the maternal plasma samples, all four groups of molecules could be readily distinguished, including each of the two alleles of the mother and each of the two alleles of the fetus. Thus, by combining the genotype information with the methylation status at the imprinted loci, we could readily distinguish the maternally inherited fetal DNA molecules from the background maternal DNA molecules (L. L. Poon et al. 2002).

This approach could be used to detect uniparental disomy. For example, if the father of this fetus is known to be homozygous for the G-allele, the failure to detect the unmethylated G-allele in maternal plasma signifies the lack of contribution of the paternal allele. In addition, under such a circumstance, when both methylated G-allele and methylated A-allele were detected in the plasma of this pregnancy, it would suggest that the fetus has heterodisomy from the mother, i.e. inheriting two different alleles from the mother with no inheritance from the father. Alternatively, if both methylated A-allele (fetal allele inherited from the mother) and unmethylated A-allele (maternal allele inherited from the maternal grandfather) were detected in maternal plasma without the unmethylated G-allele (paternal allele that should have been inherited by the fetus), it would suggest that the fetus has isodisomy from the mother, i.e. inheriting two identical alleles from the mother with no inheritance from the father.

For NESP, the mother was a GA heterozygote at the SNP while the fetus was homozygous for the G-allele. The paternal allele was methylated for NESP. In the maternal plasma samples, the paternally-inherited fetal G-alleles that were methylated could be readily distinguished from the background maternal G-alleles which were unmethylated.

VIII. Cancer/Donors

Some embodiments can be used for the detection, screening, monitoring (e.g. for relapse, remission, or response (e.g. presence or absence) to treatment), staging, classification (e.g. for aid in choosing the most appropriate treatment modality) and prognostication of cancer using methylation analysis of circulating plasma/serum DNA.

Cancer DNA is known to demonstrate aberrant DNA methylation (J. G. Herman et al. 2003 N Engl J Med; 349: 2042-2054). For example, the CpG island promoters of gene, e.g. tumor suppressor genes, are hypermethylated while the CpG sites in the gene body are hypomethylated when compared with non-cancer cells. Provided that the methylation profile of the cancer cells could be reflected by the methylation profile of the tumor-derived plasma DNA molecules using methods herein described, we expect that the overall methylation profile in plasma would be different between individuals with cancer when compared with those healthy individuals without cancer or when compared with those whose cancer had been cured. The types of differences in the methylation profile could be in terms of quantitative differences in the methylation densities of the genome and/or methylation densities of segments of the genomes. For example, due to the general hypomethylated nature of DNA from cancer tissues (Gama-Sosa M A et al. 1983 Nucleic Acids Res; 11: 6883-6894), reduction in methylation densities in the plasma methylome or segments of the genome would be observed in plasma of cancer patients.

Qualitative changes in the methylation profile should also be reflected among the plasma methylome data. For example, plasma DNA molecules originating from genes that are hypermethylated only in cancer cells would show hypermethylation in plasma of a cancer patient when compared with plasma DNA molecules originating from the same genes but in a sample of a healthy control. Because aberrant methylation occurs in most cancers, the methods herein described could be applied to the detection of all forms of malignancies with aberrant methylation, for example, malignancies in, but not limited to, the lung, breast, colorectum, prostate, nasopharynx, stomach, testes, skin, nervous system, bone, ovary, liver, hematologic tissues, pancreas, uterus, kidney, lymphoid tissues, etc. The malignancies may be of a variety of histological subtypes, for example, carcinomas, adenocarcinomas, sarcomas, fibroadenocarcinoma, neuroendocrine, undifferentiated.

On the other hand, we expect that tumor-derived DNA molecules can be distinguished from the background non-tumor-derived DNA molecules because the overall short size profile of tumor-derived DNA is accentuated for DNA molecules originating from loci with tumor-associated aberrant hypomethylation which would have an additional effect on the size of the DNA molecule. Also, tumor-derived plasma DNA molecules can be distinguished from the background non-tumor-derived plasma DNA molecules using multiple characteristic features that are associated with tumor DNA, including but not limited to single nucleotide variants, copy number gains and losses, translocations, inversions, aberrant hyper- or hypo-methylation and size profiling. As all of these changes could occur independently, the combined use of these features may provide additive advantage for the sensitive and specific detection of cancer DNA in plasma.

A. Size and Cancer

The size of tumor-derived DNA molecules in plasma also resemble the sizes of mononucleosomal units and are shorter than the background non-tumor-derived DNA molecules, which co-exists in plasma of cancer patients. Size parameters have been shown to be correlated with cancer, as described in U.S. patent application Ser. No. 13/789,553, which is incorporated by reference for all purposes.

Since both fetal-derived and maternal-derived DNA in plasma showed a relationship between the size and methylation status of the molecule, tumor-derived DNA molecules are expected to exhibit the same trend. For example, the hypomethylated molecules would be shorter than the hyper-methylated molecules in the plasma of cancer patients or in subjects screened for cancer.

B. Methylation Densities of Different Tissues in a Cancer Patient

In this example, we analyzed the plasma and tissue samples of a hepatocellular carcinoma (HCC) patient. Blood samples were collected from the HCC patient before and at 1 week after surgical resection of the tumor. Plasma and buffy coat were harvested after centrifugation of the blood samples. The resected tumor and the adjacent non-tumor liver tissue were collected. The DNA samples extracted from the plasma and tissue samples were analyzed using massively parallel sequencing with and without prior bisulfite treatment. The plasma DNA from four healthy individuals without cancer was also analyzed as controls. The bisulfite treatment of a DNA sample would convert the unmethylated cytosine residues to uracil. In the downstream polymerase chain reaction and sequencing, these uracil residues would behave as thymidine. On the other hand, the bisulfite treatment would not convert the methylated cytosine residues to uracil. After massively parallel sequencing, the sequencing reads were analyzed by the Methy-Pipe (P. Jiang, et al. Methy-Pipe: An integrated bioinformatics data analysis pipeline for whole genome methylome analysis, paper presented at the IEEE International Conference on Bioinformatics and Biomedicine Workshops, Hong Kong, 18 to 21 Dec. 2010), to determine the methylation status of the cytosine residues at all CG dinucleotide positions, i.e CpG sites.

FIG. 21A is a table 2100 showing the methylation densities of the pre-operative plasma and the tissue samples of an HCC patient. The CpG methylation density for the regions of interest (e.g. CpG sites, promoter, or repeat regions etc.) refers to the proportion of reads showing CpG methylation over the total number of reads covering genomic CpG dinucleotides. The methylation densities of the buffy coat and the non-tumoral liver tissue are similar. The overall methylation density of the tumor tissue, based on data from all autosomes, was 25% lower than those of the buffy coat and the non-tumoral liver tissue. The hypomethylation was consistent across each individual chromosome. The methylation density of the plasma was between the values of the non-malignant tissues and the cancer tissues. This observation is consistent with the fact that both cancer and non-cancer tissues would contribute to the circulating DNA of a cancer patient. It has been shown that the hematopoietic system is the main source of the circulating DNA in individuals without an active malignant condition (Y. Y. Lui, et al. 2002 Clin Chem; 48: 421-7). We therefore also analyzed plasma samples obtained from four healthy controls. The number of sequence reads and the sequencing depth achieved per sample are shown in table 2150 of FIG. 21B.

FIG. 22 is a table 220 showing the methylation densities in the autosomes ranged from 71.2% to 72.5% in the plasma samples of the healthy controls. These data showed the expected level of DNA methylation in plasma samples obtained from individuals without a source of tumor DNA. In a cancer patient, the tumor-tissue would also release DNA into the circulation (K. C. Chan et al. 2013 Clin Chem; 59: 211-224); R. J. Leary et al. 2012 Sci Transl Med; 4: 162ra154). Due to the hypomethylated nature of the HCC tumor, the presence of both tumor- and non-tumor-derived DNA in the pre-operative plasma of the patient resulted in a reduction in the methylation density when compared with plasma levels of healthy controls. In fact, the methylation density of the pre-operative plasma sample was between the methylation densities of the tumor tissue and the plasma of the healthy controls. The reason is because the methylation level of the plasma DNA of cancer patients would be influenced by the degree of degree of aberrant methylation, hypomethylation in this case, of the tumor tissue and the fractional concentration of the tumor-derived DNA in the circulation. A lower methylation density of the tumor tissue and a higher fractional concentration of tumor-derived DNA in the circulation would lead to a lower methylation density of the plasma DNA in a cancer patient. Most tumors are reported to show global hypomethylation (J. G. Herman et al. 2003 N Engl J Med; 349: 2042-2054; Gama-Sosa M A et al. 1983 Nucleic Acids Res; 11: 6883-6894). Thus, the current observations seen in the HCC samples should also be applicable to other types of tumors.

In one embodiment, the methylation density of the plasma DNA can be used to determine the fractional concentration of tumor-derived DNA in a plasma/serum sample when the methylation level of the tumor tissue is known. The methylation level, e.g. methylation density, of the tumor tissue can be obtained if the tumor sample is available or a biopsy of the tumor is available. In another embodiment, the information regarding the methylation level of the tumor tissue can be obtained from survey of the methylation level in a group of tumors of a similar type and this information (e.g. a mean level or a median level) is applied to the patient to be analyzed using the technology described in this invention. The methylation level of the tumor tissue can be determined by the analysis of the tumor tissue of the patient or inferred from the analysis of the tumor tissues of other patients with the same or a similar cancer type. The methylation of tumor tissues can be determined using a range of methylation-aware platforms, including but not limited to massively parallel sequencing, single molecular sequencing, microarray (such as methylated cytosine immunoprecipitation or methylation-aware restriction enzyme digestion followed by microarray analysis, or oligonucleotide arrays), or mass spectrometry (such as the Epityper, Sequenom, Inc., analysis). When the methylation level of a tumor is known, the fractional concentration of tumor DNA in the plasma of cancer patients could be calculated after plasma methylome analysis.

The relationship between the plasma methylation level, P, with the fractional tumor DNA concentration, f, and the tumor tissue methylation level, TUM, can be described as: $P=BKG \times (1-f) + TUM \times f$, where BKG is the background DNA methylation level in plasma derived from blood cells and other internal organs. For example, the overall methylation density of all autosomes was shown to be 42.9% in the tumor biopsy tissue obtained from this HCC patient, i.e. the TUM value for this case. The mean methylation density of the plasma samples from the four healthy controls was 71.6%, i.e. the BKG value of this case. The plasma methylation density for the pre-operative plasma was 59.7%. Using these values, f is estimated to be 41.5%

In another embodiment, the methylation level of the tumor tissue can be estimated noninvasively based on the plasma methylome data when the fractional concentration of the tumor-derived DNA in the plasma sample is known. The fractional concentration of the tumor-derived DNA in the plasma sample can be determined by other genetic analysis, for example the genomewide analysis of allelic loss (GAAL) and the analysis of single nucleotide mutations as previously described (U.S. patent application Ser. No. 13/308,473; Chan K C et al. 2013 Clin Chem; 59: 211-24). The calculation is based on the same relationship described above except that in this embodiment, the value off is known and the value of TUM becomes the unknown. The deduction can be performed for the whole genome or for parts of the genome, similar to the data observed for the context of determining the placental tissue methylation level from maternal plasma data.

In another embodiment, one can use the inter-bin variation or profile in the methylation densities to differentiate subjects with cancer and those without cancer. The resolution of the methylation analysis can be further increased by dividing the genome into bins of a particular size, e.g., 1 Mb. In such an embodiment, the methylation density of each 1 Mb bin was calculated for the collected samples, e.g., buffy coat, the resected HCC tissue, the non-tumoral liver tissue adjacent to the tumor and the plasma collected before and after tumor resection. In another embodiment, the bin sizes do not need to be kept constant. In one implementation, the number of CpG sites is kept constant within each bin while the bin itself can vary in size.

Figure 23A:
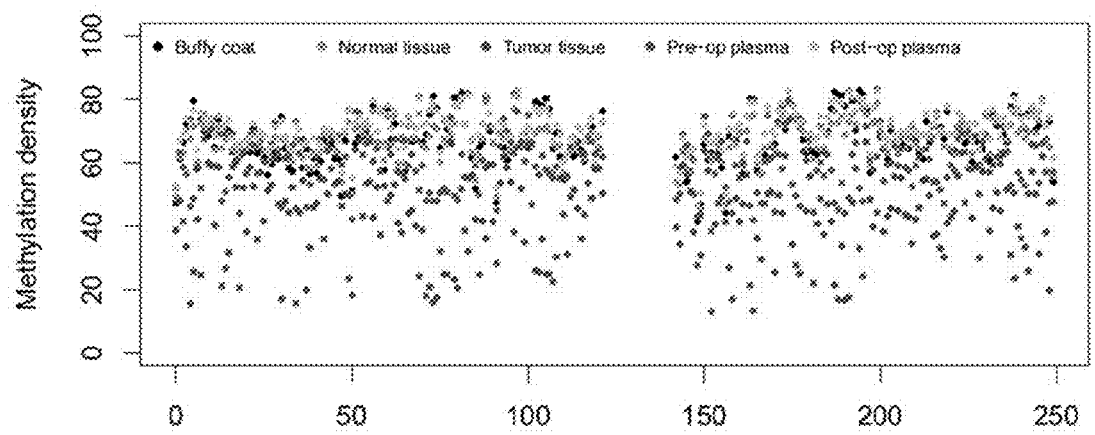
FIGS. 23A and 23B shows methylation density of buffy coat, tumor tissue, non-tumoral liver tissue, the pre-operative plasma and post-operative plasma of the HCC patient.
Figure 23B:
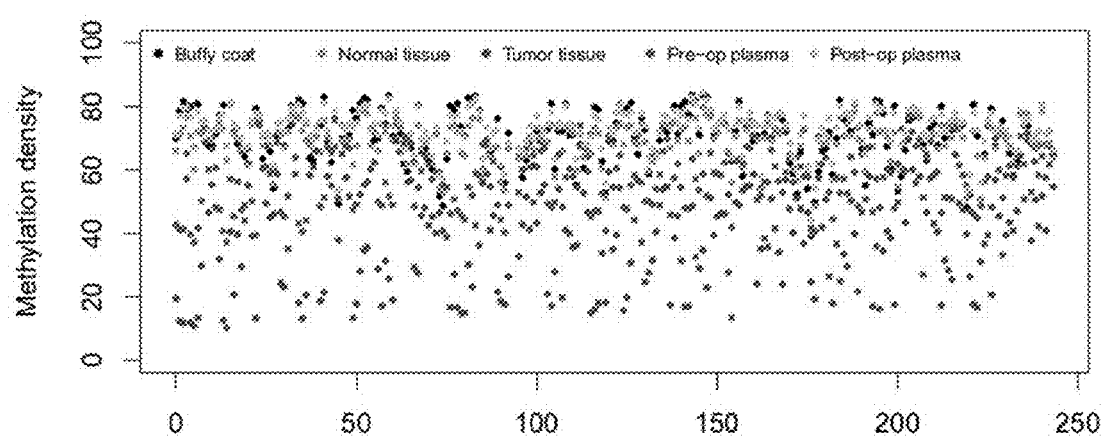

FIGS. 23A and 23B shows methylation density of buffy coat, tumor tissue, non-tumoral liver tissue, the pre-operative plasma and post-operative plasma of the HCC patient. FIG. 23A is a plot 2300 of results for chromosome 1. FIG. 23B is a plot 2350 of results for chromosome 2.

For most of the 1 Mb windows, the methylation densities for the buffy coat and the non-tumoral liver tissue adjacent to the tumor were similar whereas those of the tumor tissues were lower. Similar to the results in the whole chromosome analyses as shown in Table 1, the methylation densities of the pre-operative plasma lie between those of the tumor and the non-malignant tissues. The methylation densities of the interrogated genomic regions in the tumor tissues could be deduced using the methylation data of the pre-operative plasma and the fractional tumor DNA concentration. The method is same as described above using the methylations density values of all the autosomes. The deduction of the tumor methylation described can also be performed using this higher resolution methylation data of the plasma DNA. Other bin sizes, such as 300 kb, 500 kb, 2 Mb, 3 Mb, 5 Mb or more than 5 Mb can also be used. In one embodiment, the bin sizes do not need to be kept constant. In one implementation, the number of CpG sites is kept constant within each bin while the bin itself can vary in size.

C. Comparison of Plasma Methylation Density Between the Cancer Patient and Healthy Individuals As shown in 2100, the methylation densities of the pre-operative plasma DNA were lower than those of the non-malignant tissues in the cancer patient. This is likely to result from the presence of DNA from the tumor tissue which was hypomethylated. This lower plasma DNA methylation density can potentially be used as a biomarker for the detection and monitoring of cancer. For cancer monitoring, if a cancer is progressing, then there will be an increased amount of cancer-derived DNA in plasma with time. In this example, an increased amount of circulating cancer-derived DNA in plasma will lead to a further reduction in the plasma DNA methylation density on a genome wide level.

Conversely, if a cancer responds to treatment, then the amount of cancer-derived DNA in plasma will decrease with time. In this example, a decrease in the amount of cancer-derived DNA in plasma will lead to an increase in the plasma DNA methylation density. For example, if a lung cancer patient with epidermal growth factor receptor mutation has been treated with a targeted therapy, e.g. tyrosine kinase inhibition, then an increase in plasma DNA methylation density would signify a response. Subsequently, the emergence of a tumor clone resistant to tyrosine kinase inhibition would be associated with a decrease in plasma DNA methylation density which would indicate a relapse.

Plasma methylation density measurements can be performed serially and the rate of change of such measurements can be calculated and used to predict or correlate with clinical progression or remission or prognosis. For selected genomic loci which are hypermethylated in cancer tissues but hypomethylated in normal tissues, e.g. the promoter regions of a number of tumor suppressor genes, the relationship between cancer progression and favorable response to treatment will be opposite to the patterns described above.

To demonstrate the feasibility of this approach, we compared the DNA methylation densities of plasma samples collected from the cancer patient before and after surgical removal of the tumor with plasma DNA obtained from four healthy control subjects.

Table 2200 shows the DNA methylation densities of each autosome and the combined values of all autosomes of the pre-operative and post-operative plasma samples of the cancer patient and that of the four healthy control subjects. For all chromosomes, the methylation densities of the pre-operative plasma DNA sample was lower than the post-operative sample and the plasma samples from the four healthy subjects. The difference in the plasma DNA methylation densities between the pre-operative and post-operative samples provided supportive evidence that the lower methylation densities in the pre-operative plasma sample were due to the presence of DNA from the HCC tumor.

The reversal of the DNA methylation densities in the post-operative plasma sample levels similar to the plasma samples of the healthy controls suggested that much of the tumor-derived DNA had disappeared due to the surgical removal of the source, i.e. tumor. These data suggest that the methylation density of the pre-operative plasma as determined using data available from a large genomic regions, such as all autosomes or individual chromosomes, was of a lower methylation level than that of the healthy controls to allow the identification, i.e. diagnosis or screening, of the test case as having cancer.

The data of the pre-operative plasma also showed much lower methylation level than that of the post-operative plasma indicating that the plasma methylation level could also be used to monitor the tumor load, hence prognosticate and monitor the progress of cancer in the patient. Reference values can be determined from plasma of healthy controls or persons at-risk for the cancer but currently without cancer. Persons at risk for HCC include those with chronic hepatitis B or hepatitis C infection, those with hemochromatosis, and those with liver cirrhosis.

Plasma methylation density values beyond, for example lower than, a defined cutoff based on the reference values can be used to assess if a nonpregnant person's plasma has tumor DNA or not. To detect the presence of hypomethylated circulating tumor DNA, the cutoff can be defined as lower than the $5^{th}$ or $1^{st}$ percentiles of the values of the control population, or based on a number of standard deviations, for example, 2 or 3 standard deviations (SDs), below the mean methylation density values of the controls, or based on determining a multiple of the median (MoM). For hypermethylated tumor DNA, the cutoff can be defined as higher than the $95^{th}$ or $99^{th}$ percentile of the values of the control population, or based on a number of standard deviations, for example, 2 or 3 SDs, above the mean methylation density values of the controls, or based on determining a multiple of the median (MoM). In one embodiment, the control population is matched in age to the test subject. The age matching does not need to be exact and can be performed in age bands (e.g. 30 to 40 years, for a test subject of 35 years).

We next compared the methylation densities of 1 Mb bins between the plasma samples of the cancer patient and the four control subjects. For illustration purpose, the results of chromosome 1 are shown.

Figure 24A:
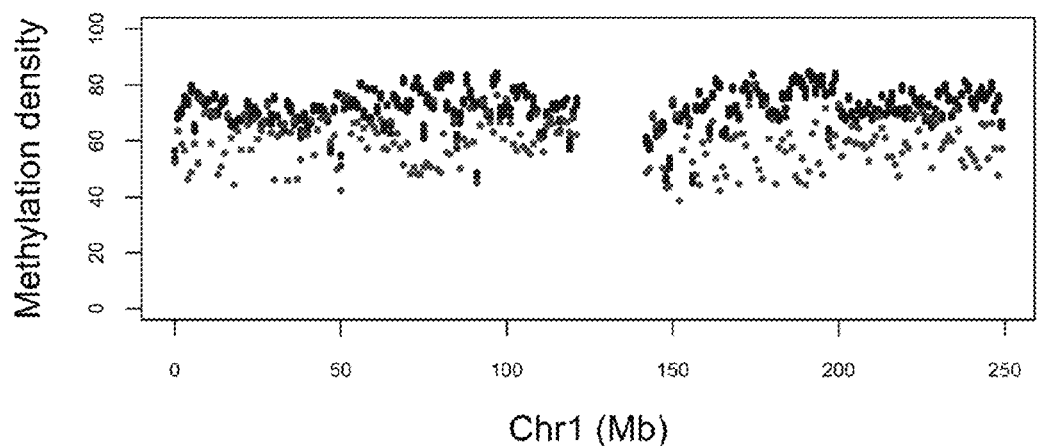
FIG. 24A is a plot 2400 showing the methylation densities of the pre-operative plasma from the HCC patient.
Figure 24B:
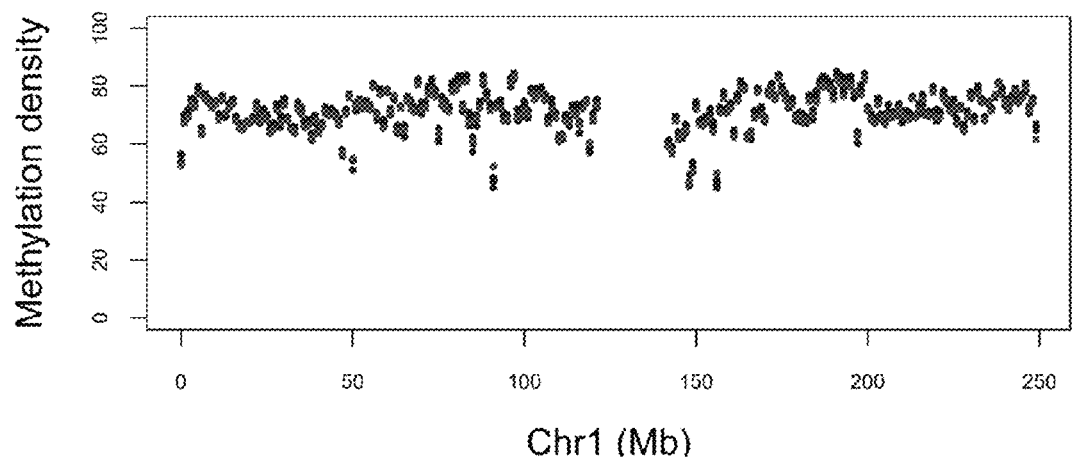
FIG. 24B is a plot 2450 showing the methylation densities of the post-operative plasma from the HCC patient.

FIG. 24A is a plot 2400 showing the methylation densities of the pre-operative plasma from the HCC patient. FIG. 24B is a plot 2450 showing the methylation densities of the post-operative plasma from the HCC patient. The blue dots represent the results of the control subjects, the red dots represent the results of the plasma sample of the HCC patient.

As shown in FIG. 24A, the methylation densities of the pre-operative plasma from the HCC patient were lower than those of the control subjects for most of the bins. Similar patterns were observed for other chromosomes. As shown in FIG. 24B, the methylation densities of the post-operative plasma from the HCC patient were similar to those of the control subjects for most of the bins. Similar patterns were observed for other chromosomes.

To assess if a tested subject is having cancer, the result of the tested subject would be compared to the values of a reference group. In one embodiment, the reference group can comprise of a number of healthy subjects. In another embodiment, the reference group can comprise of subjects with non-malignant conditions, for example, chronic hepatitis B infection or cirrhosis. The difference in the methylation densities between the tested subject and the reference group can then be quantified.

In one embodiment, a reference range can be derived from the values of the control group. Then deviations in the result of the tested subject from the upper or lower limits of the reference group can be used to determine if the subject has a tumor. This quantity would be affected by the fractional concentration of tumor-derived DNA in the plasma and the difference in the level of methylation between malignant and non-malignant tissues. Higher fractional concentration of tumor-derived DNA in plasma would lead to larger methylation density differences between the test plasma sample and the controls. A larger degree of difference in the methylation level of the malignant and non-malignant tissues are also associated with larger methylation density differences between the test plasma sample and the controls. In yet another embodiment, different reference groups are chosen for test subjects of different age ranges.

In another embodiment, the mean and SD of the methylation densities of the four control subjects were calculated for each 1 Mb bin. Then for corresponding bins, the difference between the methylation densities of the HCC patient and the mean value of the control subjects was calculated. In one embodiment, this difference was then divided by the SD of the corresponding bin to determine the z-score. In other words, the z-score represents the difference in methylation densities between the test and control plasma samples expressed as a number of SDs from the mean of the control subjects. A z-score >3 of a bin indicates that the plasma DNA of the HCC patient is more hypermethylated than the control subjects by more than 3 SDs in that bin whereas a z-score of <−3 in a bin indicates that the plasma DNA of the HCC patient is more hypomethylated than the control subjects by more than 3 SDs in that bin.

Figure 25A:
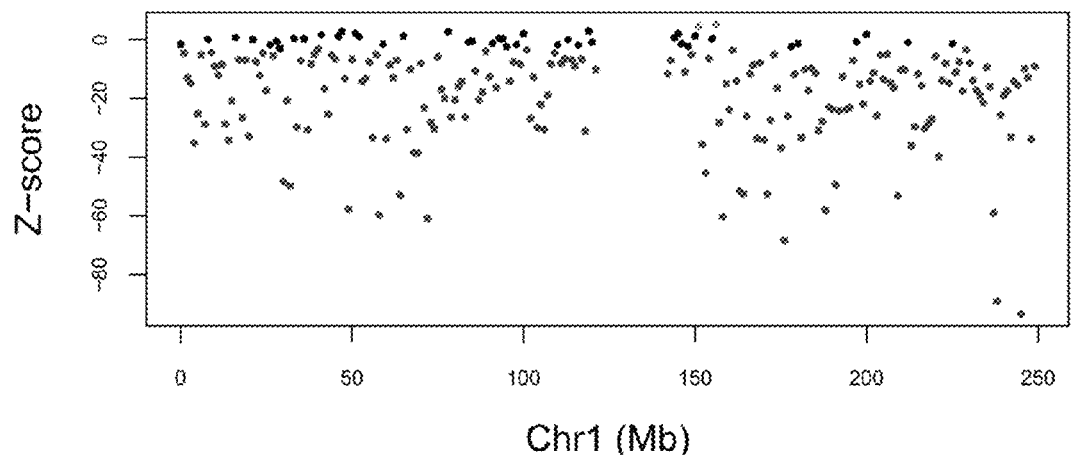
FIGS. 25A and 25B show z-scores of the plasma DNA methylation densities for the pre-operative (plot 2500) and post-operative (plot 2550) plasma samples of the HCC patient using the plasma methylome data of the four healthy control subjects as reference for chromosome 1.
Figure 25B:
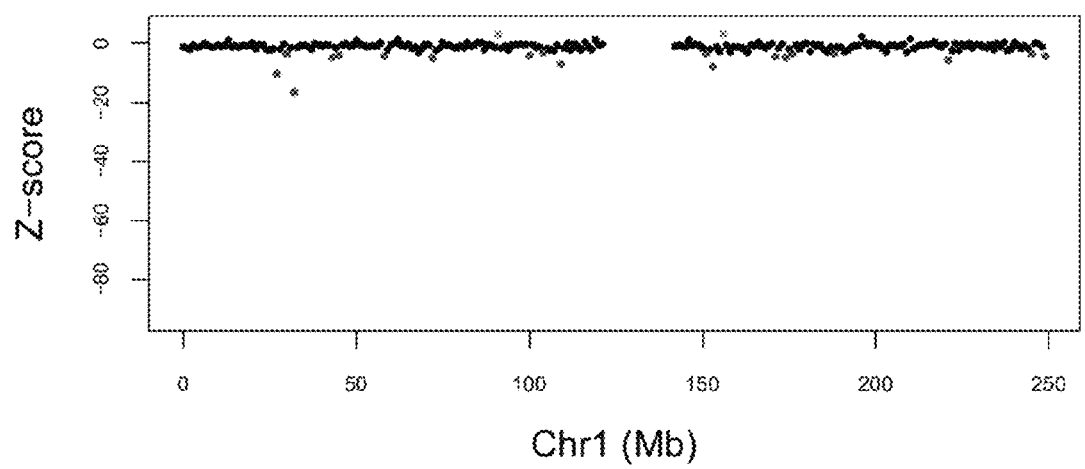

FIGS. 25A and 25B show z-scores of the plasma DNA methylation densities for the pre-operative (plot 2500) and post-operative (plot 2550) plasma samples of the HCC patient using the plasma methylome data of the four healthy control subjects as reference for chromosome 1. Each dot represents the result of one 1 Mb bin. The black dots represent the bins with z-score between −3 and 3. Red dots represent bins with z-score <−3.

Figures 26A, 26B:
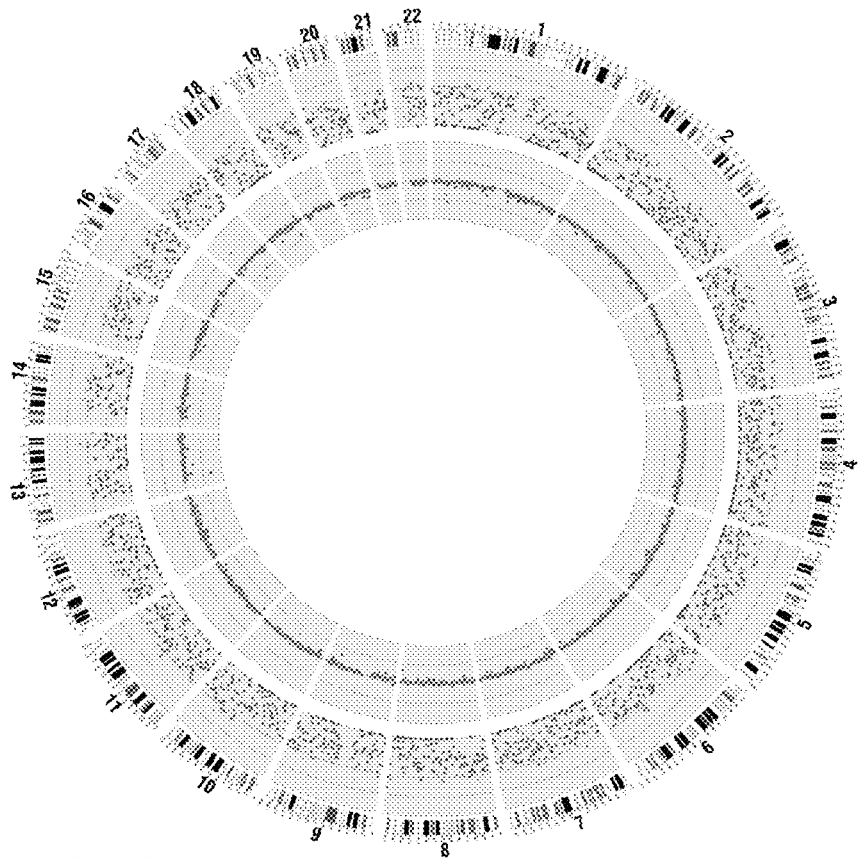
FIG. 26A is a table 2600 showing data for z-scores for pre-operative and post-operative plasma.
FIG. 26B is a Circos plot 2620 showing the z-score of the plasma DNA methylation densities for the pre-operative and post-operative plasma samples of the HCC patient using the four healthy control subjects as reference for 1 Mb bins analyzed from all autosomes.

FIG. 26A is a table 2600 showing data for z-scores for pre-operative and post-operative plasma. Most of the bins on chromosome 1 (80.9%) in the pre-operative plasma sample had a z-score of <−3 indicating that the pre-operative plasma DNA of the HCC patient was significantly more hypomethylated than that of the control subjects. On the contrary, the number of red dots decreased substantially in the post-operative plasma sample (8.3% of the bins on chromosome 1) suggesting that most of the tumor DNA had been removed from the circulation due to surgical resection of the source of circulating tumor DNA.

FIG. 26B is a Circos plot 2620 showing the z-score of the plasma DNA methylation densities for the pre-operative and post-operative plasma samples of the HCC patient using the four healthy control subjects as reference for 1 Mb bins analyzed from all autosomes. The outermost ring shows the ideograms of the human autosomes. The middle ring shows the data for the pre-operative plasma sample. The innermost ring shows that data for the post-operative plasma sample. Each dot represents the result of one 1 Mb bin. The black dots represent the bins with z-scores between −3 and 3. The red dots represent bins with z-scores <−3. The green dots represent bins with z-scores >3.

FIG. 26C is a table 2640 showing a distribution of the z-scores of the 1 Mb bins for the whole genome in both the pre-operative and post-operative plasma samples of the HCC patient. The results indicate that the pre-operative plasma DNA of the HCC patient was more hypomethylated than that of the controls for the majority of regions (85.2% of the 1 Mb bins) in the whole genome. On the contrary, majority of the regions (93.5% of the 1 Mb bins) in the post-operative plasma sample showed no significant hypermethylation or hypomethylation compared with controls. These data indicate that much of the tumor DNA, mainly hypomethylated in nature for this HCC, was no longer present in the post-operative plasma sample.

In one embodiment, the number, percentage or proportion of bins with z-scores <−3 can be used to indicate if a cancer is present. For example, as shown in table 2640, 2330 of the 2734 bins analyzed (85.2%) showed z-scores <−3 in the pre-operative plasma while only 171 of the 2734 analyzed bins (6.3%) showed z-scores <−3 in the post-operative plasma. The data indicated that the tumor DNA load in the pre-operative plasma was much higher than in the post-operative plasma.

The cutoff values of the number of bins may be determined using statistical methods. For example, approximately 0.15% of the bins would be expected to have a z-score of <−3 based on a normal distribution. Therefore, the cutoff number of bins can be 0.15% of the total number of bins being analyzed. In other words, if a plasma sample from a nonpregnant individual shows more than 0.15% of bins with z-scores <−3, there is a source of hypomethylated DNA in plasma, namely cancer. For example, 0.15% of the 2734 1 Mb bins that we have analyzed in this example is about 4 bins. Using this value as a cutoff, both the pre-operative and post-operative plasma samples contained hypomethylated tumor-derived DNA, though the amount is much more in the pre-operative plasma sample than the post-operative plasma sample. For the four healthy control subjects, none of the bins showed significant hypermethylation or hypomethylation.

In another embodiment, the cutoff number can be determined by receiver operator characteristic (ROC) curve analysis by analyzing a number of cancer patients and individuals without cancer. To further validate the specificity of this approach, a plasma sample from a patient seeking medical consultation for a non-malignant condition (C06) was analyzed. 1.1% of the bins had a z-score of <−3. In one embodiment, different thresholds can be used to classify different levels of disease status. A lower percentage threshold can be used to differentiate healthy status from benign conditions and a higher percentage threshold to differentiate benign conditions from malignancies.

In yet another embodiment, the sum of the z-scores for all the bins can be used to determine if cancer is present or used for the monitoring of the serial changes of the level of plasma DNA methylation. Due to the overall hypomethylated nature of tumor DNA, the sum of z-scores would be lower in plasma collected from an individual with cancer than healthy controls. The sum of z-scores for the pre- and post-operative plasma sample of the HCC patient were −49843.8 and −3132.13, respectively.

In other embodiments, other methods can be used to survey the methylation level of plasma DNA. For example, the proportion of methylated cytosine residues over the total content of cytosine residues can be determined using mass spectrometry (M. L. Chen et al. 2013 Clin Chem; doi: 10.1373/clinchem.2012.193938) or massively parallel sequencing. However, as most of the cytosine residues are not in the CpG dinucleotide context, the proportion of methylated cytosine among total cytosine residuals would be relatively small when compared to methylation levels estimated in the context of CpG dinucleotides. We determined the methylation level of the tissue and plasma samples obtained from the HCC patient as well as the four plasma samples obtained from the healthy controls. The methylation levels were measured in the context of CpGs, any cytosines, in CHG and CHH contexts using the genome-wide massively parallel sequencing data. H refers to adenine, thymine or cytosine residues.

FIG. 26D is a table 2660 showing the methylation levels of the tumor tissue and pre-operative plasma sample overlapped with some of the control plasma samples when using the CHH and CHG contexts. The methylation levels of the tumor tissue and pre-operative plasma sample were consistently lower when compared with the buffy coat, non-tumor liver tissue, post-operative plasma sample and healthy control plasma samples in both among the CpGs and unspecified cytosines. However, the data based on the methylated CpGs, i.e. methylation densities, showed a wider dynamic range than the data based on the methylated cytosines.

In other embodiments, the methylation status of the plasma DNA can be determined by methods using antibodies against methylated cytosine, for example, methylated DNA immunoprecipitation (MeDIP). However, the precision of these methods are expected to be inferior to sequencing-based methods because of the variability in antibody binding. In yet another embodiment, the level of 5-hydroxymethylcytosine in plasma DNA can be determined. In this regard, a reduction in the level of 5-hydroxymethylcytosine has been found to be an epigenetic feature of certain cancer, e.g. melanoma (C. G. Lian, et al. 2012 Cell; 150: 1135-1146).

Figure 27A:
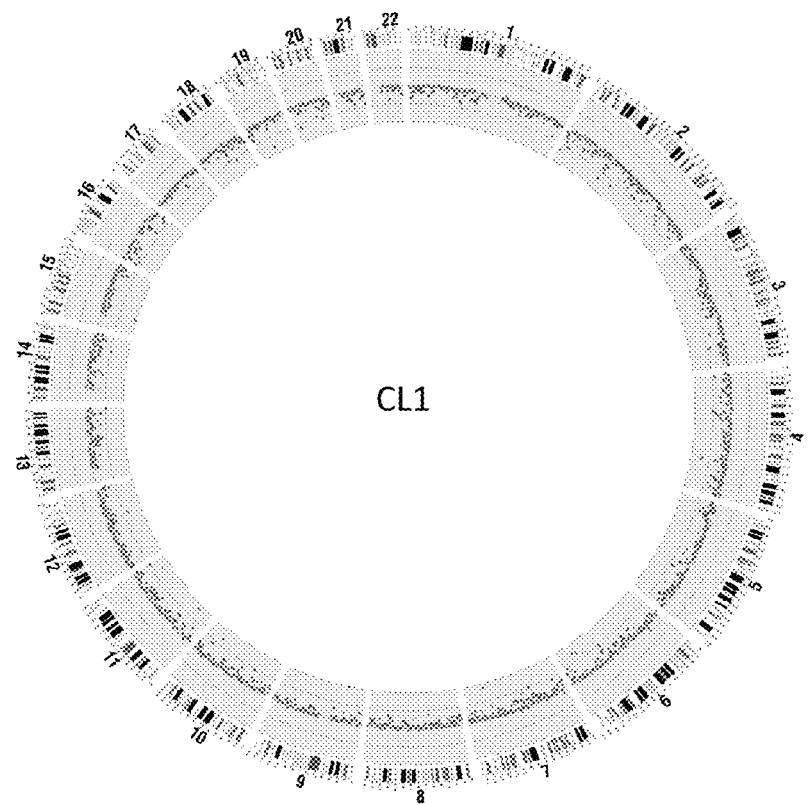
FIG. 27A-H show Circos plots of methylation density of 8 cancer patients according to embodiments of the present invention.
Figure 27B:
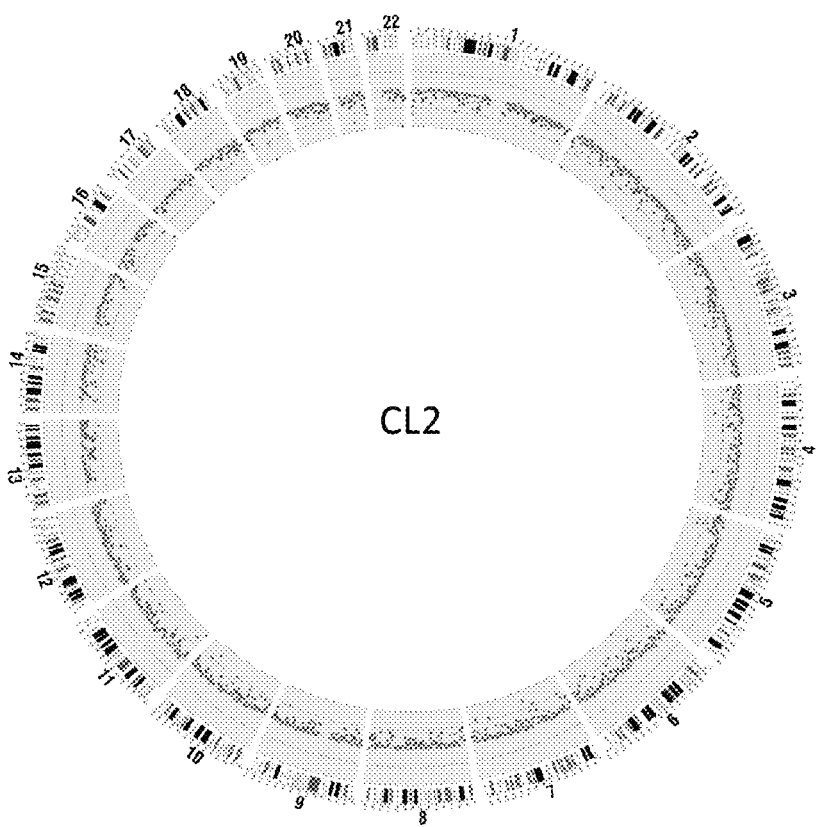
Figure 27C:
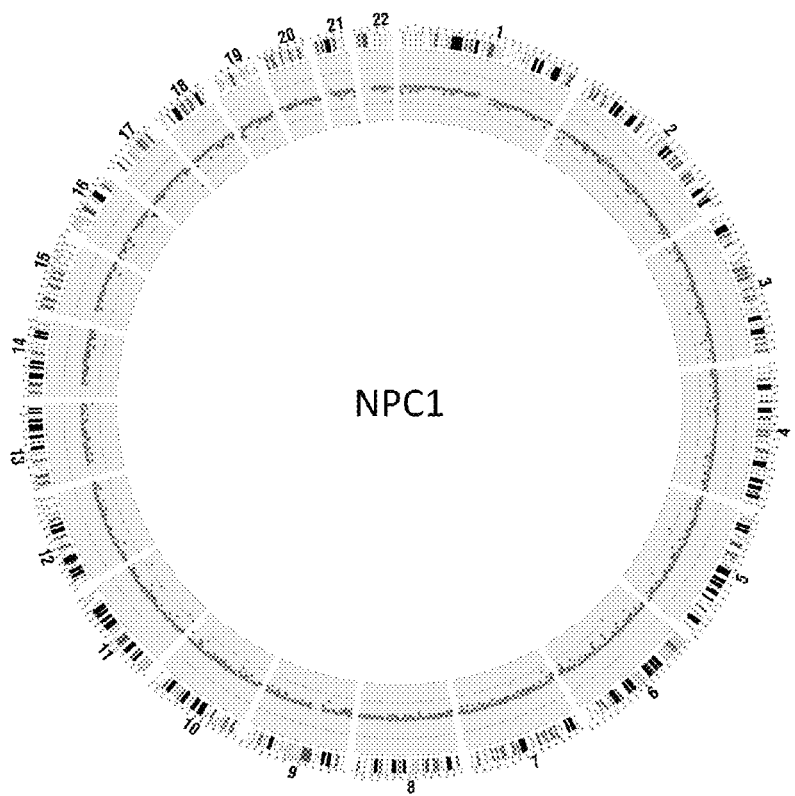
Figure 27D:
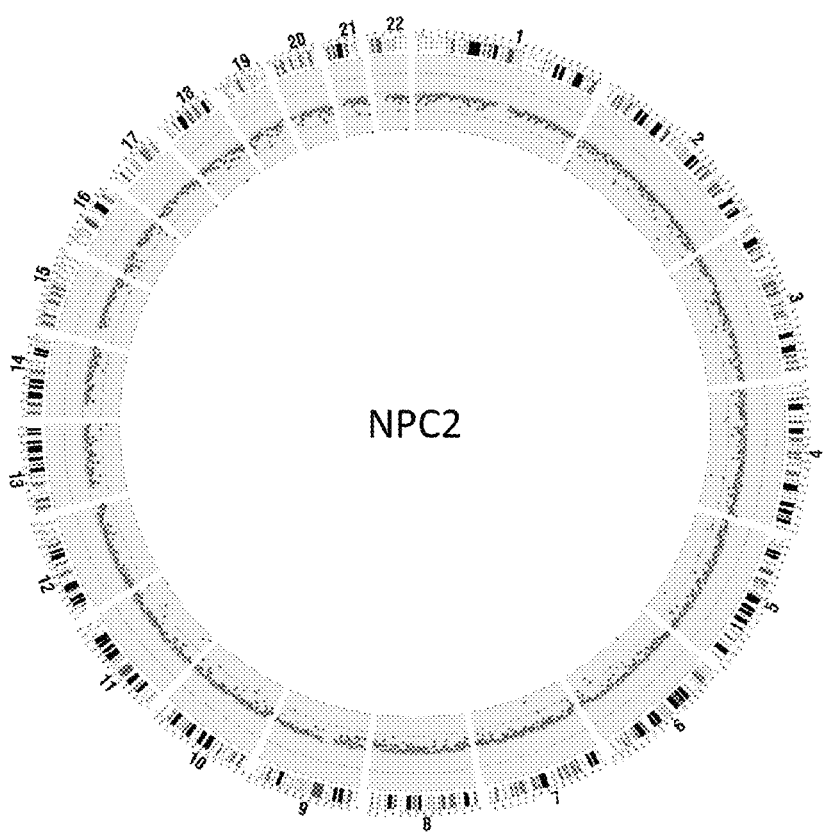
Figure 27E:
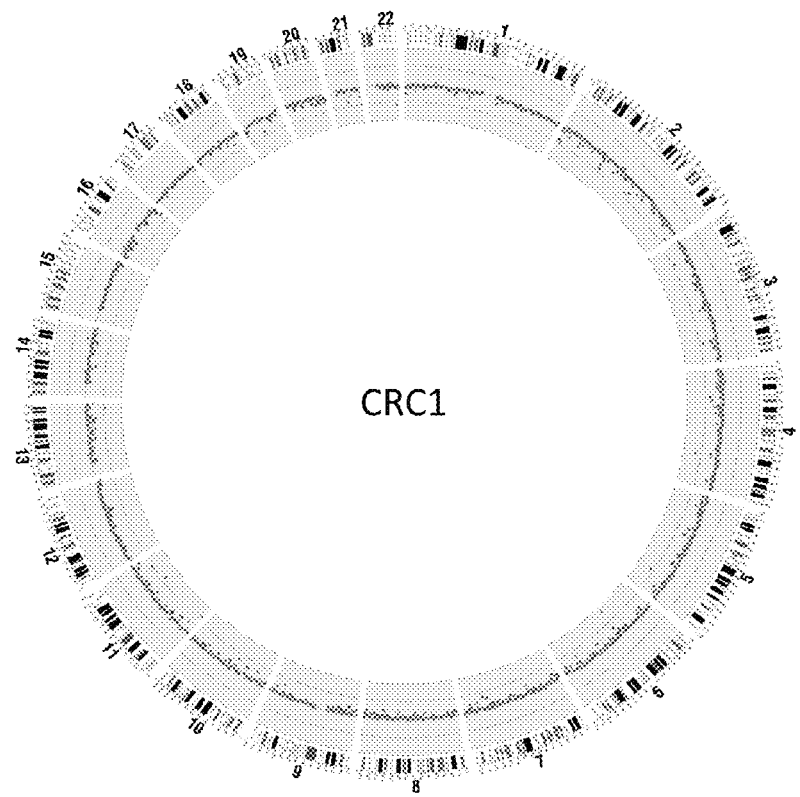
Figure 27F:
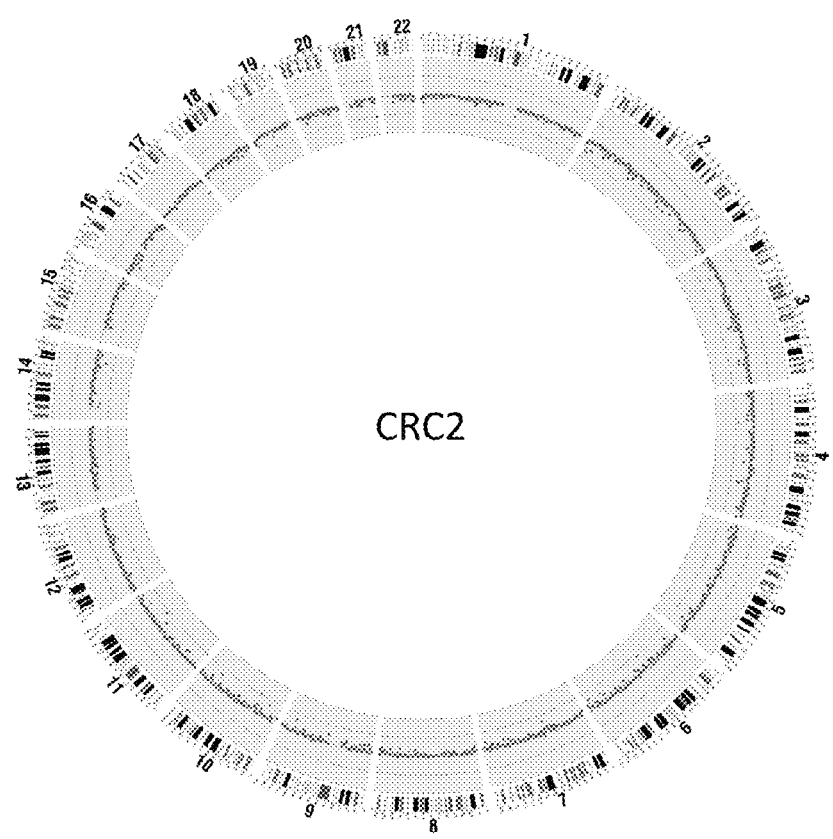
Figure 27G:
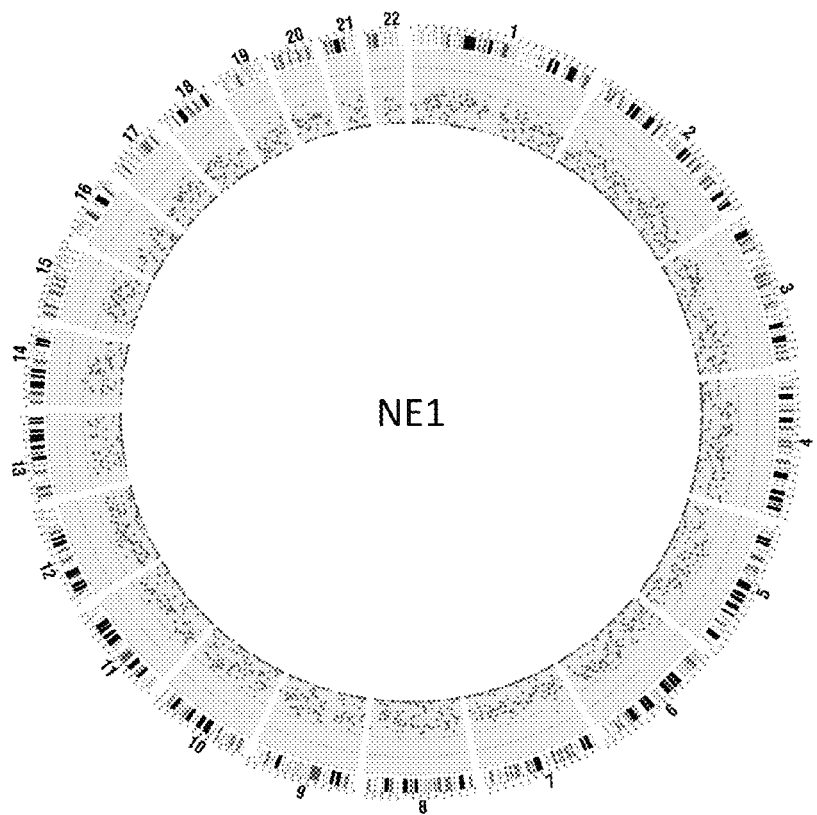
Figure 27H:
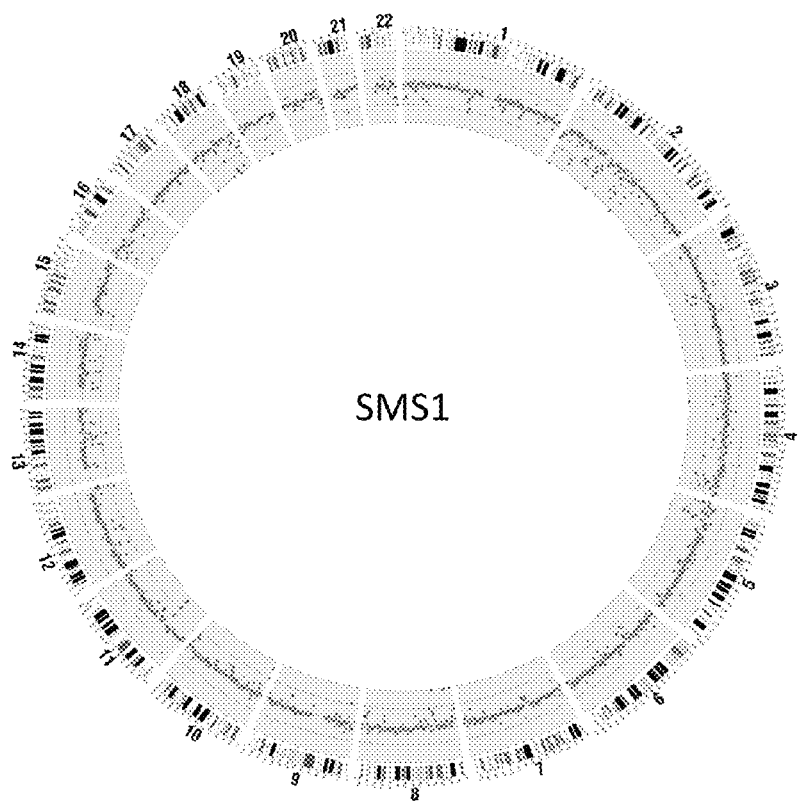

In addition to HCC, we also investigated if this approach could be applied to other types of cancers. We analyzed the plasma samples from 2 patients with adenocarcinoma of the lung (CL1 and CL2), 2 patients with nasopharyngeal carcinoma (NPC1 and NPC2), 2 patients with colorectal cancer (CRC1 and CRC2), 1 patient with metastatic neuroendocrine tumor (NE1) and 1 patient with metastatic smooth muscle sarcoma (SMS1). The plasma DNA of these subjects was bisulfite-converted and sequenced using the Illumina HiSeq2000 platform for 50 bp at one end. The four healthy control subjects mentioned above were used as a reference group for the analysis of these 8 patients. 50 bp of the sequence reads at one end were used. The whole genome was divided into 1 Mb bins. The mean and SD of methylation density were calculated for each bin using the data from the reference group. Then the results of the 8 cancer patients were expressed as z-scores which represent the number of SDs from the mean of the reference group. A positive value indicates that the methylation density of the test case is lower than the mean of the reference group, and vice versa. The number of sequence reads and the sequencing depth achieved per sample are shown in table 2780 of FIG. 27I.

FIG. 27A-H show Circos plots of methylation density of 8 cancer patients according to embodiments of the present invention. Each dot represents the result of a 1 Mb bin. The black dots represent the bins with z-scores between −3 and 3. The red dots represent bins with z-scores <−3. The green dots represent bins with z-scores >3. The interval between two consecutive lines represents a z-score difference of 20.

Significant hypomethylation was observed in multiple regions across the genomes for patients with most types of cancers, including lung cancer, nasopharyngeal carcinoma, colorectal cancer and metastatic neuroendocrine tumor. Interestingly, in addition to hypomethylation, significant hypermethylation was observed in multiple regions across the genome in the case with metastatic smooth muscle sarcoma. The embryonic origin of the smooth muscle sarcoma is the mesoderm whereas the embryonic origin of the other types of cancers in the remaining 7 patients is the ectoderm. Therefore, it is possible that the DNA methylation pattern of sarcoma may be different from that of carcinoma.

As can be seen from this case, the methylation pattern of plasma DNA can also be useful for differentiating different types of cancer, which in this example is a differentiation of carcinoma and sarcoma. These data also suggest that the approach could be used to detect aberrant hypermethylation associated with the malignancy. For all these 8 cases, only plasma samples were available and no tumor tissue had been analyzed. This showed that even without the prior methylation profile or methylation levels of the tumor tissue, tumor-derived DNA can be readily detected in plasma using the methods described.

FIG. 27J is a table 2790 is a table showing a distribution of the z-scores of the 1 Mb bins for the whole genome in plasma of patients with different malignancies. The percentages of bins with z-score <−3, −3 to 3 and >3 are shown for each case. More than 5% of the bins had a z-score of <−3 for all the cases. Therefore, if we use a cutoff of 5% of the bins being significantly hypomethylated for classifying a sample being positive for cancer, then all of these cases would be classified as positive for cancer. Our results show that hypomethylation is likely to be a general phenomenon for different types of cancers and the plasma methylome analysis would be useful for detecting different types of cancers.

D. Method

Figure 28:
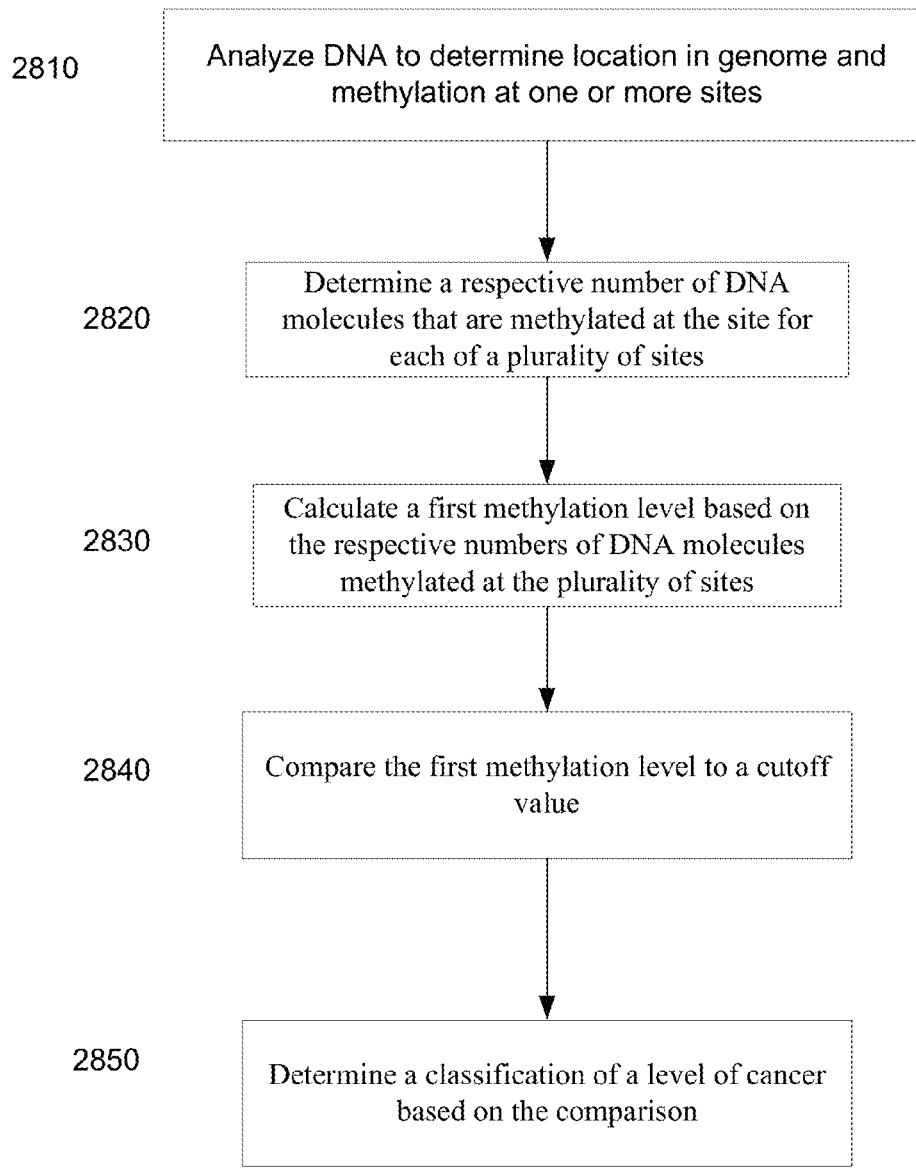
FIG. 28 is a flowchart of method 2800 of analyzing a biological sample of an organism to determine a classification of a level of cancer according to embodiments of the present invention.

FIG. 28 is a flowchart of method 2800 of analyzing a biological sample of an organism to determine a classification of a level of cancer according to embodiments of the present invention. The biological sample includes DNA originating from normal cells and may potentially include DNA from cells associated with cancer. At least some of the DNA may be cell-free in the biological sample.

At block 2810, a plurality of DNA molecules from the biological sample are analyzed. The analysis of a DNA molecule can include determining a location of the DNA molecule in a genome of the organism and determining whether the DNA molecule is methylated at one or more sites. The analysis can be performed by receiving sequence reads from a methylation-aware sequencing, and thus the analysis can be performed just on data previously obtained from the DNA. In other embodiments, the analysis can include the actual sequencing or other active steps of obtaining the data.

At block 2820, a respective number of DNA molecules that are methylated at the site is determined for each of a plurality of sites. In one embodiment, the sites are CpG sites, and may be only certain CpG sites, as selected using one or more criteria mentioned herein. The number of DNA that are methylated is equivalent to determining the number that are unmethylated once normalization is performed using a total number of DNA molecules analyzed at a particular site, e.g., a total number of sequence reads. For example, an increase in the CpG methylation density of a region is equivalent to a decrease in the density of unmethylated CpGs of the same region.

At block 2830, a first methylation level is calculated based on the respective numbers of DNA molecules methylated at the plurality of sites. The first methylation level can correspond to a methylation density that is determined based on the number of DNA molecules corresponding to the plurality of sites. The sites can correspond to a plurality of loci or just one locus.

At block 2840, the first methylation level is compared to a first cutoff value. The first cutoff value may be a reference methylation level or be related to a reference methylation level (e.g., a specified distance from a normal level). The reference methylation level may be determined from samples of individuals without cancer or from loci or the organism that are known to not be associated with a cancer of the organism. The first cutoff value may be established from a reference methylation level determined from a previous biological sample of the organism obtained previous to the biological sample being tested.

In one embodiment, the first cutoff value is a specified distance (e.g., a specified number of standard deviations) from a reference methylation level established from a biological sample obtained from a healthy organism. The comparison can be performed by determining a difference between the first methylation level and a reference methylation level, and then comparing the difference to a threshold corresponding to the first cutoff value (e.g., to determine if the methylation level is statistically different than the reference methylation level).

At block 2850, a classification of a level of cancer is determined based on the comparison. Examples of a level of cancer includes whether the subject has cancer or a premalignant condition, or an increased likelihood of developing cancer. In one embodiment, the first cutoff value may be determined from a previously obtained sample from the subject (e.g., a reference methylation level may be determined from the previous sample).

In some embodiments, the first methylation level can correspond to a number of regions whose methylation levels exceed a threshold value. For example, a plurality of regions of a genome of the organism can be identified. The regions can be identified using criteria mentioned herein, e.g., of certain lengths or certain number of sites. One or more sites (e.g., CpG sites) can be identified within each of the regions. A region methylation level can be calculated for each region. The first methylation level is for a first region. Each of the region methylation levels are compared to a respective region cutoff value, which may be the same or vary among regions. The region cutoff value for the first region is the first cutoff value. The respective region cutoff values can be a specified amount (e.g., 0.5) from a reference methylation level, thereby counting only regions that have a significant difference from a reference, which may be determined from non-cancer subjects.

A first number of regions whose region methylation level exceeds the respective region cutoff value can be determined, and compared to a threshold value to determine the classification. In one implementation, the threshold value is a percentage. Comparing the first number to a threshold value can include dividing the first number of regions by a second number of regions (e.g., all of the regions) before comparing to the threshold value, e.g., as part of a normalization process.

As described above, a fractional concentration of tumor DNA in the biological sample can be used to calculate the first cutoff value. The fractional concentration can simply be estimated to be greater than a minimum value, where as a sample with less can be flagged, e.g., as not being suitable for analysis. The minimum value can be determined based on an expected difference in methylation levels for a tumor relative to a reference methylation level. For example, if a difference if 0.5 (e.g., as used as a cutoff value), then a certain tumor concentration would be required to be high enough to see this difference.

Specific techniques from method 1300 can be applied for method 2800. In method 1300, copy number variations can be determined for a tumor (e.g., where the first chromosomal region of a tumor can be tested for having a copy number change relative to a second chromosomal region of the tumor). Thus, method 1300 can presume that a tumor exists. In method 2800, a sample can be tested for whether there is an indication of any tumor to exist at all, regardless of any copy number characteristics. Some techniques of the two methods can be similar. However, the cutoff values and methylation parameters (e.g., normalized methylation levels) for method 2800 can detect a statistical difference from a reference methylation level for non-cancer DNA as opposed to a difference from a reference methylation level for a mixture of cancer DNA and non-cancer DNA with some regions possibly having copy number variations. Thus, the reference values for method 2800 can be determined from samples without cancer, such as from organisms without cancer or from non-cancer tissue of the same patient (e.g., plasma taken previously or from contemporaneously acquired samples that are known to not have cancer, which may be determined from cellular DNA).

E. Prediction of the Minimal Fractional Concentration of Tumor-DNA to be Detected Using Plasma DNA Methylation Analysis One way to measure the sensitivity of the approach to detect cancer using the methylation level of plasma DNA is related to the minimal fractional tumor-derived DNA concentration that is required to reveal a change in plasma DNA methylation level when compared with those of controls. The test sensitivity is also dependent on the extent of difference in DNA methylation between the tumor tissue and baseline plasma DNA methylations levels in healthy controls or blood cell DNA. Blood cells are the predominant source of DNA in plasma of healthy individuals. The larger the difference, the easier the cancer patients can be discriminated from the non-cancer individuals and would be reflected as a lower detection limit of tumor-derived in plasma and a higher clinical sensitivity in detecting the cancer patients. In addition, the variations in the plasma DNA methylation in the healthy subjects or in subjects with different ages (G. Hannum et al. 2013 Mol Cell; 49: 359-367) would also affect the sensitivity of detecting the methylation changes associated with the presence of a cancer. A smaller variation in the plasma DNA methylation in the healthy subjects would make the detection of the change caused by the presence of a small amount of cancer-derived DNA easier.

Figure 29A:
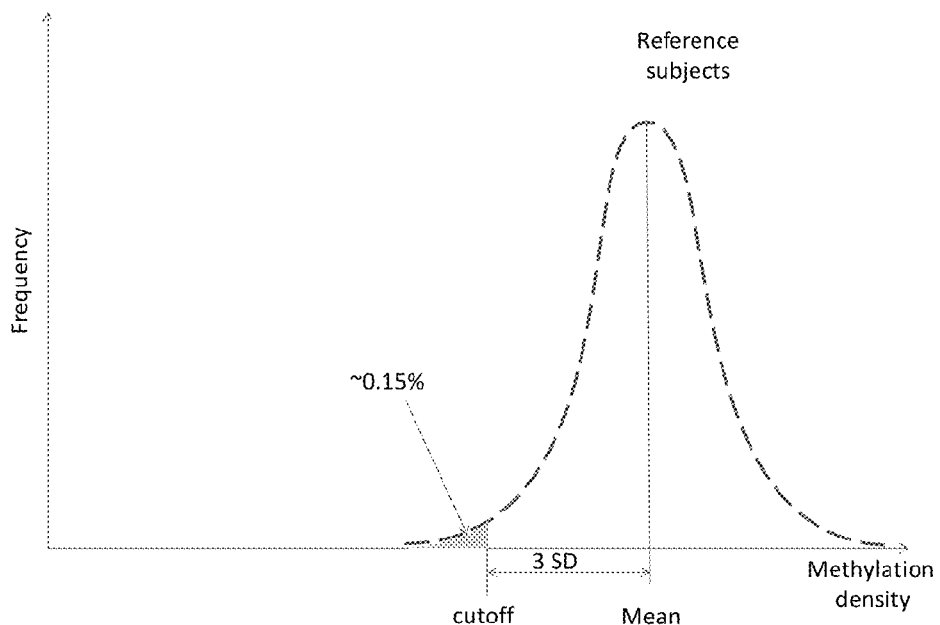
FIG. 29A is a plot 2900 showing the distribution of the methylation densities in reference subjects assuming that this distribution follows a normal distribution.

FIG. 29A is a plot 2900 showing the distribution of the methylation densities in reference subjects assuming that this distribution follows a normal distribution. This analysis is based on each plasma sample only provides one methylation density value, for example, the methylation density of all autosomes or of a particular chromosome. It illustrates how the specificity of the analysis would be affected. In one embodiment, a cutoff of 3 SDs below the mean DNA methylation density of the reference subjects is used to determine if a tested sample is significantly more hypomethylated than samples from the reference subjects. When this cutoff is used, it is expected that approximately 0.15% of non-cancer subjects would have false-positive results of being classified as having cancer resulting in a specificity of 99.85%.

Figure 29B:
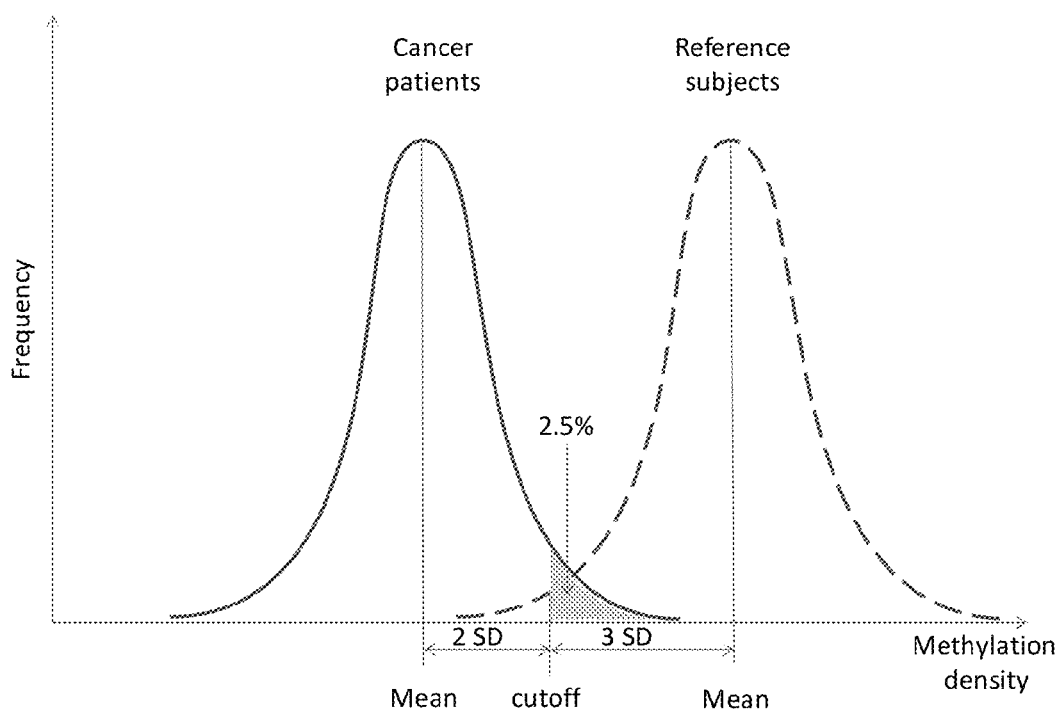
FIG. 29B is a plot 2950 showing the distribution of the methylation densities in cancer subjects assuming that this distribution follows a normal distribution and the mean methylation level is 2 standard deviations below the cutoff.

FIG. 29B is a plot 2950 showing the distributions of methylation densities in reference subjects and cancer patients. The cutoff value is 3 SDs below the mean of the methylation densities of the reference subjects. If the mean of methylation densities of the cancer patients is 2 SDs below the cutoff value (i.e. 5 SDs below the mean of the reference subjects), 97.5% of the cancer subjects would be expected to have a methylation density below the cutoff value. In other words, the expected sensitivity would be 97.5% if one methylation density value is provided for each subject, for example when the total methylation density of the whole genome, of all autosomes or a particular chromosome is analyzed. The difference between the mean methylation densities of the two populations is affected by two factors, namely the degree of difference in the methylation level between cancer and non-cancer tissues and the fractional concentration of tumor-derived DNA in the plasma sample. The higher the values of these two parameters, the higher the difference in value of the methylation densities of these two populations would be. In addition, the lower is the SD of the distributions of methylation densities of the two populations, the lesser is the overlapping of the distributions of the methylation densities of the two populations.

Here we use a hypothetical example to illustrate this concept. Let's assume that the methylation density of the tumor tissue is approximately 0.45 and that of the plasma DNA of the healthy subjects is approximately 0.7. These assumed values are similar to those obtained from our HCC patient where the overall methylation density of the autosomes is 42.9% and the mean methylation density of the autosomes for the plasma samples from healthy controls was 71.6% Assuming that the CV of measuring the plasma DNA methylation density for the whole genome is 1%, the cutoff value would be 0.7×(100%−3×1%)=0.679. To achieve a sensitivity of 97.5%, the mean methylation density of the plasma DNA for the cancer patients need to be approximately 0.679−0.7×(2×1%)=0.665. Let f represents the fractional concentration of tumor-derived DNA in the plasma sample. Then f can be calculated as (0.7−0.45)×f=0.7−0.665. Therefore, f is approximately 14%. From this calculation, it is estimated that the minimal fractional concentration that can be detected in the plasma is 14% so as to achieve a diagnostic sensitivity of 97.5% if the total methylation density of the whole genome is used as the diagnostic parameter.

Next we performed this analysis on the data obtained from the HCC patient. For this illustration, only one methylation density measurement based on the value estimated from all autosomes was made for each sample. The mean methylation density was 71.6% among the plasma samples obtained from the healthy subjects. The SD of the methylation densities of these four samples was 0.631%. Therefore, the cutoff value for plasma methylation density would need to be 71.6%−3×0.631%=69.7% to reach a z-score <−3 and a specificity of 99.85%. To achieve a sensitivity of a 97.5%, the mean plasma methylation density of the cancer patients would need to be 2 SDs below the cutoff, i.e. 68.4%. Since the methylation density of the tumor tissue was 42.9% and using the formula: P=BKG×(1−f)+TUM×f, f would need to be at least 11.1%.

In another embodiment, the methylation densities of different genomic regions can be analyzed separately as shown in FIG. 3 or 4. In other words, multiple measurements of the methylation level were made for each sample. As shown below, significant hypomethylation could be detected at much lower fractional tumor DNA concentration in plasma and thus the diagnostic performance of the plasma DNA methylation analysis for cancer detection would be enhanced. The number of genomic regions showing a significant deviation in methylation densities from the reference population can be counted. Then the number of genomic regions can be compared to a cutoff value to determine if there is an overall significant hypomethylation of plasma DNA across the population of genomic regions surveyed, for example, the 1 Mb bins of the whole genome. The cutoff value can be established by the analysis of a group of reference subjects without a cancer or derived mathematically, for example, according to normal distribution function.

Figure 30:
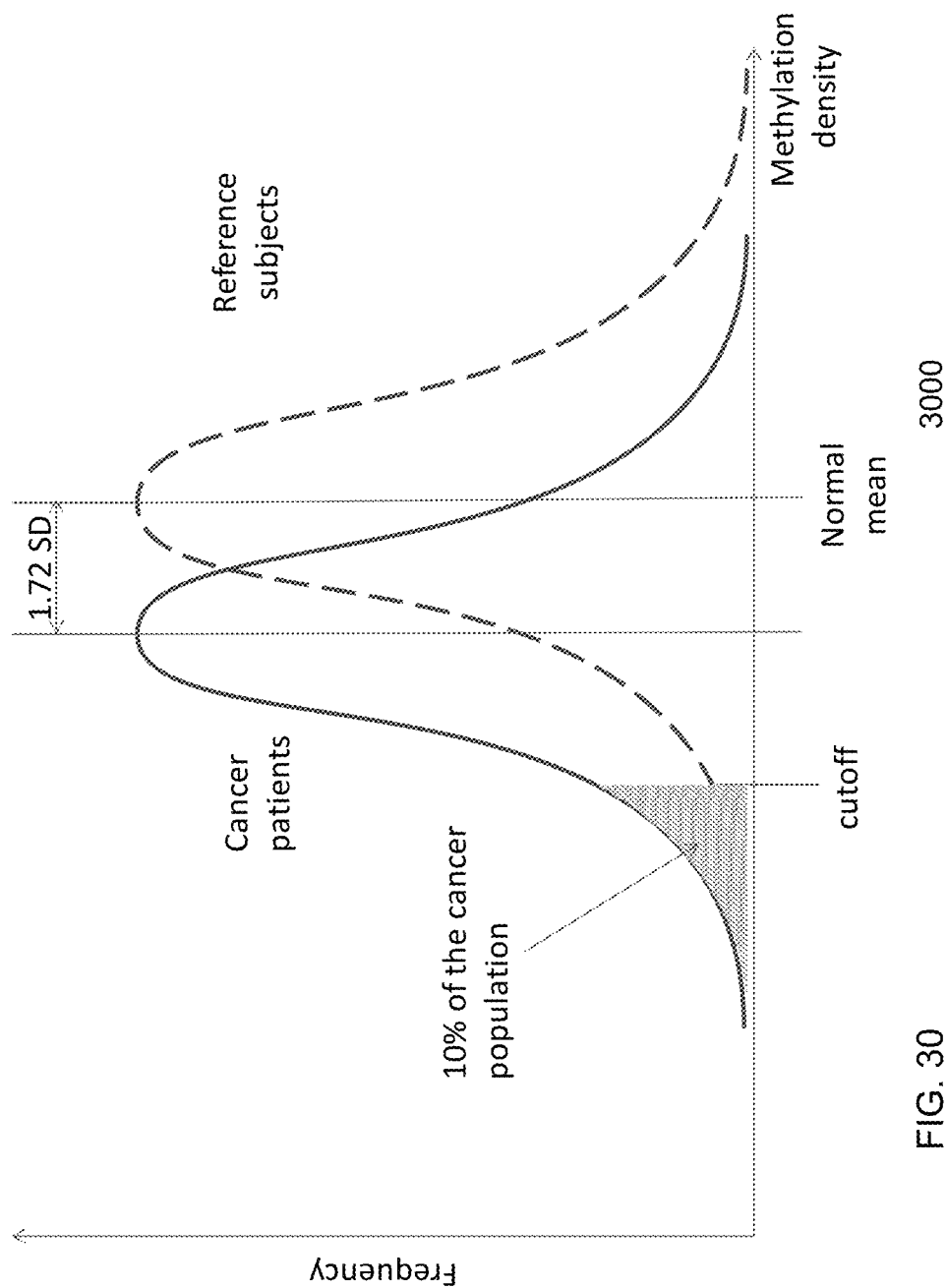
FIG. 30 is a plot 3000 showing the distribution of methylation densities of the plasma DNA of healthy subjects and cancer patients.

FIG. 30 is a plot 3000 showing the distribution of methylation densities of the plasma DNA of healthy subjects and cancer patients. The methylation density of each 1 Mb bin is compared with the corresponding values of the reference group. The percentage of bins showing significant hypomethylation (3 SDs below the mean of the reference group) was determined. A cutoff of 10% being significantly hypomethylated was used to determine if tumor-derived DNA is present in the plasma sample. Other cutoff values such as 5%, 15%, 20%, 25%, 30%, 35%, 40%, 45%, 50%, 60%, 70%, 80% or 90% can also be used according to the desired sensitivity and specificity of the test.

For example, to classify a sample as containing tumor-derived DNA, we can use 10% of the 1 Mb bins showing significant hypomethylation (z-score <−3) as a cutoff. If there are more than 10% of the bins being significantly more hypomethylated than the reference group, then the sample is classified as positive for the cancer test. For each 1 Mb bin, a cutoff of 3 SDs below the mean methylation density of the reference group is used to define a sample as significantly more hypomethylated. For each of the 1 Mb bins, if the mean plasma DNA methylation density of the cancer patients is 1.72 SDs lower than the mean plasma DNA methylation densities of the reference subjects, then there is a 10% chance that the methylation density value of any particular bin of a cancer patient would be lower than the cutoff (i.e. z-score <−3) and gives a positive result. Then, if we look at all the 1 Mb bins for the whole genome, then approximately 10% of the bins would be expected to show positive results of having significantly lower methylation densities (i.e. z-scores <−3). Assuming that the overall methylation density of the plasma DNA of the healthy subjects is approximately 0.7 and the coefficient of variation (CV) of measuring the plasma DNA methylation density for each 1 Mb bin is 1%, the mean methylation density of the plasma DNA of the cancer patients would need to be 0.7×(100%−1.72×1%)=0.68796. Let f be the fractional concentration of tumor-derived DNA in plasma so as to achieve this mean plasma DNA methylation density. Assuming that the methylation density of the tumor tissue is 0.45, then f can be calculated using the equation $$(\overline{M}_{P_{ref}} - M_{tumor}) \times f = \overline{M}_{P_{ref}} - \overline{M}_{P_{cancer}}$$

where $\overline{M}_{P_{ref}}$ represents the mean methylation density of plasma DNA in the reference individuals; $M_{tumor}$ represents the methylation density of the tumor tissue in the cancer patient; and $\overline{M}_{P_{cancer}}$ represents the mean methylation density of plasma DNA in the cancer patients Using this equation, $(0.7−0.45) \times f = 0.7−0.68796$. Thus, the minimal fractional concentration can be detected using this approach would be deduced as 4.8%. The sensitivity can be further enhanced by decreasing the cutoff percentage of bins being significantly more hypomethylated, for example, from 10% to 5%.

As shown in the above example, the sensitivity of this method is determined by the degree of difference in methylation level between cancer and non-cancer tissues, for example, blood cells. In one embodiment, only the chromosomal regions which show a large difference in methylation densities between the plasma DNA of the non-cancer subjects and the tumor tissue are selected. In one embodiment, only regions with a difference in methylation density of >0.5. In other embodiments a difference of 0.4, 0.6, 0.7, 0.8 or 0.9 can be used for selecting the suitable regions. In yet another embodiments, the physical size of the genomic regions is not fixed. Instead, the genomic regions are defined, for example, based on a fixed read depth or a fixed number of CpG sites. The methylation levels at a multiple of these genomic regions are assessed for each sample.

Figure 31:
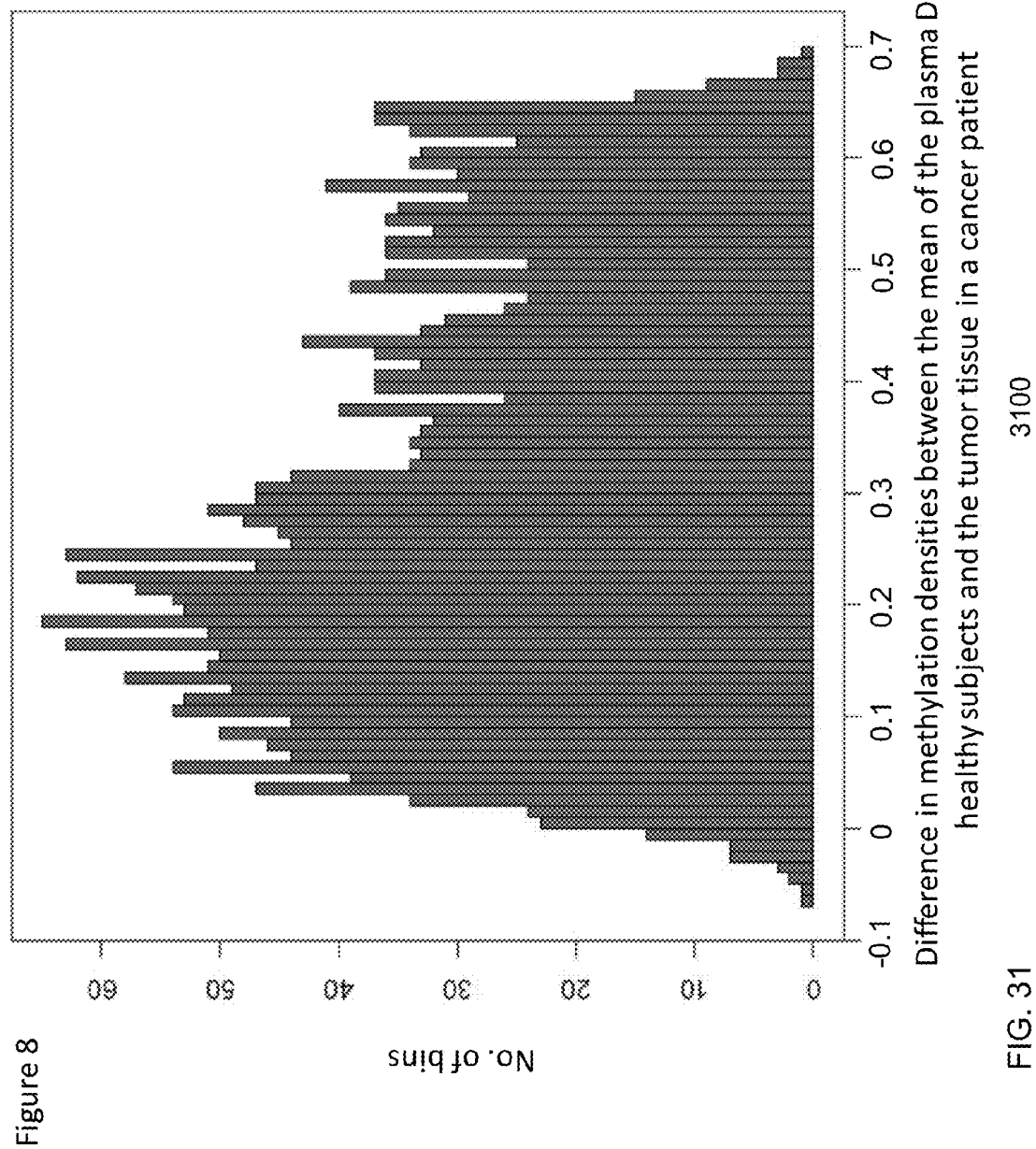
FIG. 31 is a graph 3100 showing the distribution of the differences in methylation densities between the mean of the plasma DNA of healthy subjects and the tumor tissue of the HCC patient.

FIG. 31 is a graph 3100 showing the distribution of the differences in methylation densities between the mean of the plasma DNA of healthy subjects and the tumor tissue of the HCC patient. A positive value signifies that the methylation density is higher in the plasma DNA of the healthy subjects and a negative value signifies that the methylation density is higher in the tumor tissue.

In one embodiment, the bins with the greatest difference between the methylation density of the cancer and non-cancer tissues can be selected, for example, those with a difference of >0.5, regardless of whether the tumor is hypomethylated or hypermethylated for these bins. The detection limit of fractional concentration of tumor-derived DNA in plasma can be lowered by focusing on these bins because of the greater differences between the distributions of the plasma DNA methylation levels between cancer and non-cancer subjects given the same fractional concentration of tumor-derived DNA in the plasma. For example, if only bins with differences >0.5 are used and a cutoff of 10% of the bins being significantly more hypomethylated is adopted to determine if a tested individual has a cancer, the minimal fractional concentration (f) of tumor derived DNA detected can be calculated using the following equation: $(\overline{M}_{P_{ref}} - M_{tumor}) \times f = \overline{M}_{P_{ref}} - \overline{M}_{P_{cancer}}$, where $\overline{M}_{P_{ref}}$ represents the mean methylation density of plasma DNA in the reference individuals; $M_{tumor}$ represents the methylation density of the tumor tissue in the cancer patient; and $\overline{M}_{P_{cancer}}$ represents the mean methylation density of plasma DNA in the cancer patients.

While the difference in methylation density between the plasma of the reference subjects and the tumor tissues is at least 0.5. Then, we have $0.5 \times f = 0.7 - 0.68796$ and f=2.4%. Therefore, by focusing on bins with a higher difference in methylation density between cancer and non-cancer tissues, the lower limit of fractional tumor-derived DNA can be lowered from 4.8% to 2.4%. The information regarding which bins would show larger degrees of methylation differences between cancer and non-cancer tissues, for example, blood cells, could be determined from tumor tissues of the same organ or same histological type obtained from other individuals.

In another embodiment, a parameter can be derived from the methylation density of the plasma DNA of all bins and taking into account the difference in methylation densities between cancer and non-cancer tissues. Bins with greater difference can be given a heavier weight. In one embodiment, the difference in methylation density between cancer and non-cancer tissue of each bin can directly be used as the weight if the particular bin in calculating the final parameter.

In yet another embodiment, different types of cancer may have different patterns of methylation in the tumor tissue. A cancer-specific weight profile can be derived from the degree of methylation of the specific type of cancer.

In yet another embodiment, the inter-bin relationship of methylation density can be determined in subjects with and without cancer. In FIG. 8, we can observe that in a small number of bins, the tumor tissues were more methylated than the plasma DNA of the reference subjects. Thus, the bins with the most extreme values of difference, e.g. difference >0.5 and difference <0, can be selected. The ratio of the methylation density of these bins can then be used to indicate if the tested individual has a cancer. In other embodiments, the difference and quotient of the methylation density of different bins can be used as parameters for indicating the inter-bin relationship.

We further assessed the detection sensitivity of the approach to detect or assess tumor using the methylation densities of multiple genomic regions as illustrated by the data obtained from the HCC patient. First, we mixed reads from the pre-operative plasma with those obtained from the plasma samples of the healthy controls to simulate plasma samples that contained fractional tumor DNA that ranged from 20% to 0.5%. We then scored the percentage of 1 Mb bins (out of 2,734 bins in the whole genome) with methylation densities equivalent to z-scores <−3. When the fractional tumor DNA concentration in plasma was 20%, 80.0% of the bins showed significant hypomethylation. The corresponding data for fractional tumor DNA concentration in plasma of 10%, 5%, 2%, 1% and 0.5% were 67.6%, 49.7%, 18.9%, 3.8% and 0.77% of the bins showing hypomethylation, respectively. Since the theoretical limit of the number of bins showing z-scores <−3 in the controls samples is 0.15%, our data show that there were still more bins (0.77%) beyond the theoretical cutoff limit even when the tumor fractional concentration was just 0.5%.

FIG. 32A is a table 3200 showing the effect of reducing the sequencing depth when the plasma sample contained 5% or 2% tumor DNA. A high proportion of bins (>0.15%) showing significant hypomethylation could still be detected when the mean sequencing depth was just 0.022 times the haploid genome.

FIG. 32B is a graph 3250 showing the methylation densities of the repeat elements and non-repeat regions in the plasma of the four healthy control subjects, the buffy coat, the normal liver tissue, the tumor tissue, the pre-operative plasma and the post-operative plasma samples of the HCC patient. It can be observed that the repeat elements were more methylated (higher methylation density) than the non-repeat regions in both cancer and non-cancer tissues. However, the difference in methylation between repeat elements and non-repeat regions was bigger in the non-cancer tissues and the plasma DNA of the healthy subjects when compared with the tumor tissues.

As a result, the plasma DNA of the cancer patient had a larger reduction in methylation density at the repeat elements than in the non-repeat regions. The difference in plasma DNA methylation density between the mean of the four healthy controls and the HCC patient was 0.163 and 0.088 for the repeat elements and the non-repeat regions, respectively. The data on the pre-operative and post-operative plasma samples also showed that the dynamic range in the change in methylation density was larger in the repeat than the non-repeat regions. In one embodiment, the plasma DNA methylation density of the repeat elements can be used for determining if a patient is affected by cancer or the monitoring of the disease progression.

As discussed above, the variation in methylation densities in the plasma of the reference subjects would also affect the accuracy of differentiating cancer patients from non-cancer individuals. The tighter the distribution of methylation densities (i.e. smaller standard deviation), the more accurate it would be to differentiate cancer and non-cancer subjects. In another embodiment, the coefficient of variation (CV) of the methylation densities of the 1 Mb bins can be used as a criterion for selecting the bins with low variability of plasma DNA methylation densities in the reference group. For example, only bins with CV<1% are selected. Other values, for example 0.5%, 0.75%, 1.25% and 1.5% can also be used as criteria for selecting the bins with low variability in methylation density. In yet another embodiment, the selection criteria can include both the CV of the bin and the difference in methylation density between cancer and non-cancer tissues.

The methylation density can also be used to estimate the fractional concentration of tumor-derived DNA in a plasma sample when the methylation density of the tumor tissue is known. This information can be obtained by the analysis of the tumor of the patient or from the survey of the tumors from a number of patients having the same type of cancer. As discussed above, the plasma methylation density (P) can be expressed using the following equation: $P = BKG \times (1-f) + TUM \times f$ where BKG is the background methylation density from the blood cells and other organs, TUM is the methylation density in the tumor tissue, and f is the fractional concentration of tumor-derived DNA in the plasma sample. This can be rewritten as:

$$f = \frac{BKG - P}{BKG - TUM}.$$

The values of BKG can be determined by analyzing the patient's plasma sample at a time point that the cancer is not present or from the survey of a reference group of individuals without cancer. Therefore, after measuring the plasma methylation density, f can be determined.

F. Combination

The methylation analysis approach described in this invention can be used in combination with other methods that are based on the genetic changes of tumor-derived DNA in plasma. Examples of such methods include the analysis for cancer-associated chromosomal aberrations (K. C. Chan et al. 2013 Clin Chem; 59:211-224; R. J. Leary et al. 2012 Sci Transl Med; 4:162ra154) and cancer-associated single nucleotide variations in plasma (K. C. Chan et al. 2013 Clin Chem; 59:211-224). There are advantages of the methylation analysis approach over those genetic approaches.

As shown in FIG. 21A, the hypomethylation of the tumor DNA is a global phenomenon involving regions distributed across almost the entire genome. Therefore, the DNA fragments from all chromosomal regions would be informative regarding the potential contribution of the tumor-derived hypomethylated DNA to the plasma/serum DNA in the patient. In contrast, chromosomal aberrations (either amplification or deletion of a chromosomal region) are only present in some chromosomal and the DNA fragments from the regions without a chromosome aberration in the tumor tissue would not be informative in the analysis (K. C. Chan et al. 2013 Clin Chem; 59: 211-224). Similarly only a few thousand of single nucleotide alterations are observed in each cancer genome (K. C. Chan et al. 2013 Clin Chem; 59: 211-224). DNA fragments that do not overlap with these single nucleotide changes would not be informative in determining if tumor-derived DNA is present in the plasma. Therefore, this methylation analysis approach is potentially more cost-effective than those genetic approaches for detecting cancer-associated changes in the circulation.

In one embodiment, the cost-effectiveness of plasma DNA methylation analysis can further be enhanced by enriching for DNA fragments from the most informative regions, for example regions with highest differential methylation difference between cancer and non-cancer tissues. Examples for the methods of enriching for these regions include the use of hybridization probes (e.g. Nimblegen SeqCap system and Agilent SureSelect Target Enrichment system), PCR amplification and solid phase hybridization (e.g. Illumina TruSeq Enrichment kit).

G. Tissue-Specific Analysis/Donors

Tumor-derived cells invade and metastasize to adjacent or distant organs. The invaded tissues or metastatic foci contribute DNA into plasma as a result of cell death. By analyzing the methylation profile of DNA in the plasma of cancer patients and detecting the presence of tissue-specific methylation signatures, one could detect the types of tissues that are involved in the disease process. This approach provides a noninvasive anatomic scan of the tissues involved in the cancerous process to aid in the identification of the organs involved as the primary and metastatic sites. Monitoring the relative concentrations of the methylation signatures of the involved organs in plasma would also allow one to assess the tumor burden of those organs and determine if the cancer process in that organ is deteriorating or improving or had been cured. For example, if a gene X is specifically methylated in the liver. Then, metastatic involvement of the liver by a cancer (e.g. colorectal cancer) will be expected to increase the concentration of methylated sequences from gene X in the plasma. There would also be another sequence or groups of sequences with similar methylation characteristics as gene X. One could then combine the results from such sequences. Similar considerations are applicable to other tissues, e.g. the brain, bones, lungs and kidneys, etc.

On the other hand, DNA from different organs is known to exhibit tissue-specific methylation signatures (B. W. Futscher et al. 2002 Nat Genet; 31:175-179; S. S. C. Chim et al. 2008 Clin Chem; 54: 500-511). Thus, methylation profiling in plasma can be used for elucidating the contribution of tissues from various organs into plasma. The elucidation of such contribution can be used for assessing organ damage, as plasma DNA is believed to be released when cells die. For example, liver pathology such as hepatitis (e.g. by viruses, autoimmune processes, etc) or hepatoxicity (e.g. drug overdose (such as by paracetamol) or toxins (such as alcohol) caused by drugs is associated with liver cell damage and will be expected to be associated with increased level of liver-derived DNA in plasma. For example, if a gene X is specifically methylated in the liver. Then, liver pathology will be expected to increase the concentration of methylated sequences from gene X in the plasma. Conversely, if a gene Y is specifically hypomethylated in the liver. Then, liver pathology will be expected to decrease the concentration of methylated sequences from gene Y in the plasma.

The present described approach could also be applied to the assessment of donor-derived DNA in the plasma of organ transplantation recipients (Y. M. D. Lo et al. 1998 Lancet; 351:1329-1330). Polymorphic differences between the donor and recipient had been used to distinguish the donor-derived DNA from the recipient-derived DNA in plasma (Y. W. Zheng et al. 2012 Clin Chem; 58: 549-558). We propose that tissue-specific methylation signatures of the transplanted organ could also be used as a method to detect the donor's DNA in the recipient's plasma.

By monitoring the concentration of the donor's DNA, one could noninvasively assess the status of the transplanted organ. For example, transplant rejection is associated with higher rate of cell death and hence the concentration of the donor's DNA, as reflected by the methylation signature of the transplanted organ, would be increased when compared with the time when the patient is in stable condition or when compared to other stable transplant recipients or healthy controls without transplantation. Similar to what has been described for cancer, the donor-derived DNA could be identified in the plasma of transplantation recipients by detecting for all or some of the characteristic features, including polymorphic differences, shorter size DNA for the transplanted solid organs (Y. W. Zheng et al. 2012 Clin Chem; 58: 549-558) and tissue-specific methylation profile.

IX. Materials and Methods

A. Preparation of Bisulfite-Treated DNA Libraries and Sequencing

Genomic DNA (5 µg) added with 0.5% (w/w) unmethylated lambda DNA (Promega) was fragmented by a Covaris 5220 System (Covaris) to approximately 200 bp in length. DNA libraries were prepared using the Paired-End Sequencing Sample Preparation Kit (Illumina) according to the manufacturer's instructions, except that methylated adapters (Illumina) were ligated to the DNA fragments. Following two rounds of purification using AMPure XP magnetic beads (Beckman Coulter), the ligation products were split into 2 portions, one of which was subjected to 2 rounds of bisulfite modification with an EpiTect Bisulfite Kit (Qiagen). Unmethylated cytosines at CpG sites in the inserts were converted to uracils while the methylated cytosines remained unchanged. The adapter-ligated DNA molecules, either treated or untreated with sodium bisulfite, were enriched by 10 cycles of PCR using the following recipe: 2.5 U PfuTurboCx hotstart DNA polymerase (Agilent Technologies), 1×PfuTurboCx reaction buffer, 25 µM dNTPs, 1 µl PCR Primer PE 1.0 and 1 µl PCR Primer PE 2.0 (Illumina) in a 50 µl-reaction. The thermocycling profile was: 95° C. for 2 min, 98° C. for 30 s, then 10 cycles of 98° C. for 15 s, 60° C. for 30 s and 72° C. for 4 min, with a final step of 72° C. for 10 min (R. Lister, et al. 2009 Nature 462, 315-322). The PCR products were purified using AMPure XP magnetic beads.

Plasma DNA extracted from 3.2-4 ml of maternal plasma samples was spiked with fragmented lambda DNA (25 pg per ml plasma) and subjected to library construction as described above (R. W. K. Chiu et al. 2011 BMJ; 342: c7401). After ligating to the methylated adapters, the ligation products were split into 2 halves and a portion was subjected to 2 rounds of bisulfite modification. The bisulfite-treated or untreated ligation products were then enriched by 10 cycles of PCR as described above.

Bisulfite-treated or untreated DNA libraries were sequenced for 75 bp in a paired-end format on HiSeq2000 instruments (Illumina). DNA clusters were generated with a Paired-End Cluster Generation Kit v3 on a cBot instrument (Illumina). Real-time image analysis and base calling were performed using the HiSeq Control Software (HCS) v1.4 and Real Time Analysis (RTA) Software v1.13 (Illumina), by which the automated matrix and phasing calculations were based on the spiked-in PhiX control v3 sequenced with the DNA libraries.

B. Sequence Alignment and Identification of Methylated Cytosines

After base calling, adapter sequences and low quality bases (i.e. quality score <20) on the fragment ends were removed. The trimmed reads in FASTQ format were then processed by a methylation data analysis pipeline called Methy-Pipe (P. Jiang, et al. Methy-Pipe: An integrated bioinformatics data analysis pipeline for whole genome methylome analysis, paper presented at the IEEE International Conference on Bioinformatics and Biomedicine Workshops, Hong Kong, 18 to 21 Dec. 2010). In order to align the bisulfite converted sequencing reads, we first performed in silico conversion of all cytosine residues to thymines, on the Watson and Crick strands separately, using the reference human genome (NCBI build 36/hg18). We then performed in silico conversion of each cytosine to thymine in all the processed reads and kept the position information of each converted residue. SOAP2 (R. Li, et al. 2009 Bioinformatics; 25: 1966-1967) was used to align the converted reads to the two pre-converted reference human genomes, with a maximum of two mismatches allowed for each aligned read. Only reads mappable to a unique genomic location were selected. Ambiguous reads which mapped to both the Watson and Crick strands and duplicated (clonal) reads which had the same start and end genomic positions were removed. Sequenced reads with insert size ≤600 bp were retained for the methylation and size analyses.

Cytosine residues in the CpG dinucleotide context were the major targets for the downstream DNA methylation studies. After alignment, the cytosines originally present on the sequenced reads were recovered based on the positional information kept during the in silico conversion. The recovered cytosines among the CpG dinucleotides were scored as methylated. Thymines among the CpG dinucleotides were scored as unmethylated. The unmethylated lambda DNA included during library preparation served as an internal control for estimating the efficiency of sodium bisulfite modification. All cytosines on the lambda DNA should have been converted to thymines if the bisulfite conversion efficiency was 100%.

X. Summary

With the use of embodiments described herein, one could screen, detect, monitor or prognosticate cancer noninvasively using for example the plasma of a subject. One could also carry out prenatal screening, diagnosis, investigation or monitoring of a fetus by deducing the methylation profile of fetal DNA from maternal plasma. To illustrate the power of the approach, we showed that information that was conventionally obtained via the study of placental tissues could be assessed directly from maternal plasma. For example, the imprinting status of gene loci, identification of loci with differential methylation between the fetal and maternal DNA and the gestational variation in the methylation profile of gene loci were achieved through the direct analysis of maternal plasma DNA. The major advantage of our approach is that the fetal methylome could be assessed comprehensively during pregnancy without disruption to the pregnancy or the need for invasive sampling of fetal tissues. Given the known association between altered DNA methylation status and the many pregnancy-associated conditions, the approach described in this study can serve as an important tool for investigating the pathophysiology of and the identification of biomarkers for those conditions. By focusing on the imprinted loci, we showed that both the paternally-transmitted as well as the maternally-transmitted fetal methylation profiles could be assessed from maternal plasma. This approach may potentially be useful for the investigation of imprinting diseases. Embodiments can also be applied directly for the prenatal assessment of fetal or pregnancy-associated diseases.

This is also the first study where genome-wide bisulfite sequencing has been applied to investigate the DNA methylation profile of placental tissues. There are approximately 28M CpG sites in the human genome (C. Clark, et al. 2012 PLoS One; 7: e50233). Our bisulfite sequencing data of the CVS and term placental tissue sample covered more than 80% of the CpGs. This represents a substantially broader coverage than those achievable using other high-throughput platforms. For example, the Illumina Infinium HumanMethylation 27K beadchip array that was used in a previous study on placental tissues (T. Chu, et al. 2011 PLoS One; 6: e14723). only covered 0.1% of the CpGs in the genome. The Illumina Infinium HumanMethylation 450K beadchip array that was available more recently only covered 1.7% of the CpGs (C. Clark, et al. 2012). Because the MPS approach is free from restrictions related to probe design, hybridization efficiency or strength of antibody capture, CpGs within or beyond CpG islands and in most sequence contexts could be assessed.

XI. Computer System

Figure 33:
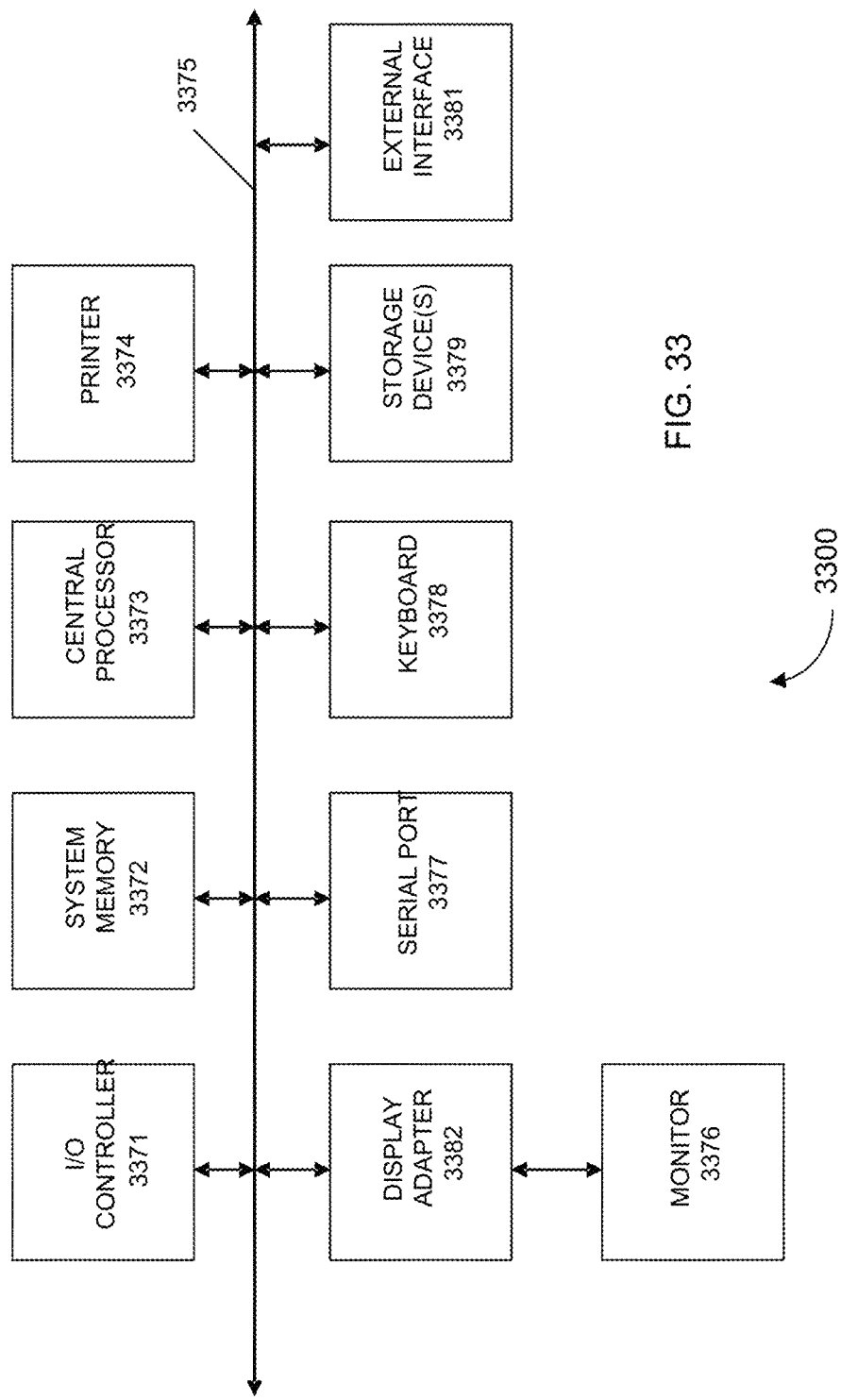
FIG. 33 shows a block diagram of an example computer system 3300 usable with system and methods according to embodiments of the present invention.

Any of the computer systems mentioned herein may utilize any suitable number of subsystems. Examples of such subsystems are shown in FIG. 33 in computer apparatus 3300. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 33 are interconnected via a system bus 3375. Additional subsystems such as a printer 3374, keyboard 3378, storage device(s) 3379, monitor 3376, which is coupled to display adapter 3382, and others are shown. Peripherals and input/output (I/O) devices, which couple to I/O controller 3371, can be connected to the computer system by any number of means known in the art, such as serial port 3377. For example, serial port 3377 or external interface 3381 (e.g. Ethernet, Wi-Fi, etc.) can be used to connect computer system 3300 to a wide area network such as the Internet, a mouse input device, or a scanner. The interconnection via system bus 3375 allows the central processor 3373 to communicate with each subsystem and to control the execution of instructions from system memory 3372 or the storage device(s) 3379 (e.g., a fixed disk), as well as the exchange of information between subsystems. The system memory 3372 and/or the storage device(s) 3379 may embody a computer readable medium. Any of the values mentioned herein can be output from one component to another component and can be output to the user.

A computer system can include a plurality of the same components or subsystems, e.g., connected together by external interface 3381 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

TABLE S2A

List of 100 most hypermethylated regions identified from first trimester chorionic villus sample and maternal blood cells.

| Chromosome | Start | End | Size (bp) | Maternal blood cells | CVS | P-values | Methylation Difference |
|---|---|---|---|---|---|---|---|
| chr13 | 113063600 | 113064100 | 500 | 0.009 | 0.9 | 3.67E−15 | 0.891 |
| chr6 | 36279700 | 36280200 | 500 | 0.0068 | 0.8957 | 2.39E−22 | 0.8889 |
| chr16 | 66876000 | 66876500 | 500 | 0.0327 | 0.9211 | 3.82E−21 | 0.8884 |
| chr10 | 163500 | 164000 | 500 | 0.0195 | 0.9034 | 3.60E−35 | 0.8839 |
| chr9 | 3518300 | 3518800 | 500 | 0.0263 | 0.9045 | 1.32E−26 | 0.8782 |
| chr12 | 31877100 | 31877600 | 500 | 0.007 | 0.8784 | 3.08E−22 | 0.8714 |
| chr22 | 37477400 | 37478400 | 1000 | 0.0152 | 0.8848 | 0.00E+00 | 0.8696 |
| chr4 | 148940500 | 148941000 | 500 | 0.0055 | 0.8717 | 4.40E−29 | 0.8662 |
| chr5 | 131836300 | 131836800 | 500 | 0.075 | 0.9403 | 1.54E−10 | 0.8653 |
| chr17 | 26661700 | 26663600 | 1900 | 0.0187 | 0.875 | 2.95E−38 | 0.8563 |
| chr2 | 105758600 | 105759600 | 1000 | 0.0305 | 0.8828 | 1.19E−53 | 0.8523 |
| chr22 | 39188800 | 39189800 | 1000 | 0 | 0.8514 | 2.05E−46 | 0.8514 |
| chr3 | 153443900 | 153444900 | 1000 | 0.0436 | 0.8945 | 5.43E−34 | 0.8509 |
| chr6 | 25149600 | 25150600 | 1000 | 0.0135 | 0.8632 | 0.00E+00 | 0.8497 |
| chr5 | 98296800 | 98297300 | 500 | 0.0432 | 0.8925 | 4.97E−23 | 0.8493 |
| chr7 | 150679900 | 150680400 | 500 | 0.0496 | 0.8944 | 6.50E−17 | 0.8448 |
| chr7 | 107563100 | 107563600 | 500 | 0.0495 | 0.8895 | 9.58E−26 | 0.84 |
| chr7 | 37348300 | 37349300 | 1000 | 0.0012 | 0.8409 | 0.00E+00 | 0.8397 |
| chr14 | 58837800 | 58838300 | 500 | 0.0097 | 0.848 | 3.35E−16 | 0.8383 |
| chr6 | 119238100 | 119238600 | 500 | 0.0899 | 0.928 | 2.38E−19 | 0.8381 |
| chr15 | 93669900 | 93670400 | 500 | 0.0753 | 0.913 | 2.19E−10 | 0.8377 |
| chr17 | 26669200 | 26670200 | 1000 | 0.0221 | 0.859 | 1.44E−29 | 0.8369 |
| chr2 | 88108100 | 88108600 | 500 | 0.075 | 0.9109 | 3.55E−17 | 0.8359 |
| chr13 | 98363800 | 98364300 | 500 | 0.11 | 0.9457 | 1.28E−11 | 0.8357 |
| chr16 | 66948000 | 66948500 | 500 | 0.0331 | 0.8685 | 0.00E+00 | 0.8354 |
| chr6 | 42098000 | 42098500 | 500 | 0.0484 | 0.8835 | 3.73E−16 | 0.8351 |

TABLE S2A-continued

List of 100 most hypermethylated regions identified from first trimester chorionic villus sample and maternal blood cells.

| Chromosome | Start | End | Size (bp) | Maternal blood cells | CVS | P-values | Methylation Difference |
|---|---|---|---|---|---|---|---|
| chr3 | 129876000 | 129876500 | 500 | 0.0565 | 0.8897 | 8.81E−17 | 0.8332 |
| chr3 | 142700300 | 142700800 | 500 | 0.0063 | 0.8393 | 2.59E−22 | 0.833 |
| chr8 | 145883800 | 145884300 | 500 | 0.0392 | 0.872 | 0.00E+00 | 0.8328 |
| chr10 | 8320700 | 8321200 | 500 | 0.0566 | 0.8871 | 9.40E−09 | 0.8305 |
| chr3 | 120438100 | 120438600 | 500 | 0.102 | 0.9292 | 7.09E−16 | 0.8272 |
| chr3 | 173792600 | 173793100 | 500 | 0.0182 | 0.8453 | 2.84E−39 | 0.8271 |
| chr17 | 40320700 | 40321200 | 500 | 0.0539 | 0.8788 | 6.50E−30 | 0.8249 |
| chr15 | 72076200 | 72076700 | 500 | 0.0299 | 0.8525 | 6.48E−10 | 0.8226 |
| chr16 | 29663900 | 29665400 | 1500 | 0.0081 | 0.8305 | 0.00E+00 | 0.8224 |
| chr11 | 66961100 | 66962100 | 1000 | 0.0489 | 0.8712 | 0.00E+00 | 0.8223 |
| chr9 | 27083100 | 27084100 | 1000 | 0.097 | 0.9177 | 2.37E−55 | 0.8207 |
| chr9 | 111249600 | 111250100 | 500 | 0.0613 | 0.8795 | 1.99E−20 | 0.8182 |
| chr14 | 101412400 | 101412900 | 500 | 0 | 0.8167 | 8.26E−32 | 0.8167 |
| chr1 | 242549200 | 242549700 | 500 | 0 | 0.8155 | 3.50E−21 | 0.8155 |
| chr8 | 38642800 | 38643300 | 500 | 0.0191 | 0.8346 | 3.22E−41 | 0.8155 |
| chr4 | 85893600 | 85894100 | 500 | 0.0394 | 0.8533 | 1.45E−15 | 0.8139 |
| chr5 | 142368600 | 142369100 | 500 | 0.0385 | 0.8523 | 1.18E−18 | 0.8138 |
| chr8 | 130969500 | 130970000 | 500 | 0.069 | 0.8824 | 2.42E−24 | 0.8134 |
| chr2 | 196783900 | 196784400 | 500 | 0 | 0.8123 | 3.63E−40 | 0.8123 |
| chr16 | 49258100 | 49258600 | 500 | 0.0733 | 0.8851 | 4.29E−18 | 0.8118 |
| chr1 | 232601200 | 232601700 | 500 | 0.0594 | 0.8707 | 1.73E−13 | 0.8113 |
| chr1 | 109039500 | 109040000 | 500 | 0.0366 | 0.8471 | 1.07E−11 | 0.8105 |
| chr17 | 59491300 | 59491800 | 500 | 0.0662 | 0.8758 | 2.15E−17 | 0.8096 |
| chr21 | 42194100 | 42194600 | 500 | 0.11 | 0.9182 | 1.61E−12 | 0.8082 |
| chr9 | 116174500 | 116175500 | 1000 | 0.0062 | 0.8132 | 1.98E−60 | 0.807 |
| chr15 | 73429200 | 73429700 | 500 | 0 | 0.8066 | 9.81E−33 | 0.8066 |
| chr6 | 157462800 | 157463300 | 500 | 0.0758 | 0.8819 | 7.94E−16 | 0.8061 |
| chr3 | 16858500 | 16859500 | 1000 | 0.0021 | 0.8068 | 4.76E−08 | 0.8047 |
| chr9 | 96662800 | 96663300 | 500 | 0.0614 | 0.8651 | 6.79E−28 | 0.8037 |
| chr9 | 88143000 | 88143500 | 500 | 0.1538 | 0.9559 | 7.43E−09 | 0.8021 |
| chr19 | 16090000 | 16091000 | 1000 | 0.0899 | 0.8904 | 1.60E−53 | 0.8005 |
| chr15 | 29436300 | 29437300 | 1000 | 0.0553 | 0.8559 | 1.18E−80 | 0.8003 |
| chr11 | 77816100 | 77816600 | 500 | 0.1069 | 0.9068 | 2.31E−17 | 0.7999 |
| chr10 | 30346800 | 30347300 | 500 | 0.1212 | 0.9211 | 7.48E−07 | 0.7999 |
| chr1 | 89510300 | 89511300 | 1000 | 0.0203 | 0.8191 | 3.53E−77 | 0.7988 |
| chr3 | 125986100 | 125986600 | 500 | 0.1686 | 0.9674 | 5.24E−22 | 0.7988 |
| chr19 | 60162800 | 60163300 | 500 | 0.0127 | 0.8113 | 9.99E−19 | 0.7986 |
| chr16 | 73655900 | 73656900 | 1000 | 0.082 | 0.8806 | 4.48E−41 | 0.7986 |
| chr16 | 30104300 | 30105800 | 1500 | 0.0298 | 0.8282 | 0.00E+00 | 0.7984 |
| chr10 | 118642400 | 118642900 | 500 | 0.0588 | 0.8571 | 8.63E−11 | 0.7983 |
| chr16 | 4495000 | 4496000 | 1000 | 0.0632 | 0.8615 | 2.27E−44 | 0.7983 |
| chr1 | 2048300 | 2048800 | 500 | 0.0309 | 0.8289 | 1.19E−80 | 0.798 |
| chr2 | 136481800 | 136482800 | 1000 | 0.0554 | 0.8533 | 8.50E−48 | 0.7979 |
| chr10 | 29959200 | 29959700 | 500 | 0.1429 | 0.94 | 2.60E−08 | 0.7971 |
| chr6 | 139642400 | 139642900 | 500 | 0.0618 | 0.8585 | 2.16E−29 | 0.7967 |
| chr14 | 69825300 | 69825800 | 500 | 0.0654 | 0.8615 | 6.85E−14 | 0.7961 |
| chr8 | 49739700 | 49740200 | 500 | 0.0324 | 0.828 | 2.88E−30 | 0.7956 |
| chr17 | 42205700 | 42206200 | 500 | 0.057 | 0.852 | 2.11E−30 | 0.795 |
| chr4 | 77445300 | 77445800 | 500 | 0.0442 | 0.8377 | 1.79E−35 | 0.7935 |
| chr17 | 53762700 | 53766300 | 3600 | 0.0003 | 0.7926 | 0.00E+00 | 0.7923 |
| chr17 | 44269900 | 44270400 | 500 | 0.026 | 0.8182 | 3.49E−21 | 0.7922 |
| chr6 | 42462700 | 42463200 | 500 | 0.0761 | 0.8678 | 4.74E−22 | 0.7917 |
| chr2 | 23396200 | 23396700 | 500 | 0.0333 | 0.8235 | 1.25E−14 | 0.7902 |
| chr9 | 100921100 | 100921600 | 500 | 0.0244 | 0.814 | 3.32E−21 | 0.7896 |
| chr7 | 74016100 | 74016600 | 500 | 0.1442 | 0.9333 | 6.74E−10 | 0.7891 |
| chr6 | 157879000 | 157879500 | 500 | 0.133 | 0.9219 | 6.36E−17 | 0.7889 |
| chr3 | 3189400 | 3190400 | 1000 | 0.0693 | 0.8571 | 1.38E−24 | 0.7878 |
| chr16 | 29581500 | 29584500 | 3000 | 0.0081 | 0.7956 | 0.00E+00 | 0.7875 |
| chr17 | 42201800 | 42202800 | 1000 | 0.0884 | 0.8751 | 0.00E+00 | 0.7867 |
| chr11 | 94257000 | 94257500 | 500 | 0.1122 | 0.8986 | 4.29E−10 | 0.7864 |
| chr10 | 14741600 | 14742100 | 500 | 0.0139 | 0.8 | 1.73E−20 | 0.7861 |
| chr21 | 33826900 | 33827400 | 500 | 0.0879 | 0.8739 | 2.81E−11 | 0.786 |
| chr4 | 130057200 | 130057700 | 500 | 0.0893 | 0.875 | 1.76E−13 | 0.7857 |
| chr21 | 35343400 | 35343900 | 500 | 0 | 0.7853 | 7.43E−18 | 0.7853 |
| chr12 | 105372800 | 105373300 | 500 | 0.0923 | 0.8767 | 8.67E−22 | 0.7844 |
| chr5 | 10799800 | 10800300 | 500 | 0.1429 | 0.9263 | 8.21E−17 | 0.7834 |
| chr5 | 16753100 | 16753600 | 500 | 0.041 | 0.8241 | 1.40E−15 | 0.7831 |
| chr3 | 135746000 | 135746500 | 500 | 0.1429 | 0.9259 | 2.86E−09 | 0.783 |
| chr6 | 53708300 | 53708800 | 500 | 0.0412 | 0.8235 | 2.74E−31 | 0.7823 |
| chr2 | 128122900 | 128123400 | 500 | 0.0634 | 0.8455 | 4.82E−21 | 0.7821 |
| chr5 | 150574200 | 150574700 | 500 | 0.0876 | 0.8696 | 1.56E−20 | 0.782 |
| chr16 | 84326000 | 84327000 | 1000 | 0.1071 | 0.8891 | 3.58E−61 | 0.782 |

TABLE S2A-continued

List of 100 most hypermethylated regions identified from first trimester chorionic villus sample and maternal blood cells.

| Chromosome | Start | End | Size (bp) | Maternal blood cells | CVS | P-values | Methylation Difference |
|---|---|---|---|---|---|---|---|
| chr1 | 26744500 | 26745500 | 1000 | 0.0336 | 0.8152 | 0.00E+00 | 0.7816 |
| chr2 | 234882000 | 234882500 | 500 | 0.0392 | 0.819 | 7.63E−14 | 0.7798 |

TABLE S2B

List of 100 most hypomethylated regions identified from first trimester chorionic villus sample and maternal blood cells.

| Chromosome | Start | End | Size (bp) | Maternal blood cells | CVS | P-values | Methylation Difference |
|---|---|---|---|---|---|---|---|
| chr18 | 12217500 | 12218500 | 1000 | 0.9873 | 0 | 3.05E−25 | 0.9873 |
| chr17 | 22885400 | 22885900 | 500 | 0.9714 | 0.0161 | 8.92E−12 | 0.9553 |
| chr3 | 184827100 | 184827600 | 500 | 0.9875 | 0.033 | 4.79E−16 | 0.9545 |
| chr5 | 148968300 | 148968800 | 500 | 0.98 | 0.0426 | 6.70E−09 | 0.9374 |
| chr10 | 104794500 | 104795000 | 500 | 0.973 | 0.0385 | 9.33E−10 | 0.9345 |
| chr4 | 84977900 | 84978400 | 500 | 0.9643 | 0.0417 | 2.98E−08 | 0.9226 |
| chr3 | 180395300 | 180395800 | 500 | 0.9877 | 0.0667 | 6.72E−08 | 0.921 |
| chr2 | 138908300 | 138908800 | 500 | 0.939 | 0.0208 | 1.10E−16 | 0.9182 |
| chr6 | 139873100 | 139873600 | 500 | 0.9667 | 0.0526 | 1.29E−07 | 0.914 |
| chr8 | 59604700 | 59605200 | 500 | 0.9468 | 0.033 | 2.88E−14 | 0.9138 |
| chr6 | 167622300 | 167622800 | 500 | 0.9452 | 0.0316 | 3.86E−14 | 0.9136 |
| chr3 | 175701300 | 175701800 | 500 | 0.9846 | 0.0735 | 7.43E−10 | 0.9111 |
| chr13 | 59246400 | 59246900 | 500 | 0.9402 | 0.0313 | 2.31E−11 | 0.9089 |
| chr12 | 71263600 | 71264100 | 500 | 0.9296 | 0.0213 | 1.08E−08 | 0.9083 |
| chr5 | 39459400 | 39459900 | 500 | 0.9219 | 0.014 | 5.01E−22 | 0.9079 |
| chr17 | 24904700 | 24905200 | 500 | 0.9161 | 0.0092 | 5.04E−35 | 0.9069 |
| chr12 | 31889900 | 31890400 | 500 | 0.9524 | 0.0465 | 6.78E−13 | 0.9059 |
| chr3 | 152897800 | 152898300 | 500 | 0.9402 | 0.0345 | 1.70E−17 | 0.9057 |
| chr1 | 40378700 | 40379200 | 500 | 0.9565 | 0.0526 | 3.31E−09 | 0.9039 |
| chr12 | 43979300 | 43979800 | 500 | 0.952 | 0.05 | 6.68E−13 | 0.902 |
| chr18 | 1395900 | 1397400 | 1500 | 0.9308 | 0.0293 | 0.00E+00 | 0.9015 |
| chr1 | 223482900 | 223483400 | 500 | 0.9579 | 0.0575 | 3.36E−24 | 0.9004 |
| chr9 | 130357000 | 130357500 | 500 | 0.9282 | 0.0286 | 9.19E−13 | 0.8996 |
| chr3 | 72878300 | 72878800 | 500 | 0.9612 | 0.0625 | 8.20E−14 | 0.8987 |
| chr7 | 84347200 | 84348700 | 1500 | 0.9401 | 0.0418 | 0.00E+00 | 0.8983 |
| chr15 | 37317500 | 37318000 | 500 | 0.9358 | 0.0385 | 7.58E−14 | 0.8973 |
| chr8 | 42528600 | 42529100 | 500 | 0.9302 | 0.0337 | 1.73E−14 | 0.8965 |
| chr6 | 134914000 | 134914500 | 500 | 0.9037 | 0.0076 | 4.84E−21 | 0.8961 |
| chr13 | 56207100 | 56208100 | 1000 | 0.9184 | 0.0245 | 0.00E+00 | 0.894 |
| chr2 | 209074000 | 209074500 | 500 | 0.9309 | 0.037 | 6.13E−27 | 0.8938 |
| chr12 | 74021100 | 74022100 | 1000 | 0.9513 | 0.058 | 0.00E+00 | 0.8933 |
| chr4 | 118939300 | 118939800 | 500 | 0.9192 | 0.0276 | 6.58E−27 | 0.8916 |
| chr5 | 12626600 | 12628600 | 2000 | 0.9266 | 0.0355 | 0.00E+00 | 0.8911 |
| chr5 | 105517300 | 105518300 | 1000 | 0.927 | 0.0359 | 0.00E+00 | 0.891 |
| chr12 | 70056300 | 70057300 | 1000 | 0.9488 | 0.0609 | 0.00E+00 | 0.888 |
| chr6 | 153238200 | 153239200 | 1000 | 0.9123 | 0.0244 | 0.00E+00 | 0.8879 |
| chr17 | 60374800 | 60375300 | 500 | 0.9655 | 0.0777 | 3.64E−14 | 0.8878 |
| chr14 | 68272700 | 68273200 | 500 | 0.9389 | 0.0523 | 1.23E−22 | 0.8866 |
| chr19 | 54533800 | 54534800 | 1000 | 0.9117 | 0.0262 | 0.00E+00 | 0.8855 |
| chr12 | 15392200 | 15393200 | 1000 | 0.9307 | 0.0457 | 0.00E+00 | 0.885 |
| chr1 | 212517400 | 212517900 | 500 | 0.9266 | 0.0417 | 9.81E−12 | 0.8849 |
| chr10 | 49344400 | 49345400 | 1000 | 0.9422 | 0.0579 | 0.00E+00 | 0.8844 |
| chr3 | 47410400 | 47410900 | 500 | 0.9213 | 0.0381 | 5.59E−16 | 0.8832 |
| chr3 | 879500 | 880000 | 500 | 0.9455 | 0.0625 | 8.06E−06 | 0.883 |
| chr2 | 31572400 | 31573400 | 1000 | 0.9176 | 0.0357 | 0.00E+00 | 0.8819 |
| chr1 | 89131200 | 89131700 | 500 | 0.9314 | 0.0498 | 5.15E−70 | 0.8816 |
| chr8 | 94832000 | 94832500 | 500 | 0.9156 | 0.0351 | 2.16E−65 | 0.8805 |
| chr7 | 14008300 | 14009800 | 1500 | 0.9349 | 0.0545 | 0.00E+00 | 0.8804 |
| chr12 | 12971300 | 12972300 | 1000 | 0.9361 | 0.0559 | 0.00E+00 | 0.8802 |
| chr5 | 43114700 | 43115200 | 500 | 0.9638 | 0.0842 | 1.79E−13 | 0.8796 |
| chr11 | 107872400 | 107872900 | 500 | 0.9472 | 0.0677 | 2.31E−32 | 0.8794 |
| chr8 | 49757600 | 49758100 | 500 | 0.9048 | 0.0269 | 3.15E−52 | 0.8779 |
| chr13 | 33106400 | 33106900 | 500 | 0.9384 | 0.0606 | 9.54E−15 | 0.8778 |
| chr3 | 190658800 | 190659300 | 500 | 0.9388 | 0.0617 | 2.71E−22 | 0.877 |
| chr1 | 181508000 | 181508500 | 500 | 0.9259 | 0.0495 | 3.78E−15 | 0.8764 |
| chr1 | 180436900 | 180437400 | 500 | 0.9412 | 0.0652 | 2.36E−13 | 0.876 |
| chr6 | 122642800 | 122643800 | 1000 | 0.9218 | 0.0458 | 0.00E+00 | 0.8759 |
| chr5 | 166429300 | 166429800 | 500 | 0.9551 | 0.08 | 5.26E−05 | 0.8751 |

TABLE S2B-continued

List of 100 most hypomethylated regions identified from first trimester chorionic villus sample and maternal blood cells.

| Chromosome | Start | End | Size (bp) | Maternal blood cells | CVS | P-values | Methylation Difference |
|---|---|---|---|---|---|---|---|
| chr12 | 14972900 | 14973400 | 500 | 0.9483 | 0.0733 | 2.10E−18 | 0.8749 |
| chr5 | 123933900 | 123934400 | 500 | 0.943 | 0.0683 | 1.12E−39 | 0.8746 |
| chr2 | 15969400 | 15970400 | 1000 | 0.8939 | 0.0196 | 9.43E−46 | 0.8743 |
| chr3 | 167635200 | 167636200 | 1000 | 0.9363 | 0.0625 | 9.03E−41 | 0.8738 |
| chr5 | 159442700 | 159443200 | 500 | 0.9174 | 0.044 | 6.27E−14 | 0.8734 |
| chr4 | 48027200 | 48027700 | 500 | 0.9839 | 0.1111 | 8.89E−06 | 0.8728 |
| chr6 | 140071500 | 140072000 | 500 | 0.9234 | 0.0506 | 4.39E−33 | 0.8728 |
| chr10 | 22356300 | 22356800 | 500 | 0.9548 | 0.0822 | 1.04E−18 | 0.8726 |
| chr8 | 61007300 | 61007800 | 500 | 0.9197 | 0.0476 | 1.24E−15 | 0.8721 |
| chr11 | 95463500 | 95464000 | 500 | 0.9348 | 0.0629 | 1.16E−20 | 0.8718 |
| chr2 | 216399800 | 216400300 | 500 | 0.938 | 0.0667 | 5.98E−06 | 0.8713 |
| chr18 | 57359700 | 57360200 | 500 | 0.9293 | 0.0584 | 1.77E−19 | 0.871 |
| chr3 | 102734400 | 102734900 | 500 | 0.8917 | 0.0207 | 7.94E−22 | 0.871 |
| chr1 | 173605700 | 173606200 | 500 | 0.96 | 0.0891 | 5.46E−13 | 0.8709 |
| chr2 | 86993700 | 86995700 | 2000 | 0.8965 | 0.0261 | 0.00E+00 | 0.8704 |
| chr3 | 162621100 | 162621600 | 500 | 0.9226 | 0.0526 | 7.89E−38 | 0.8699 |
| chr12 | 10144800 | 10145300 | 500 | 0.929 | 0.0598 | 3.45E−17 | 0.8691 |
| chr3 | 113855100 | 113855600 | 500 | 0.9667 | 0.0982 | 3.97E−14 | 0.8685 |
| chr2 | 156958200 | 156959200 | 1000 | 0.9252 | 0.0571 | 8.89E−50 | 0.8681 |
| chr2 | 55775000 | 55776000 | 1000 | 0.9159 | 0.0483 | 0.00E+00 | 0.8676 |
| chr6 | 124898400 | 124898900 | 500 | 0.8987 | 0.0313 | 1.91E−15 | 0.8675 |
| chr5 | 42003700 | 42004700 | 1000 | 0.9262 | 0.0588 | 0.00E+00 | 0.8674 |
| chr3 | 24162200 | 24162700 | 500 | 0.883 | 0.0161 | 1.75E−27 | 0.8668 |
| chr6 | 35394000 | 35395000 | 1000 | 0.9204 | 0.0539 | 0.00E+00 | 0.8665 |
| chr17 | 8451800 | 8453300 | 1500 | 0.9376 | 0.0714 | 0.00E+00 | 0.8662 |
| chr14 | 53487700 | 53488700 | 1000 | 0.9013 | 0.0353 | 0.00E+00 | 0.866 |
| chr7 | 98572800 | 98573300 | 500 | 0.9651 | 0.0995 | 8.37E−26 | 0.8656 |
| chr6 | 52298700 | 52299200 | 500 | 0.9427 | 0.0772 | 1.31E−28 | 0.8655 |
| chr6 | 159047900 | 159048400 | 500 | 0.908 | 0.0426 | 3.34E−08 | 0.8655 |
| chr14 | 22152600 | 22153100 | 500 | 0.9085 | 0.0435 | 4.43E−17 | 0.865 |
| chr12 | 103285000 | 103285500 | 500 | 0.9321 | 0.0674 | 0.00E+00 | 0.8647 |
| chr7 | 43302200 | 43302700 | 500 | 0.968 | 0.1037 | 6.40E−16 | 0.8643 |
| chr14 | 22247400 | 22247900 | 500 | 0.9804 | 0.1163 | 3.83E−06 | 0.8641 |
| chr2 | 66780900 | 66781400 | 500 | 0.9355 | 0.0714 | 8.37E−09 | 0.8641 |
| chr12 | 97393000 | 97393500 | 500 | 0.9045 | 0.0408 | 3.46E−21 | 0.8637 |
| chr5 | 162797900 | 162798900 | 1000 | 0.9271 | 0.0635 | 1.75E−57 | 0.8636 |
| chr2 | 83598400 | 83599400 | 1000 | 0.9354 | 0.0719 | 0.00E+00 | 0.8635 |
| chr11 | 111358800 | 111359300 | 500 | 0.9156 | 0.0523 | 4.15E−24 | 0.8632 |
| chr11 | 104891100 | 104892600 | 1500 | 0.9164 | 0.0533 | 0.00E+00 | 0.863 |
| chr1 | 184583600 | 184584100 | 500 | 0.9647 | 0.1026 | 3.02E−13 | 0.8621 |
| chr5 | 132350500 | 132351500 | 1000 | 0.9042 | 0.0426 | 1.86E−36 | 0.8616 |
| chr5 | 53268300 | 53268800 | 500 | 0.972 | 0.1111 | 4.76E−16 | 0.8609 |

TABLE S2C

List of 100 most hypermethylated regions identified from third trimester placental tissue and maternal blood cells.

| Chromosome | Start | End | Size (bp) | Maternal blood cells | Term placenta | P-values | Methylation Difference |
|---|---|---|---|---|---|---|---|
| chr4 | 78129700 | 78130200 | 500 | 0.0488 | 0.9747 | 3.97E−33 | 0.926 |
| chr5 | 131467400 | 131467900 | 500 | 0.0213 | 0.9275 | 7.10E−27 | 0.9063 |
| chr17 | 26661700 | 26663600 | 1900 | 0.0187 | 0.9226 | 1.79E−41 | 0.9039 |
| chr4 | 148940500 | 148941000 | 500 | 0.0055 | 0.9079 | 1.82E−29 | 0.9024 |
| chr9 | 100921100 | 100921600 | 500 | 0.0244 | 0.9242 | 1.38E−25 | 0.8998 |
| chr6 | 137114200 | 137114700 | 500 | 0 | 0.8934 | 8.87E−14 | 0.8934 |
| chr3 | 173792600 | 173793100 | 500 | 0.0182 | 0.9091 | 1.70E−42 | 0.8908 |
| chr5 | 98296800 | 98297300 | 500 | 0.0432 | 0.9333 | 2.58E−23 | 0.8901 |
| chr12 | 44898000 | 44898500 | 500 | 0 | 0.8889 | 4.47E−11 | 0.8889 |
| chr3 | 197328900 | 197329400 | 500 | 0.0169 | 0.9048 | 5.55E−10 | 0.8878 |
| chr8 | 49739700 | 49740200 | 500 | 0.0324 | 0.9194 | 5.71E−34 | 0.887 |
| chr12 | 122279300 | 122279800 | 500 | 0.0135 | 0.8969 | 3.46E−21 | 0.8834 |
| chr17 | 43092200 | 43092700 | 500 | 0 | 0.8824 | 4.34E−10 | 0.8824 |
| chr7 | 107563100 | 107563600 | 500 | 0.0495 | 0.931 | 1.05E−28 | 0.8815 |
| chr11 | 72543200 | 72543700 | 500 | 0.0377 | 0.9167 | 2.94E−09 | 0.8789 |
| chr14 | 58837800 | 58838300 | 500 | 0.0097 | 0.886 | 9.16E−18 | 0.8763 |
| chr3 | 153443900 | 153444900 | 1000 | 0.0436 | 0.9197 | 6.24E−39 | 0.876 |
| chr3 | 16953200 | 16953700 | 500 | 0.0896 | 0.9655 | 6.78E−09 | 0.876 |

TABLE S2C-continued

List of 100 most hypermethylated regions identified from third trimester placental tissue and maternal blood cells.

| Chromosome | Start | End | Size (bp) | Maternal blood cells | Term placenta | P-values | Methylation Difference |
|---|---|---|---|---|---|---|---|
| chr17 | 42205700 | 42206200 | 500 | 0.057 | 0.933 | 1.13E−31 | 0.8759 |
| chr6 | 53217600 | 53218100 | 500 | 0.0818 | 0.9571 | 1.54E−19 | 0.8754 |
| chr3 | 112749000 | 112749500 | 500 | 0.0403 | 0.9154 | 4.11E−22 | 0.8752 |
| chr8 | 22453700 | 22454203 | 500 | 0.003 | 0.8765 | 1.64E−50 | 0.8735 |
| chr1 | 162860900 | 162861400 | 500 | 0.023 | 0.8932 | 8.37E−14 | 0.8702 |
| chr6 | 36279700 | 36280200 | 500 | 0.0068 | 0.8762 | 1.14E−21 | 0.8694 |
| chr5 | 80962500 | 80963000 | 500 | 0 | 0.8679 | 2.08E−15 | 0.8679 |
| chr16 | 11312500 | 11313000 | 500 | 0 | 0.8679 | 2.14E−10 | 0.8679 |
| chr16 | 29663900 | 29665400 | 1500 | 0.0081 | 0.8759 | 0.00E+00 | 0.8678 |
| chr3 | 120438100 | 120438600 | 500 | 0.102 | 0.9639 | 2.98E−45 | 0.8618 |
| chr8 | 134157000 | 134157500 | 500 | 0.0625 | 0.9219 | 6.10E−20 | 0.8594 |
| chr6 | 42620900 | 42621400 | 500 | 0 | 0.8571 | 5.68E−08 | 0.8571 |
| chr5 | 131836300 | 131836800 | 500 | 0.075 | 0.9315 | 1.26E−40 | 0.8565 |
| chr14 | 60290000 | 60290500 | 500 | 0 | 0.8544 | 5.63E−14 | 0.8544 |
| chr6 | 42850300 | 42851300 | 1000 | 0.0676 | 0.9211 | 2.38E−24 | 0.8534 |
| chr8 | 28974100 | 28974600 | 500 | 0.0394 | 0.8927 | 2.03E−51 | 0.8533 |
| chr22 | 22368500 | 22369000 | 500 | 0.0248 | 0.8178 | 1.18E−70 | 0.8529 |
| chr14 | 69825300 | 69825800 | 500 | 0.0654 | 0.9174 | 2.73E−14 | 0.852 |
| chr3 | 142700300 | 142700800 | 500 | 0.0063 | 0.8582 | 2.56E−23 | 0.8519 |
| chr17 | 59491300 | 59491800 | 500 | 0.0662 | 0.9175 | 1.81E−16 | 0.8513 |
| chr15 | 30881700 | 30882200 | 500 | 0.0493 | 0.8995 | 2.38E−26 | 0.8502 |
| chr15 | 91496300 | 91496800 | 500 | 0 | 0.85 | 3.13E−17 | 0.85 |
| chr17 | 18745300 | 18745800 | 500 | 0.0294 | 0.8775 | 3.47E−51 | 0.848 |
| chr15 | 29436500 | 29437000 | 500 | 0.0336 | 0.8811 | 2.62E−66 | 0.8476 |
| chr2 | 217795300 | 217795800 | 500 | 0 | 0.8472 | 1.78E−22 | 0.8472 |
| chr11 | 16328100 | 16328600 | 500 | 0.0278 | 0.875 | 3.43E−11 | 0.8472 |
| chr13 | 113063500 | 113064000 | 500 | 0.0102 | 0.8571 | 1.82E−15 | 0.8469 |
| chr5 | 40472400 | 40472900 | 500 | 0.0197 | 0.8664 | 7.54E−35 | 0.8467 |
| chr1 | 242549200 | 242549700 | 500 | 0 | 0.8462 | 8.53E−23 | 0.8462 |
| chr11 | 58099100 | 58099600 | 500 | 0.0162 | 0.8612 | 4.45E−35 | 0.845 |
| chr9 | 16020400 | 16020900 | 500 | 0.0132 | 0.8555 | 8.05E−23 | 0.8423 |
| chr8 | 37550700 | 37551200 | 500 | 0.0093 | 0.8512 | 1.11E−16 | 0.8419 |
| chr5 | 75722400 | 75722900 | 500 | 0.1215 | 0.9627 | 5.97E−23 | 0.8411 |
| chr19 | 60454700 | 60455200 | 500 | 0.0316 | 0.8722 | 2.44E−62 | 0.8405 |
| chr4 | 99587100 | 99587600 | 500 | 0.0128 | 0.8526 | 1.49E−12 | 0.8398 |
| chr6 | 25149600 | 25150600 | 1000 | 0.0135 | 0.8514 | 0.00E+00 | 0.8379 |
| chr1 | 32065200 | 32065700 | 500 | 0 | 0.8371 | 1.09E−44 | 0.8371 |
| chr7 | 5337200 | 5337700 | 500 | 0.0727 | 0.9098 | 2.18E−14 | 0.8371 |
| chr17 | 44269900 | 44270400 | 500 | 0.026 | 0.8621 | 3.94E−22 | 0.8361 |
| chr1 | 36180800 | 36181300 | 500 | 0.0714 | 0.9067 | 1.23E−09 | 0.8352 |
| chr18 | 10472700 | 10473700 | 1000 | 0.0713 | 0.9064 | 9.35E−70 | 0.8351 |
| chr5 | 350000 | 350500 | 500 | 0.0297 | 0.8643 | 1.49E−16 | 0.8346 |
| chr2 | 136481800 | 136482800 | 1000 | 0.0554 | 0.8887 | 1.87E−52 | 0.8332 |
| chr4 | 89241100 | 89241600 | 500 | 0.1091 | 0.9423 | 1.05E−12 | 0.8332 |
| chr17 | 40320700 | 40321200 | 500 | 0.0539 | 0.8859 | 6.94E−31 | 0.832 |
| chr7 | 133897200 | 133897700 | 500 | 0.0769 | 0.9077 | 1.64E−24 | 0.8308 |
| chr8 | 98060600 | 98061100 | 500 | 0.0741 | 0.9048 | 3.11E−07 | 0.8307 |
| chr8 | 134141500 | 134142000 | 500 | 0 | 0.829 | 2.77E−58 | 0.829 |
| chr14 | 80250600 | 80251100 | 500 | 0.0839 | 0.9122 | 2.05E−18 | 0.8283 |
| chr2 | 100730900 | 100731400 | 500 | 0.0787 | 0.9067 | 4.85E−11 | 0.828 |
| chr2 | 88108100 | 88108600 | 500 | 0.075 | 0.901 | 2.10E−16 | 0.826 |
| chr19 | 16338500 | 16339500 | 1000 | 0.0011 | 0.8259 | 0.00E+00 | 0.8247 |
| chr5 | 141791900 | 141792900 | 1000 | 0.0225 | 0.8467 | 0.00E+00 | 0.8243 |
| chr11 | 116227400 | 116227900 | 500 | 0 | 0.8242 | 1.01E−17 | 0.8242 |
| chr22 | 48705500 | 48706000 | 500 | 0.0649 | 0.8891 | 4.00E−76 | 0.8242 |
| chr9 | 3518300 | 3518800 | 500 | 0.0263 | 0.8493 | 6.66E−25 | 0.823 |
| chr11 | 16791000 | 16791500 | 500 | 0.1095 | 0.9322 | 1.05E−22 | 0.8228 |
| chr3 | 135746000 | 135746500 | 500 | 0.1429 | 0.9651 | 7.63E−10 | 0.8223 |
| chr1 | 19323400 | 19323900 | 500 | 0.0411 | 0.8624 | 2.36E−20 | 0.8213 |
| chr9 | 96662800 | 96663300 | 500 | 0.0614 | 0.8826 | 1.07E−28 | 0.8212 |
| chr7 | 37348300 | 37349300 | 1000 | 0.0012 | 0.821 | 0.00E+00 | 0.8198 |
| chr2 | 234882000 | 234882500 | 500 | 0.0392 | 0.8591 | 5.36E−15 | 0.8198 |
| chr6 | 44694000 | 44694500 | 500 | 0.1024 | 0.9222 | 5.68E−19 | 0.8198 |
| chr17 | 18320500 | 18321000 | 500 | 0 | 0.8197 | 2.78E−39 | 0.8197 |
| chr22 | 28992000 | 28994000 | 2000 | 0.0012 | 0.8195 | 0.00E+00 | 0.8183 |
| chr17 | 53762700 | 53766300 | 3600 | 0.0003 | 0.8179 | 0.00E+00 | 0.8176 |
| chr1 | 114215500 | 114216000 | 500 | 0 | 0.8169 | 2.24E−20 | 0.8169 |
| chr6 | 13381700 | 13382700 | 1000 | 0.0037 | 0.8206 | 1.03E−40 | 0.8169 |
| chr5 | 17045400 | 17045900 | 500 | 0.0235 | 0.84 | 3.24E−13 | 0.8165 |
| chr12 | 110924300 | 110924800 | 500 | 0.0855 | 0.9016 | 1.01E−18 | 0.816 |
| chr1 | 200499800 | 200500300 | 500 | 0.011 | 0.8269 | 9.73E−24 | 0.8159 |
| chr4 | 8311000 | 8311500 | 500 | 0.053 | 0.8687 | 7.82E−18 | 0.8157 |
| chr8 | 6535300 | 6535800 | 500 | 0.0667 | 0.8824 | 5.25E−09 | 0.8157 |

TABLE S2C-continued

List of 100 most hypermethylated regions identified from third trimester placental tissue and maternal blood cells.

| Chromosome | Start | End | Size (bp) | Maternal blood cells | Term placenta | P-values | Methylation Difference |
|---|---|---|---|---|---|---|---|
| chr6 | 42462700 | 42463200 | 500 | 0.0761 | 0.8919 | 5.78E−23 | 0.8157 |
| chr1 | 91969900 | 91970400 | 500 | 0.0172 | 0.8325 | 5.23E−18 | 0.8152 |
| chr2 | 105758600 | 105759600 | 1000 | 0.0305 | 0.8455 | 5.15E−52 | 0.815 |
| chr21 | 37538500 | 37539000 | 500 | 0.1595 | 0.9745 | 8.81E−16 | 0.815 |
| chr9 | 92953000 | 92953500 | 500 | 0.0189 | 0.8333 | 1.88E−15 | 0.8145 |
| chr16 | 30104400 | 30105900 | 1500 | 0.0505 | 0.8636 | 0.00E+00 | 0.8131 |
| chr1 | 234184400 | 234185400 | 1000 | 0.0346 | 0.8477 | 9.66E−31 | 0.813 |
| chr8 | 19116400 | 19116900 | 500 | 0 | 0.8125 | 9.33E−11 | 0.8125 |
| chr4 | 141194300 | 141195300 | 1000 | 0.0865 | 0.899 | 5.46E−30 | 0.8125 |

TABLE S2D

List of 100 most hypomethylated regions identified from third trimester placental tissue and maternal blood cells.

| Chromosome | Start | End | Size (bp) | Maternal blood cells | Term placenta | P-values | Methylation Difference |
|---|---|---|---|---|---|---|---|
| chr9 | 40380300 | 40380800 | 500 | 0.9667 | 0 | 1.13E−06 | 0.9667 |
| chr1 | 31769200 | 31769700 | 500 | 0.9548 | 0.0256 | 5.57E−25 | 0.9291 |
| chr18 | 12217600 | 12218100 | 500 | 0.9873 | 0.0602 | 1.63E−19 | 0.9271 |
| chr20 | 19704400 | 19704900 | 500 | 0.9426 | 0.018 | 4.34E−18 | 0.9246 |
| chr15 | 37317500 | 37318000 | 500 | 0.9358 | 0.0132 | 1.90E−25 | 0.9226 |
| chrX | 83368400 | 83368900 | 500 | 0.913 | 0 | 3.15E−07 | 0.913 |
| chr11 | 27549100 | 27549600 | 500 | 0.9224 | 0.0123 | 3.92E−24 | 0.9101 |
| chr18 | 58141500 | 58142000 | 500 | 0.9737 | 0.0645 | 1.07E−09 | 0.9092 |
| chr1 | 159897000 | 159897500 | 500 | 0.9067 | 0 | 2.53E−16 | 0.9067 |
| chr7 | 84347200 | 84348700 | 1500 | 0.9401 | 0.0407 | 0.00E+00 | 0.8994 |
| chr2 | 216916100 | 216916600 | 500 | 0.9695 | 0.0714 | 2.13E−16 | 0.8981 |
| chr7 | 144200000 | 144200500 | 500 | 0.9294 | 0.0317 | 1.24E−10 | 0.8977 |
| chr1 | 241331600 | 241332100 | 500 | 0.9198 | 0.0227 | 0.00E+00 | 0.8971 |
| chr7 | 123190000 | 123191000 | 1000 | 0.9341 | 0.0384 | 0.00E+00 | 0.8957 |
| chr5 | 12626600 | 12628600 | 2000 | 0.9266 | 0.0321 | 0.00E+00 | 0.8944 |
| chr12 | 12971300 | 12972300 | 1000 | 0.9361 | 0.0438 | 0.00E+00 | 0.8923 |
| chr22 | 20936500 | 20937000 | 500 | 0.9528 | 0.0606 | 1.87E−06 | 0.8922 |
| chr13 | 31321900 | 31322400 | 500 | 0.9231 | 0.0313 | 1.43E−06 | 0.8918 |
| chr22 | 21701500 | 21702000 | 500 | 0.9579 | 0.0667 | 1.30E−09 | 0.8912 |
| chr10 | 104794400 | 104794900 | 500 | 1 | 0.1111 | 6.10E−09 | 0.8889 |
| chr7 | 21835800 | 21836300 | 500 | 0.9156 | 0.0267 | 3.85E−13 | 0.8889 |
| chr10 | 16134800 | 16135300 | 500 | 0.95 | 0.0635 | 4.79E−10 | 0.8865 |
| chr3 | 47410400 | 47410900 | 500 | 0.9213 | 0.0357 | 6.63E−17 | 0.8855 |
| chr10 | 49344400 | 49345400 | 1000 | 0.9422 | 0.0571 | 0.00E+00 | 0.8851 |
| chr2 | 209073900 | 209074400 | 500 | 0.9196 | 0.0353 | 1.63E−22 | 0.8843 |
| chr1 | 89131200 | 89131700 | 500 | 0.9314 | 0.0472 | 1.05E−75 | 0.8842 |
| chr3 | 167118500 | 167119500 | 1000 | 0.9365 | 0.0527 | 0.00E+00 | 0.8838 |
| chr18 | 1395900 | 1397400 | 1500 | 0.9308 | 0.0472 | 0.00E+00 | 0.8836 |
| chr2 | 59670300 | 59670800 | 500 | 0.9433 | 0.0599 | 5.09E−23 | 0.8834 |
| chr14 | 28368900 | 28369400 | 500 | 0.9446 | 0.0619 | 5.03E−64 | 0.8827 |
| chr3 | 126028800 | 126029300 | 500 | 0.9379 | 0.0556 | 1.83E−20 | 0.8823 |
| chr9 | 69378900 | 69379900 | 1000 | 0.8816 | 0 | 6.02E−51 | 0.8816 |
| chr5 | 105517300 | 105518300 | 1000 | 0.927 | 0.0461 | 0.00E+00 | 0.8808 |
| chr2 | 31572400 | 31573400 | 1000 | 0.9176 | 0.037 | 0.00E+00 | 0.8806 |
| chr5 | 42003700 | 42004700 | 1000 | 0.9262 | 0.0462 | 0.00E+00 | 0.88 |
| chr14 | 94718300 | 94718800 | 500 | 0.9548 | 0.0764 | 6.67E−19 | 0.8784 |
| chr19 | 56417800 | 56418300 | 500 | 0.9615 | 0.0833 | 1.71E−06 | 0.8782 |
| chr2 | 70183000 | 70183500 | 500 | 0.9694 | 0.0914 | 9.49E−39 | 0.878 |
| chr4 | 118939300 | 118939800 | 500 | 0.9192 | 0.0412 | 2.20E−34 | 0.878 |
| chr13 | 59246400 | 59246900 | 500 | 0.9402 | 0.0633 | 5.40E−12 | 0.8769 |
| chr12 | 74021100 | 74022100 | 1000 | 0.9513 | 0.0752 | 0.00E+00 | 0.8761 |
| chr2 | 173432500 | 173433000 | 500 | 0.9529 | 0.0778 | 5.39E−12 | 0.8752 |
| chr16 | 24004400 | 24004900 | 500 | 0.9239 | 0.0488 | 3.25E−23 | 0.8751 |
| chr13 | 27596300 | 27597300 | 1000 | 0.9538 | 0.0795 | 0.00E+00 | 0.8743 |
| chr15 | 88904300 | 88904800 | 500 | 0.9212 | 0.0481 | 7.69E−27 | 0.8731 |
| chr18 | 12720200 | 12721200 | 1000 | 0.9346 | 0.0618 | 0.00E+00 | 0.8728 |
| chr15 | 60975900 | 60976900 | 1000 | 0.9311 | 0.0587 | 0.00E+00 | 0.8724 |
| chr21 | 39630100 | 39631100 | 1000 | 0.9423 | 0.07 | 4.68E−43 | 0.8723 |
| chr5 | 123933900 | 123934400 | 500 | 0.943 | 0.0707 | 2.60E−38 | 0.8722 |
| chr8 | 77382600 | 77383600 | 1000 | 0.9117 | 0.0395 | 0.00E+00 | 0.8722 |
| chr21 | 32238800 | 32239300 | 500 | 0.9396 | 0.0677 | 1.28E−18 | 0.8719 |

TABLE S2D-continued

List of 100 most hypomethylated regions identified from third trimester placental tissue and maternal blood cells.

| Chromosome | Start | End | Size (bp) | Maternal blood cells | Term placenta | P-values | Methylation Difference |
|---|---|---|---|---|---|---|---|
| chr5 | 175019600 | 175020100 | 500 | 0.9542 | 0.0828 | 4.34E−20 | 0.8714 |
| chr8 | 134437400 | 134438400 | 1000 | 0.9083 | 0.037 | 4.79E−29 | 0.8713 |
| chr5 | 69668800 | 69669300 | 500 | 0.9194 | 0.0492 | 2.88E−09 | 0.8702 |
| chr1 | 60877900 | 60878900 | 1000 | 0.9378 | 0.068 | 0.00E+00 | 0.8698 |
| chr16 | 80650400 | 80650900 | 500 | 0.9309 | 0.0611 | 2.49E−32 | 0.8698 |
| chr18 | 59388800 | 59389300 | 500 | 0.9706 | 0.1008 | 4.84E−15 | 0.8697 |
| chr2 | 15969400 | 15970400 | 1000 | 0.8939 | 0.0244 | 3.07E−52 | 0.8695 |
| chr13 | 56207100 | 56208100 | 1000 | 0.9184 | 0.0505 | 0.00E+00 | 0.868 |
| chr3 | 180395300 | 180395800 | 500 | 0.9877 | 0.12 | 1.73E−09 | 0.8677 |
| chr6 | 153238200 | 153239200 | 1000 | 0.9123 | 0.0452 | 0.00E+00 | 0.8671 |
| chr18 | 61635100 | 61635600 | 500 | 0.9268 | 0.06 | 2.77E−13 | 0.8668 |
| chr3 | 177562200 | 177563200 | 1000 | 0.9121 | 0.0455 | 0.00E+00 | 0.8666 |
| chr4 | 160368300 | 160370200 | 1900 | 0.9272 | 0.0606 | 0.00E+00 | 0.8665 |
| chr6 | 144626900 | 144627400 | 500 | 0.9114 | 0.046 | 2.10E−12 | 0.8654 |
| chr16 | 59885500 | 59886500 | 1000 | 0.9407 | 0.0757 | 1.12E−62 | 0.865 |
| chr1 | 55667100 | 55667600 | 500 | 0.9095 | 0.0446 | 8.62E−39 | 0.8649 |
| chr2 | 83598300 | 83599300 | 1000 | 0.9366 | 0.0718 | 0.00E+00 | 0.8648 |
| chr4 | 105135200 | 105136200 | 1000 | 0.913 | 0.0486 | 0.00E+00 | 0.8644 |
| chr14 | 32048400 | 32048900 | 500 | 0.9142 | 0.0499 | 5.43E−53 | 0.8643 |
| chr1 | 223482700 | 223483700 | 1000 | 0.9636 | 0.0997 | 2.69E−34 | 0.864 |
| chr14 | 47487700 | 47488200 | 500 | 0.915 | 0.0514 | 5.45E−33 | 0.8636 |
| chr3 | 104515000 | 104515500 | 500 | 1 | 0.1373 | 1.08E−06 | 0.8627 |
| chr7 | 14008300 | 14009800 | 1500 | 0.9349 | 0.0725 | 0.00E+00 | 0.8624 |
| chr1 | 243134000 | 243135500 | 1500 | 0.9208 | 0.0588 | 0.00E+00 | 0.8619 |
| chr10 | 14156400 | 14156900 | 500 | 0.9105 | 0.0489 | 0.00E+00 | 0.8616 |
| chr2 | 118616200 | 118617200 | 1000 | 0.9178 | 0.0565 | 0.00E+00 | 0.8613 |
| chr17 | 8455500 | 8456000 | 500 | 0.8941 | 0.0331 | 1.94E−18 | 0.8611 |
| chr12 | 15392200 | 15393200 | 1000 | 0.9307 | 0.0697 | 0.00E+00 | 0.861 |
| chr8 | 81275900 | 81276900 | 1000 | 0.9291 | 0.0684 | 0.00E+00 | 0.8606 |
| chr1 | 234269300 | 234269800 | 500 | 0.9471 | 0.087 | 2.25E−25 | 0.8602 |
| chr1 | 181970300 | 181970800 | 500 | 0.9167 | 0.0566 | 2.15E−08 | 0.8601 |
| chr2 | 55775000 | 55776000 | 1000 | 0.9159 | 0.0559 | 0.00E+00 | 0.8599 |
| chr3 | 88338000 | 88339000 | 1000 | 0.8909 | 0.0311 | 0.00E+00 | 0.8598 |
| chr5 | 140078700 | 140079200 | 500 | 0.8852 | 0.0253 | 0.00E+00 | 0.8598 |
| chr21 | 16720900 | 16721400 | 500 | 0.9317 | 0.0721 | 1.38E−15 | 0.8596 |
| chr11 | 104891100 | 104892600 | 1500 | 0.9164 | 0.0569 | 0.00E+00 | 0.8595 |
| chr1 | 184204700 | 184205200 | 500 | 0.9194 | 0.0603 | 8.16E−16 | 0.859 |
| chr6 | 160732500 | 160733000 | 500 | 0.9191 | 0.0606 | 1.31E−10 | 0.8585 |
| chr8 | 37134300 | 37134800 | 500 | 0.9151 | 0.0567 | 1.21E−26 | 0.8584 |
| chr18 | 5869800 | 5870300 | 500 | 0.913 | 0.0548 | 1.21E−09 | 0.8582 |
| chr1 | 98448100 | 98448600 | 500 | 0.9574 | 0.1 | 2.08E−05 | 0.8574 |
| chr3 | 152897800 | 152898300 | 500 | 0.9402 | 0.0828 | 3.28E−18 | 0.8574 |
| chr1 | 110304000 | 110304500 | 500 | 0.9783 | 0.121 | 2.60E−18 | 0.8572 |
| chr2 | 86993600 | 86995600 | 2000 | 0.8965 | 0.0395 | 0.00E+00 | 0.857 |
| chr19 | 15428100 | 15430600 | 2500 | 0.9424 | 0.0862 | 0.00E+00 | 0.8563 |
| chr13 | 75176800 | 75177800 | 1000 | 0.9258 | 0.0697 | 3.09E−47 | 0.8561 |
| chr13 | 24126700 | 24127200 | 500 | 0.9498 | 0.0938 | 1.57E−17 | 0.856 |
| chr16 | 28238500 | 28240500 | 2000 | 0.9427 | 0.0868 | 0.00E+00 | 0.8559 |
| chr2 | 158079500 | 158080500 | 1000 | 0.9199 | 0.0642 | 0.00E+00 | 0.8557 |

TABLE S3A

List of the top 100 loci deduced to be hypermethylated from the first trimester maternal plasma bisulfite-sequencing data.

| Chromosome | Start | End | Maternal blood cells | CVS | Methylation difference |
|---|---|---|---|---|---|
| chr22 | 39189067 | 39189863 | 0 | 0.8444 | 0.8444 |
| chr17 | 53763065 | 53764027 | 0 | 0.7922 | 0.7922 |
| chr7 | 41887694 | 41888212 | 0 | 0.7614 | 0.7614 |
| chr2 | 1.14E+08 | 1.14E+08 | 0 | 0.751 | 0.751 |
| chr12 | 25096242 | 25097206 | 0 | 0.7098 | 0.7098 |
| chr1 | 66574104 | 66574793 | 0 | 0.7025 | 0.7025 |
| chr6 | 11489985 | 11490755 | 0 | 0.7004 | 0.7004 |
| chr6 | 1.07E+08 | 1.07E+08 | 0 | 0.6978 | 0.6978 |
| chr10 | 30858286 | 30858871 | 0 | 0.6693 | 0.6693 |
| chr17 | 21131574 | 21132167 | 0 | 0.6496 | 0.6496 |
| chr18 | 13454740 | 13455292 | 0 | 0.5468 | 0.5468 |
| chr16 | 11298755 | 11299326 | 0 | 0.5373 | 0.5373 |
| chr2 | 1.75E+08 | 1.75E+08 | 0 | 0.5196 | 0.5196 |
| chr19 | 44060511 | 44061036 | 0 | 0.5128 | 0.5128 |
| chr6 | 1.08E+08 | 1.08E+08 | 0 | 0.5 | 0.5 |
| chr3 | 71261611 | 71262501 | 0 | 0.4587 | 0.4587 |
| chr9 | 36247847 | 36248885 | 0 | 0.447 | 0.447 |
| chr19 | 17819240 | 17820082 | 0 | 0.4279 | 0.4279 |
| chr17 | 53769900 | 53770731 | 0 | 0.4102 | 0.4102 |
| chr1 | 1.12E+08 | 1.12E+08 | 0.0002 | 0.6167 | 0.6166 |
| chr7 | 1.34E+08 | 1.34E+08 | 0.0003 | 0.4351 | 0.4348 |
| chr3 | 11658550 | 11659929 | 0.0004 | 0.4299 | 0.4295 |

TABLE S3A-continued

List of the top 100 loci deduced to be hypermethylated from the first trimester maternal plasma bisulfite-sequencing data.

| Chromosome | Start | End | Maternal blood cells | CVS | Methylation difference |
|---|---|---|---|---|---|
| chr17 | 53764417 | 53765963 | 0.0005 | 0.7967 | 0.7961 |
| chr10 | 11246762 | 11249052 | 0.0005 | 0.4002 | 0.3997 |
| chr22 | 28992647 | 28993434 | 0.0006 | 0.8092 | 0.8087 |
| chr15 | 62460278 | 62461007 | 0.0006 | 0.4334 | 0.4328 |
| chr1 | 31002038 | 31003474 | 0.0007 | 0.5926 | 0.5919 |
| chr19 | 3129246 | 3132159 | 0.0008 | 0.7725 | 0.7717 |
| chr12 | 1.21E+08 | 1.21E+08 | 0.0008 | 0.7303 | 0.7295 |
| chr19 | 12304446 | 12305741 | 0.0009 | 0.6986 | 0.6978 |
| chr3 | 67788734 | 67789395 | 0.001 | 0.9131 | 0.9121 |
| chr9 | 1.32E+08 | 1.32E+08 | 0.001 | 0.7047 | 0.7037 |
| chr19 | 6723370 | 6724479 | 0.001 | 0.689 | 0.688 |
| chr3 | 1.84E+08 | 1.84E+08 | 0.001 | 0.4384 | 0.4374 |
| chr2 | 53848089 | 53849214 | 0.001 | 0.4368 | 0.4358 |
| chr17 | 59450886 | 59452113 | 0.0012 | 0.469 | 0.4678 |
| chr5 | 1.72E+08 | 1.72E+08 | 0.0014 | 0.578 | 0.5766 |
| chr21 | 35342527 | 35343373 | 0.0014 | 0.5392 | 0.5378 |
| chr21 | 45164804 | 45165437 | 0.0015 | 0.4251 | 0.4236 |
| chrX | 3742417 | 3744601 | 0.0016 | 0.4486 | 0.447 |
| chr21 | 45158293 | 45159003 | 0.0017 | 0.7799 | 0.7782 |
| chr7 | 39839340 | 39839876 | 0.0017 | 0.4074 | 0.4057 |
| chr2 | 1.75E+08 | 1.75E+08 | 0.0018 | 0.4816 | 0.4797 |
| chr12 | 1.24E+08 | 1.24E+08 | 0.0019 | 0.6306 | 0.6287 |
| chr3 | 50352688 | 50353823 | 0.002 | 0.624 | 0.622 |
| chr9 | 97264382 | 97265523 | 0.0021 | 0.5008 | 0.4987 |
| chr7 | 64178628 | 64179354 | 0.0021 | 0.4088 | 0.4066 |
| chr9 | 94767202 | 94767802 | 0.0023 | 0.7568 | 0.7544 |
| chr5 | 42986308 | 42988304 | 0.0023 | 0.4882 | 0.4859 |
| chr17 | 63854127 | 63854693 | 0.0024 | 0.8266 | 0.8242 |
| chr12 | 1.22E+08 | 1.22E+08 | 0.0024 | 0.4869 | 0.4844 |
| chr17 | 16260170 | 16260909 | 0.0026 | 0.6404 | 0.6378 |
| chr4 | 39874787 | 39875456 | 0.0027 | 0.7233 | 0.7206 |
| chr12 | 6441080 | 6441608 | 0.0027 | 0.6228 | 0.6201 |
| chr19 | 45015653 | 45016886 | 0.0028 | 0.5444 | 0.5416 |
| chr6 | 30757752 | 30758823 | 0.0028 | 0.4783 | 0.4755 |
| chr6 | 41636176 | 41637112 | 0.0028 | 0.4254 | 0.4226 |
| chr12 | 6315199 | 6315765 | 0.0029 | 0.4613 | 0.4584 |
| chr14 | 76576283 | 76577070 | 0.0029 | 0.4365 | 0.4336 |
| chr16 | 48857790 | 48858300 | 0.0031 | 0.5625 | 0.5594 |
| chr5 | 1.7E+08 | 1.7E+08 | 0.0031 | 0.4752 | 0.4721 |
| chr13 | 26897813 | 26898557 | 0.0032 | 0.4354 | 0.4322 |
| chr14 | 52753948 | 52754571 | 0.0032 | 0.4221 | 0.4189 |
| chr1 | 1.66E+08 | 1.66E+08 | 0.0033 | 0.5579 | 0.5545 |
| chr12 | 56157424 | 56158348 | 0.0033 | 0.47 | 0.4667 |
| chr22 | 16079971 | 16080532 | 0.0034 | 0.6226 | 0.6193 |
| chr7 | 1946410 | 1946975 | 0.0036 | 0.6826 | 0.6789 |
| chr11 | 258799 | 259749 | 0.0036 | 0.5072 | 0.5037 |
| chr6 | 13381944 | 13382477 | 0.0037 | 0.5945 | 0.5908 |
| chr7 | 1.27E+08 | 1.27E+08 | 0.0037 | 0.5096 | 0.5058 |
| chr13 | 23743886 | 23744467 | 0.0037 | 0.4534 | 0.4497 |
| chr2 | 1.21E+08 | 1.21E+08 | 0.0038 | 0.7175 | 0.7137 |
| chr21 | 25855853 | 25857105 | 0.0039 | 0.4661 | 0.4622 |
| chr2 | 43211724 | 43212565 | 0.0039 | 0.4345 | 0.4306 |
| chr12 | 1.08E+08 | 1.08E+08 | 0.0041 | 0.6024 | 0.5983 |
| chr15 | 92928924 | 92929575 | 0.0041 | 0.4074 | 0.4033 |
| chr19 | 10731043 | 10731636 | 0.0042 | 0.5868 | 0.5826 |
| chr6 | 1.45E+08 | 1.45E+08 | 0.0043 | 0.5783 | 0.574 |
| chr1 | 52875323 | 52875907 | 0.0044 | 0.4145 | 0.4101 |
| chr14 | 75058186 | 75058956 | 0.0045 | 0.602 | 0.5975 |
| chr12 | 1.21E+08 | 1.21E+08 | 0.0045 | 0.4821 | 0.4776 |
| chr17 | 76873737 | 76874471 | 0.0046 | 0.6012 | 0.5966 |
| chr2 | 2.38E+08 | 2.38E+08 | 0.0049 | 0.7654 | 0.7604 |
| chr2 | 1.98E+08 | 1.98E+08 | 0.0049 | 0.7228 | 0.7179 |
| chr6 | 1.47E+08 | 1.47E+08 | 0.0049 | 0.4967 | 0.4918 |
| chr9 | 1.36E+08 | 1.36E+08 | 0.0049 | 0.4584 | 0.4535 |
| chr1 | 67545402 | 67546771 | 0.005 | 0.4971 | 0.4921 |
| chr6 | 1.58E+08 | 1.58E+08 | 0.0052 | 0.6145 | 0.6093 |
| chr3 | 1.7E+08 | 1.7E+08 | 0.0052 | 0.5845 | 0.5794 |
| chr1 | 2.34E+08 | 2.34E+08 | 0.0053 | 0.7033 | 0.6979 |
| chr10 | 80715722 | 80716751 | 0.0053 | 0.6515 | 0.6462 |
| chr4 | 48602901 | 48603736 | 0.0053 | 0.6315 | 0.6262 |
| chr19 | 13957965 | 13958580 | 0.0053 | 0.599 | 0.5937 |
| chr1 | 90081114 | 90082367 | 0.0053 | 0.4574 | 0.4521 |
| chr2 | 1.06E+08 | 1.06E+08 | 0.0054 | 0.8858 | 0.8804 |
| chr16 | 29664213 | 29665369 | 0.0054 | 0.8339 | 0.8285 |
| chr1 | 1.59E+08 | 1.59E+08 | 0.0054 | 0.7663 | 0.7608 |
| chr13 | 97926489 | 97927025 | 0.0054 | 0.6229 | 0.6175 |
| chr1 | 41604452 | 41605277 | 0.0054 | 0.6011 | 0.5956 |
| chr9 | 1.28E+08 | 1.28E+08 | 0.0054 | 0.5871 | 0.5818 |

TABLE S3B

List of top 100 loci deduced to be hypomethylated from the first trimester maternal plasma bisulfite-sequencing data

| Chromosome | Start | End | Maternal blood cells | CVS | Methylation difference |
|---|---|---|---|---|---|
| chr1 | 235771917 | 235772426 | 0.9868 | 0.549 | 0.4377 |
| chr1 | 97357972 | 97358622 | 0.9835 | 0.4805 | 0.503 |
| chr1 | 4490516 | 4491074 | 0.9826 | 0.4793 | 0.5032 |
| chr4 | 181124168 | 181124671 | 0.9825 | 0.4725 | 0.5099 |
| chr16 | 71908694 | 71909213 | 0.982 | 0.5581 | 0.4239 |
| chr3 | 182727915 | 182728477 | 0.981 | 0.3577 | 0.6233 |
| chr5 | 115339535 | 115340038 | 0.9802 | 0.5455 | 0.4347 |
| chr3 | 195855575 | 195856122 | 0.9801 | 0.3793 | 0.6008 |
| chr6 | 155437621 | 155438161 | 0.9799 | 0.5991 | 0.3808 |
| chr9 | 20468093 | 20468904 | 0.9798 | 0.4271 | 0.5527 |
| chr10 | 90702298 | 90702987 | 0.9787 | 0.3324 | 0.6463 |
| chr1 | 170581654 | 170582162 | 0.9785 | 0.4817 | 0.4968 |
| chr3 | 108816849 | 108817794 | 0.9783 | 0.4793 | 0.4989 |
| chr20 | 36912749 | 36913319 | 0.9783 | 0.5 | 0.4783 |
| chr13 | 72517281 | 72517839 | 0.9782 | 0.4855 | 0.4927 |
| chr12 | 103553001 | 103553677 | 0.9774 | 0.492 | 0.4854 |
| chr22 | 27638905 | 27639408 | 0.9766 | 0.5385 | 0.4382 |
| chr7 | 17290850 | 17291462 | 0.9763 | 0.59 | 0.3863 |
| chr6 | 17227866 | 17228510 | 0.976 | 0.4058 | 0.5703 |
| chr15 | 56998547 | 56999107 | 0.9754 | 0.3766 | 0.5988 |
| chr7 | 70965945 | 70966842 | 0.9753 | 0.5893 | 0.386 |
| chr3 | 32159338 | 32160065 | 0.9752 | 0.5379 | 0.4372 |
| chr16 | 17043258 | 17043854 | 0.9752 | 0.5521 | 0.4231 |
| chr16 | 22776223 | 22776850 | 0.9752 | 0.5735 | 0.4017 |
| chr5 | 169344029 | 169344869 | 0.9751 | 0.4211 | 0.5541 |
| chr11 | 34324955 | 34325722 | 0.975 | 0.5561 | 0.4189 |
| chr8 | 58554745 | 58555376 | 0.9747 | 0.5784 | 0.3964 |
| chr1 | 153933389 | 153934121 | 0.9746 | 0.463 | 0.5116 |
| chr14 | 88003983 | 88004485 | 0.9745 | 0.5379 | 0.4366 |
| chr3 | 151738501 | 151739120 | 0.9741 | 0.4901 | 0.484 |
| chr14 | 105618699 | 105619606 | 0.974 | 0.3457 | 0.6283 |
| chr16 | 24060085 | 24060702 | 0.9738 | 0.3991 | 0.5747 |
| chr8 | 68941792 | 68942711 | 0.9738 | 0.5449 | 0.429 |
| chr12 | 53208707 | 53209304 | 0.9737 | 0.4847 | 0.489 |
| chr7 | 76892564 | 76893249 | 0.9736 | 0.5664 | 0.4072 |
| chr3 | 69464294 | 69464971 | 0.9736 | 0.5893 | 0.3843 |
| chr19 | 61401137 | 61401745 | 0.9732 | 0.4933 | 0.4799 |
| chr11 | 124569867 | 124570490 | 0.9732 | 0.5136 | 0.4595 |
| chr18 | 42618440 | 42619096 | 0.9732 | 0.5942 | 0.379 |
| chr5 | 169398896 | 169399637 | 0.9731 | 0.498 | 0.4751 |
| chr5 | 169328124 | 169328983 | 0.9731 | 0.572 | 0.401 |
| chr20 | 34679880 | 34680448 | 0.9731 | 0.5922 | 0.3809 |
| chr16 | 9042198 | 9042702 | 0.973 | 0.4286 | 0.5444 |
| chr10 | 90205044 | 90205701 | 0.973 | 0.4407 | 0.5323 |
| chr13 | 33236454 | 33236997 | 0.973 | 0.5906 | 0.3824 |
| chr16 | 73284579 | 73285087 | 0.9729 | 0.5602 | 0.4127 |
| chr8 | 29100691 | 29101428 | 0.9728 | 0.505 | 0.4678 |
| chr2 | 202383851 | 202384447 | 0.9727 | 0.5461 | 0.4267 |
| chr3 | 179501620 | 179502300 | 0.9722 | 0.5766 | 0.3956 |
| chr6 | 107674979 | 107675906 | 0.9719 | 0.4434 | 0.5285 |
| chr6 | 107880632 | 107881161 | 0.9718 | 0.5623 | 0.4095 |
| chr12 | 56350283 | 56350933 | 0.9718 | 0.5909 | 0.3809 |
| chr19 | 40636458 | 40637339 | 0.9717 | 0.4941 | 0.4776 |
| chr2 | 223472599 | 223473287 | 0.9714 | 0.1824 | 0.7891 |
| chr22 | 20709067 | 20709787 | 0.9714 | 0.5149 | 0.4565 |

TABLE S3B-continued

List of top 100 loci deduced to be hypomethylated from the first trimester maternal plasma bisulfite-sequencing data

| Chromosome | Start | End | Maternal blood cells | CVS | Methylation difference |
|---|---|---|---|---|---|
| chr19 | 46095583 | 46096190 | 0.9713 | 0.5385 | 0.4328 |
| chr6 | 90258338 | 90259318 | 0.9712 | 0.3415 | 0.6297 |
| chr2 | 54598347 | 54598933 | 0.9712 | 0.5894 | 0.3819 |
| chr3 | 114810453 | 114811493 | 0.9711 | 0.5166 | 0.4545 |
| chr19 | 15851125 | 15851654 | 0.9711 | 0.5236 | 0.4476 |
| chr8 | 42889138 | 42890084 | 0.9711 | 0.5652 | 0.4059 |
| chr18 | 52354390 | 52355064 | 0.971 | 0.598 | 0.373 |
| chr15 | 38206236 | 38207010 | 0.9709 | 0.4186 | 0.5523 |
| chr7 | 99700554 | 99701110 | 0.9708 | 0.305 | 0.6658 |
| chr12 | 19487336 | 19487855 | 0.9708 | 0.4105 | 0.5603 |
| chr7 | 87996908 | 87997437 | 0.9708 | 0.5462 | 0.4246 |
| chr6 | 63628653 | 63629378 | 0.9707 | 0.529 | 0.4417 |
| chr15 | 38209108 | 38209618 | 0.9706 | 0.5882 | 0.3824 |
| chr19 | 6623769 | 6624450 | 0.9704 | 0.5179 | 0.4526 |
| chr2 | 10794513 | 10795242 | 0.9704 | 0.5976 | 0.3728 |
| chr2 | 118472785 | 118474454 | 0.9704 | 0.5992 | 0.3712 |
| chr5 | 57820209 | 57820801 | 0.9701 | 0.5815 | 0.3886 |
| chr10 | 100183380 | 100184702 | 0.9701 | 0.5826 | 0.3875 |
| chr2 | 8151989 | 8152646 | 0.97 | 0.4701 | 0.4999 |
| chr10 | 3938374 | 3038914 | 0.9699 | 0.1741 | 0.7958 |
| chr9 | 123724524 | 123725439 | 0.9697 | 0.57 | 0.3997 |
| chr14 | 89085469 | 89086097 | 0.9696 | 0.3278 | 0.6418 |
| chr16 | 14129437 | 14130133 | 0.9695 | 0.5304 | 0.4392 |
| chr5 | 60746367 | 60747191 | 0.9695 | 0.5571 | 0.4124 |
| chr1 | 92002953 | 92003729 | 0.9694 | 0.52 | 0.4494 |
| chr6 | 31264677 | 31265413 | 0.9693 | 0.5135 | 0.4558 |
| chr7 | 99317013 | 99318281 | 0.9692 | 0.5117 | 0.4574 |
| chr8 | 8808867 | 8809422 | 0.9692 | 0.5691 | 0.4002 |
| chr19 | 20052165 | 20052720 | 0.969 | 0.2792 | 0.6898 |
| chr8 | 129139026 | 129139573 | 0.969 | 0.3458 | 0.6232 |
| chr11 | 122314929 | 122315458 | 0.969 | 0.4232 | 0.5458 |
| chr13 | 98377663 | 98378165 | 0.9688 | 0.3319 | 0.6369 |
| chr9 | 107606194 | 107606872 | 0.9688 | 0.449 | 0.5198 |
| chr8 | 56096904 | 56097736 | 0.9688 | 0.5267 | 0.4422 |
| chr7 | 128093836 | 128094339 | 0.9688 | 0.5929 | 0.3758 |
| chr2 | 103109370 | 103109916 | 0.9686 | 0.3333 | 0.6352 |
| chr3 | 101803534 | 101804063 | 0.9686 | 0.5027 | 0.4659 |
| chr10 | 69505720 | 69506278 | 0.9684 | 0.2515 | 0.7169 |
| chr13 | 26608225 | 26608754 | 0.9683 | 0.3614 | 0.6069 |
| chr1 | 90993315 | 90993828 | 0.9683 | 0.5519 | 0.4164 |
| chr6 | 11361243 | 11361801 | 0.9681 | 0.2578 | 0.7103 |
| chr21 | 36529300 | 36529981 | 0.968 | 0.1944 | 0.7736 |
| chr21 | 37813953 | 37814521 | 0.9679 | 0.2175 | 0.7505 |
| chr2 | 15226273 | 15227211 | 0.9679 | 0.5134 | 0.4545 |
| chr19 | 4102809 | 4103443 | 0.9679 | 0.5646 | 0.4034 |

TABLE S3C

List of top 100 loci deduced to be hypermethylated from the third trimester maternal plasma bisulfite-sequencing data

| Chromosome | Start | End | Maternal blood cells | Term placenta | Methylation difference |
|---|---|---|---|---|---|
| chr17 | 53763065 | 53764027 | 0.0000 | 0.8680 | 0.8680 |
| chr22 | 39189067 | 39189863 | 0.0000 | 0.8233 | 0.8233 |
| chr10 | 30858286 | 30858871 | 0.0000 | 0.7713 | 0.7713 |
| chr7 | 41887694 | 41888212 | 0.0000 | 0.7578 | 0.7578 |
| chr2 | 1.14E+08 | 1.14E+08 | 0.0000 | 0.7500 | 0.7500 |
| chr12 | 25096242 | 25097206 | 0.0000 | 0.7332 | 0.7332 |
| chr6 | 1.07E+08 | 1.07E+08 | 0.0000 | 0.7229 | 0.7229 |
| chr1 | 66574104 | 66574793 | 0.0000 | 0.7136 | 0.7136 |
| chr16 | 11298755 | 11299326 | 0.0000 | 0.7005 | 0.7005 |
| chr6 | 11489985 | 11490755 | 0.0000 | 0.6935 | 0.6935 |
| chr18 | 13454740 | 13455292 | 0.0000 | 0.6594 | 0.6594 |
| chr6 | 1.08E+08 | 1.08E+08 | 0.0000 | 0.6231 | 0.6231 |
| chrX | 3627885 | 3628549 | 0.0000 | 0.6133 | 0.6133 |
| chr12 | 7979754 | 7980413 | 0.0000 | 0.6118 | 0.6118 |
| chr3 | 71261611 | 71262501 | 0.0000 | 0.5938 | 0.5938 |

TABLE S3C-continued

List of top 100 loci deduced to be hypermethylated from the third trimester maternal plasma bisulfite-sequencing data

| Chromosome | Start | End | Maternal blood cells | Term placenta | Methylation difference |
|---|---|---|---|---|---|
| chr17 | 53769900 | 53770731 | 0.0000 | 0.5586 | 0.5586 |
| chr11 | 1.18E+08 | 1.18E+08 | 0.0000 | 0.5558 | 0.5558 |
| chr19 | 44060511 | 44061036 | 0.0000 | 0.5464 | 0.5464 |
| chr2 | 2.38E+08 | 2.38E+08 | 0.0000 | 0.5330 | 0.5330 |
| chr1 | 1.91E+08 | 1.91E+08 | 0.0000 | 0.5294 | 0.5294 |
| chr1 | 1.44E+08 | 1.44E+08 | 0.0000 | 0.4857 | 0.4857 |
| chr2 | 1.75E+08 | 1.75E+08 | 0.0000 | 0.4785 | 0.4785 |
| chr4 | 15366889 | 15367646 | 0.0000 | 0.4729 | 0.4729 |
| chr2 | 19537237 | 19537737 | 0.0000 | 0.4599 | 0.4599 |
| chr1 | 1.15E+08 | 1.15E+08 | 0.0000 | 0.4351 | 0.4351 |
| chr1 | 1.54E+08 | 1.54E+08 | 0.0000 | 0.4299 | 0.4299 |
| chr14 | 51383387 | 51384149 | 0.0000 | 0.4186 | 0.4186 |
| chr1 | 1.12E+08 | 1.12E+08 | 0.0002 | 0.5350 | 0.5348 |
| chr3 | 11658550 | 11659929 | 0.0004 | 0.5579 | 0.5575 |
| chr17 | 53764417 | 53765963 | 0.0005 | 0.7894 | 0.7889 |
| chr22 | 28992647 | 28993434 | 0.0006 | 0.8053 | 0.8047 |
| chr6 | 27214981 | 27215823 | 0.0006 | 0.4593 | 0.4587 |
| chr1 | 31002038 | 31003474 | 0.0007 | 0.6309 | 0.6302 |
| chr12 | 1.21E+08 | 1.21E+08 | 0.0008 | 0.7360 | 0.7352 |
| chr19 | 3129246 | 3132159 | 0.0008 | 0.7257 | 0.7249 |
| chr19 | 12304446 | 12305741 | 0.0009 | 0.6397 | 0.6388 |
| chr6 | 28723918 | 28724965 | 0.0009 | 0.4344 | 0.4335 |
| chr19 | 6723370 | 6724479 | 0.0010 | 0.7280 | 0.7270 |
| chr2 | 53848089 | 53849214 | 0.0010 | 0.4060 | 0.4050 |
| chr9 | 1.32E+08 | 1.32E+08 | 0.0010 | 0.7558 | 0.7548 |
| chr3 | 67788734 | 67789395 | 0.0010 | 0.9219 | 0.9209 |
| chr19 | 18276368 | 18277132 | 0.0011 | 0.5136 | 0.5125 |
| chr17 | 59450886 | 59452113 | 0.0012 | 0.5196 | 0.5184 |
| chr17 | 74243852 | 74244670 | 0.0012 | 0.4117 | 0.4105 |
| chr3 | 1.85E+08 | 1.85E+08 | 0.0014 | 0.4961 | 0.4948 |
| chr21 | 35342527 | 35343373 | 0.0014 | 0.5126 | 0.5112 |
| chr5 | 1.72E+08 | 1.72E+08 | 0.0014 | 0.6531 | 0.6516 |
| chr21 | 45164504 | 45165437 | 0.0015 | 0.4364 | 0.4349 |
| chrX | 3742417 | 3744601 | 0.0016 | 0.7517 | 0.7501 |
| chr21 | 45158293 | 45159003 | 0.0017 | 0.8180 | 0.8163 |
| chr2 | 1.75E+08 | 1.75E+08 | 0.0018 | 0.6214 | 0.6196 |
| chr12 | 1.24E+08 | 1.24E+08 | 0.0019 | 0.5906 | 0.5887 |
| chr3 | 50352688 | 50353823 | 0.0020 | 0.6082 | 0.6062 |
| chr9 | 94767202 | 94767802 | 0.0023 | 0.8327 | 0.8304 |
| chr17 | 63854127 | 63854693 | 0.0024 | 0.7886 | 0.7862 |
| chr12 | 1.22E+08 | 1.22E+08 | 0.0024 | 0.5021 | 0.4997 |
| chr17 | 16260170 | 16260909 | 0.0026 | 0.5780 | 0.5754 |
| chr12 | 6441080 | 6441608 | 0.0027 | 0.7471 | 0.7444 |
| chr4 | 39874787 | 39875456 | 0.0027 | 0.7962 | 0.7935 |
| chr18 | 50536032 | 50536649 | 0.0027 | 0.4920 | 0.4893 |
| chr6 | 30757752 | 30758823 | 0.0028 | 0.4029 | 0.4001 |
| chr19 | 2571763 | 2572292 | 0.0031 | 0.4200 | 0.4169 |
| chr5 | 1.7E+08 | 1.7E+08 | 0.0031 | 0.4218 | 0.4187 |
| chr13 | 26897813 | 26898557 | 0.0032 | 0.6485 | 0.6453 |
| chr12 | 56157424 | 56158348 | 0.0033 | 0.5541 | 0.5508 |
| chr1 | 1.66E+08 | 1.66E+08 | 0.0033 | 0.5147 | 0.5113 |
| chr22 | 16079971 | 16080532 | 0.0034 | 0.6265 | 0.6231 |
| chr6 | 16820551 | 16821134 | 0.0035 | 0.4800 | 0.4765 |
| chr11 | 258799 | 259749 | 0.0036 | 0.5475 | 0.5439 |
| chr7 | 1946410 | 1946975 | 0.0036 | 0.8251 | 0.8215 |
| chr6 | 13381944 | 13382477 | 0.0037 | 0.8221 | 0.8183 |
| chr7 | 1.27E+08 | 1.27E+08 | 0.0037 | 0.4767 | 0.4730 |
| chr2 | 1.21E+08 | 1.21E+08 | 0.0038 | 0.6734 | 0.6697 |
| chr2 | 43211724 | 43212565 | 0.0039 | 0.4256 | 0.4217 |
| chr15 | 92928924 | 92929575 | 0.0041 | 0.5605 | 0.5564 |
| chr12 | 1.08E+08 | 1.08E+08 | 0.0041 | 0.7313 | 0.7271 |
| chr19 | 10731043 | 10731636 | 0.0042 | 0.5668 | 0.5626 |
| chr6 | 1.45E+08 | 1.45E+08 | 0.0043 | 0.5910 | 0.5867 |
| chr1 | 52875323 | 52875907 | 0.0044 | 0.6115 | 0.6071 |
| chr12 | 1.21E+08 | 1.21E+08 | 0.0045 | 0.5884 | 0.5839 |
| chr14 | 75058186 | 75058956 | 0.0045 | 0.6534 | 0.6489 |
| chr17 | 76873737 | 76874417 | 0.0046 | 0.5658 | 0.5612 |
| chr6 | 1.47E+08 | 1.47E+08 | 0.0049 | 0.5826 | 0.5777 |
| chr2 | 1.98E+08 | 1.98E+08 | 0.0049 | 0.7944 | 0.7895 |
| chr2 | 2.38E+08 | 2.38E+08 | 0.0049 | 0.7328 | 0.7278 |
| chr8 | 1.42E+08 | 1.42E+08 | 0.0050 | 0.7728 | 0.7679 |
| chr3 | 1.7E+08 | 1.7E+08 | 0.0052 | 0.7227 | 0.7176 |
| chr6 | 1.58E+08 | 1.58E+08 | 0.0052 | 0.6389 | 0.6337 |

TABLE S3C-continued

List of top 100 loci deduced to be hypermethylated from the third trimester maternal plasma bisulfite-sequencing data

| Chromosome | Start | End | Maternal blood cells | Term placenta | Methylation difference |
|---|---|---|---|---|---|
| chr2 | 2.38E+08 | 2.38E+08 | 0.0052 | 0.4238 | 0.4185 |
| chr11 | 56948854 | 56949496 | 0.0053 | 0.4484 | 0.4431 |
| chr4 | 48602901 | 48603736 | 0.0053 | 0.5920 | 0.5867 |
| chr5 | 1.31E+08 | 1.31E+08 | 0.0053 | 0.4858 | 0.4805 |
| chr10 | 80715722 | 80716751 | 0.0053 | 0.5249 | 0.5196 |
| chr19 | 13957965 | 13958580 | 0.0053 | 0.4379 | 0.4326 |
| chr1 | 2.34E+08 | 2.34E+08 | 0.0053 | 0.8440 | 0.8387 |
| chr13 | 97926489 | 97927025 | 0.0054 | 0.7233 | 0.7179 |
| chr9 | 1.28E+08 | 1.28E+08 | 0.0054 | 0.7312 | 0.7258 |
| chr2 | 1.06E+08 | 1.06E+08 | 0.0054 | 0.8513 | 0.8459 |
| chr2 | 96556705 | 96557637 | 0.0054 | 0.4095 | 0.4041 |
| chr16 | 29664213 | 29665369 | 0.0054 | 0.8837 | 0.8783 |

TABLE S3D

List of top 100 loci deduced to be hypomethylated from the

| Chromosome | Start | End | Maternal blow cells | Term placenta | Methylation difference |
|---|---|---|---|---|---|
| chr10 | 7548948 | 7549483 | 0.9866 | 0.5685 | 0.4181 |
| chr1 | 4490516 | 4491074 | 0.9826 | 0.5015 | 0.4810 |
| chr4 | 1.81E+08 | 1.81E+08 | 0.9825 | 0.5981 | 0.3843 |
| chr3 | 1.83E+08 | 1.83E+08 | 0.9810 | 0.2925 | 0.6886 |
| chr3 | 1.96E+08 | 1.96E+08 | 0.9801 | 0.4643 | 0.5158 |
| chr6 | 1.55E+08 | 1.55E+08 | 0.9799 | 0.4610 | 0.5189 |
| chr1 | 1.71E+08 | 1.71E+08 | 0.9785 | 0.5122 | 0.4662 |
| chr20 | 36912749 | 36913319 | 0.9783 | 0.4513 | 0.5269 |
| chr22 | 38583100 | 38583616 | 0.9783 | 0.5428 | 0.4355 |
| chr1 | 19391314 | 19392207 | 0.9778 | 0.5273 | 0.4505 |
| chr5 | 1.74E+08 | 1.74E+08 | 0.9770 | 0.5852 | 0.3918 |
| chr19 | 13678906 | 13679531 | 0.9760 | 0.5812 | 0.3949 |
| chr14 | 83650790 | 83651395 | 0.9760 | 0.5378 | 0.4382 |
| chr15 | 56998547 | 56999107 | 0.9754 | 0.4691 | 0.5063 |
| chr16 | 22776223 | 22776850 | 0.9752 | 0.5114 | 0.4638 |
| chr5 | 1.69E+08 | 1.69E+08 | 0.9751 | 0.4809 | 0.4943 |
| chr8 | 58554745 | 58555376 | 0.9747 | 0.5977 | 0.3770 |
| chr14 | 1.06E+08 | 1.06E+08 | 0.9740 | 0.2069 | 0.7671 |
| chr8 | 68941792 | 68942711 | 0.9738 | 0.5872 | 0.3866 |
| chr16 | 24060085 | 24060702 | 0.9738 | 0.3470 | 0.6268 |
| chr12 | 53208707 | 53209304 | 0.9737 | 0.5278 | 0.4459 |
| chr5 | 1.69E+08 | 1.69E+08 | 0.9731 | 0.5057 | 0.4673 |
| chr16 | 9042198 | 9042702 | 0.9730 | 0.1860 | 0.7869 |
| chr10 | 90205044 | 90205701 | 0.9730 | 0.5922 | 0.3808 |
| chr3 | 1.89E+08 | 1.89E+08 | 0.9720 | 0.4949 | 0.4771 |
| chr6 | 1.08E+08 | 1.08E+08 | 0.9719 | 0.5825 | 0.3894 |
| chr2 | 2.23E+08 | 2.23E+08 | 0.9714 | 0.3333 | 0.6381 |
| chr19 | 46095583 | 46096190 | 0.9713 | 0.5065 | 0.4648 |
| chr8 | 1.41E+08 | 1.41E+08 | 0.9713 | 0.5753 | 0.3959 |
| chr6 | 90258338 | 90259318 | 0.9712 | 0.4357 | 0.5355 |
| chr13 | 51403556 | 51404069 | 0.9710 | 0.3980 | 0.5731 |
| chr18 | 66875048 | 66875726 | 0.9710 | 0.5259 | 0.4451 |
| chr7 | 99700554 | 99701110 | 0.9708 | 0.3757 | 0.5951 |
| chr7 | 87996908 | 87997437 | 0.9708 | 0.5720 | 0.3988 |
| chr19 | 6623769 | 6624450 | 0.9704 | 0.4774 | 0.4930 |
| chr1 | 97639047 | 97639749 | 0.9701 | 0.4148 | 0.5553 |
| chr16 | 23892096 | 23892772 | 0.9701 | 0.5000 | 0.4701 |
| chr10 | 3938374 | 3938914 | 0.9699 | 0.1148 | 0.8551 |
| chr14 | 89085469 | 89086097 | 0.9696 | 0.2964 | 0.6732 |
| chr8 | 1.29E+08 | 1.29E+08 | 0.9690 | 0.3565 | 0.6126 |
| chr13 | 98377663 | 98378165 | 0.9688 | 0.3123 | 0.6566 |
| chr8 | 56096904 | 56097736 | 0.9688 | 0.4562 | 0.5126 |
| chr2 | 1.03E+08 | 1.03E+08 | 0.9686 | 0.3459 | 0.6227 |
| chr13 | 26608225 | 26608754 | 0.9683 | 0.4562 | 0.5121 |
| chr2 | 22738157 | 22738760 | 0.9682 | 0.5122 | 0.4560 |
| chr6 | 11361243 | 11361801 | 0.9681 | 0.2646 | 0.7035 |
| chr21 | 36529300 | 36529981 | 0.9680 | 0.1829 | 0.7852 |
| chr21 | 37813953 | 37814521 | 0.9679 | 0.3061 | 0.6619 |
| chr2 | 2.43E+08 | 2.43E+08 | 0.9679 | 0.5750 | 0.3929 |

TABLE S3D-continued

List of top 100 loci deduced to be hypomethylated from the

| Chromosome | Start | End | Maternal blow cells | Term placenta | Methylation difference |
|---|---|---|---|---|---|
| chr4 | 12413543 | 12414103 | 0.9679 | 0.5944 | 0.3735 |
| chr3 | 1.27E+08 | 1.27E+08 | 0.9677 | 0.4030 | 0.5648 |
| chr7 | 33509047 | 33509556 | 0.9676 | 0.4627 | 0.5048 |
| chr14 | 59284846 | 59285553 | 0.9674 | 0.5254 | 0.4420 |
| chr17 | 42623453 | 42624024 | 0.9673 | 0.4318 | 0.5355 |
| chr19 | 6778363 | 6779377 | 0.9671 | 0.4416 | 0.5255 |
| chr4 | 41798250 | 41798788 | 0.9670 | 0.5000 | 0.4670 |
| chr5 | 88054080 | 88054588 | 0.9669 | 0.2238 | 0.7431 |
| chr16 | 24109379 | 24110289 | 0.9669 | 0.5062 | 0.4607 |
| chr10 | 13847159 | 13847895 | 0.9667 | 0.3188 | 0.6479 |
| chr10 | 1.27E+08 | 1.27E+08 | 0.9667 | 0.5423 | 0.4244 |
| chr12 | 1.12E+08 | 1.12E+08 | 0.9663 | 0.3722 | 0.5941 |
| chr10 | 17220886 | 17221845 | 0.9662 | 0.4455 | 0.5207 |
| chr8 | 5947355 | 5947862 | 0.9662 | 0.5171 | 0.4491 |
| chr3 | 73740840 | 73741439 | 0.9659 | 0.3657 | 0.6002 |
| chr14 | 57945953 | 57946875 | 0.9658 | 0.5357 | 0.4301 |
| chr14 | 50905777 | 50906333 | 0.9658 | 0.3008 | 0.6650 |
| chr15 | 90275374 | 90276000 | 0.9657 | 0.5409 | 0.4248 |
| chr22 | 24717299 | 24718197 | 0.9657 | 0.5160 | 0.4497 |
| chr7 | 36530122 | 36530987 | 0.9656 | 0.5194 | 0.4462 |
| chr2 | 1.31E+08 | 1.31E+08 | 0.9655 | 0.4384 | 0.5271 |
| chr4 | 42116988 | 42117788 | 0.9654 | 0.5195 | 0.4459 |
| chr2 | 1.16E+08 | 1.16E+08 | 0.9653 | 0.5594 | 0.4059 |
| chr12 | 7491785 | 7492736 | 0.9652 | 0.4556 | 0.5097 |
| chr19 | 6599638 | 6600187 | 0.9652 | 0.5488 | 0.4163 |
| chr6 | 25326803 | 25327398 | 0.9651 | 0.3974 | 0.5677 |
| chr4 | 1.7E+08 | 1.7E+08 | 0.9651 | 0.4933 | 0.4718 |
| chr7 | 99875338 | 99876155 | 0.9650 | 0.2696 | 0.6953 |
| chr14 | 97144328 | 97145208 | 0.9649 | 0.5377 | 0.4272 |
| chr3 | 11718596 | 11719163 | 0.9649 | 0.5521 | 0.4128 |
| chr14 | 1E+08 | 1E+08 | 0.9649 | 0.3794 | 0.5855 |
| chr7 | 1.5E+08 | 1.5E+08 | 0.9648 | 0.3327 | 0.6322 |
| chr12 | 56357827 | 56358328 | 0.9648 | 0.4217 | 0.5430 |
| chr10 | 8275750 | 8276276 | 0.9647 | 0.3100 | 0.6547 |
| chr11 | 16999685 | 17000209 | 0.9647 | 0.2765 | 0.6882 |
| chr22 | 34419356 | 34419861 | 0.9646 | 0.4245 | 0.5401 |
| chr18 | 72453151 | 72453725 | 0.9646 | 0.4700 | 0.4946 |
| chr5 | 49919879 | 49920699 | 0.9645 | 0.3169 | 0.6476 |
| chr1 | 24580891 | 24581805 | 0.9643 | 0.3565 | 0.6078 |
| chr22 | 18233774 | 18234492 | 0.9641 | 0.5205 | 0.4436 |
| chr14 | 45356178 | 45356903 | 0.9640 | 0.3934 | 0.5706 |
| chr3 | 53007193 | 53008661 | 0.9638 | 0.4902 | 0.4737 |
| chr4 | 55027912 | 55028539 | 0.9637 | 0.5254 | 0.4384 |
| chr5 | 1.37E+08 | 1.37E+08 | 0.9637 | 0.5290 | 0.4347 |
| chr1 | 2.23E+08 | 2.23E+08 | 0.9636 | 0.0997 | 0.8640 |
| chr7 | 1.35E+08 | 1.35E+08 | 0.9636 | 0.2959 | 0.6677 |
| chr5 | 80350438 | 80351169 | 0.9636 | 0.4969 | 0.4667 |
| chr12 | 31889600 | 31890343 | 0.9636 | 0.1745 | 0.7891 |
| chr12 | 8365395 | 8366096 | 0.9636 | 0.5721 | 0.3914 |
| chr19 | 15424819 | 15425355 | 0.9635 | 0.2836 | 0.6799 |
| chr10 | 10985469 | 10986409 | 0.9635 | 0.4877 | 0.4759 |

What is claimed is:

1. A method of measuring a first methylation profile of a first tissue from a first biological sample of an organism, the method comprising:

obtaining the first biological sample, the first biological sample including cell-free DNA comprising a mixture of cell-free DNA originating from the first tissue and from a second tissue, the first tissue being fetal or placental tissue or tumor tissue, wherein the first biological sample is selected from the group consisting of blood, plasma, serum, urine, saliva, sputum, tears, and stool;

purifying the first biological sample for the mixture of cell-free DNA from a cellular portion of the first biological sample;

obtaining a second methylation profile corresponding to DNA of the second tissue, the second methylation profile providing a methylation density at each of a plurality of loci in a genome, the methylation density at a particular locus corresponding to a proportion of DNA of the second tissue that are methylated;

determining a cell-free methylation profile of the cell-free DNA of the mixture, wherein the determining the cell-free methylation profile comprises:
performing an assay on the cell-free DNA of the mixture, wherein performing the assay on the cell-free DNA of the mixture comprises:
sequencing the cell-free DNA, wherein the assay is performed at a genome-wide scale; and
detecting methylation statuses of the cell-free DNA from the mixture at the plurality of loci; and
determining, by a computer system, a methylation density at each of the plurality of loci using the methylation statuses of the cell-free DNA from the mixture at the plurality of loci;

determining, by the computer system, a percentage of the cell-free DNA in the mixture that are from the first tissue; and determining, by the computer system, the first methylation profile of the first tissue by:
for each of the plurality of loci:
calculating a differential parameter that includes a difference between the methylation density of the second methylation profile and the methylation density of the cell-free methylation profile, the difference being scaled by the percentage.

2. The method of claim 1, further comprising:
determining a first methylation level from the first methylation profile; and
comparing the first methylation level to a first cutoff value to determine a classification of a level of cancer based on the comparison.

3. The method of claim 1, further comprising:
transforming the first methylation profile to obtain a corrected first methylation profile.

4. The method of claim 3, wherein the transformation is a linear transformation.

5. The method of claim 1, wherein the differential parameter D for a locus is defined as $$D = mbc - \frac{(mbc - mp)}{f * CN},$$

where mbc denotes the methylation density of the second methylation profile at the locus, mp denotes the methylation density of the cell-free methylation profile at the locus, f is the percentage of cell-free DNA from the first tissue in the first biological sample, and CN represents a copy number at the locus.

6. The method of claim 5, wherein CN is one for the copy number of the first tissue being disomic at the locus.

7. The method of claim 5, further comprising:
identifying regions where D exceeds a threshold.

8. The method of claim 1, further comprising:
identifying the plurality of loci by selecting loci that have any one or more of the following criteria:
a GC content of greater than 50%;
a methylation density of the second methylation profile of less than a first threshold or greater than a second threshold; and
a minimum of five CpG sites in a region defined by the locus.

9. The method of claim 1, wherein the first biological sample is from a female subject pregnant with a fetus, and wherein the first tissue is from the fetus or a placenta and the second tissue corresponds to the female subject.

10. The method of claim 9, further comprising:
determining a first methylation level from the first methylation profile; and
comparing the first methylation level to a first cutoff value to determine a classification of a medical condition.

11. The method of claim 10, wherein the medical condition is preeclampsia or a chromosomal abnormality in the first tissue.

12. The method of claim 1, wherein the first tissue is from a tumor within the organism and the second tissue is from non-tumor of the organism.

13. The method of claim 1, wherein the cellular portion of the first biological sample includes cellular DNA from the second tissue, the method further comprising:
extracting the cellular DNA from the first biological sample, wherein obtaining the second methylation profile includes:
analyzing the cellular DNA from the second tissue of the first biological sample by performing an assay on the cellular DNA to determine the second methylation profile.

14. The method of claim 1, wherein the obtained second methylation profile corresponds to an average methylation profiles obtained from a group of control samples.

15. The method of claim 1, wherein determining a methylation density of the cell-free methylation profile for a first locus of the plurality of loci includes:
determining a first number of the cell-free DNA that are from the first locus;
determining whether each DNA molecule of the first number is methylated at one or more sites to obtain a second number of methylated DNA molecules; and
calculating the methylation density from the first number and the second number.

16. The method of claim 15, wherein the one or more sites are CpG sites.

17. The method of claim 1, wherein performing the assay on the cell-free DNA of the mixture includes:
treating the cell-free DNA with sodium bisulfite; and
performing random sequencing of the treated DNA.

18. The method of claim 1, wherein performing the assay on the cell-free DNA of the mixture includes:
performing single molecule sequencing of the cell-free DNA, wherein the sequencing of a single molecule includes determining whether at least one site of a DNA molecule is methylated.

19. The method of claim 1, wherein determining the cell-free methylation profile from the cell-free DNA of the mixture includes:
receiving, at the computer system, sequence reads from the sequencing of the cell-free DNA; and
analyzing, by the computer system, the sequence reads to determine locations of the sequence reads and methylation statuses at sites of the sequence reads.

20. The method of claim 13, wherein analyzing the cellular DNA from the second tissue to determine the second methylation profile includes:
receiving, at the computer system, sequence reads from a sequencing of the DNA from the second tissue; and
analyzing, by the computer system, the sequence reads to determine locations of the sequence reads and methylation statuses at sites of the sequence reads.

21. The method of claim 1, wherein the assay comprises massively parallel sequencing.

22. The method of claim 1, wherein the assay comprises digital PCR.

23. The method of claim 1, wherein the second methylation profile is generated from a second biological sample that is different than the first biological sample.

24. The method of claim 23, wherein the second biological sample and the first biological sample are from different subjects.

25. The method of claim 1, wherein the assay is performed at a single nucleotide resolution.

26. The method of claim 1, wherein the cellular portion correspond to the buffy coat of a blood sample.

* * * * *